US011427562B2

(12) United States Patent
Oh et al.

(10) Patent No.: US 11,427,562 B2
(45) Date of Patent: Aug. 30, 2022

(54) HETEROCYCLIC COMPOUND, AND ORGANIC LIGHT-EMITTING DEVICE USING SAME

(71) Applicant: LT MATERIALS CO., LTD., Yongin (KR)

(72) Inventors: Han-Kook Oh, Osan-si (KR); Jun-Tae Mo, Osan-si (KR); Yong-Geun Jung, Seoul (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin (KR)

( * ) Notice: Subject to any disclaimer, the term of this patent is extended or adjusted under 35 U.S.C. 154(b) by 488 days.

(21) Appl. No.: 16/315,271

(22) PCT Filed: Jul. 6, 2017

(86) PCT No.: PCT/KR2017/007256

§ 371 (c)(1),
(2) Date: Jan. 4, 2019

(87) PCT Pub. No.: WO2018/009009

PCT Pub. Date: Jan. 11, 2018

(65) Prior Publication Data

US 2019/0233398 A1 Aug. 1, 2019

(30) Foreign Application Priority Data

Jul. 6, 2016 (KR) ........................ 10-2016-0085746

(51) Int. Cl.
*C07D 401/06* (2006.01)
*C07D 401/14* (2006.01)
(Continued)

(52) U.S. Cl.
CPC ......... *C07D 401/14* (2013.01); *C07D 221/06* (2013.01); *C07D 401/06* (2013.01);
(Continued)

(58) Field of Classification Search
None
See application file for complete search history.

(56) References Cited

U.S. PATENT DOCUMENTS 7,318,966 B2 1/2008 Tominaga et al.

FOREIGN PATENT DOCUMENTS

CN 105061307 A 11/2015
CN 105693631 A 6/2016
(Continued)

OTHER PUBLICATIONS

SciFinder search result for Jahng et al. (Korean Journal of Medicinal Chemistry, 8(1), 22-29, 1998), 2 pages. (Year: 1998).*
Liu, Bingqing, et al. "Tuning the ground state and excited state properties of monocationic iridium (III) complexes by varying the site of benzannulation on diimine ligand." Inorganic chemistry 56.9 (2017): 5361-5370. (Year: 2017).*
Haginawa et al. Yakugaku Zasshi 99(12), 1979, 1181-1185. (Year: 1979).*
(Continued)

*Primary Examiner* — Robert S Loewe
(74) *Attorney, Agent, or Firm* — Birch, Stewart, Kolasch & Birch, LLP

(57) ABSTRACT

The present application provides a hetero-cyclic compound capable of significantly enhancing lifespan, efficiency, electrochemical stability and thermal stability of an organic light emitting device, and an organic light emitting device containing the hetero-cyclic compound in an organic compound layer.

8 Claims, 3 Drawing Sheets

(51) Int. Cl.

| | |
|---|---|
| ***C07D 221/06*** | (2006.01) |
| ***H01L 51/00*** | (2006.01) |
| ***H01L 51/50*** | (2006.01) |
| ***C09K 11/06*** | (2006.01) |
| ***C07D 401/10*** | (2006.01) |
| ***C07D 405/14*** | (2006.01) |
| ***C07D 409/14*** | (2006.01) |
| ***C07D 471/04*** | (2006.01) |

(52) U.S. Cl.

CPC ......... *C07D 401/10* (2013.01); *C07D 405/14* (2013.01); *C07D 409/14* (2013.01); *C07D 471/04* (2013.01); *C09K 11/06* (2013.01); *H01L 51/00* (2013.01); *H01L 51/0054* (2013.01); *H01L 51/0067* (2013.01); *H01L 51/0072* (2013.01); *H01L 51/0073* (2013.01); *H01L 51/0074* (2013.01); *H01L 51/50* (2013.01); *H01L 51/5012* (2013.01); *H01L 51/5016* (2013.01); *H01L 51/5044* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

FOREIGN PATENT DOCUMENTS

| | | | | |
|---|---|---|---|---|
| JP | 2002-222697 A | 8/2002 | | |
| JP | 2010-27761 A | 2/2010 | | |
| KR | 10-2015-0076029 A | 7/2015 | | |
| KR | 10-1533035 B1 | 7/2015 | | |
| WO | WO-2010062107 A1 * | 6/2010 | ........... | C07D 279/24 |

OTHER PUBLICATIONS

International Search Report (PCT/ISA/210) issued in PCT/KR2017/007256, dated Oct. 20, 2017.

Karim et al., "Unusual Product Distribution from Friedländer Reaction of Di- and Triacetylbenzenes with 3-Aminonaphthalene-2-carbaldehyde and Properties of New Benzo[g]quinoline-Derived Aza-aromatics", Molecules, 2014, vol. 19, No. 8, pp. 12842-12851. See p. 12842:formua 1.

Kuwabara et al., "Thermally Stable Multilayered Organic Electroluminescent Devices Using Novel Starburst Molecules, 4,4' ,4"-Tri(N-carbazolyl)triphenylamine (TCTA) and 4,4' ,4" -Tris(3-methylphenylphenylamino)triphenylamine (m-MTDATA), as Hole-Transport Materials", Advanced Materials, 1994, vol. 6, No. 9, pp. 677-679.

* cited by examiner

【FIG. 1】
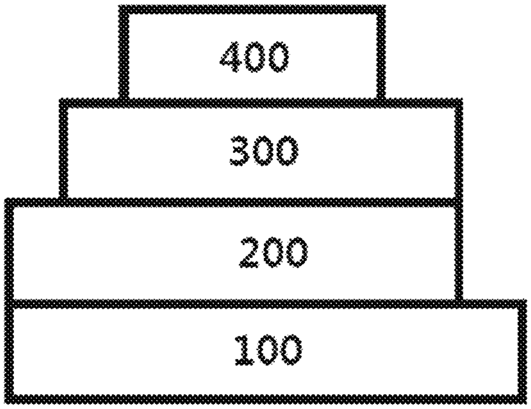
【FIG. 2】
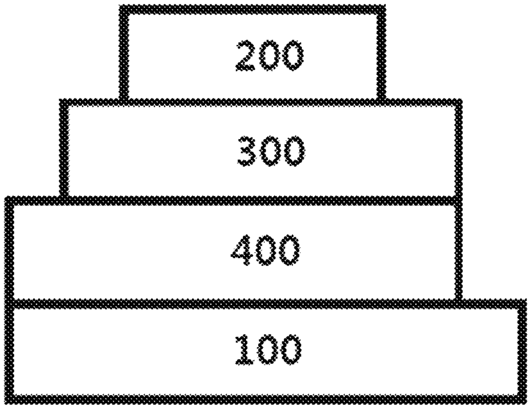

【FIG. 3】
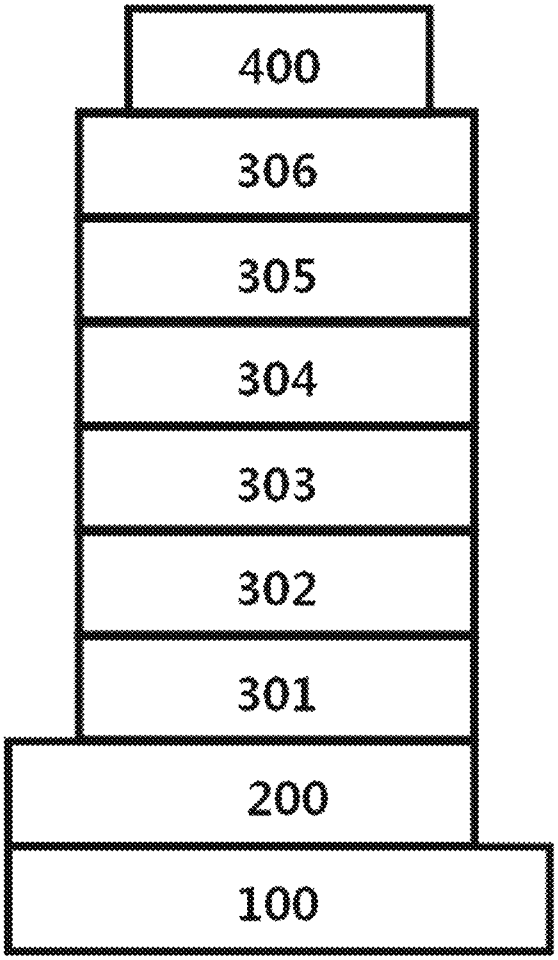

【FIG. 4】

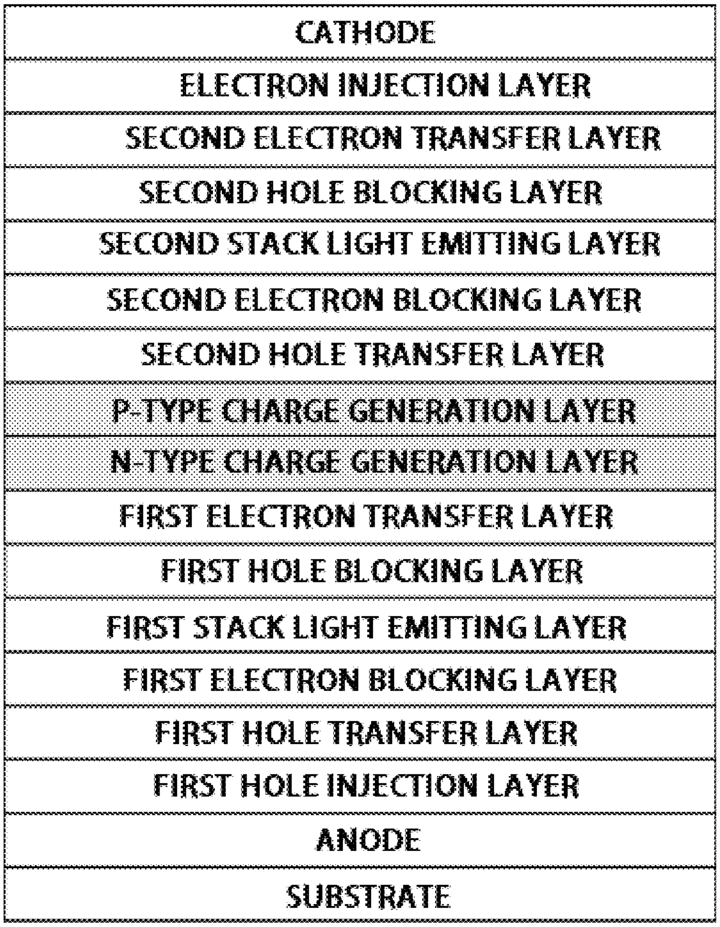

[FIG. 4]

| |
|---|
| CATHODE |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND, AND ORGANIC LIGHT-EMITTING DEVICE USING SAME

TECHNICAL FIELD

The present application claims priority to and the benefits of Korean Patent Application No. 10-2016-0085746, filed with the Korean Intellectual Property Office on Jul. 6, 2016, the entire contents of which are incorporated herein by reference.

The present application relates to a hetero-cyclic compound and an organic light emitting device using the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves may be used alone, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifespan or efficiency of an organic light emitting device.

PRIOR ART DOCUMENTS

Patent Documents

U.S. Pat. No. 4,356,429

DISCLOSURE

Technical Problem

Researches for an organic light emitting device comprising a compound capable of satisfying conditions required for materials usable in an organic light emitting device, for example, a proper energy level, electrochemical stability, thermal stability and the like, and having a chemical structure that may perform various roles required in an organic light emitting device depending on substituents have been required.

Technical Solution

One embodiment of the present application provides a hetero-cyclic compound represented by the following Chemical Formula 1:

[Chemical Formula 1]

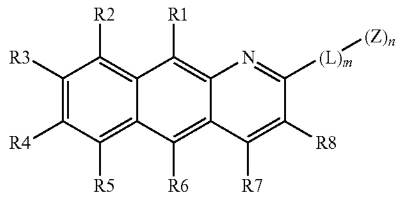

in Chemical Formula 1,

L is a direct bond; a substituted or unsubstituted $C_6$ to $C_{60}$ arylene group; or a $C_2$ to $C_{60}$ heteroarylene group, Z is selected from the group consisting of hydrogen; deuterium; a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, m is an integer of 0 to 4, n is an integer of 1 to 4, R1 to R6, and R8 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring, R7 is selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, and R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Another embodiment of the present application provides an organic light emitting device comprising an anode, a cathode, and one or more organic material layers provided between the anode and the cathode, wherein one or more layers of the organic material layers comprise the hetero-cyclic compound represented by Chemical Formula 1.

Advantageous Effects

A hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer or the like in an organic light emitting device. Particularly, the hetero-cyclic compound represented by Chemical Formula 1 can be used as a material of an electron transfer layer or a charge generation layer in an organic light emitting device. In addition, using the hetero-cyclic compound represented by Chemical Formula 1 in an organic light emitting device lowers a driving voltage of the device, enhances light efficiency, and can enhance a lifespan property of the device with thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

A hetero-cyclic compound according to one embodiment of the present application is represented by Chemical Formula 1. More specifically, the hetero-cyclic compound represented by Chemical Formula 1 is capable of being used as an organic material layer material of an organic light emitting device with such a core structure and structural characteristics of substituents.

In one embodiment of the present application, when m of Chemical Formula 1 is 2 or greater, two or more Ls may be the same as or different from each other. In addition, when n of Chemical Formula 1 is 2 or greater, two or more Zs may be the same as or different from each other.

In one embodiment of the present application, m of Chemical Formula 1 may be an integer of 1 to 4.

In one embodiment of the present application, at least one of R1 and R6 of Chemical Formula 1 is a substituted or unsubstituted $C_6$ to $C_{60}$ aryl group, and the rest may be hydrogen or deuterium.

In another embodiment, at least one of R1 and R6 of Chemical Formula 1 is a $C_6$ to $C_{60}$ aryl group, and the rest may be hydrogen or deuterium.

In another embodiment, at least one of R1 and R6 of Chemical Formula 1 is a phenyl group, and the rest may be hydrogen.

In one embodiment of the present application, Z of Chemical Formula 1 may be selected from the group consisting of hydrogen; a substituted or unsubstituted $C_1$ to $C_{60}$ alkyl group; a substituted or unsubstituted $C_6$ to $C_{60}$ aryl group; and a substituted or unsubstituted $C_2$ to $C_{60}$ heteroaryl group.

In another embodiment, Z of Chemical Formula 1 may be hydrogen; a $C_6$ to $C_{60}$ aryl group unsubstituted or substituted with one or more substituents selected from the group consisting of a $C_6$ to $C_{60}$ aryl group and a $C_2$ to $C_{60}$ heteroaryl group; or a $C_2$ to $C_{60}$ heteroaryl group unsubstituted or substituted with one or more substituents selected from the group consisting of a $C_1$ to $C_{60}$ alkyl group, a $C_6$ to $C_{60}$ aryl group and a $C_2$ to $C_{60}$ heteroaryl group.

In another embodiment, Z of Chemical Formula 1 may be hydrogen; a phenyl group; a naphthyl group unsubstituted or substituted with a phenyl group; an anthracene group; a triphenylene group; a pyrene group; a phenanthrene group; or a perylene group.

In another embodiment, Z of Chemical Formula 1 may be hydrogen; a benzoquinoline group unsubstituted or substituted with a phenyl group; a triazine group unsubstituted or substituted with one or more substituents selected from the group consisting of a phenyl group and a biphenyl group; a pyrimidine group unsubstituted or substituted with one or more substituents selected from the group consisting of a phenyl group and a biphenyl group; a pyridine group unsubstituted or substituted with one or more substituents selected from the group consisting of a phenyl group, a pyrene group, a triphenylene group, a quinoline group and a naphthyl group; a quinoline group unsubstituted or substituted with one or more substituents selected from the group consisting of a pyridine group, a phenyl group and pyrene group; a phenanthroline group unsubstituted or substituted with one or more substituents selected from the group consisting of a naphthyl group, a methyl group, a quinoline group, a phenyl group, a pyridine group and a biphenyl group; a benzimidazole group unsubstituted or substituted with a phenyl group; a dibenzothiophene group; a dibenzofuran group; or a carbazole group.

In one embodiment of the present application, Z of Chemical Formula 1 may be substituted again with one or more substituents selected from the group consisting of a $C_6$ to $C_{60}$ aryl group and a $C_6$ to $C_{60}$ heteroaryl group.

In another embodiment, Z of Chemical Formula 1 may be substituted again with one or more substituents selected from the group consisting of a pyridine group; a quinoline group; a pyrene group; and a pyrimidine group.

In one embodiment of the present application, L may be a direct bond; a substituted or unsubstituted $C_6$ to $C_{40}$ arylene group; or a substituted or unsubstituted $C_2$ to $C_{40}$ heteroarylene group.

In another embodiment, L may be a direct bond; a $C_6$ to $C_{40}$ arylene group unsubstituted or substituted with one or more substituents selected from the group consisting of a $C_1$ to $C_{40}$ alkyl group, a $C_6$ to $C_{40}$ aryl group and a $C_2$ to $C_{40}$ heteroaryl group; or a $C_2$ to $C_{40}$ heteroarylene group unsubstituted or substituted with one or more substituents selected from the group consisting of a $C_1$ to $C_{40}$ alkyl group, a $C_6$ to $C_{40}$ aryl group and a $C_2$ to $C_{40}$ heteroaryl group.

In another embodiment, L may be a direct bond; a phenylene group unsubstituted or substituted with one or more substituents selected from the group consisting of a pyridine group, a pyrimidine group, a quinoline group, a phenanthroline group, an anthracene group, a benzoquinoline group, a naphthyl group, a phenyl group, a triazine group, a dibenzofuran group, a dibenzothiophene group and a carbazole group; a divalent anthracene group unsubstituted or substituted with one or more substituents selected from the group consisting of a phenyl group, a naphthyl group, a pyridine group and a quinoline group; a biphenylene group; a naphthylene group; a phenalene group; a divalent phenanthrene group; or a divalent pyrene group.

In another embodiment, L may be a direct bond; a divalent pyridine group unsubstituted or substituted with one or more substituents selected from the group consisting of a phenyl group, a pyridine group, a pyrimidine group, a quinoline group, a phenanthroline group, an anthracene group, a benzoquinoline group, a naphthyl group and a triazine group; a divalent phenanthroline group unsubstituted or substituted with one or more substituents selected from the group consisting of a phenyl group and a methyl group; a divalent benzoquinoline group; a divalent pyrimidine group or a divalent quinoline group.

In one embodiment of the present application, L may be substituted again with one or more substituents selected from the group consisting of a $C_1$ to $C_{60}$ alkyl group; a $C_6$ to $C_{60}$ aryl group; and a $C_6$ to $C_{60}$ heteroaryl group.

In another embodiment, L may be substituted again with one or more substituents selected from the group consisting of a methyl group; a phenyl group; a biphenyl group; a naphthyl group; a pyridine group; a pyrimidine group; a quinoline group; and a benzoquinoline group.

According to one embodiment of the present application, Chemical Formula 1 may be represented by any one of the following Chemical Formulae 2 to 6.

[Chemical Formula 2]

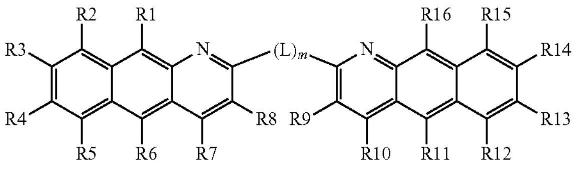

[Chemical Formula 3]

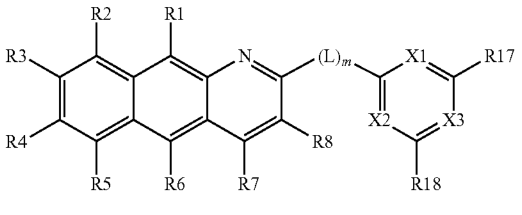

[Chemical Formula 4]

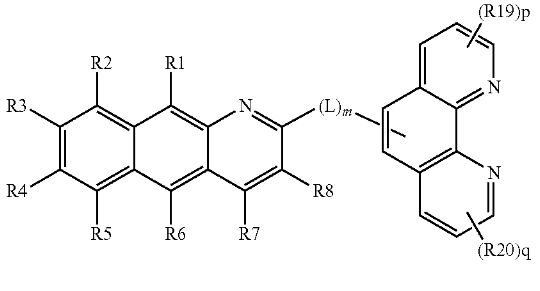

-continued

[Chemical Formula 5]

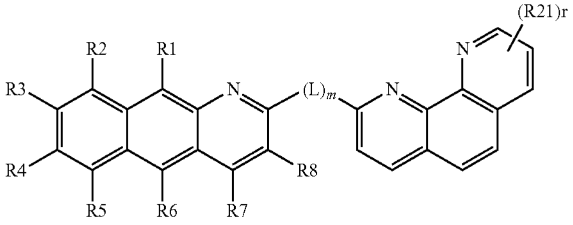

[Chemical Formula 6]

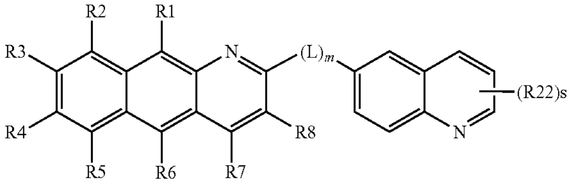

In Chemical Formulae 2 to 6,

L, R1 to R8, and m have the same definitions as in Chemical Formula 1, at least one of X1 to X3 is N, and the rest are each independently N or CR23, R9 to R23 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring, and p, q, r and s are each independently an integer of 0 to 3.

In one embodiment of the present application, R23 is hydrogen.

In one embodiment of the present application, at least one of R1 and R6 and at least one of R11 and R16 of Chemical Formulae 2 to 6 are a substituted or unsubstituted $C_6$ to $C_{60}$ aryl group, and the rest may be hydrogen or deuterium.

In another embodiment, at least one of R1 and R6 and at least one of R11 and R16 of Chemical Formulae 2 to 6 are a $C_6$ to $C_{60}$ aryl group, and the rest may be hydrogen or deuterium.

In another embodiment, at least one of R1 and R6 and at least one of R11 and R16 of Chemical Formulae 2 to 6 are a phenyl group, and the rest may be hydrogen.

In one embodiment of the present application, R2 to R5, R7 to R10, and R12 to R15 of Chemical Formulae 1 and 2 may be each independently hydrogen or deuterium.

In one embodiment of the present application, R, R' and R" of Chemical Formulae 1 and 2 are the same as or different from each other, and may be each independently hydrogen; a substituted or unsubstituted $C_1$ to $C_{60}$ alkyl group; or a substituted or unsubstituted $C_6$ to $C_{60}$ aryl group.

In one embodiment of the present application, R17 and R18 are the same as or different from each other, and may be each independently hydrogen; or a substituted or unsubstituted $C_6$ to $C_{60}$ aryl group.

In another embodiment, R17 and R18 are the same as or different from each other, and may be each independently hydrogen; or a $C_6$ to $C_{60}$ aryl group.

In another embodiment, R17 and R18 are the same as or different from each other, and may be each independently hydrogen; a phenyl group; a naphthyl group; or a biphenyl group.

In one embodiment of the present application, R19 to R21 are the same as or different from each other, and may be each independently hydrogen; a substituted or unsubstituted $C_1$ to $C_{60}$ alkyl group; a substituted or unsubstituted $C_6$ to $C_{60}$ aryl group; or a substituted or unsubstituted $C_2$ to $C_{60}$ heteroaryl 10 group.

In another embodiment, R19 to R21 are the same as or different from each other, and may be each independently hydrogen; a $C_1$ to $C_{60}$ alkyl group; a $C_6$ to $C_{60}$ aryl group; or a $C_2$ to $C_{60}$ heteroaryl group.

In another embodiment, R19 to R21 are the same as or different from each other, and may be each independently hydrogen; a methyl group; a phenyl group; a pyridine group; a naphthyl group; a quinoline group; or a benzoquinoline group.

In one embodiment of the present application, R22 may be hydrogen; a $C_1$ to $C_{60}$ alkyl group; a $C_6$ to $C_{60}$ aryl group; or a $C_2$ to $C_{60}$ heteroaryl group.

In another embodiment, R22 may be hydrogen; a phenyl group unsubstituted or substituted with one or more substituents selected from the group consisting of a quinoline group, a pyridine group and a benzoquinoline group; a pyrene group; or a pyridine group.

In the present specification, the term "substituted or unsubstituted" means being substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_{60}$ arylamine group; and a $C_2$ to $C_{60}$ heteroarylamine group, or being unsubstituted, or being substituted with a substituent bonding two or more of the above-mentioned substituents, or being substituted, or being substituted with a substituent linking two or more substituents selected from among the above-mentioned substituents, or being unsubstituted. For example, "a substituent linking two or more substituents" may comprise a biphenyl group. In other words, a biphenyl group may be an aryl group, or may be interpreted as a substituent linking two phenyl groups. The additional substituents may be further substituted. R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to one embodiment of the present application, the "substituted or unsubstituted" means being substituted with one or more substituents selected from the group consisting of deuterium, a halogen group, —CN, SiRR'R", P(=O)RR', a $C_1$ to $C_{20}$ linear or branched alkyl group, a $C_6$ to $C_{60}$ aryl group, and a $C_2$ to $C_{60}$ heteroaryl group, or being unsubstituted, and R, R' and R" are the same as or different from each other, and each independently hydrogen; deuterium; —CN; a $C_1$ to $C_{60}$ alkyl group unsubstituted or substituted with deuterium, a halogen group, —CN, a $C_1$ to $C_{20}$ alkyl group, a $C_6$ to $C_{60}$ aryl group and a $C_2$ to $C_{60}$ heteroaryl group; a $C_3$ to $C_{60}$ cycloalkyl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; a $C_6$ to $C_{60}$ aryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; or a $C_2$ to $C_{60}$ heteroaryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, however, may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, however, may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, however, may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the following spiro group may comprise any one of the groups having the following structural formulae.

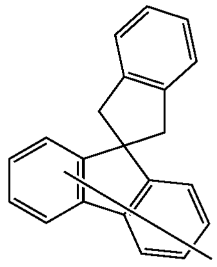

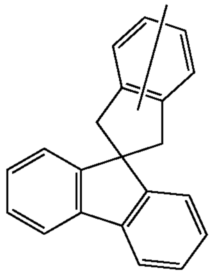

-continued

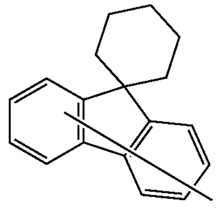

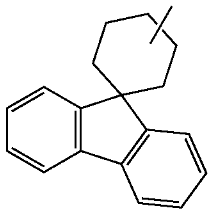

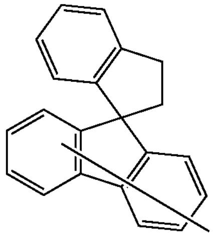

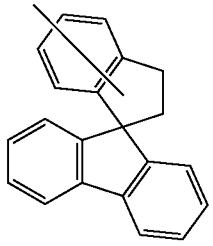

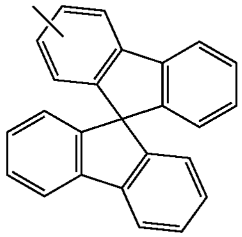

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, however, may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

According to one embodiment of the present application, Chemical Formula 1 may be represented by any one of the following compounds, but is not limited thereto.

1

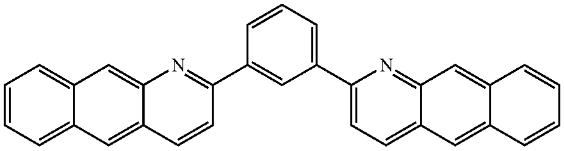

2

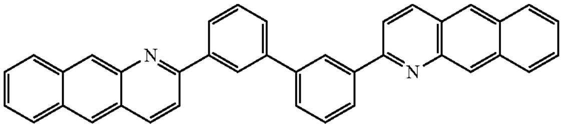

3

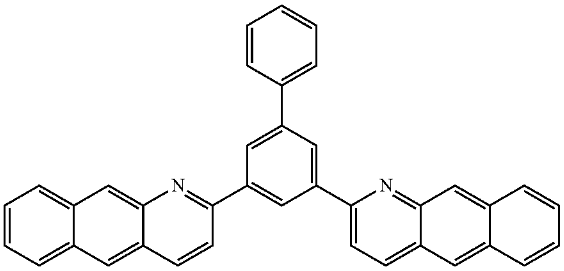

4

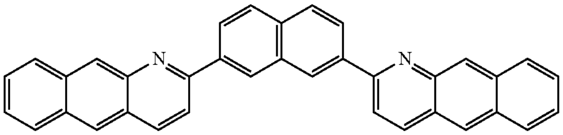

5

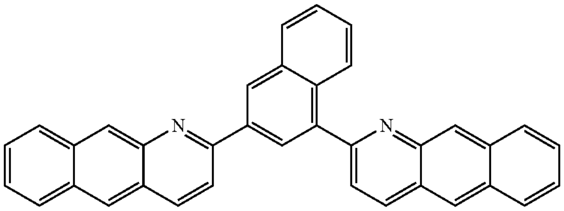

6

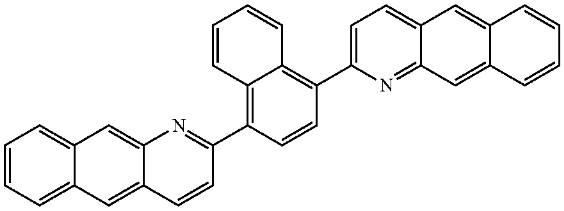

7

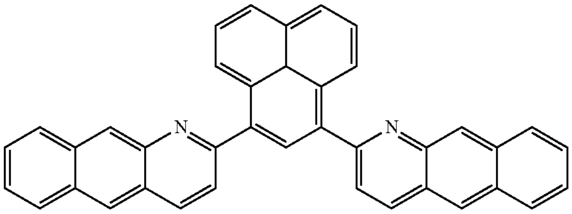

8

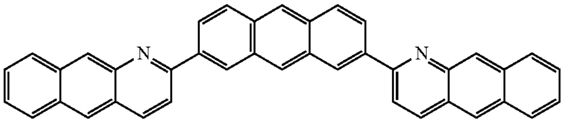

-continued
9
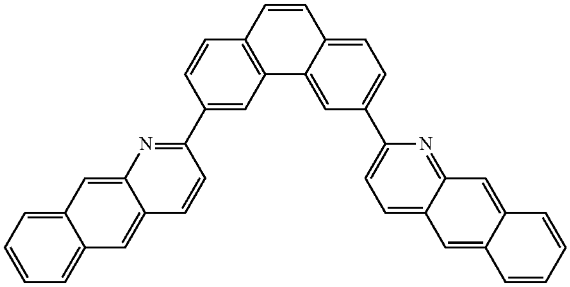
10
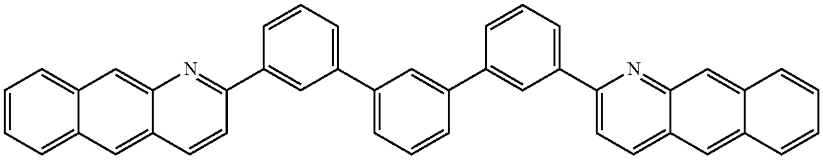
11
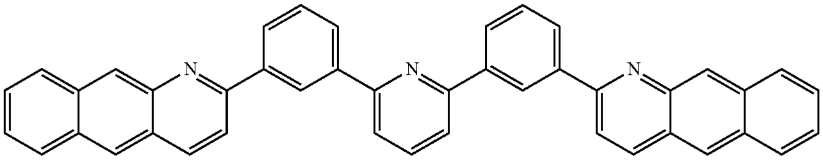
12
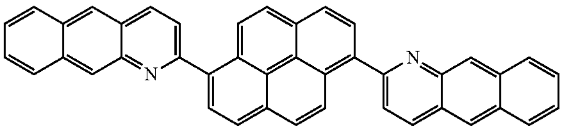
13
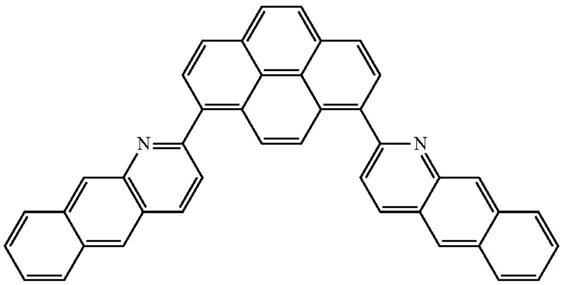
14
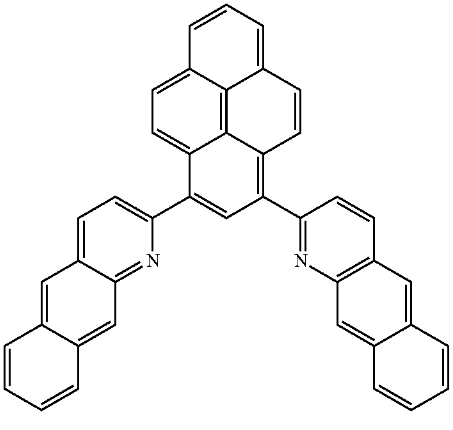
15
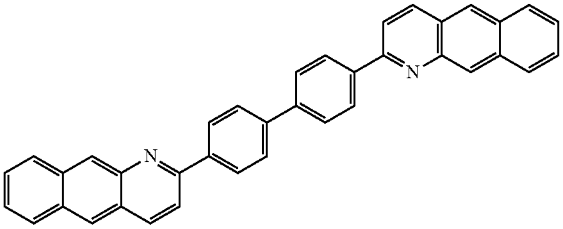
16
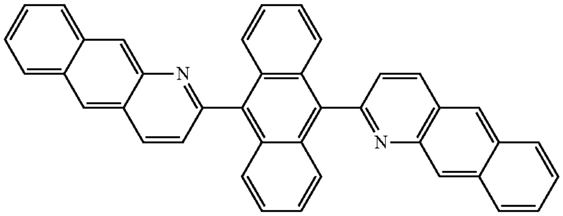
17
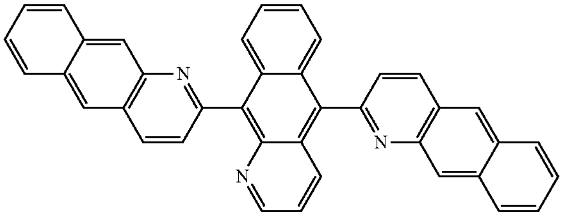

-continued
18
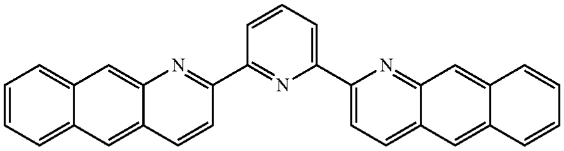
19
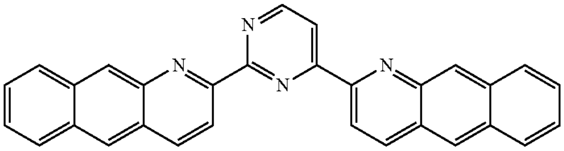
20
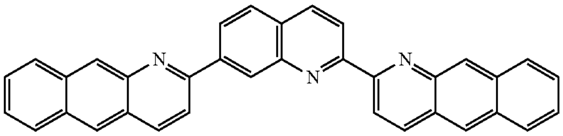
21
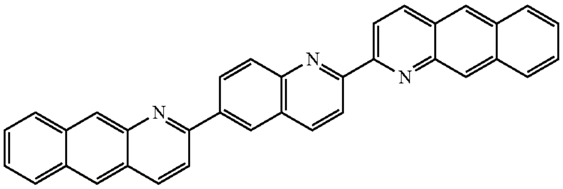
22
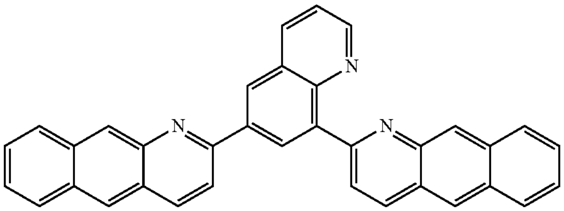
23
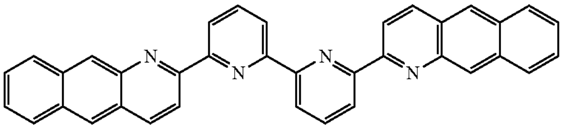
24
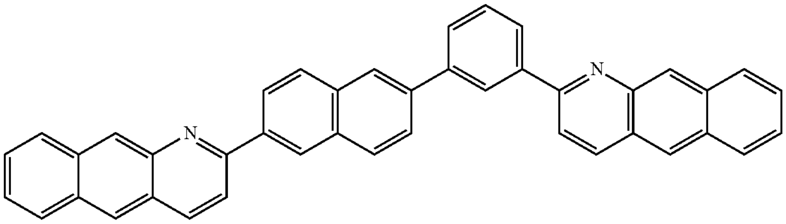
25
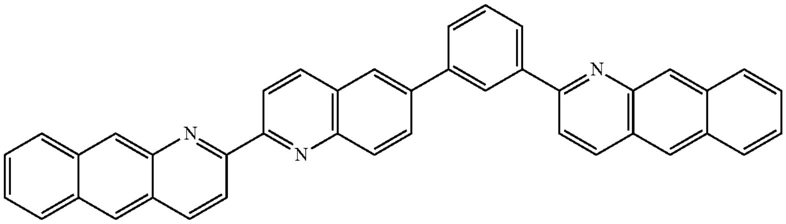
26
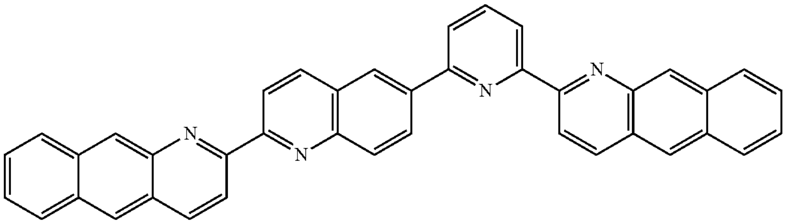
27
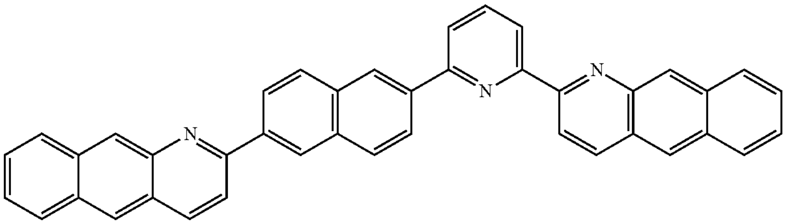

-continued
28
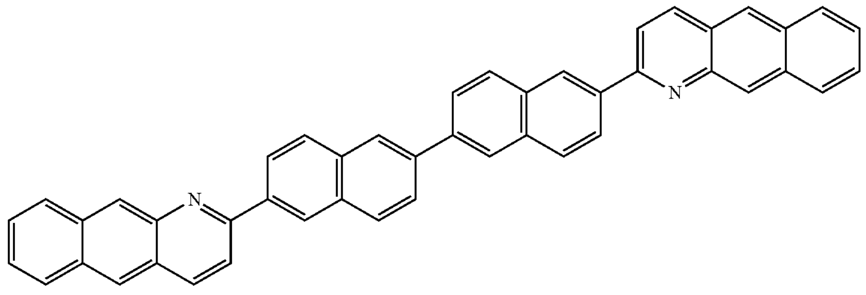
29
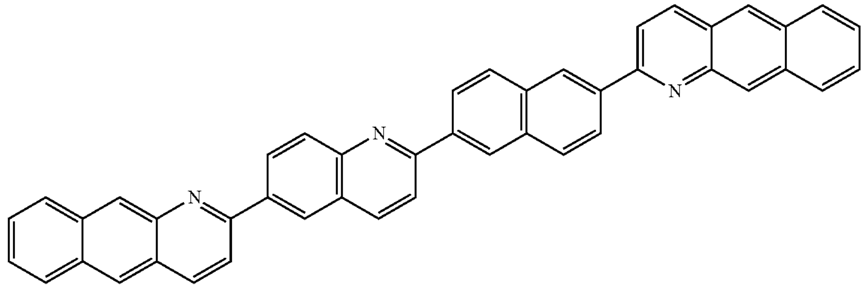
30
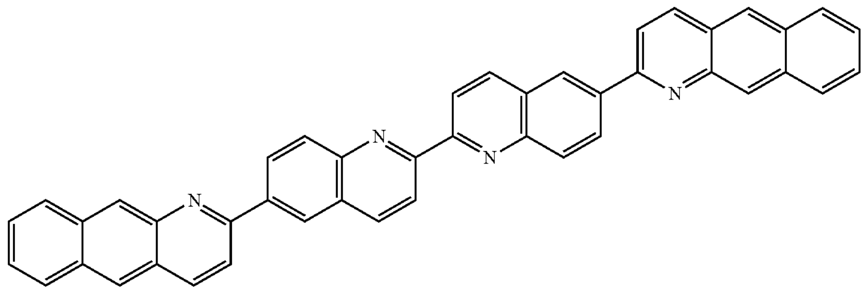
31
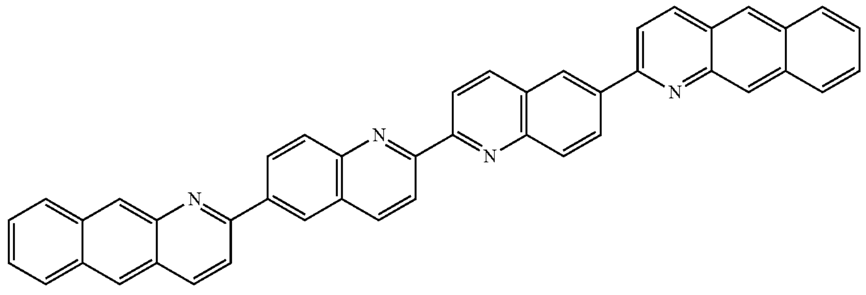
32
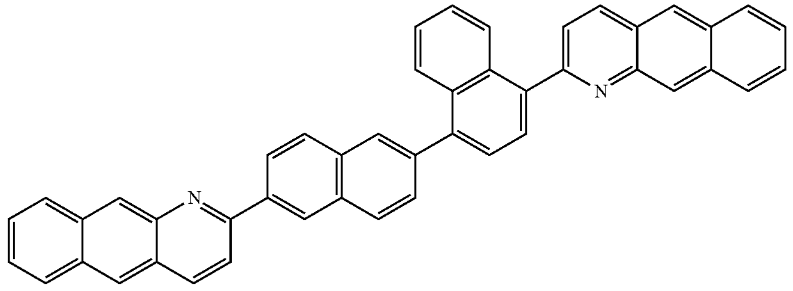

-continued
33
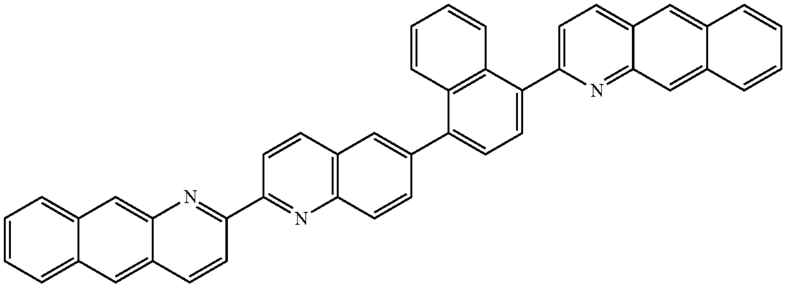
34
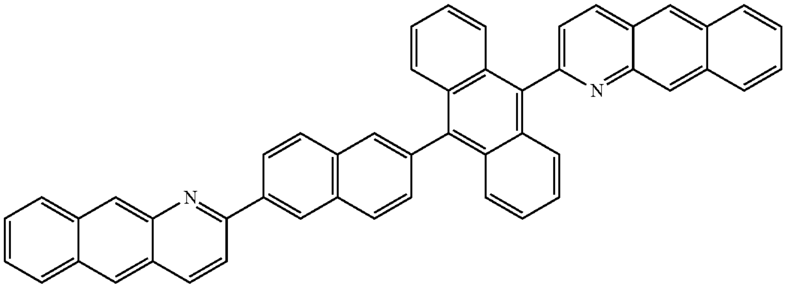
35
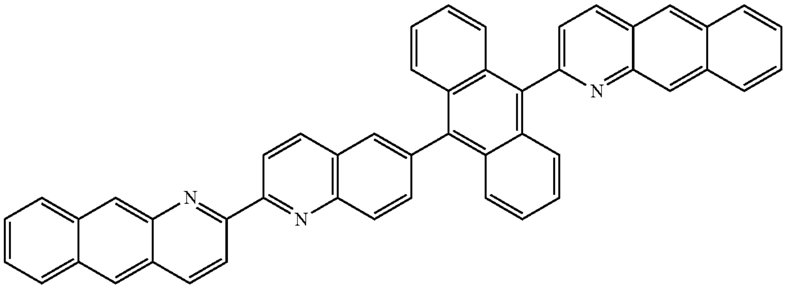
36
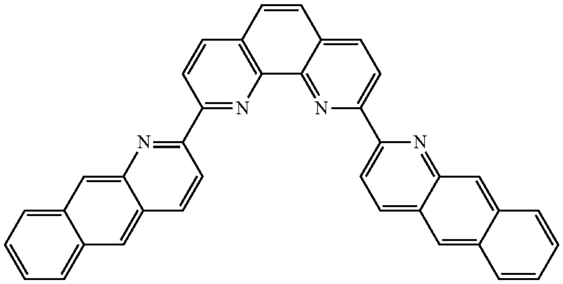
37
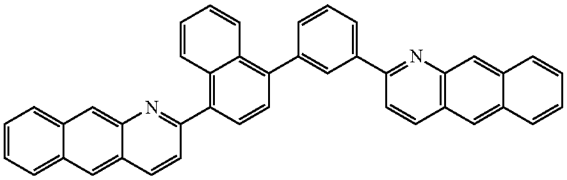
38
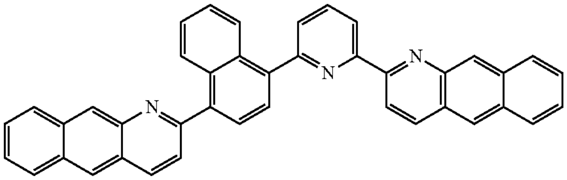
39
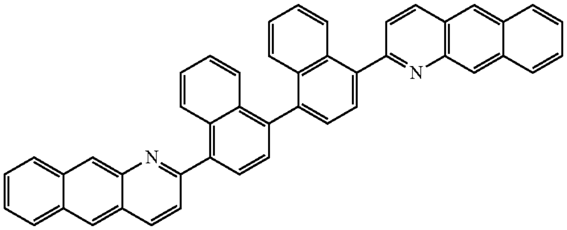

-continued
40
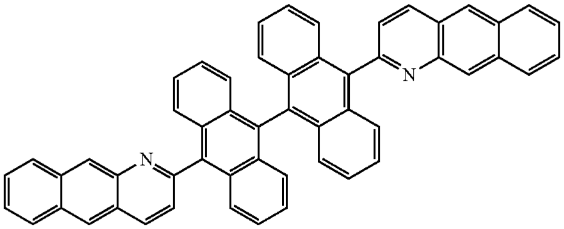
41
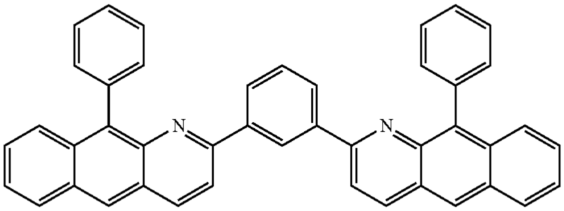
42
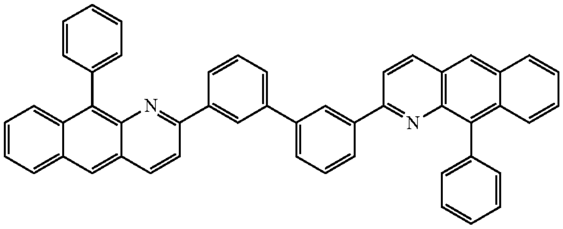
43
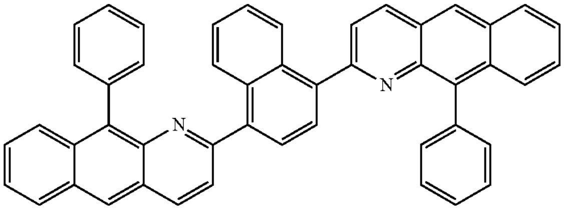
44
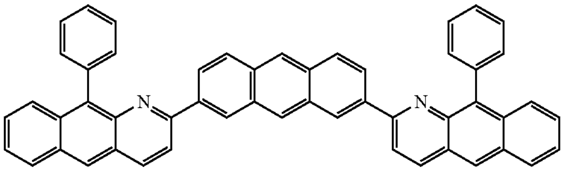
45
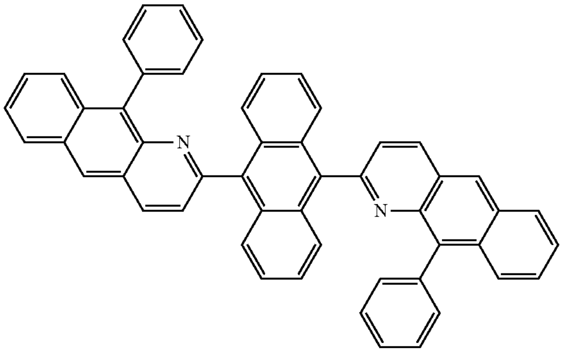
46
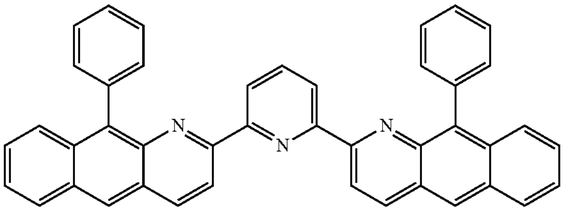
47
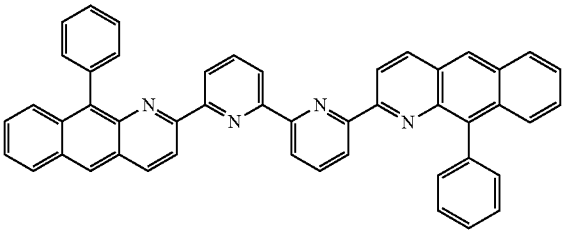
48
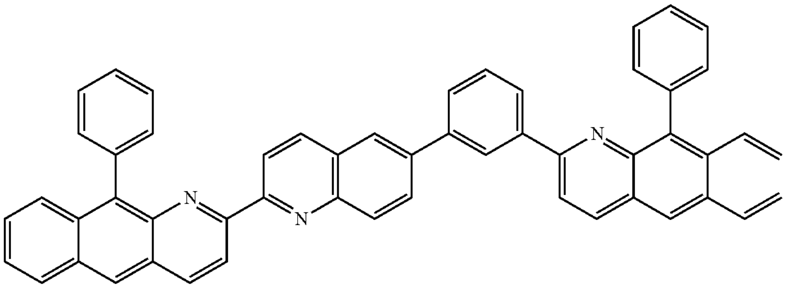

-continued
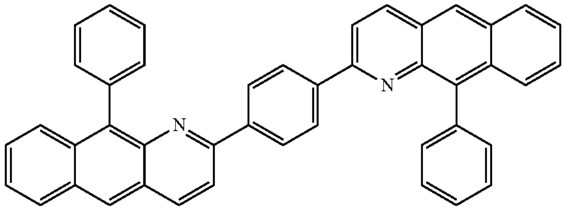
49
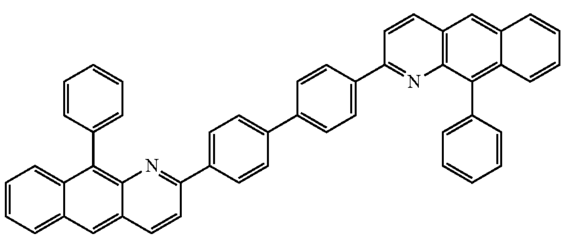
50
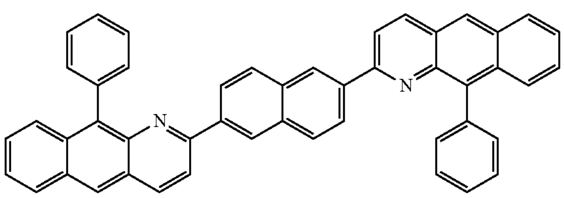
51
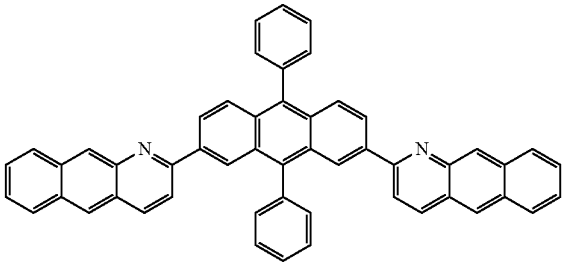
52
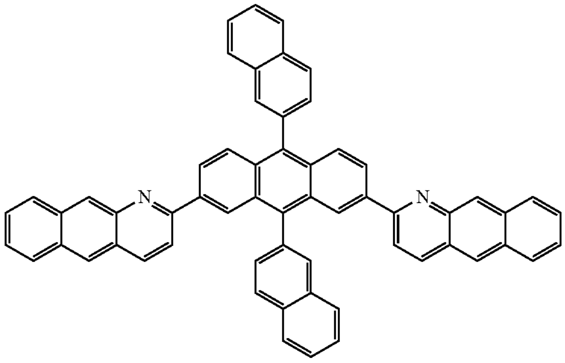
53
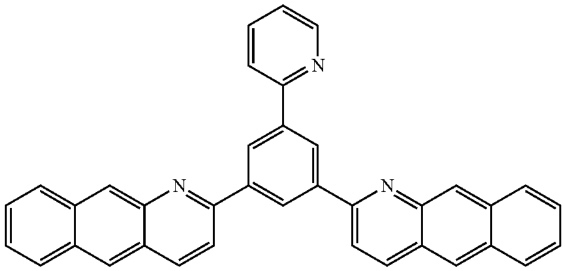
54
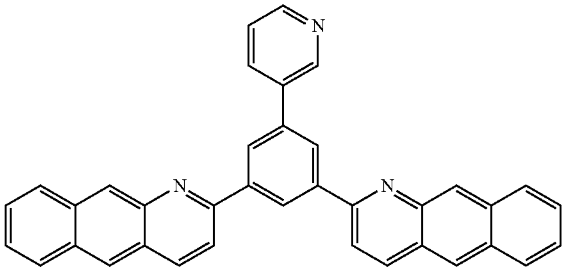
55
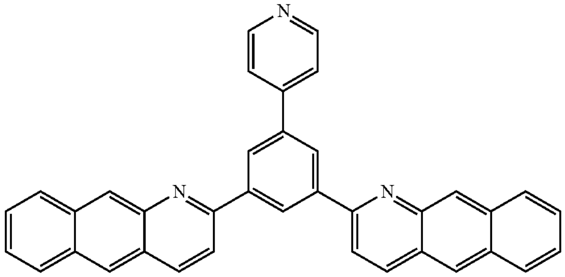
56
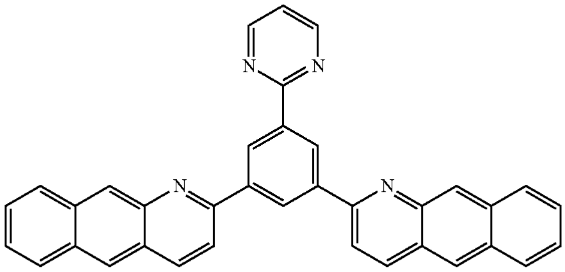
57

-continued
58
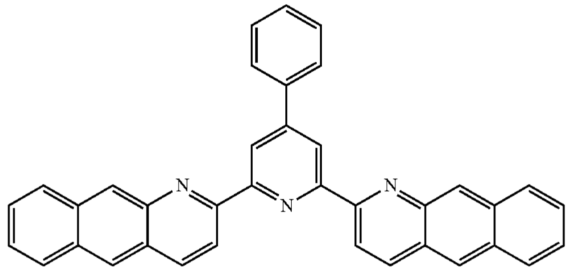
59
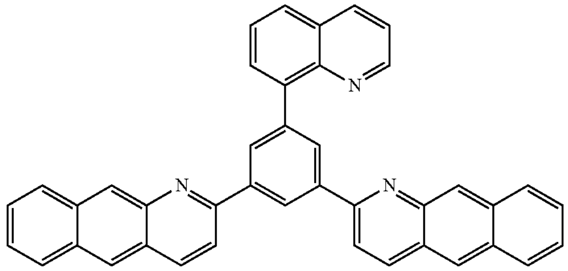
60
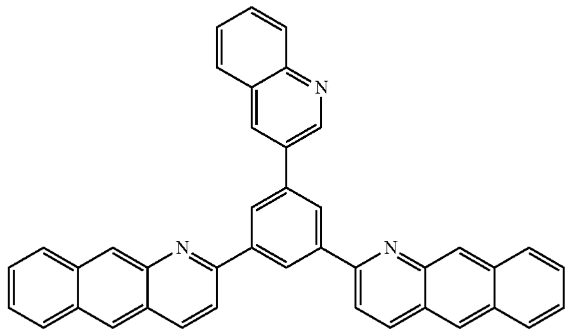
61
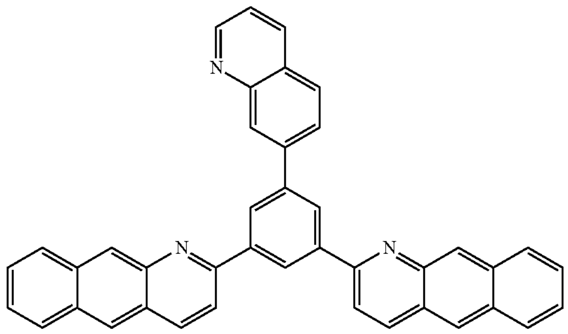
62
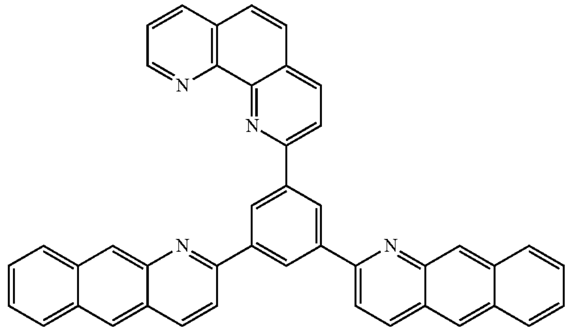
63
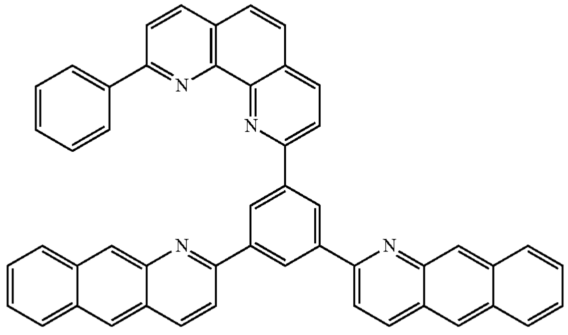
64
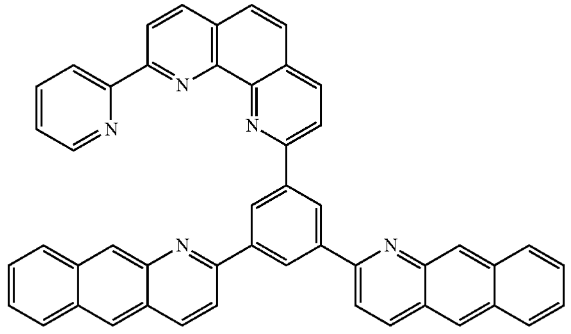
65
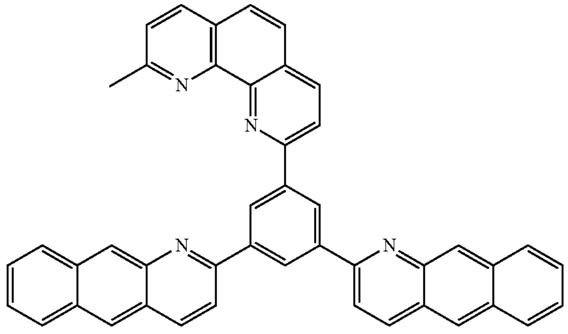

-continued
66
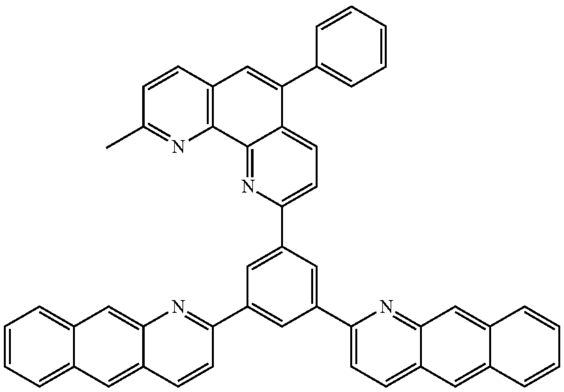
67
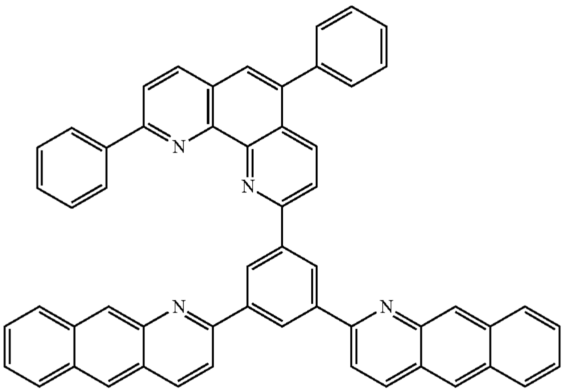
68
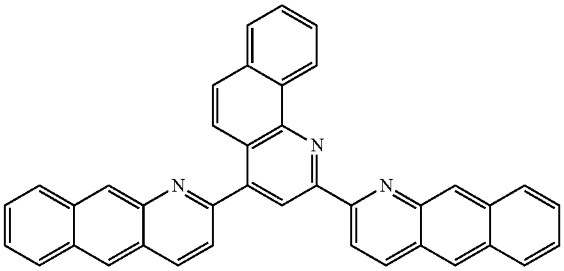
69
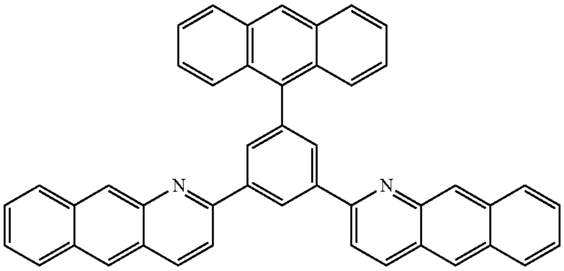
70
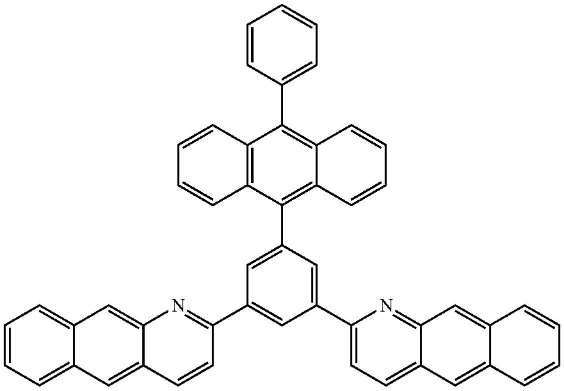
71
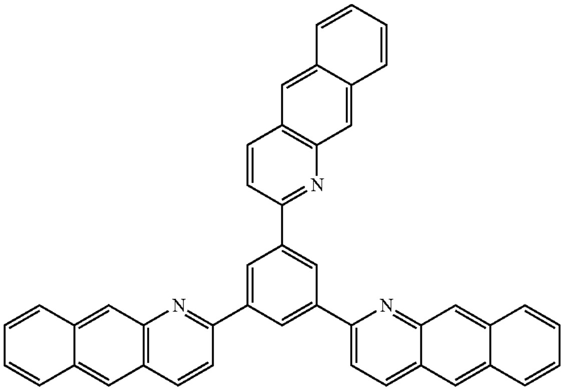
72
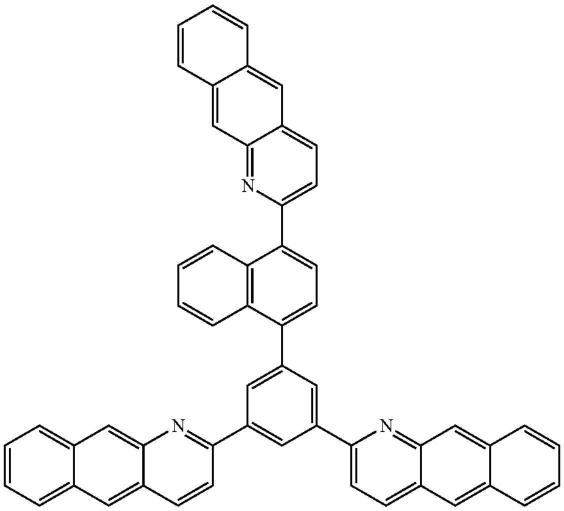
73
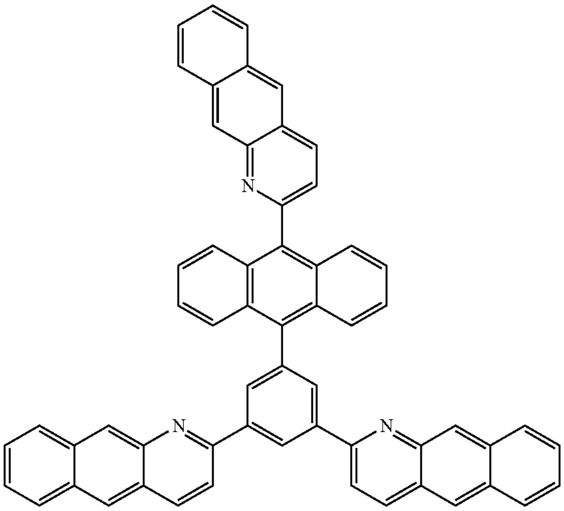

-continued
74
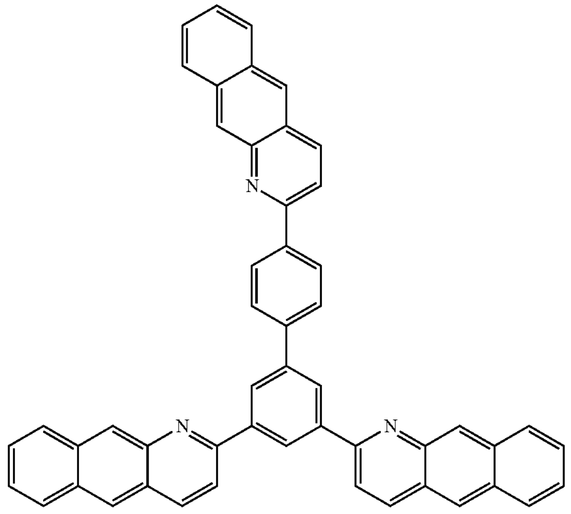
75
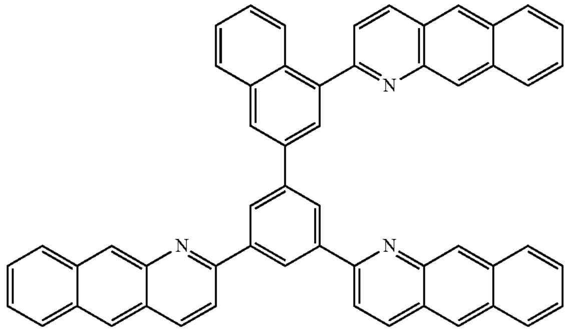
76
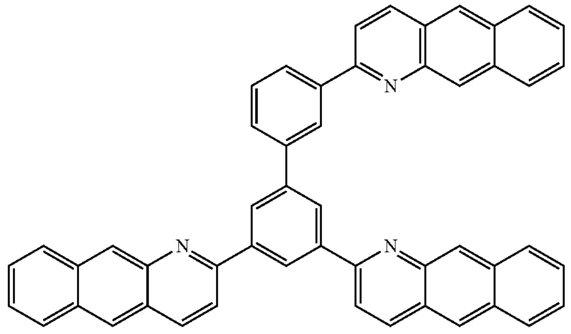
77
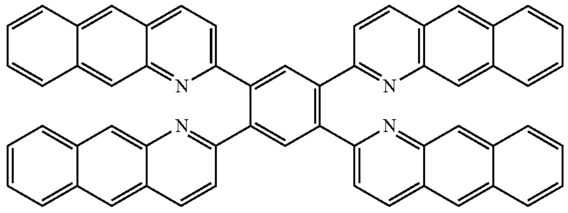
78
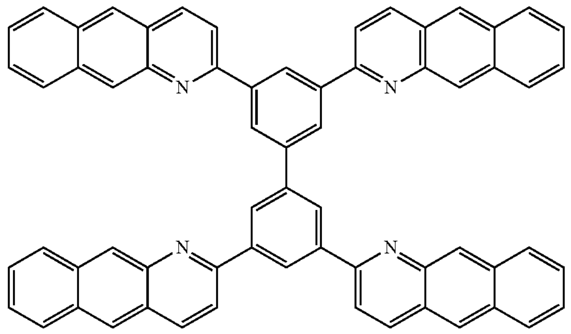
79
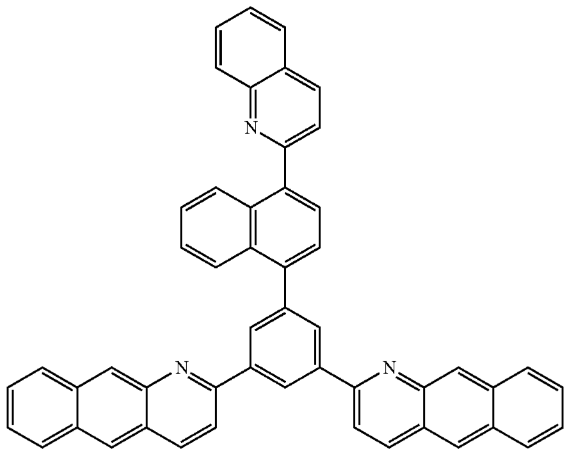

-continued
80
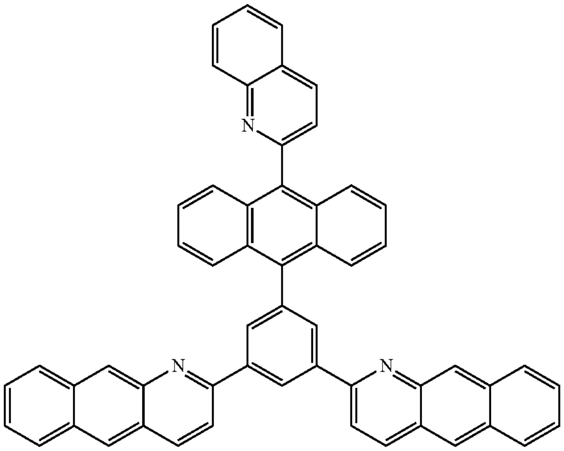
81
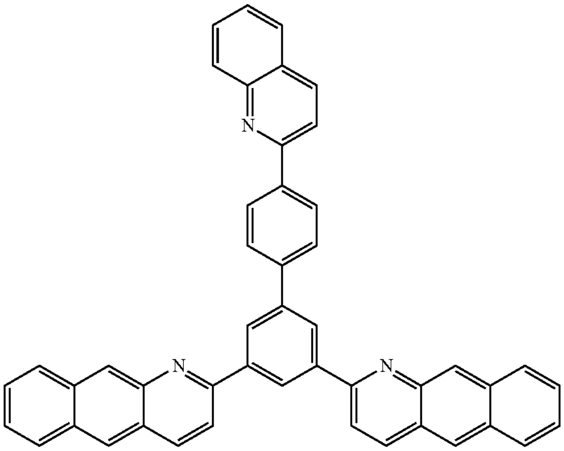
82
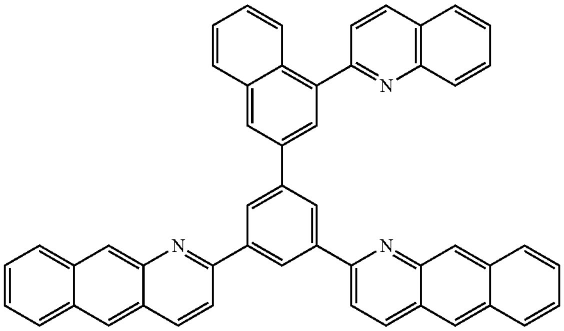
83
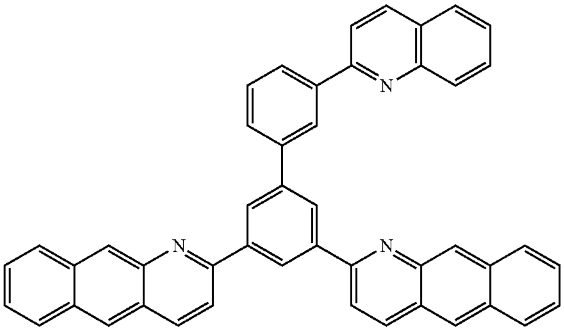
84
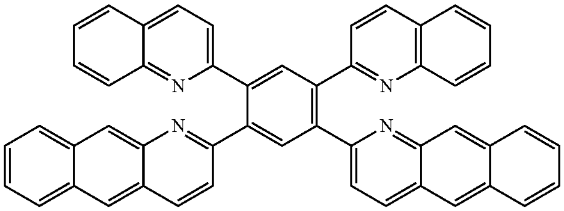
85
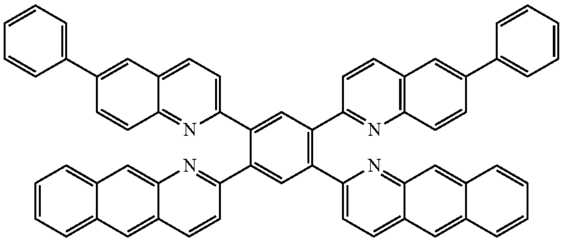
86
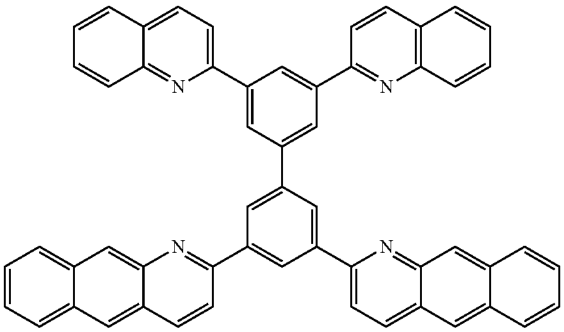
87
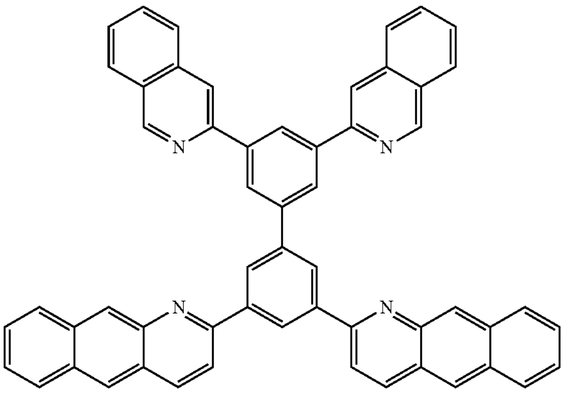

-continued
88
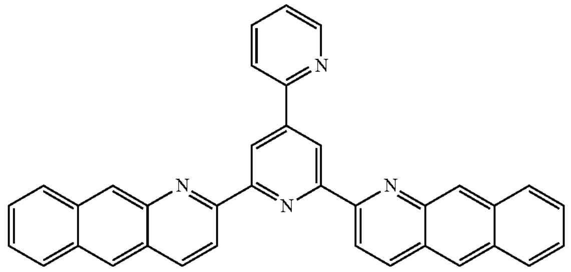
89
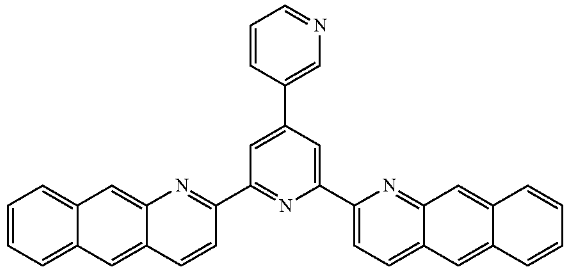
90
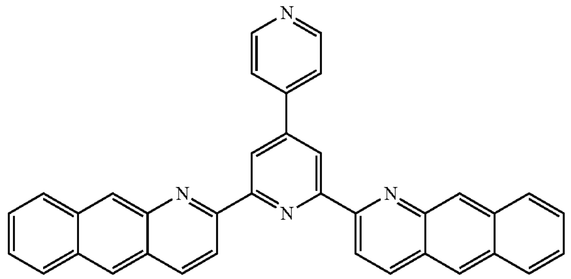
91
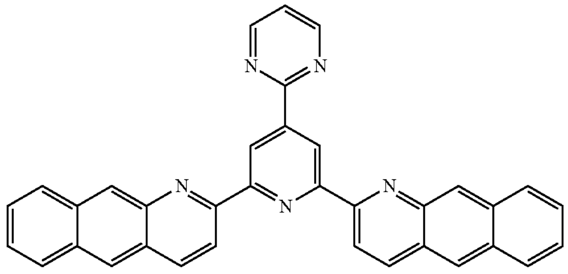
92
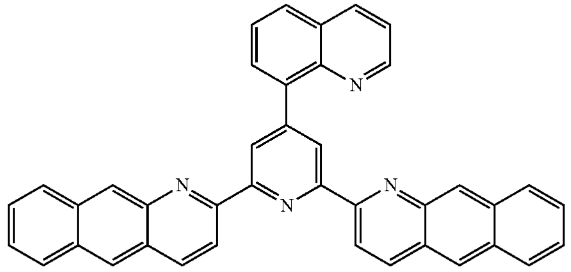
93
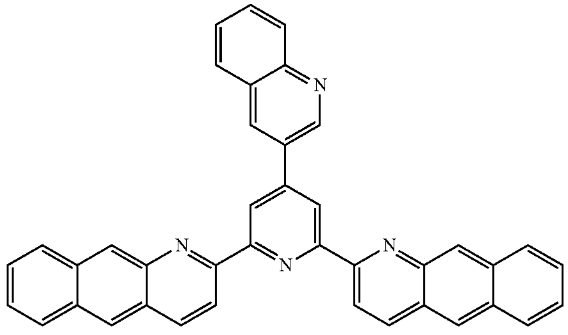
94
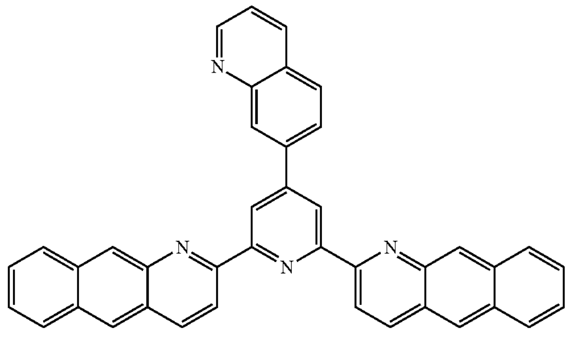
95
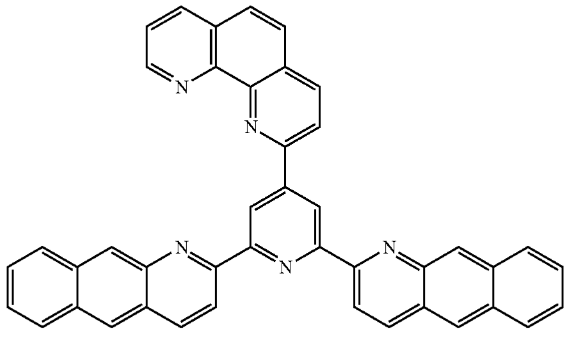

-continued
96
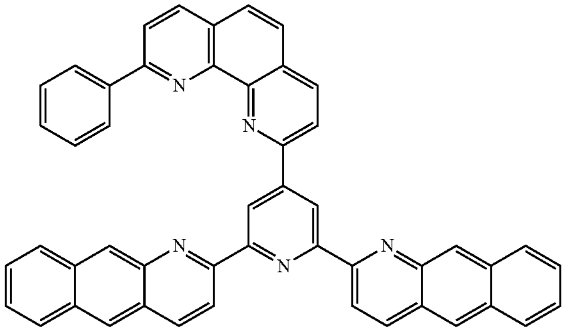
97
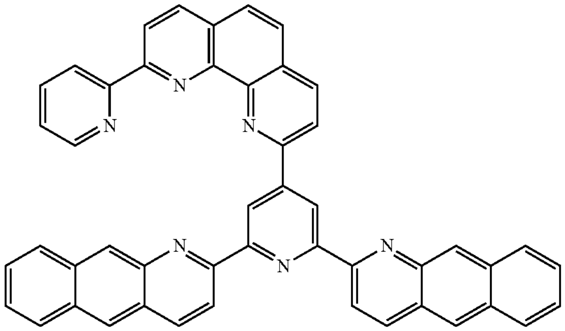
98
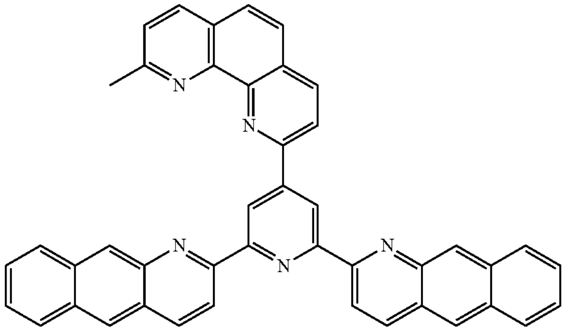
99
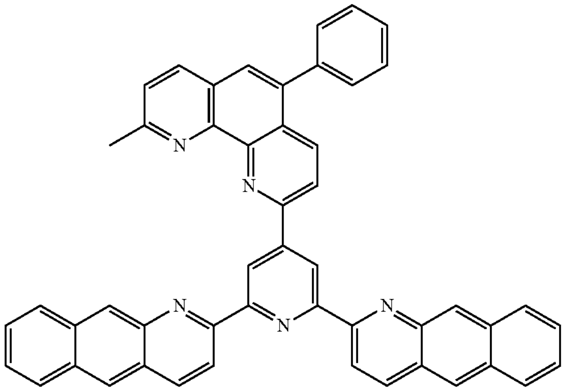
100
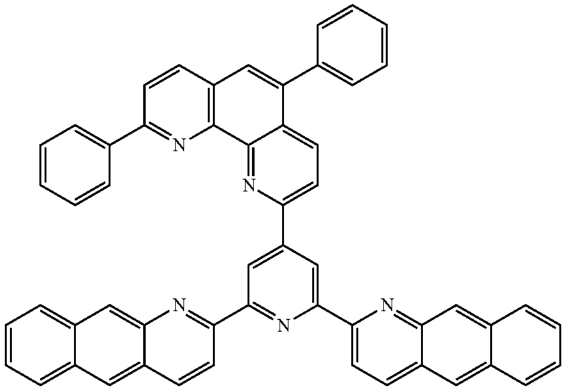
101
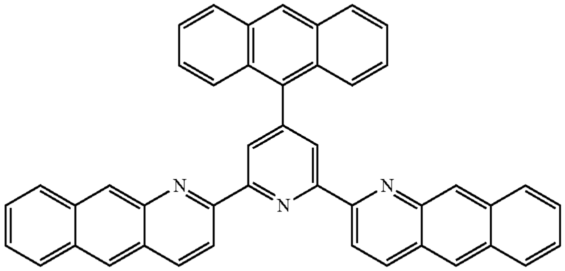
102
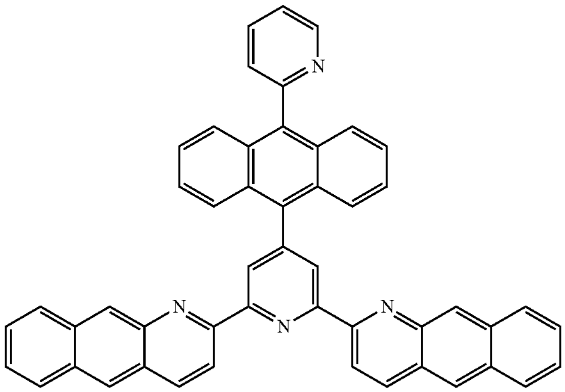
103
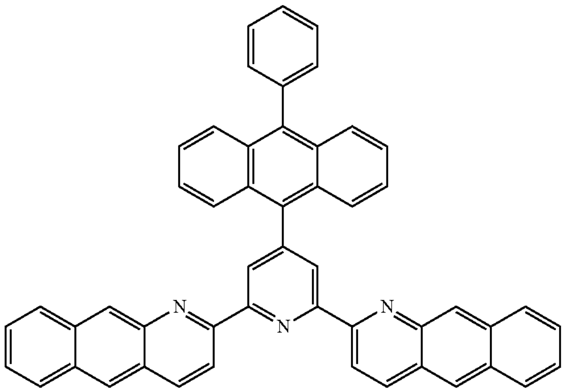

-continued
104
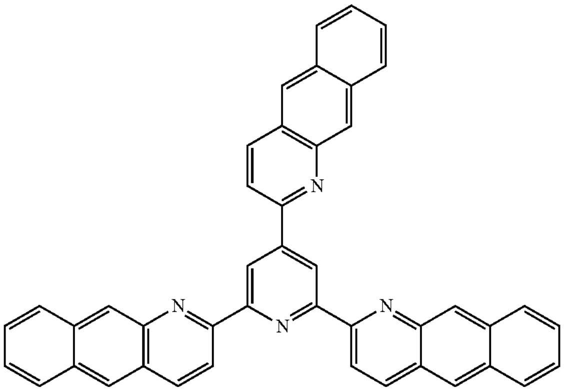
105
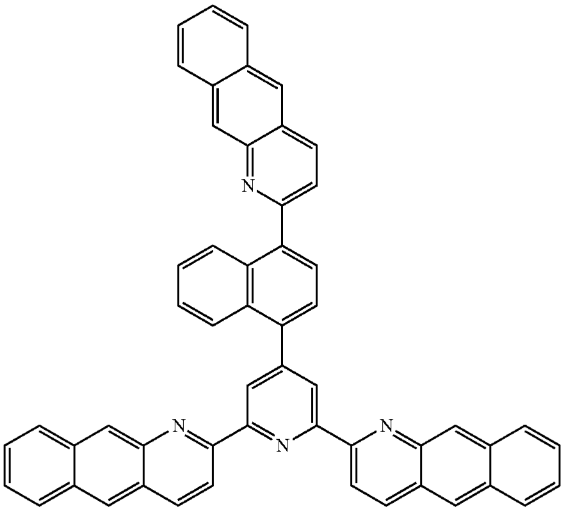
106
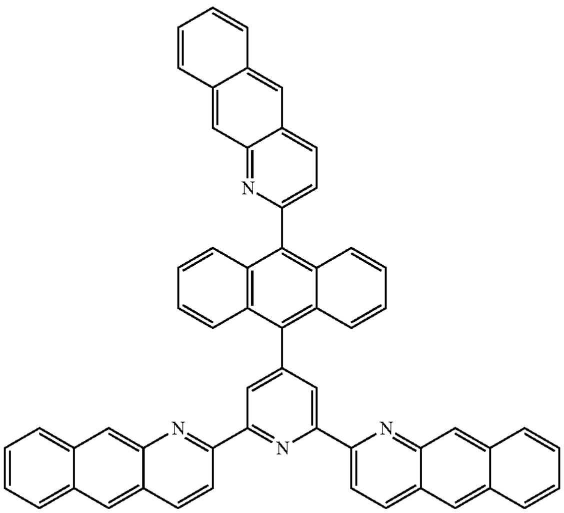
107
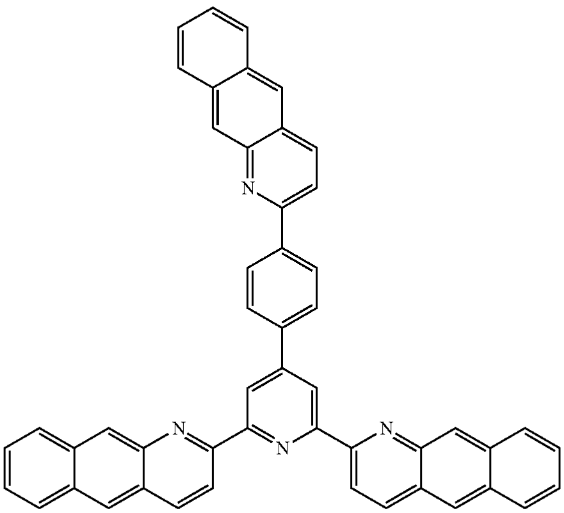
108
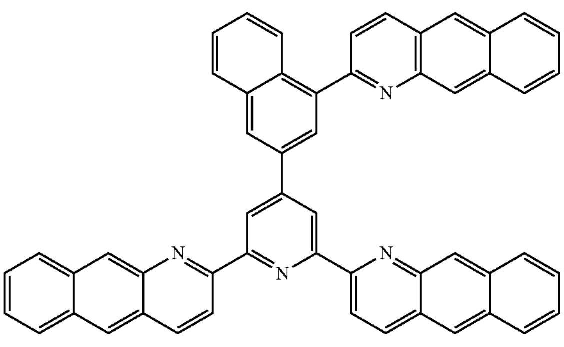
109
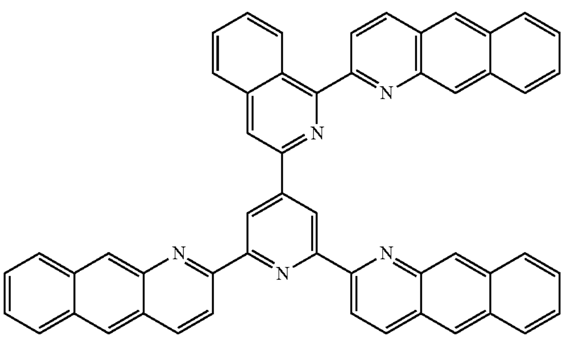

-continued
110
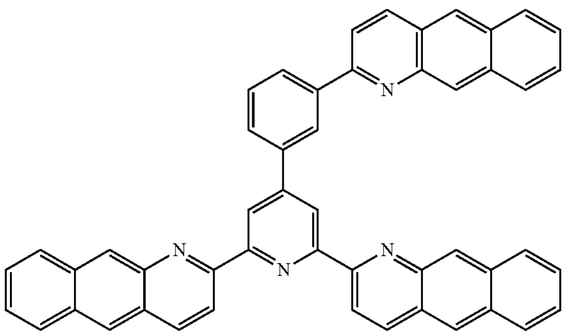
111
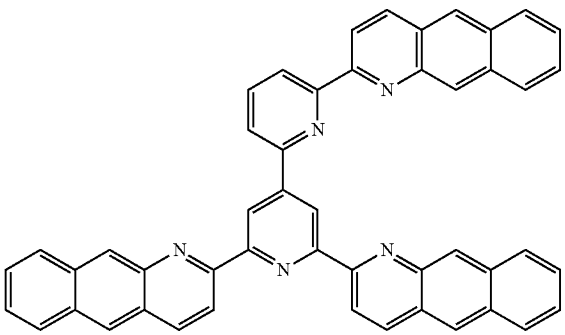
112
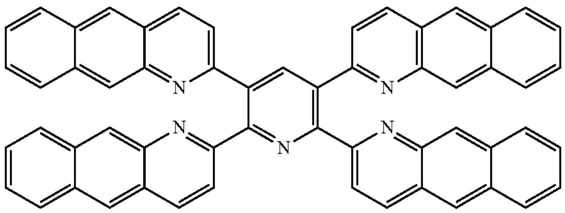
113
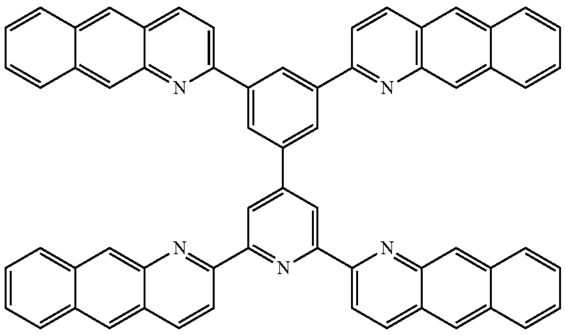
114
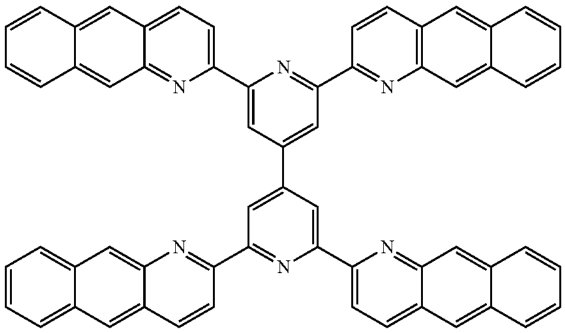
115
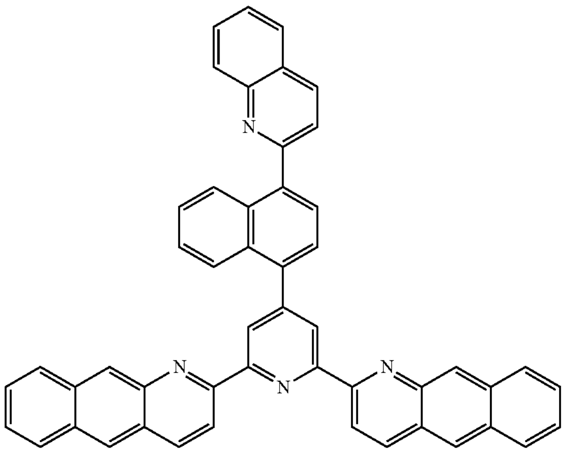
116
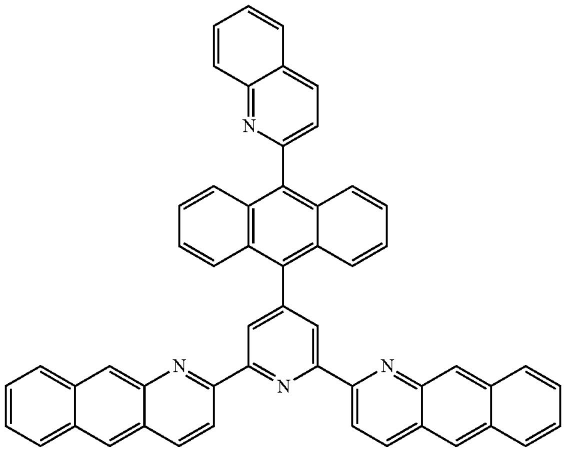
117
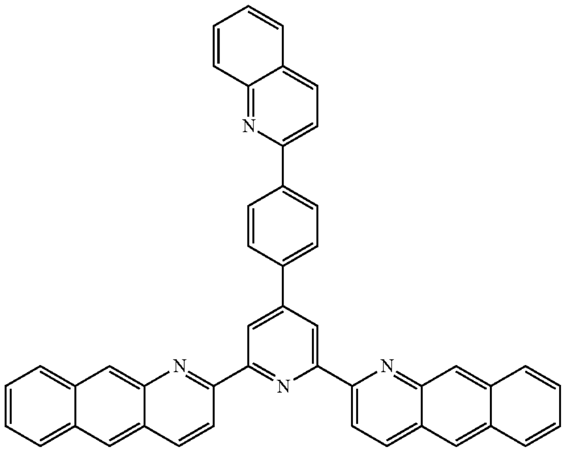

-continued
118
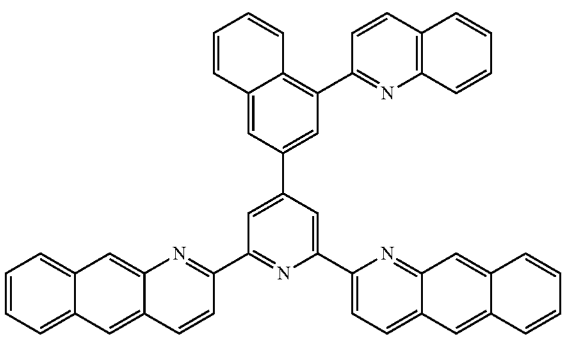
119
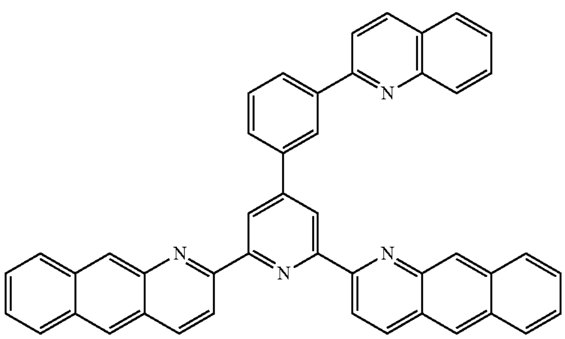
120
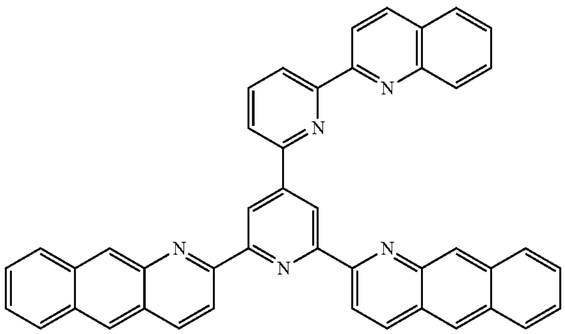
121
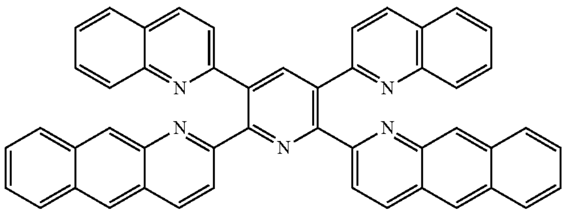
123
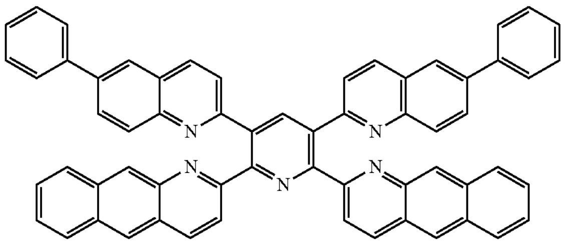
124
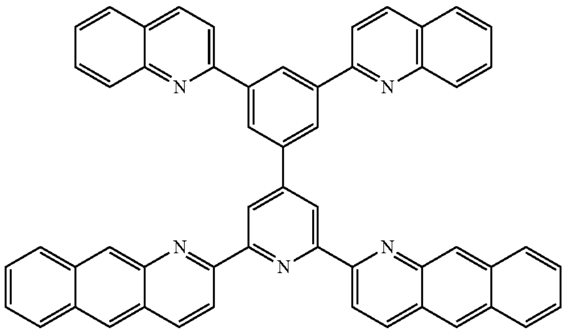
125
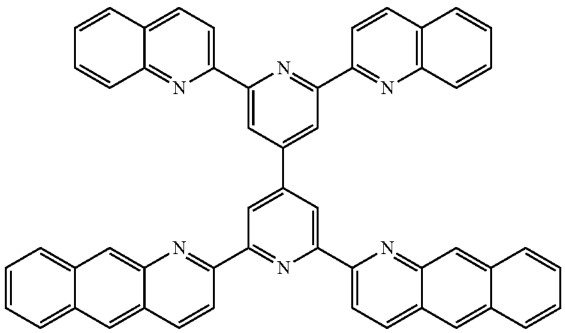
126
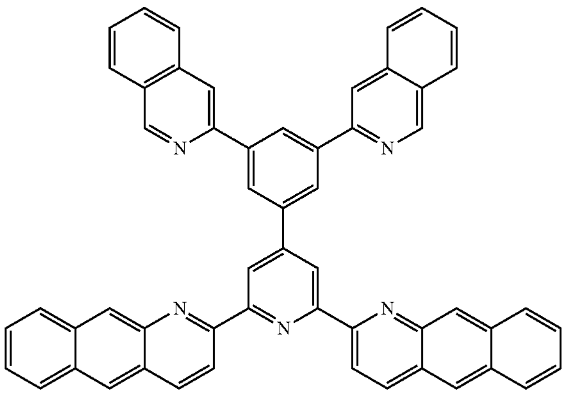

-continued
127
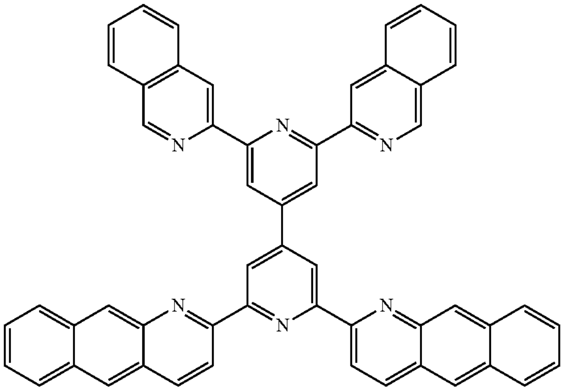
128
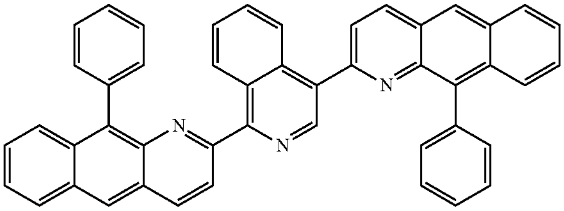
129
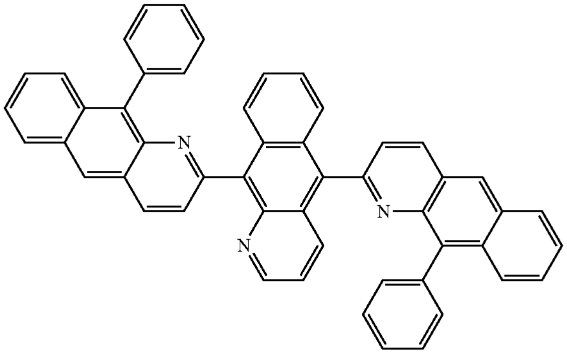
130
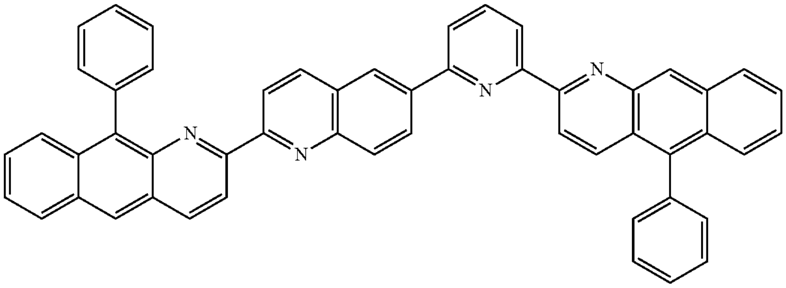
131
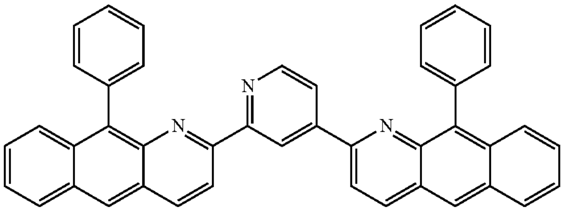
132
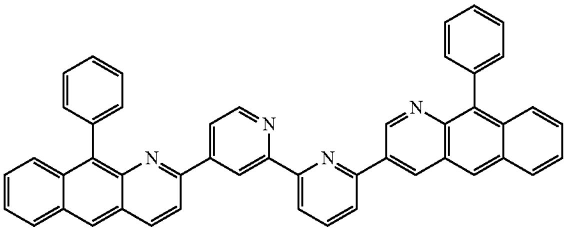

-continued
133
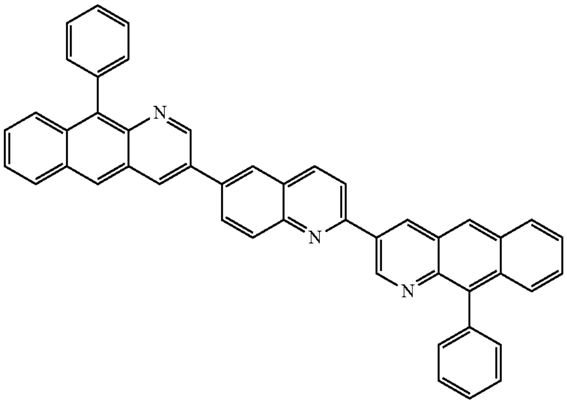
134
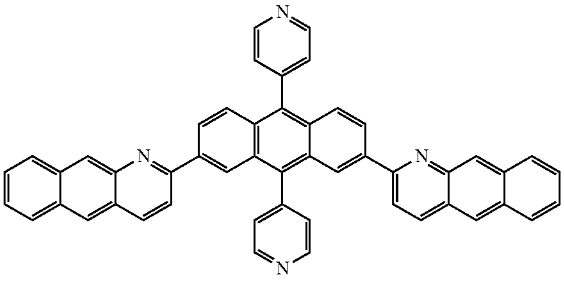
135
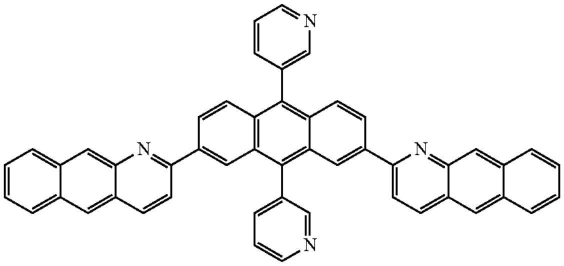
136
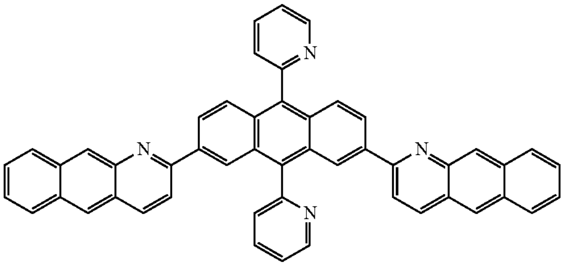
137
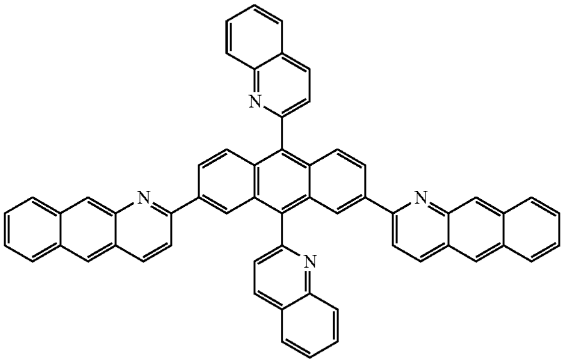
138
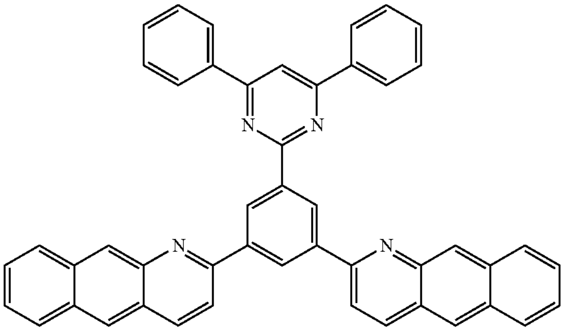
139
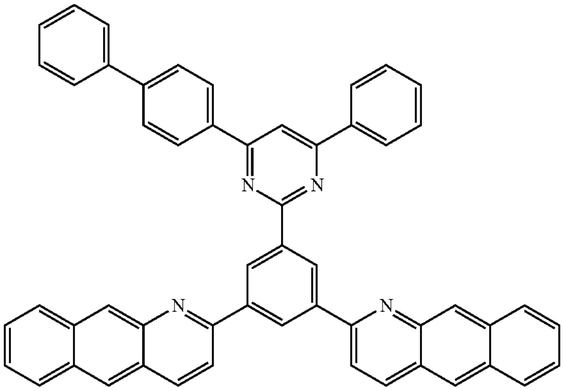
140
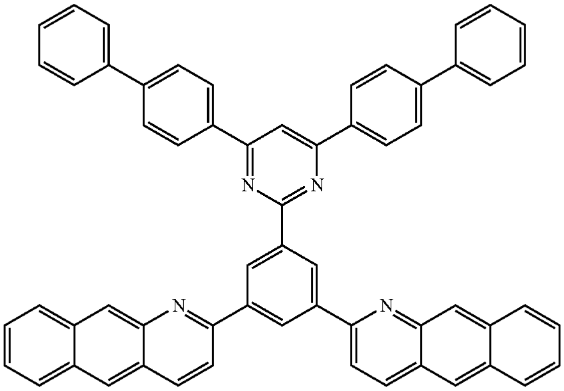

-continued
141
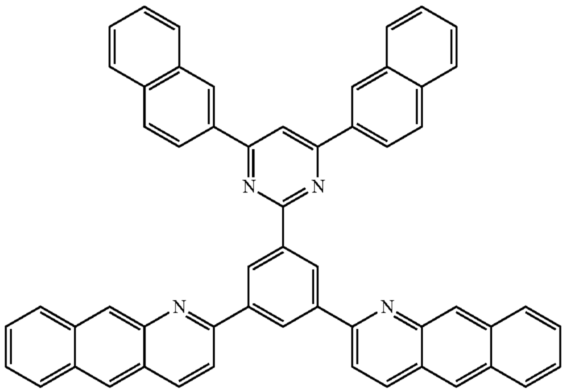
142
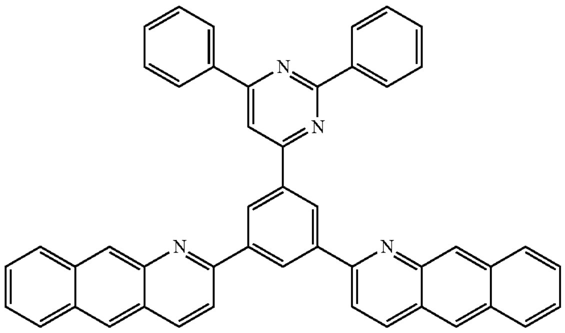
143
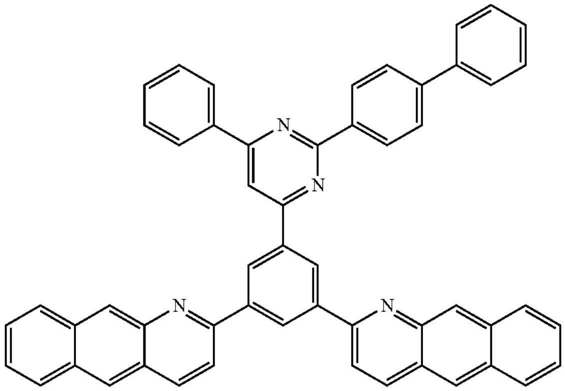
144
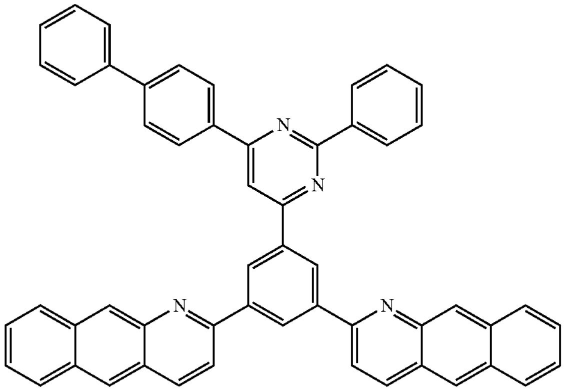
145
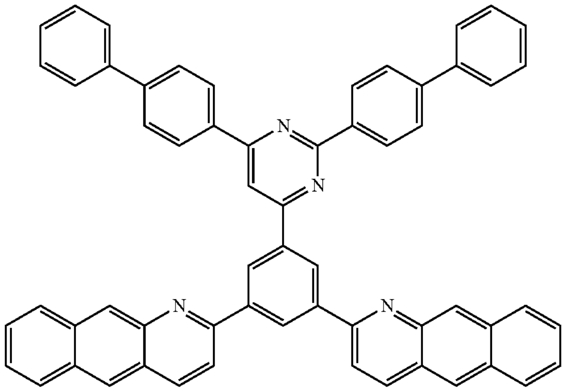
146
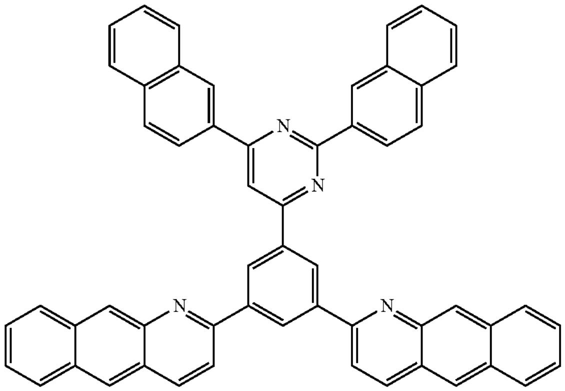
147
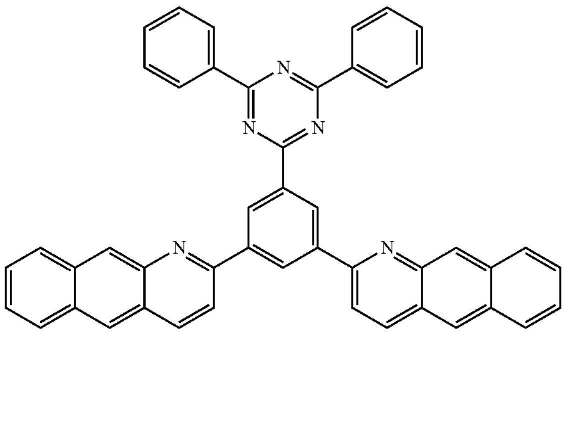
148
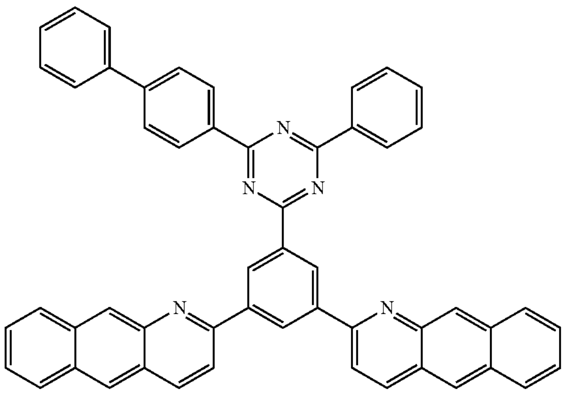

-continued
149
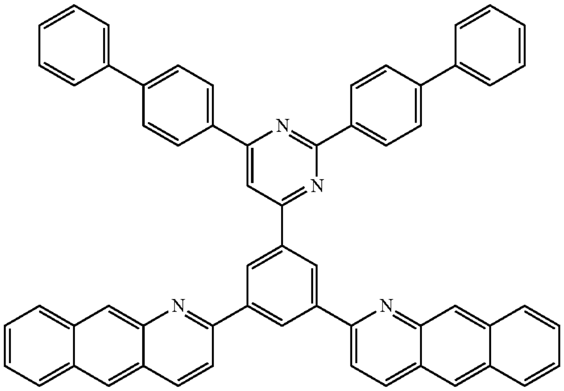
150
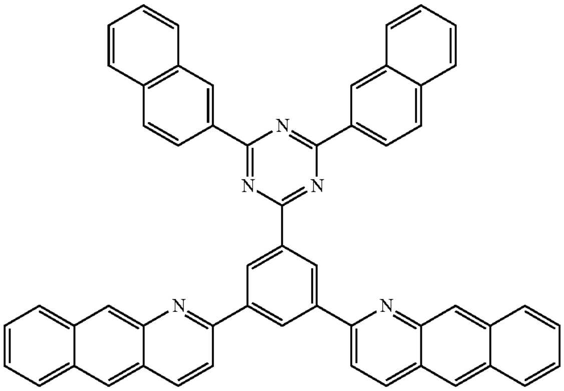
151
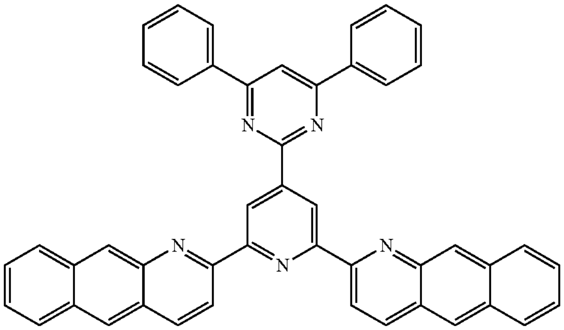
152
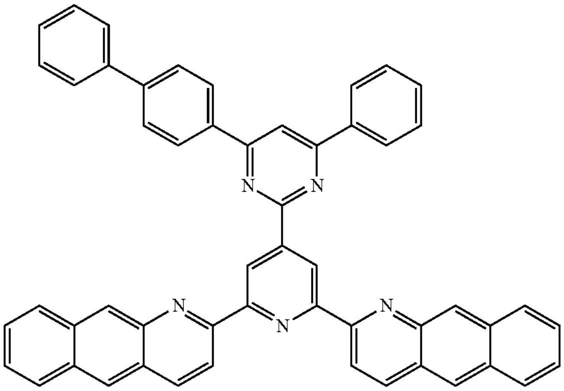
153
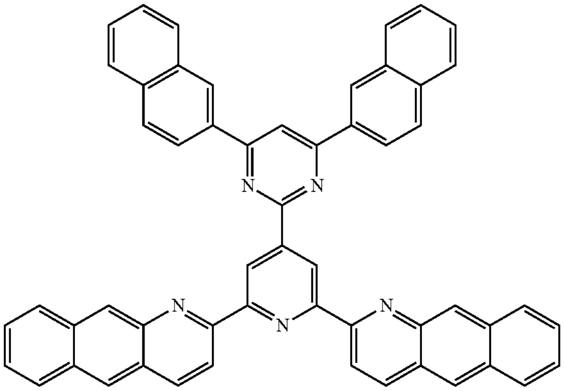
154
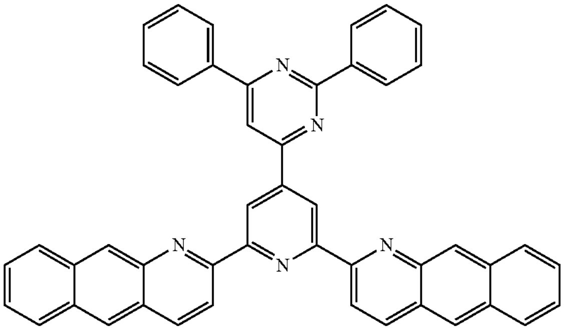
155
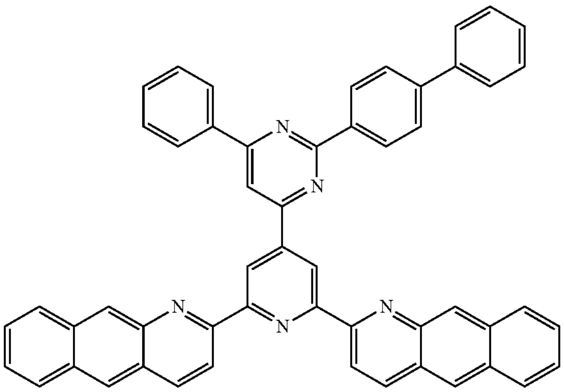
156
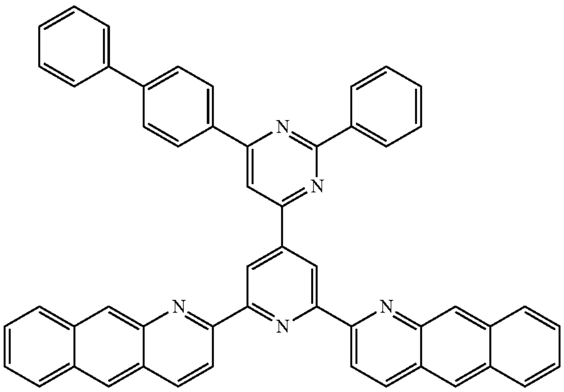

-continued
157
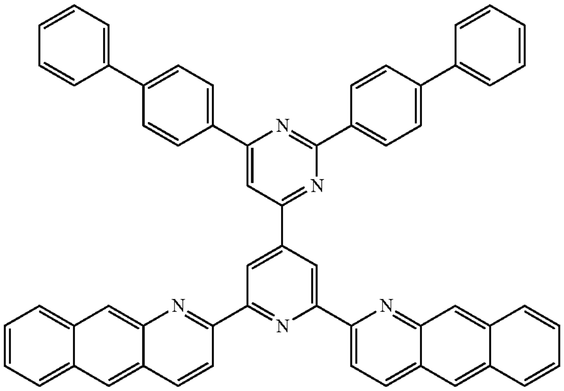
158
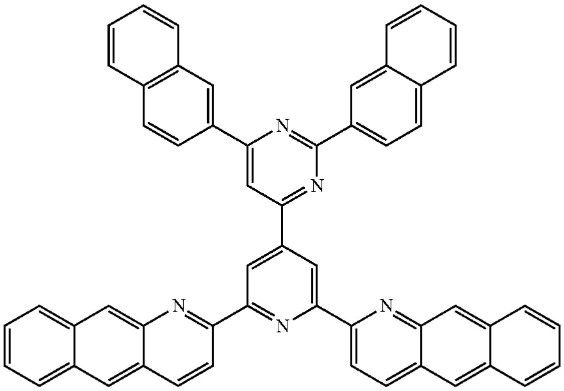
159
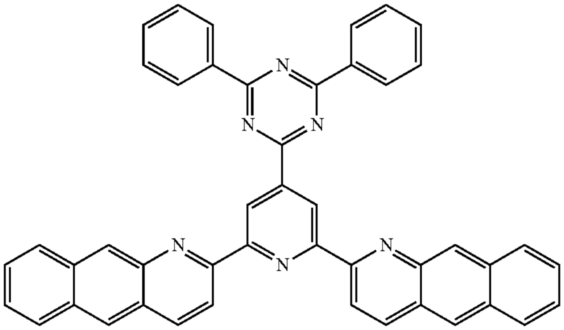
160
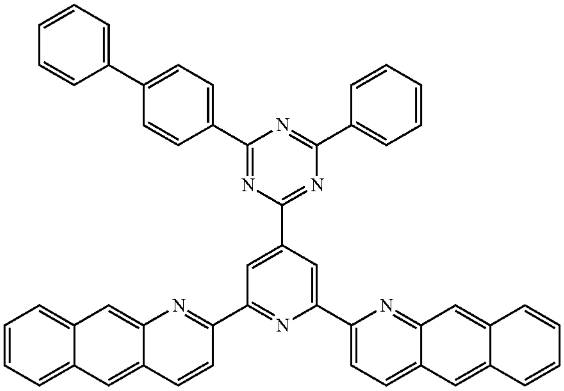
161
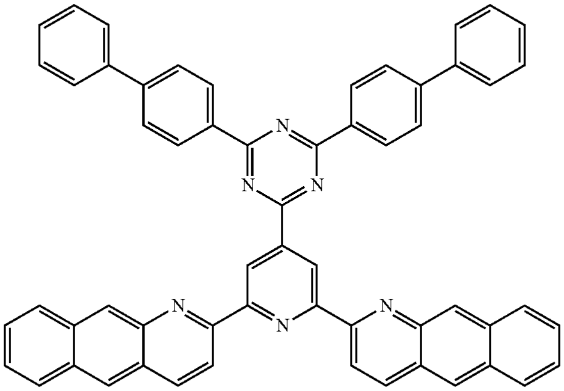
162
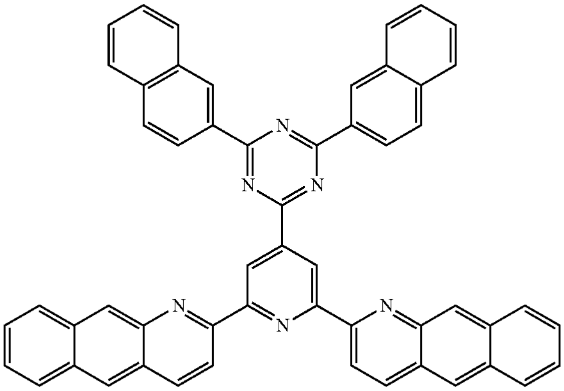
163
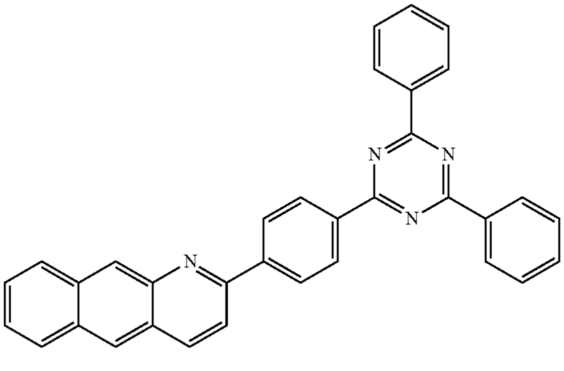
164
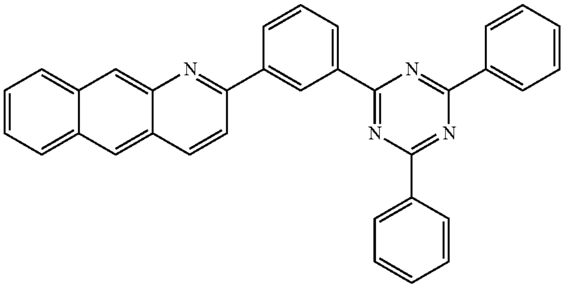

-continued
165
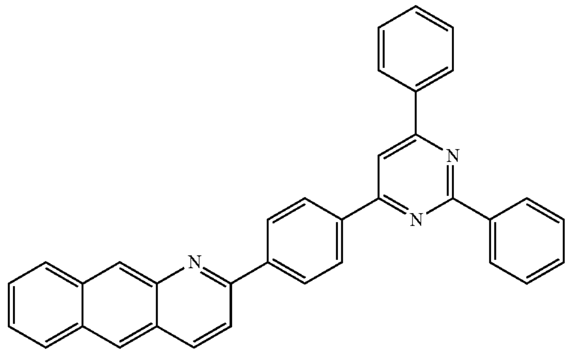
166
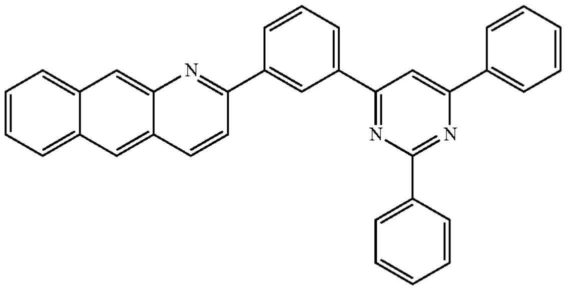
167
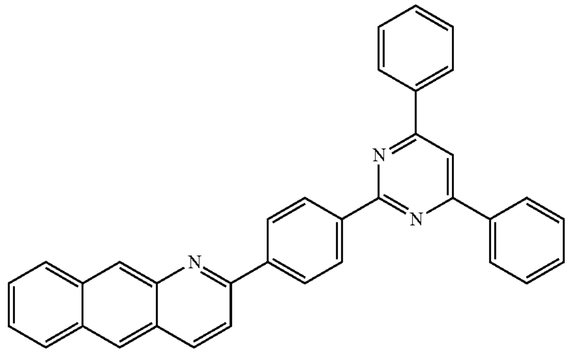
168
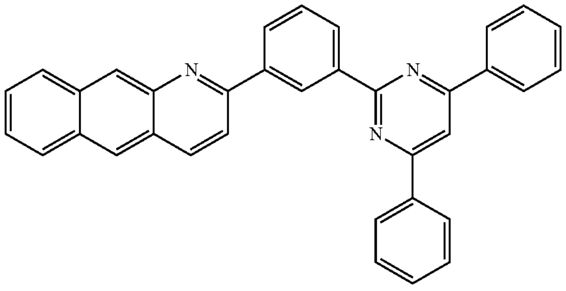
169
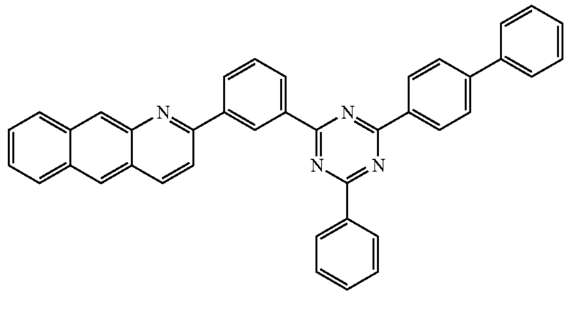
170
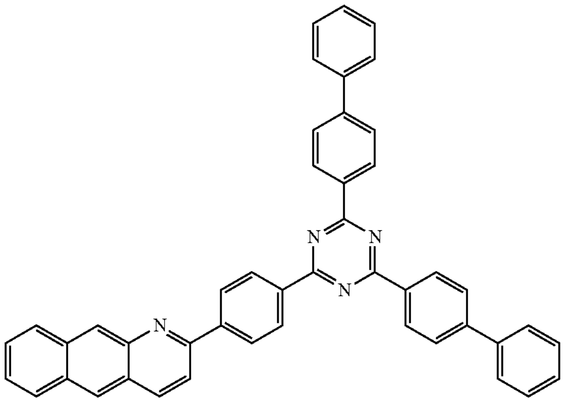

-continued
171
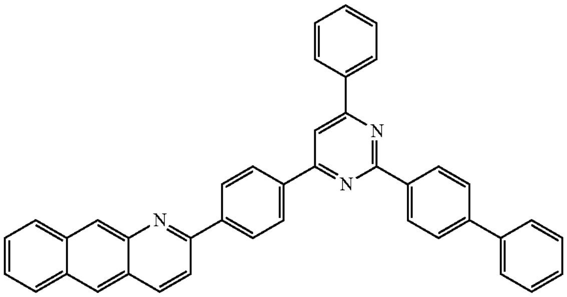
172
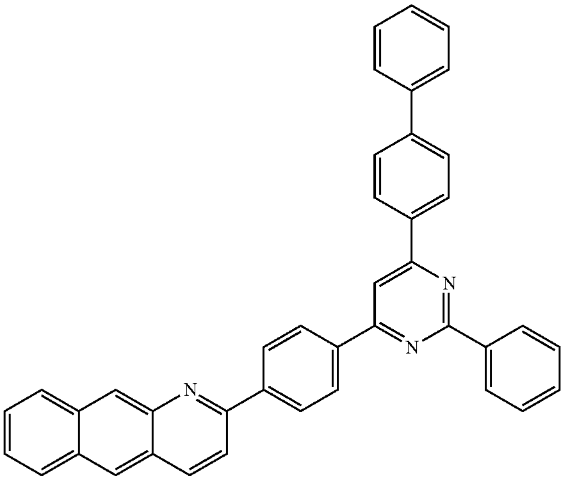
173
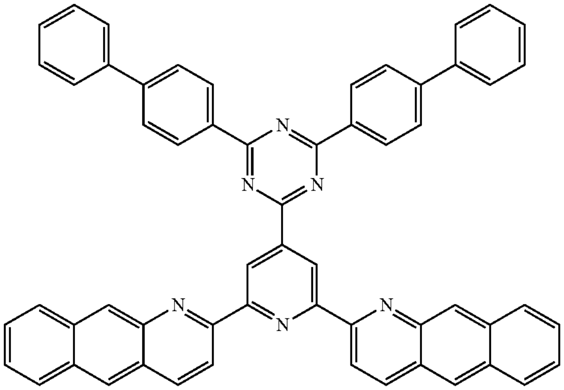
174
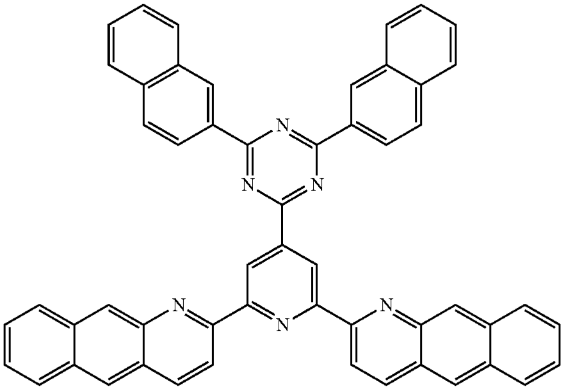
175
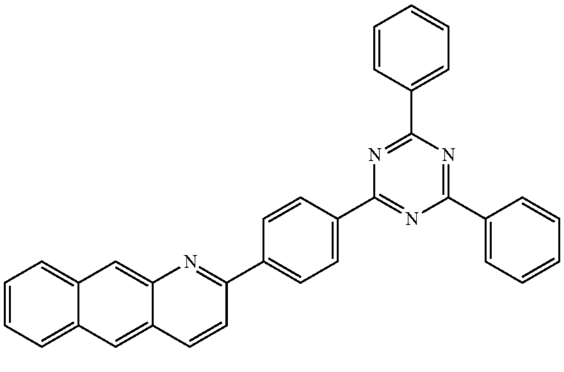
176
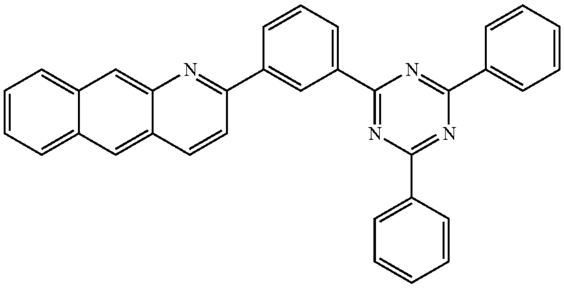

-continued
177
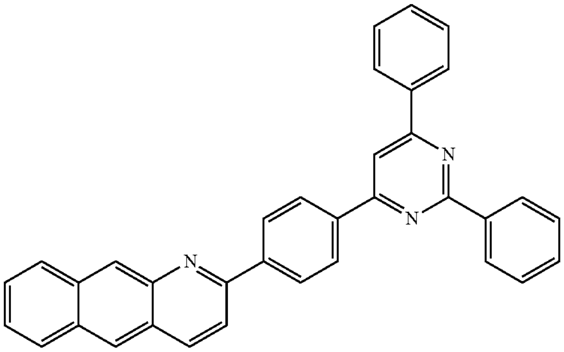
178
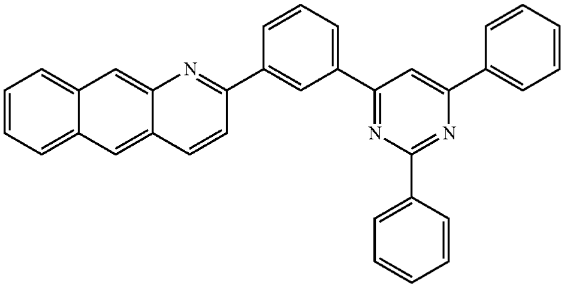
179
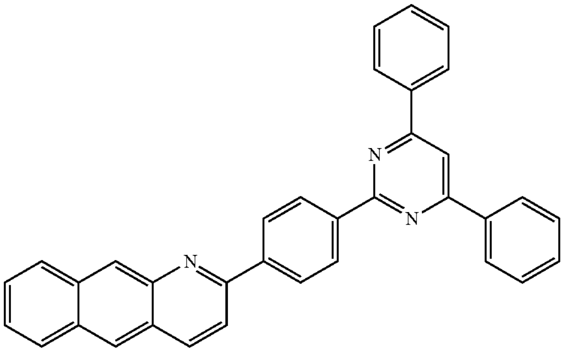
180
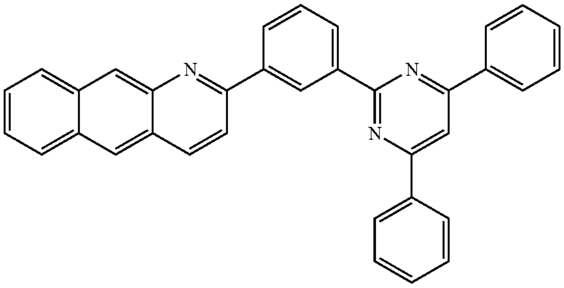
181
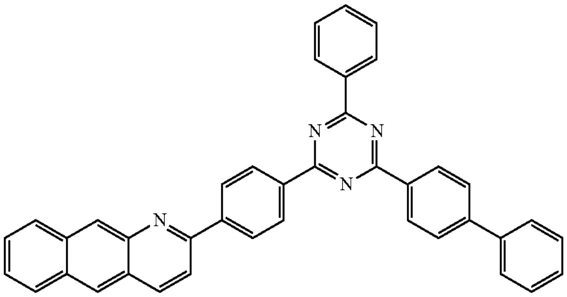
182
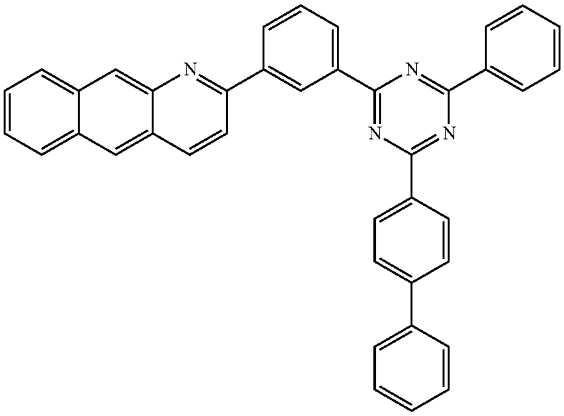
183
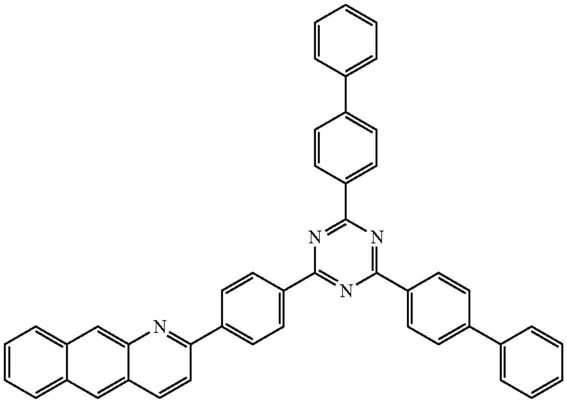
184
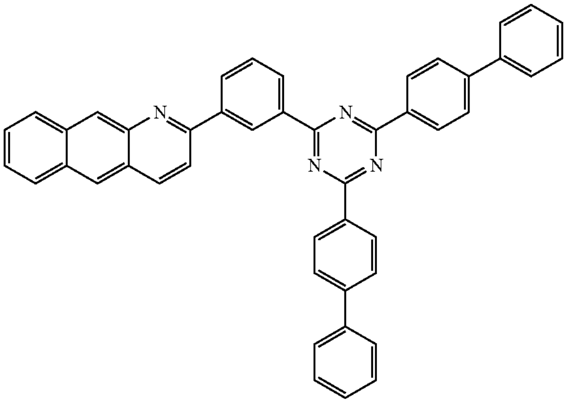

-continued
185
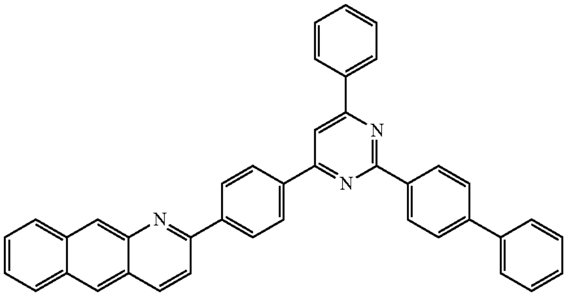
186
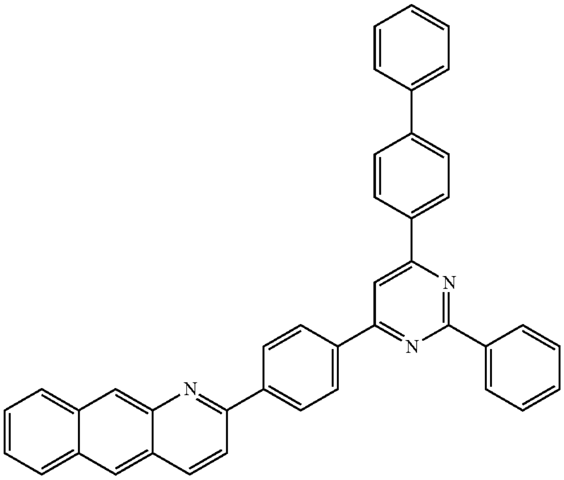
187
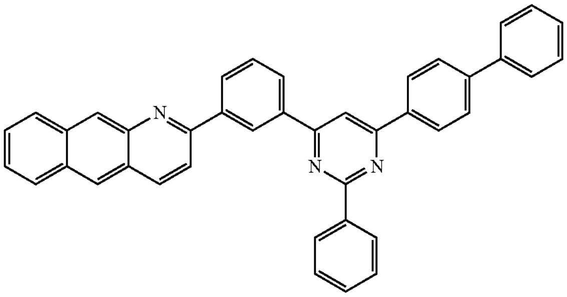
188
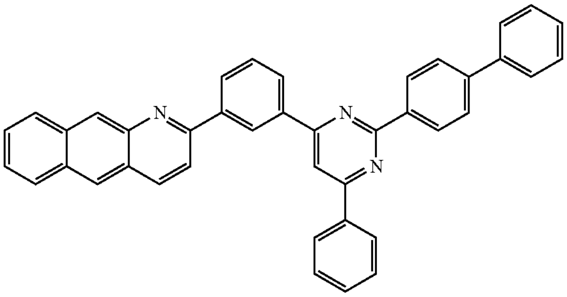
189
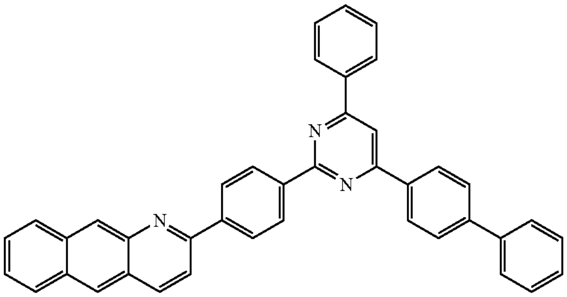
190
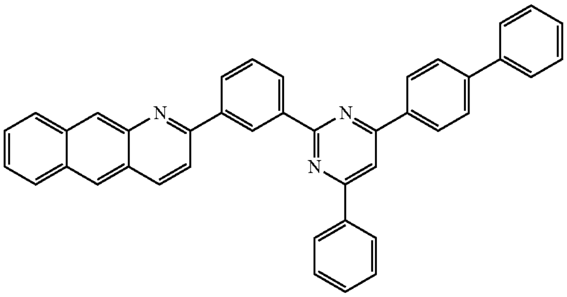
191
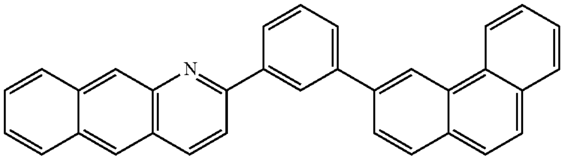
192
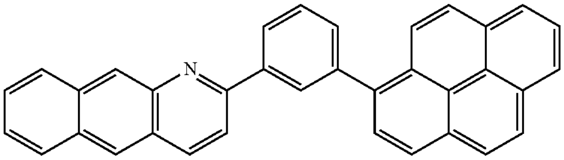
193
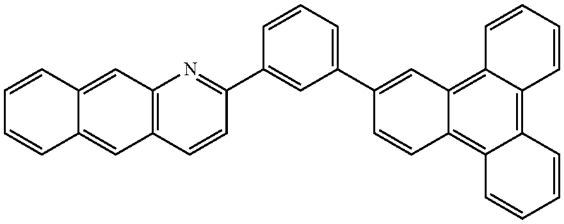
194
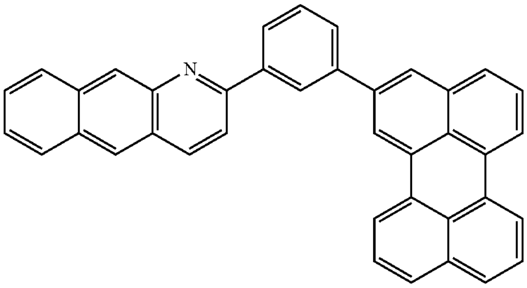

-continued
195
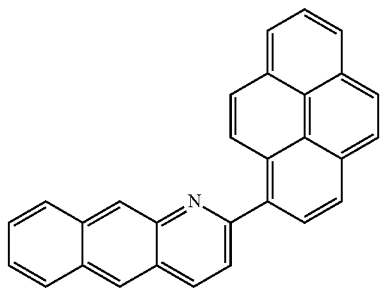
196
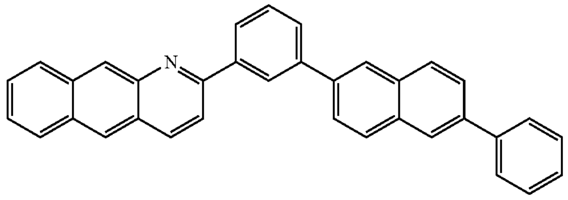
197
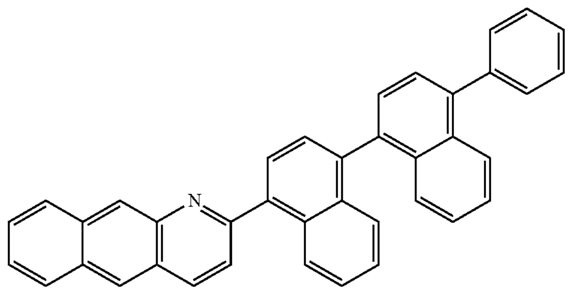
198
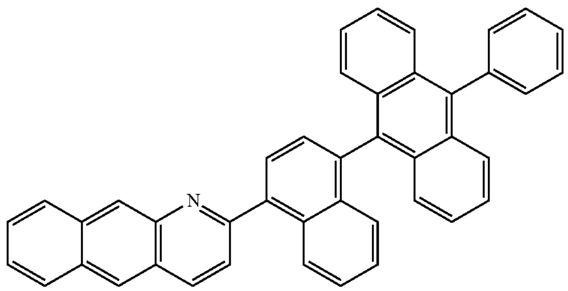
199
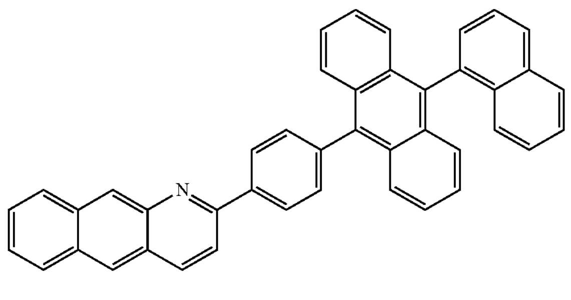
200
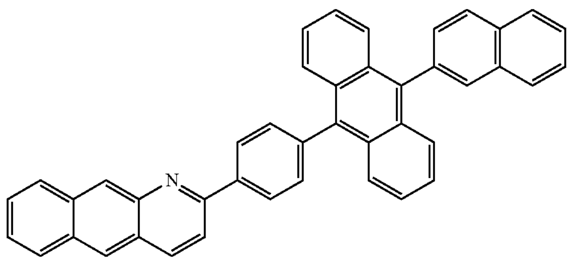
201
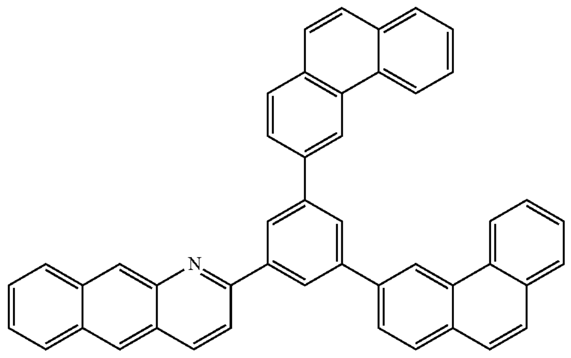
202
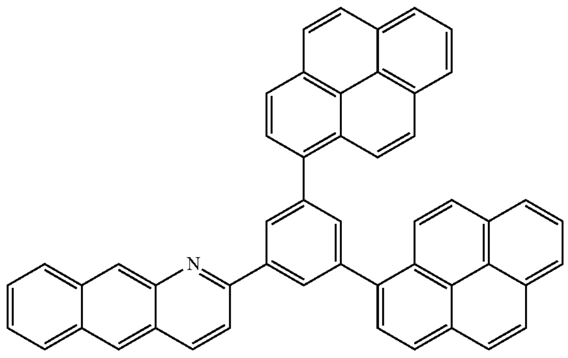

-continued
203
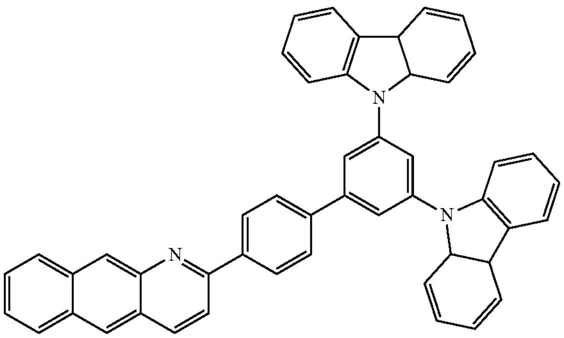
204
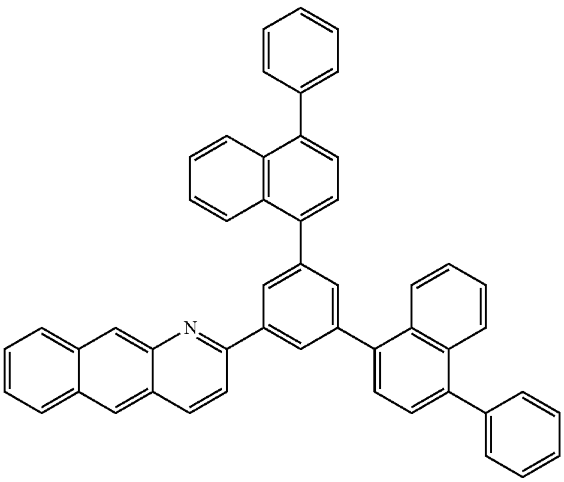
205
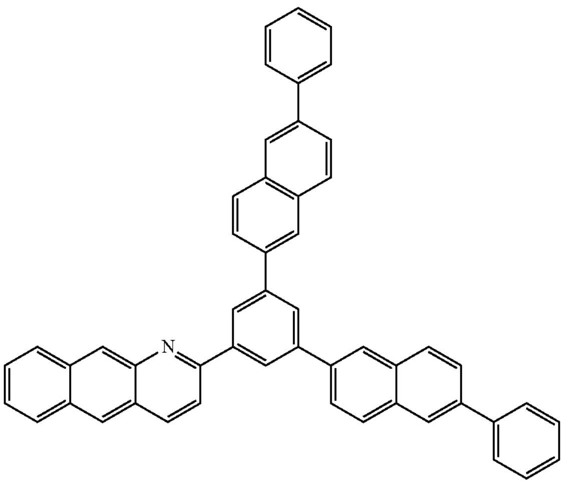
206
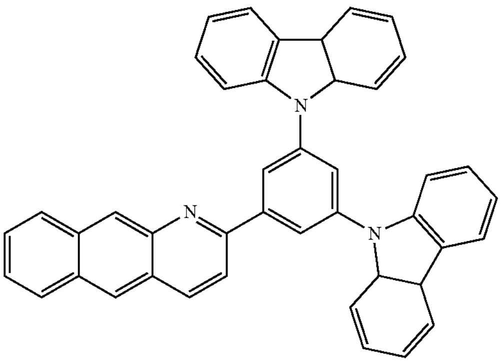
207
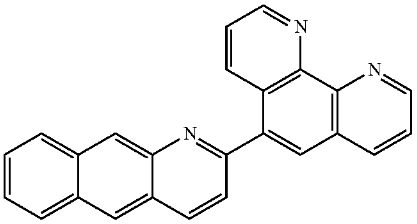
208
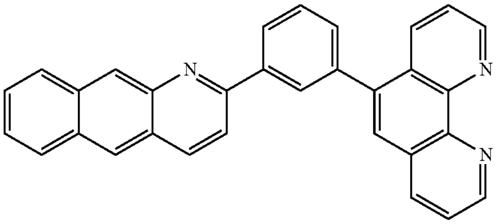
209
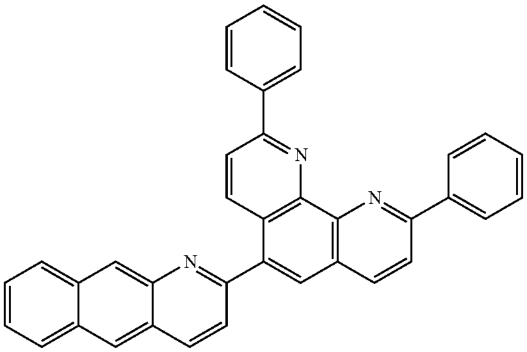
210
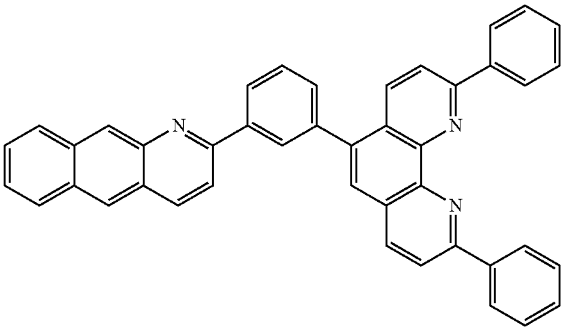

-continued
211
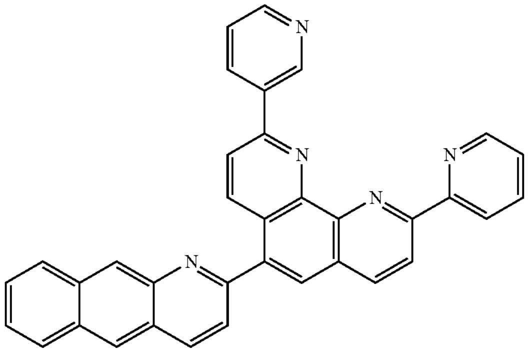
212
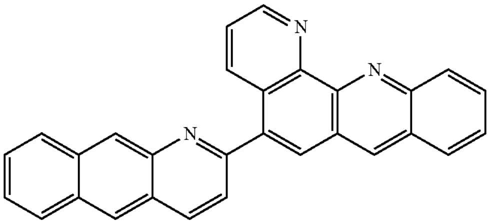
213
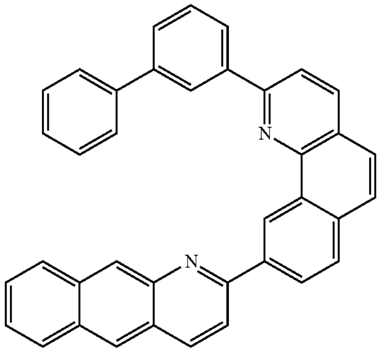
214
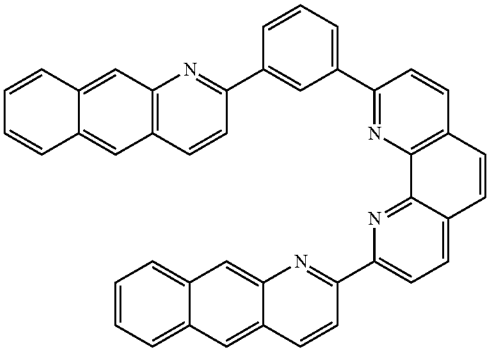
215
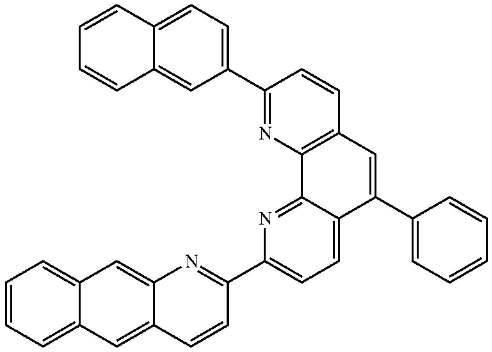
216
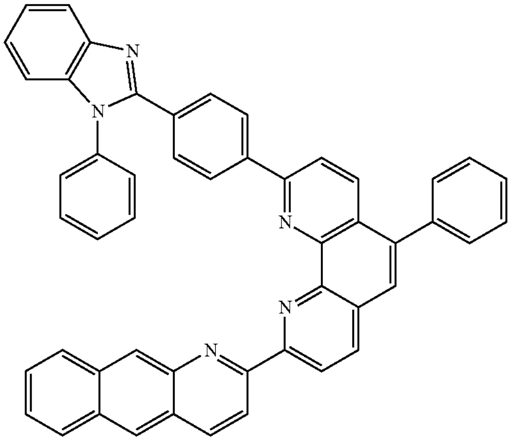
217
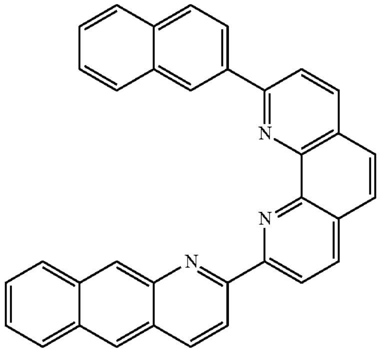
218
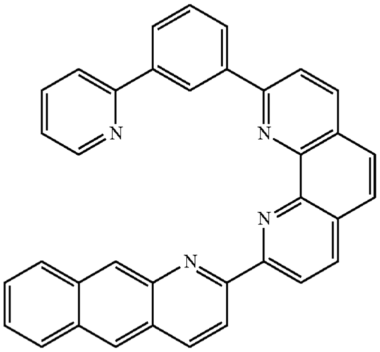

-continued
219
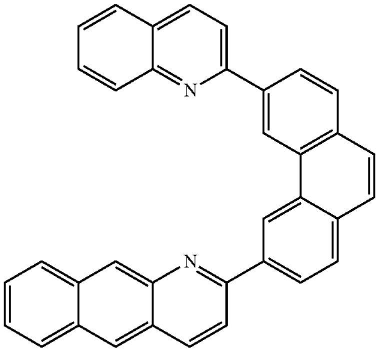
220
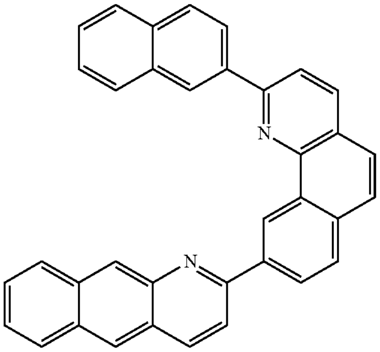
221
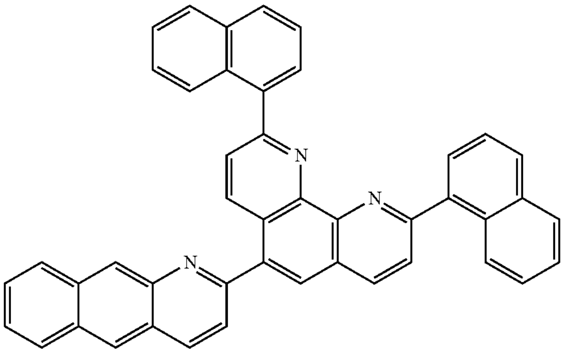
222
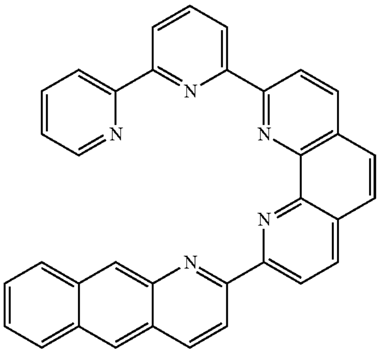
223
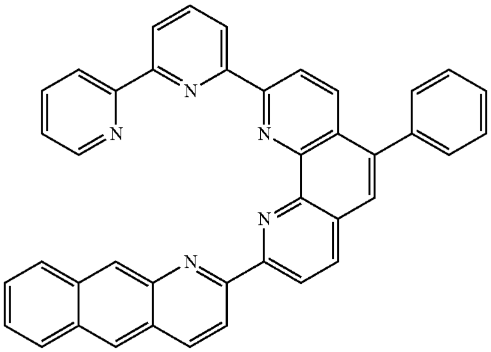
224
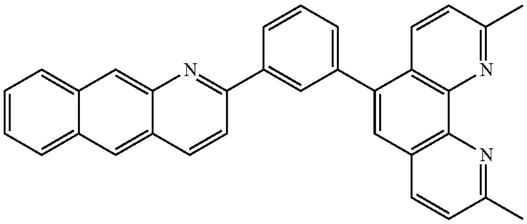
225
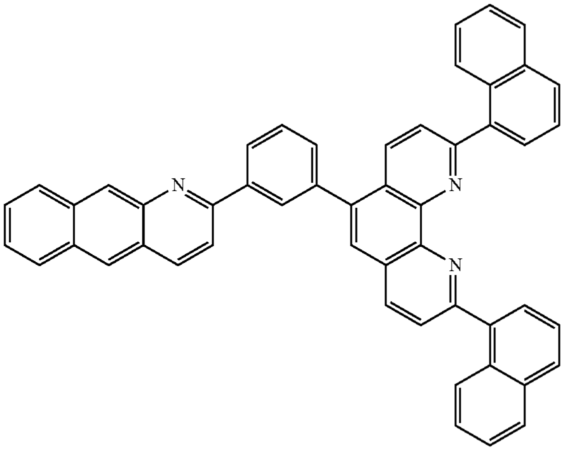
226
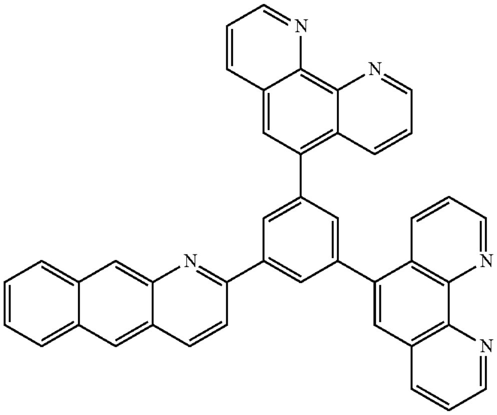

-continued
227
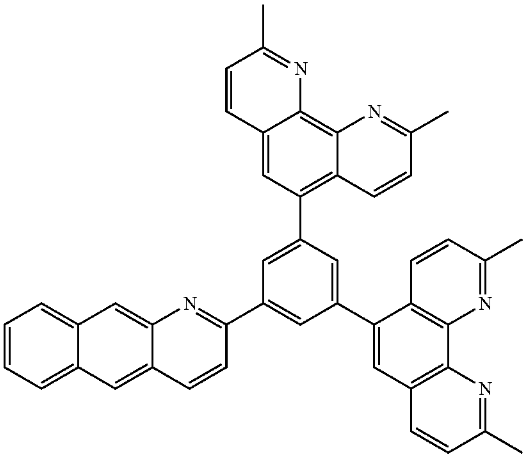
228
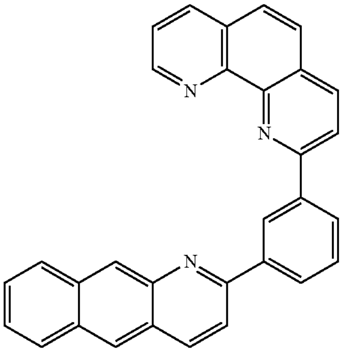
229
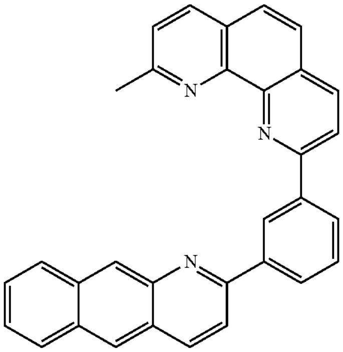
230
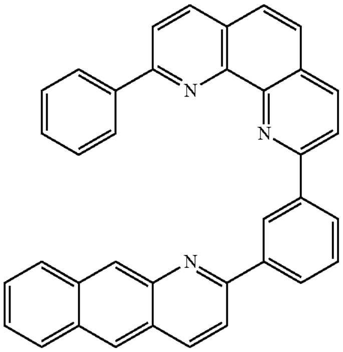
231
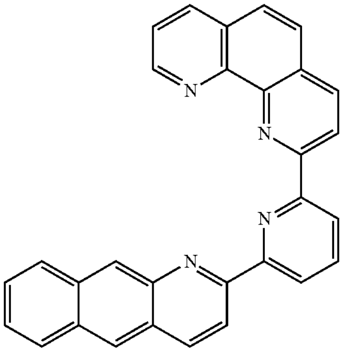
232
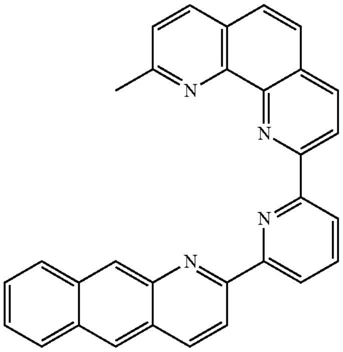
233
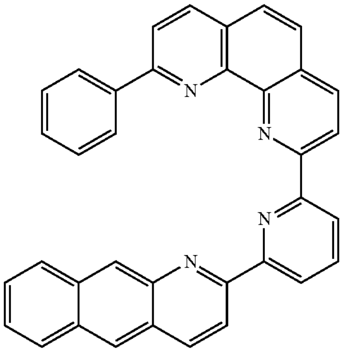
234
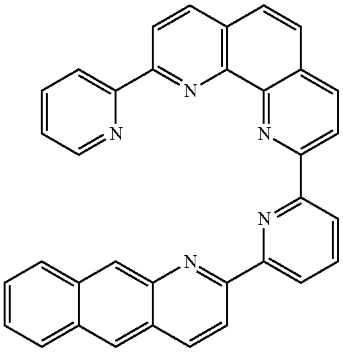

-continued
235
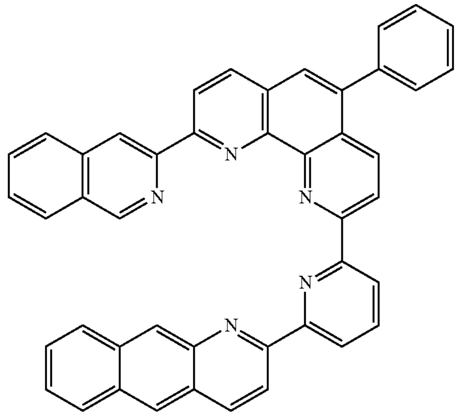
236
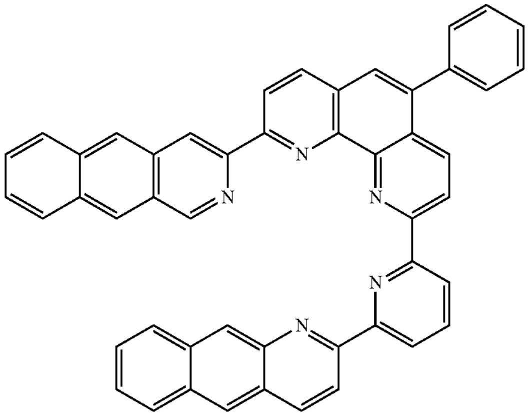
237
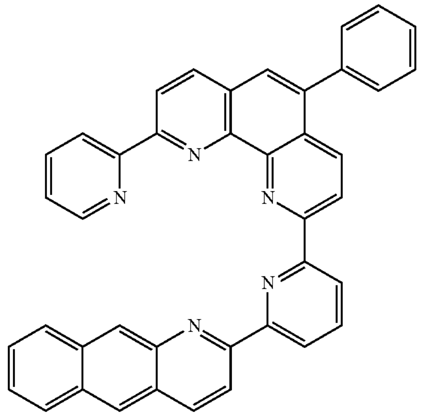
238
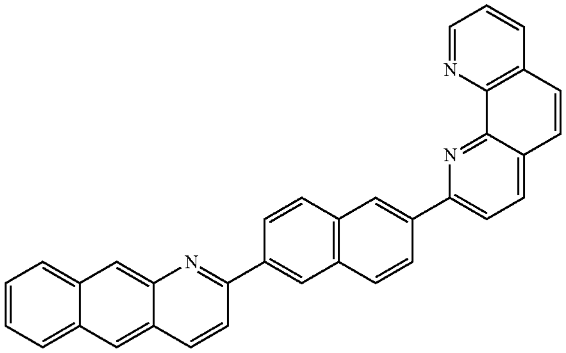
239
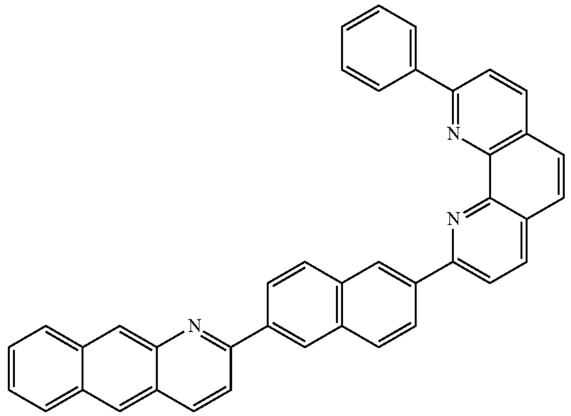
240
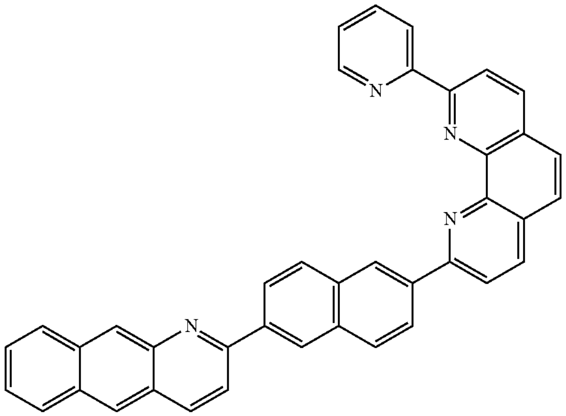

-continued
241
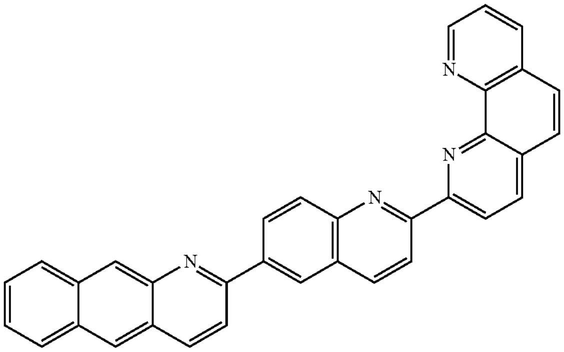
242
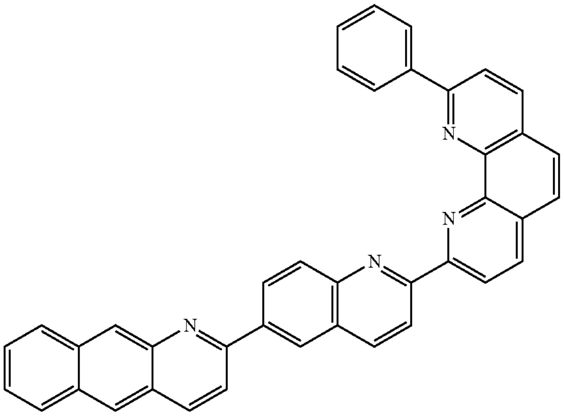
243
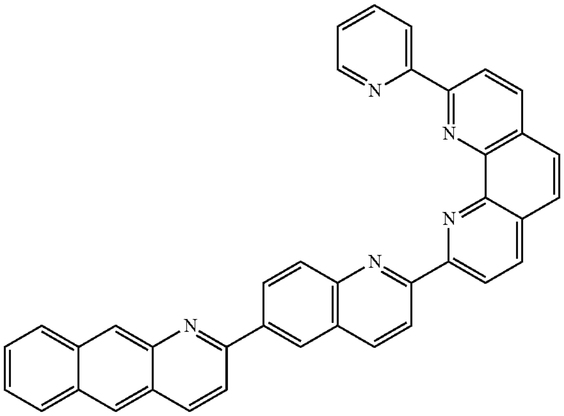
244
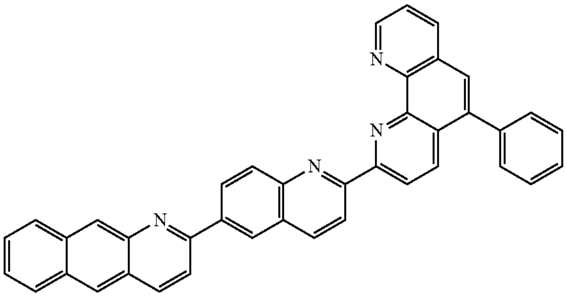
245
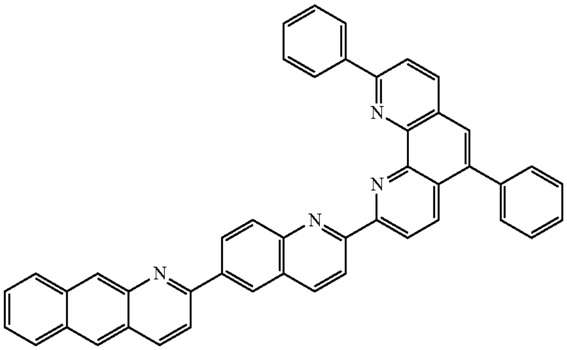
246
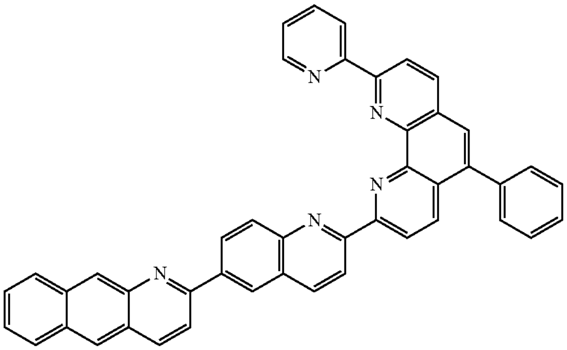
247
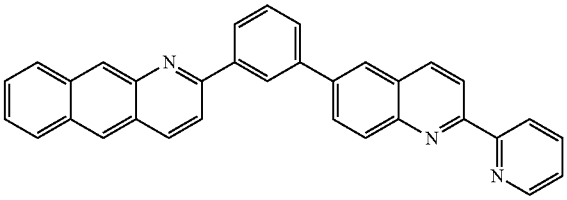
248
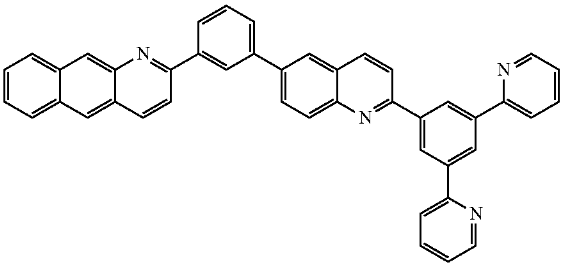

-continued
249
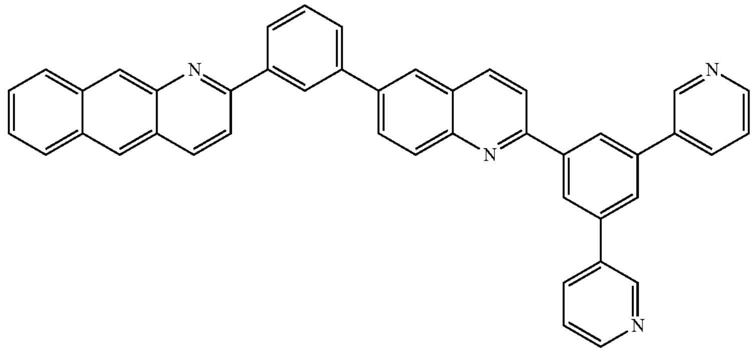
250
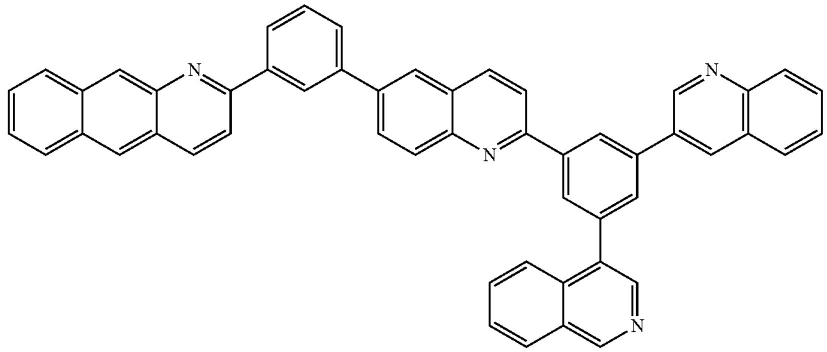
251
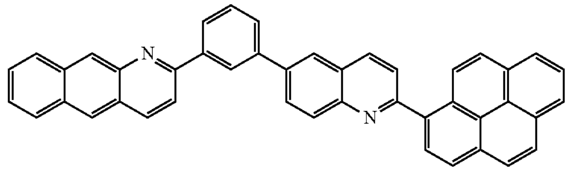
252
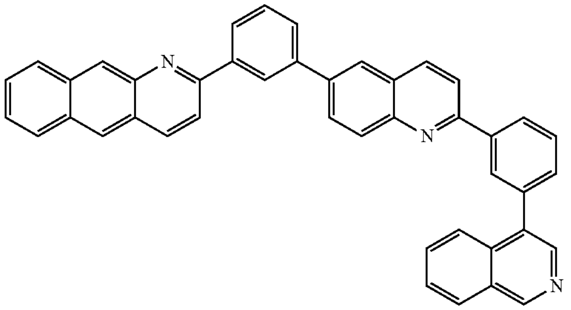
253
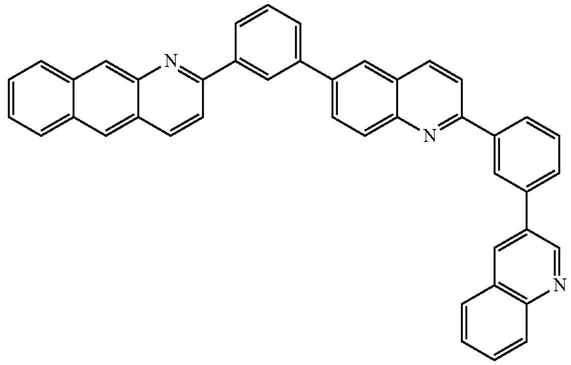
254
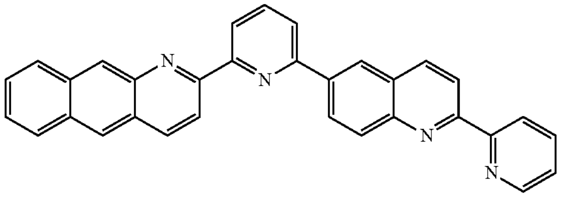

-continued
255
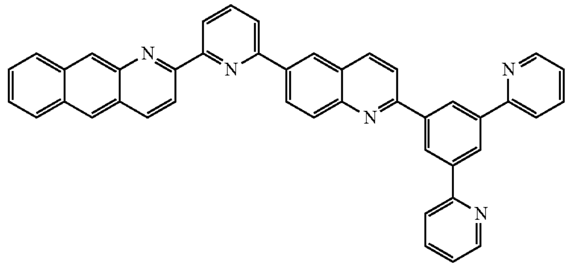
256
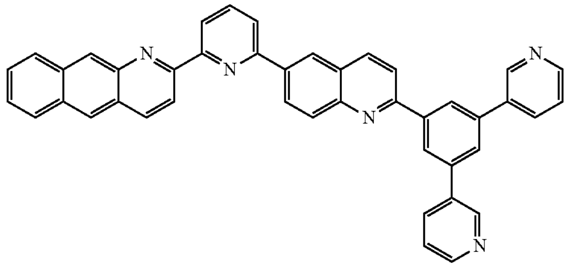
257
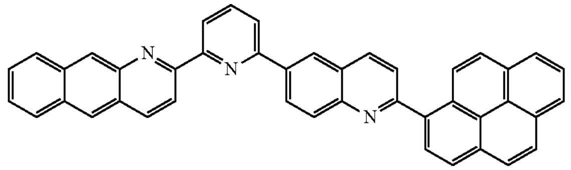
258
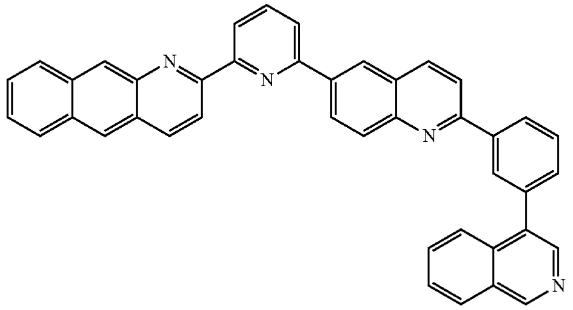
259
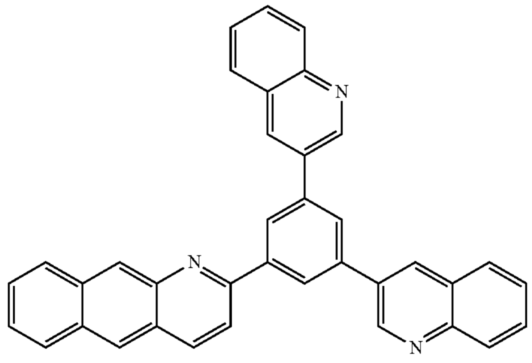
260
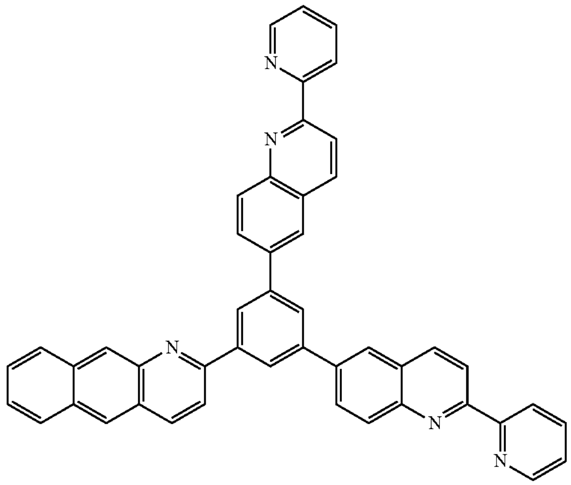
261
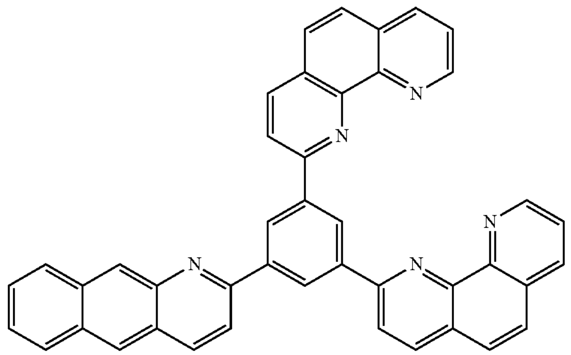
262
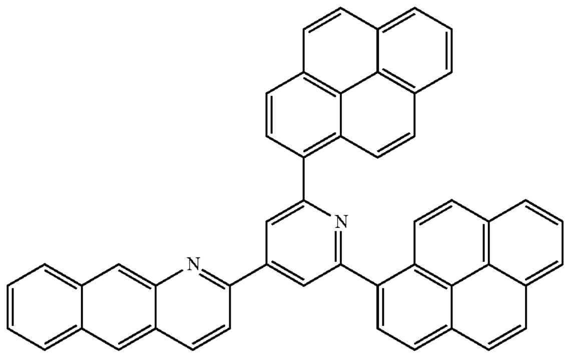

-continued
263
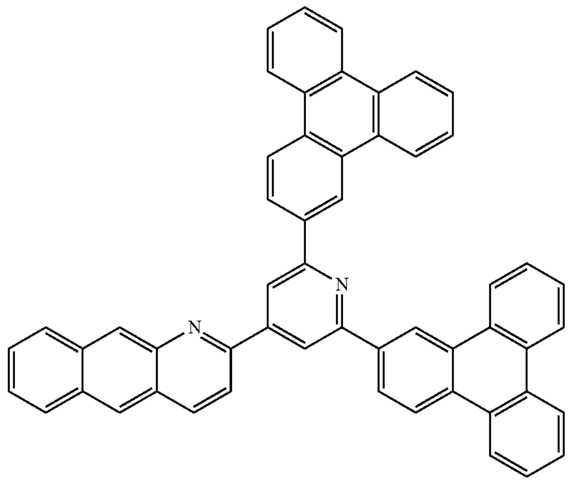
264
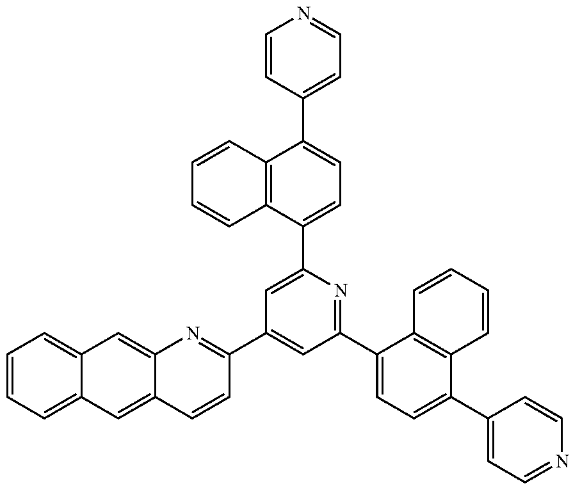
265
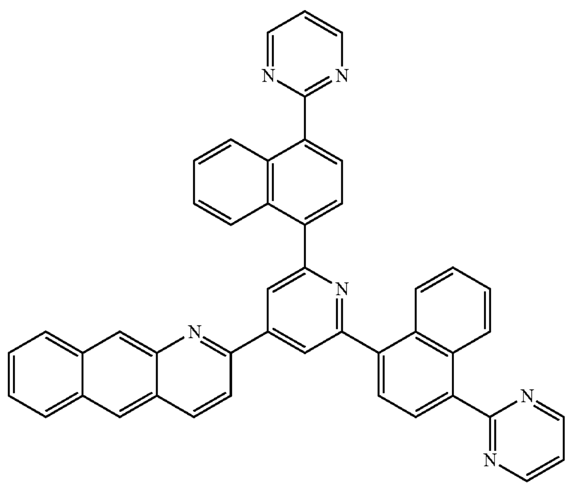
266
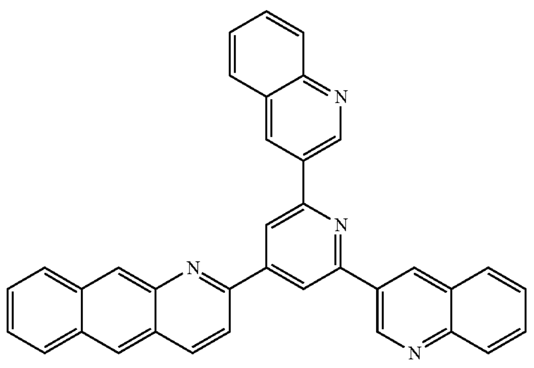
267
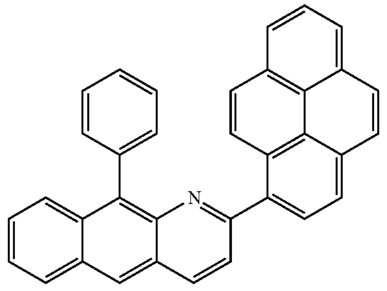
268
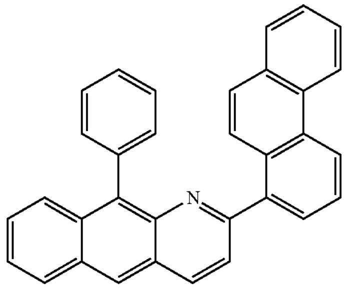
269
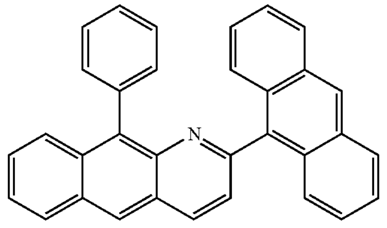
270
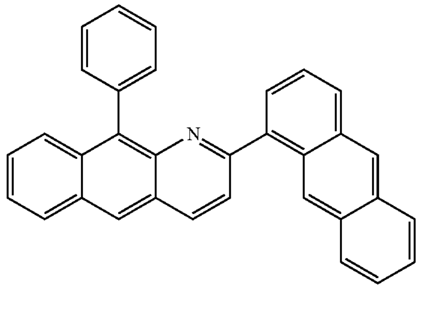

-continued
271
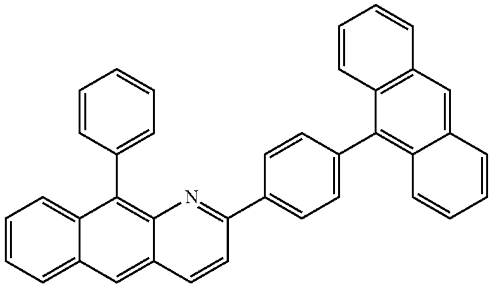
272
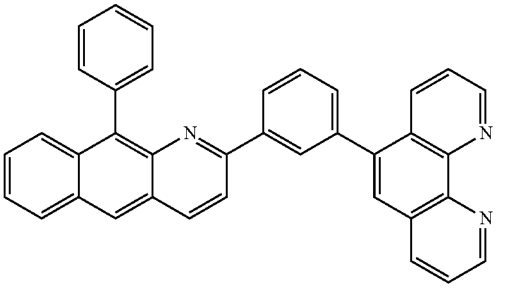
273
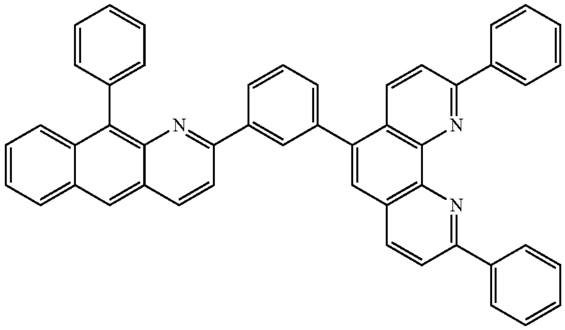
274
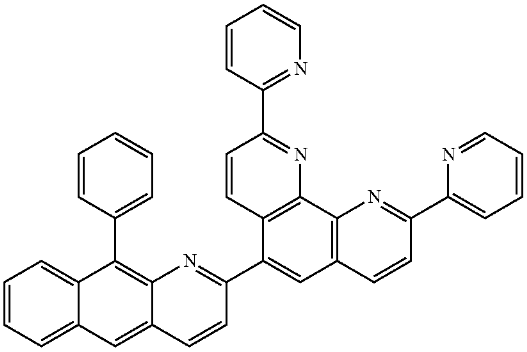
275
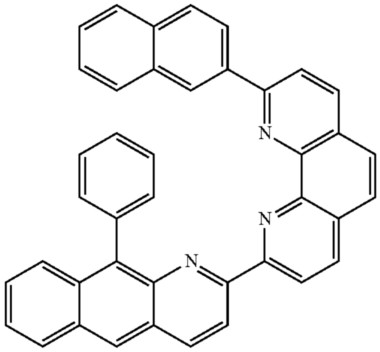
276
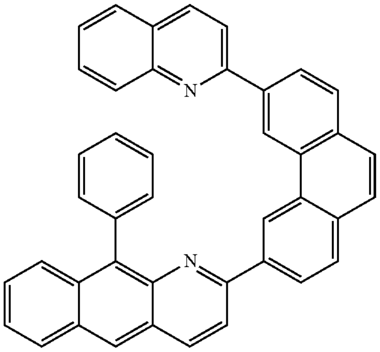
277
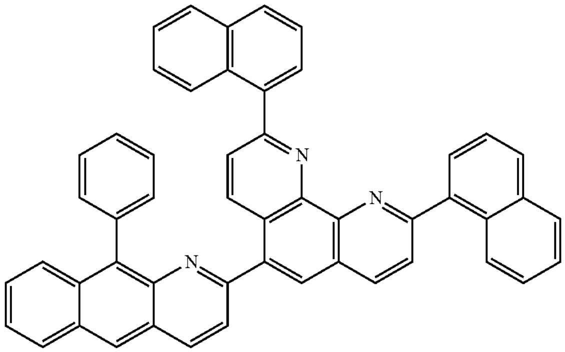
278
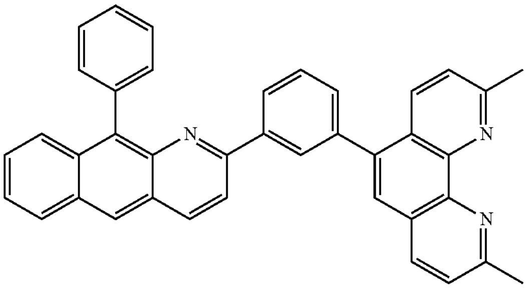

-continued
279
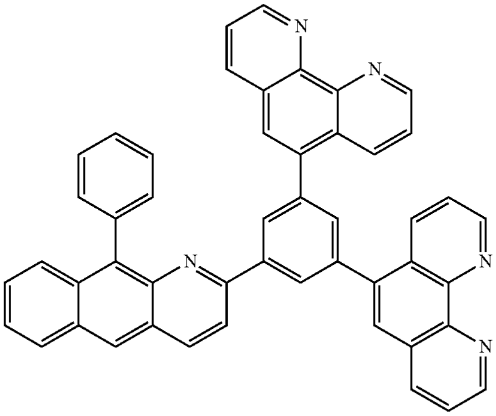
280
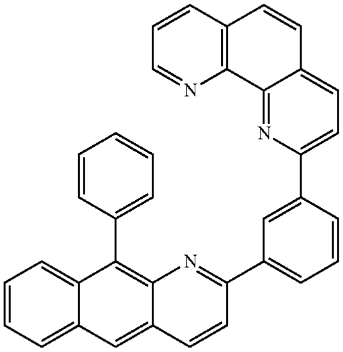
281
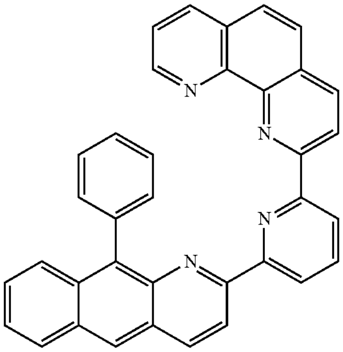
282
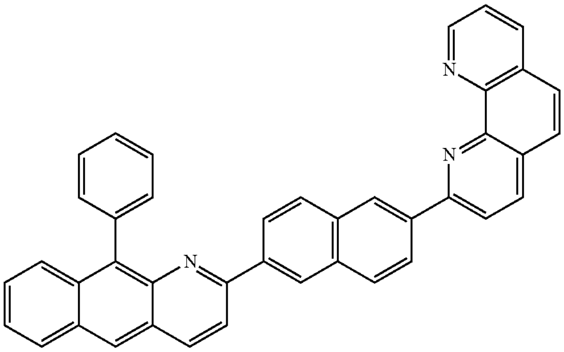
283
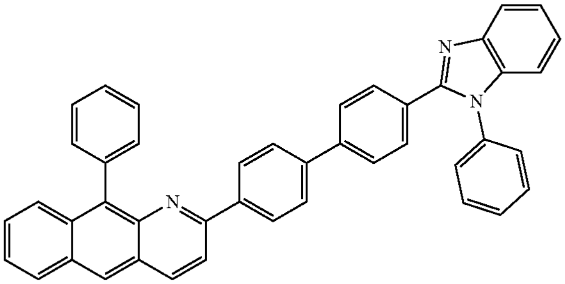
284
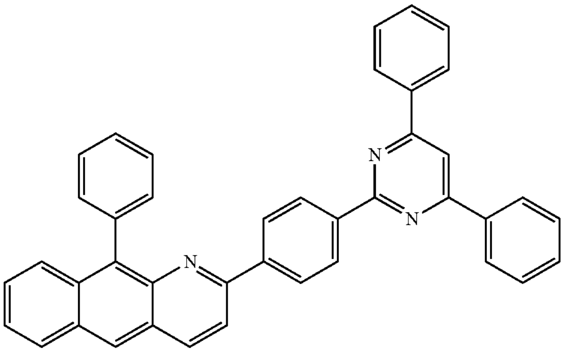
285
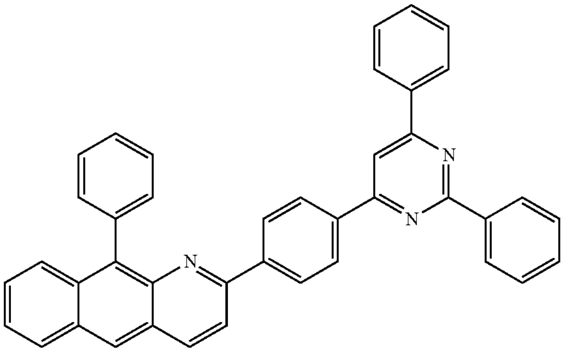
286
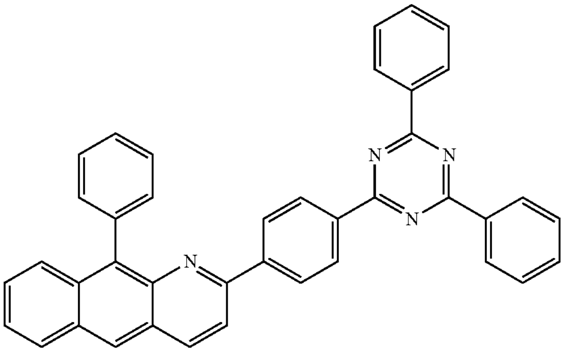

-continued
287
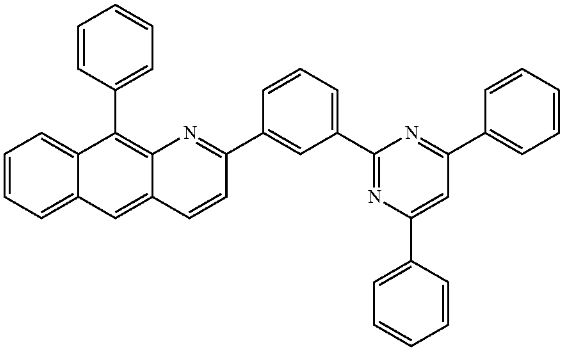
288
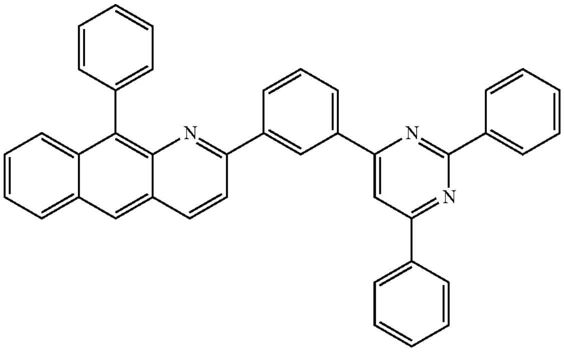
289
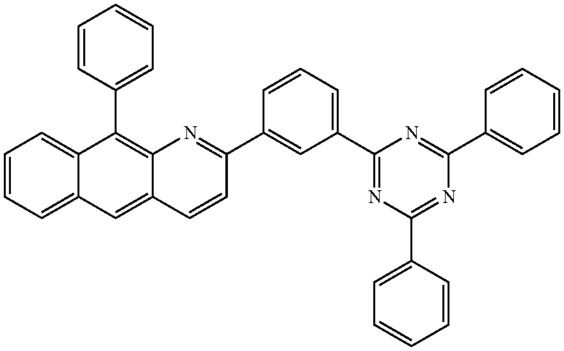
290
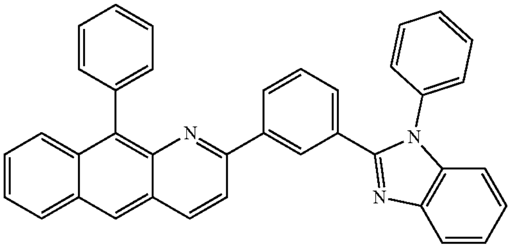
291
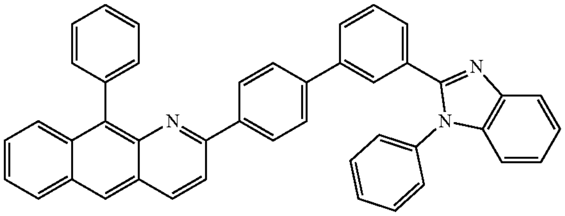
292
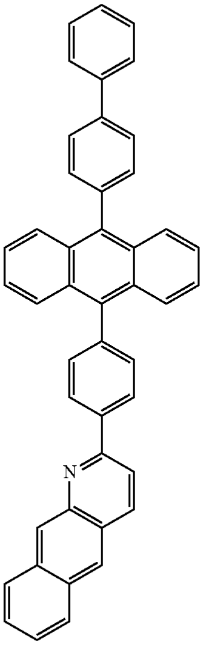

-continued
293
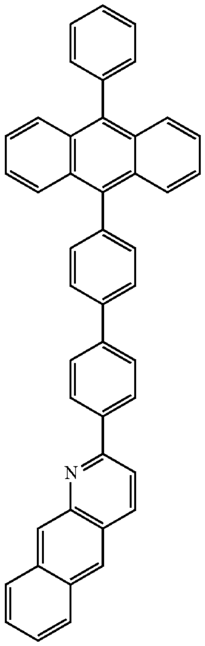
294
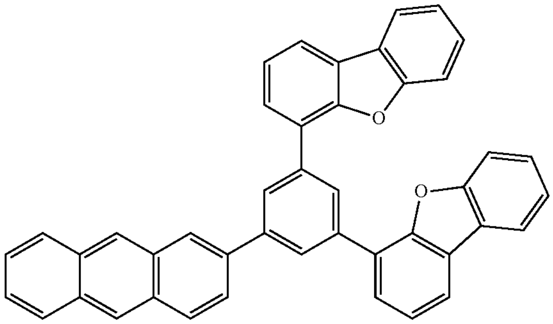
295
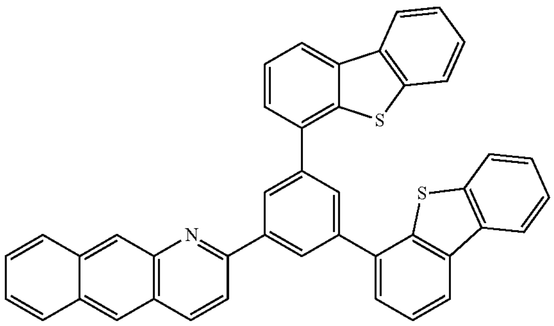
296
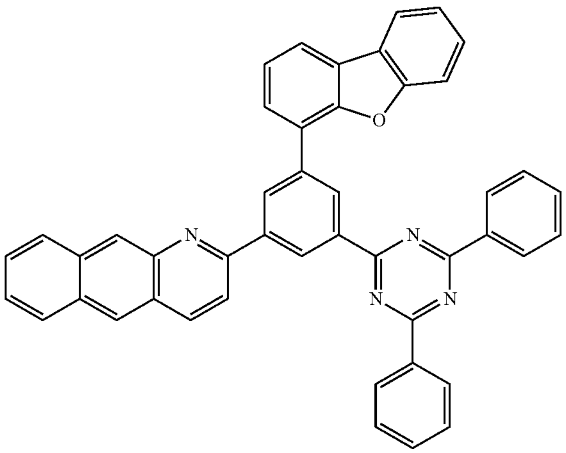
297
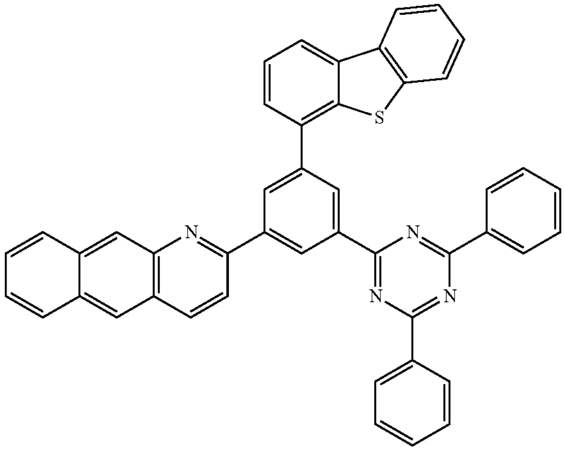
298
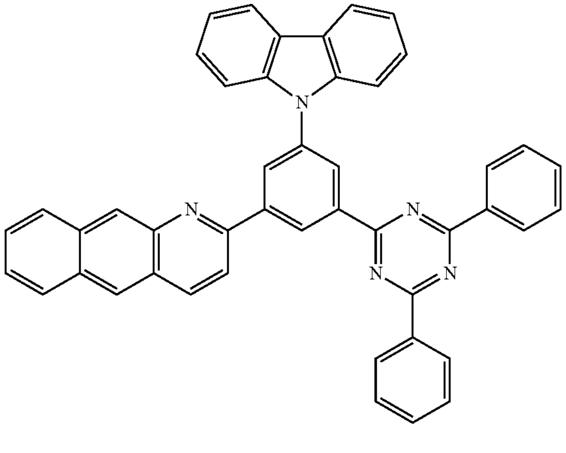

-continued
299
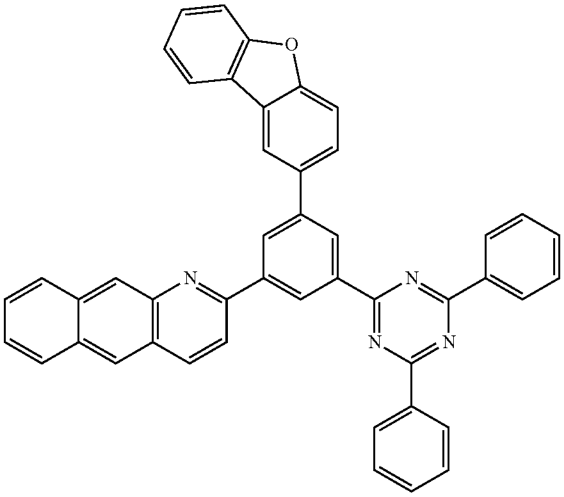
300
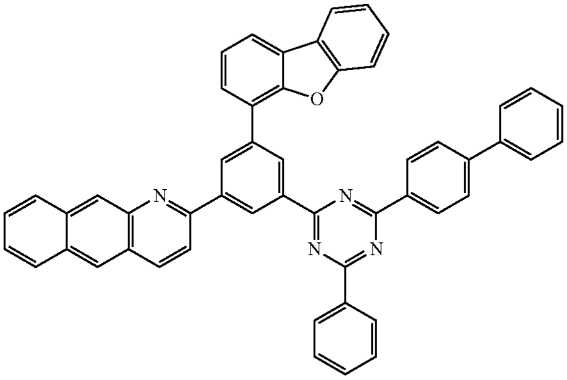
301
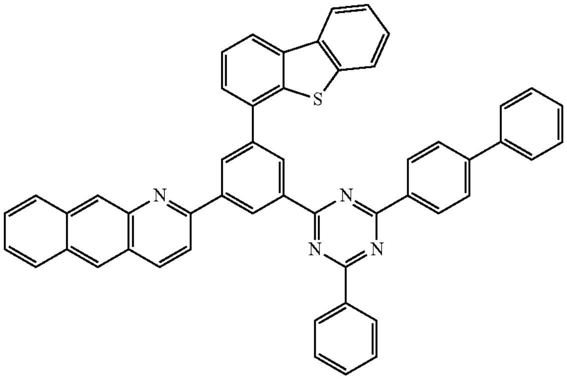
302
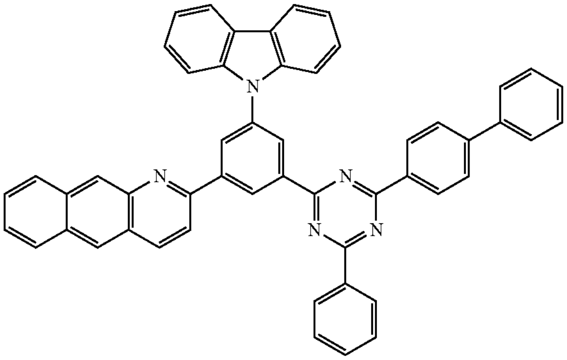
303
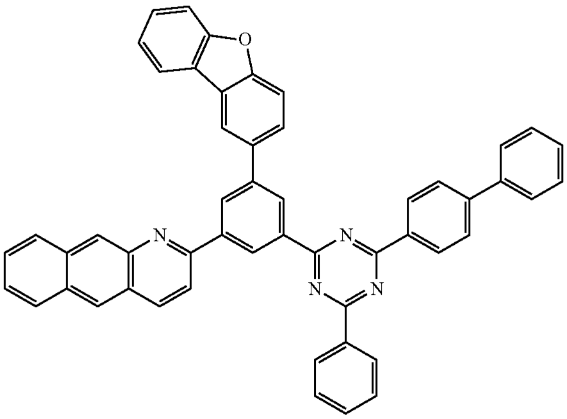
304
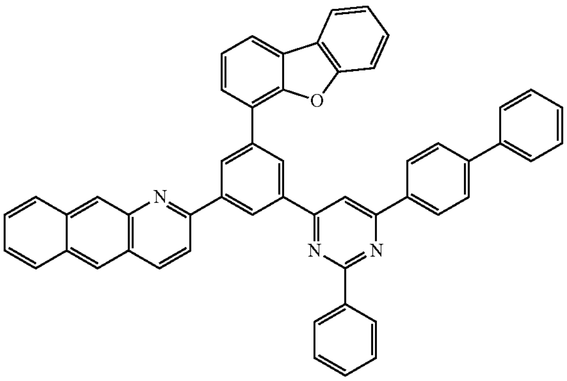

-continued
305
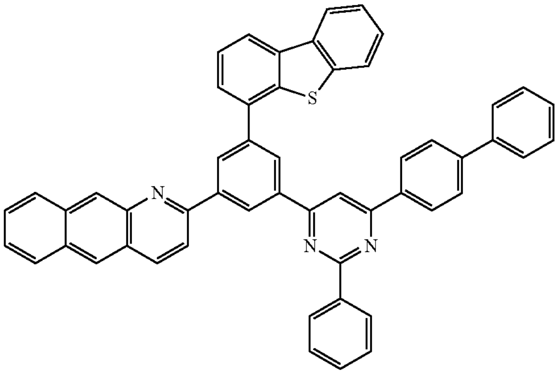
306
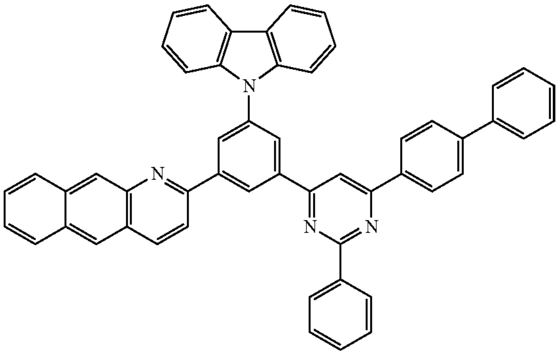
307
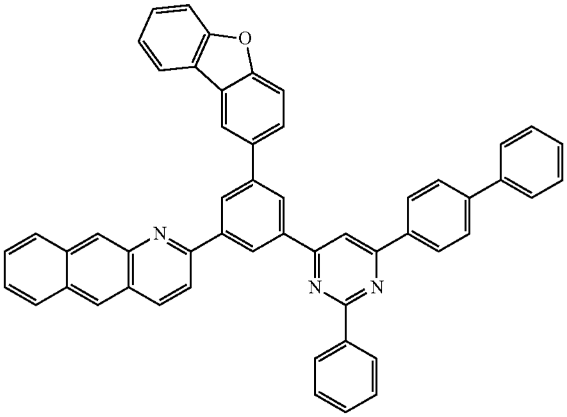
308
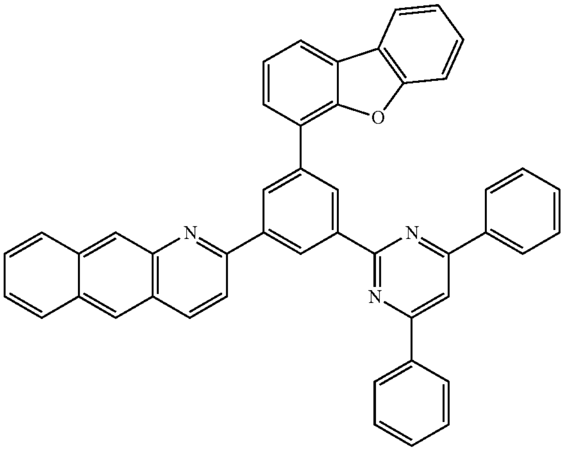
309
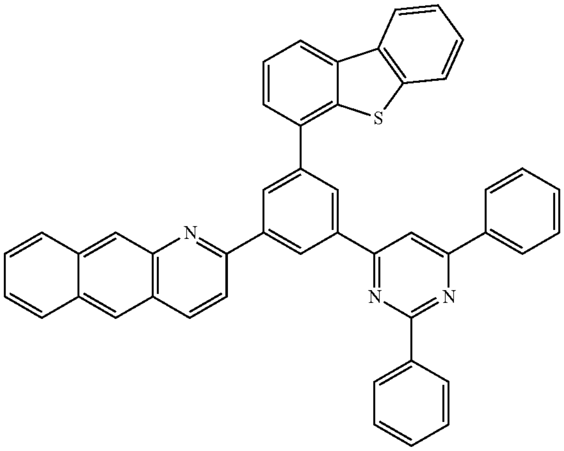
310
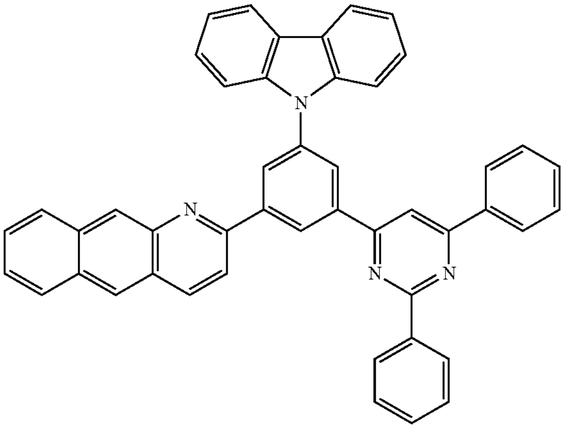

-continued

311

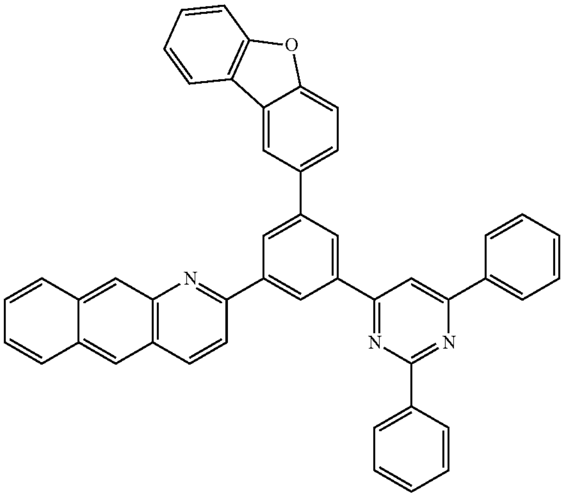

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the hetero-cyclic compound has excellent thermal stability with a high glass transition temperature (Tg). Such an increase in the thermal stability becomes an important factor in providing driving stability to a device.

The hetero-cyclic compound according to one embodiment of the present application may be prepared through a multistep chemical reaction. Some intermediate compounds are prepared first, and the compound of Chemical Formula 1 may be prepared from the intermediate compounds. More specifically, the hetero-cyclic compound according to one embodiment of the present application may be prepared based on preparation examples to be described below.

Another embodiment of the present application provides an organic light emitting device comprising the hetero-cyclic compound represented by Chemical Formula 1.

The organic light emitting device according to one embodiment of the present application may be manufactured using common organic light emitting device manufacturing methods and materials except that one or more organic material layers are formed using the hetero-cyclic compound described above.

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present application comprises an anode, a cathode, and one or more organic material layers provided between the anode and the cathode, wherein one or more layers of the organic material layers comprise the hetero-cyclic compound represented by Chemical Formula 1.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the hetero-cyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the hetero-cyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the hetero-cyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first bole blocking layer, the second hole blocking layer and the like described in FIG. 4 may not be included in some cases.

The organic light emitting device according to the present specification may be manufactured using materials and methods known in the art except that one or more layers of the organic material layers comprise the hetero-cyclic compound represented by Chemical Formula 1.

The hetero-cyclic compound represented by Chemical Formula 1 may form one or more layers of the organic material layers of the organic light emitting device alone. However, as necessary, the hetero-cyclic compound represented by Chemical Formula 1 may be mixed with other materials to form the organic material layers.

The hetero-cyclic compound represented by Chemical Formula 1 may be used as a material of the charge generation layer in the organic light emitting device.

The hetero-cyclic compound represented by Chemical Formula 1 may be used as a material of the electron transfer layer, the hole blocking layer, the light emitting layer or the like in the organic light emitting device. As one example, the hetero-cyclic compound represented by Chemical Formula 1 may be used as a material of the electron transfer layer, the hole transfer layer or the light emitting layer in the organic light emitting device.

In addition, the hetero-cyclic compound represented by Chemical Formula 1 may be used as a material of the light emitting layer in the organic light emitting device. As one example, the hetero-cyclic compound represented by Chemical Formula 1 may be used as a phosphorescent host material of the light emitting layer in the organic light emitting device.

In the organic light emitting device according to one embodiment of the present application, materials other than the hetero-cyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylcompound), poly[3,4-(ethylene-1,2-dioxy)compound](PEDOT), polypyrrole and polyaniline, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri [phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

EXAMPLE

<Preparation Example 1> Preparation of Compound 3

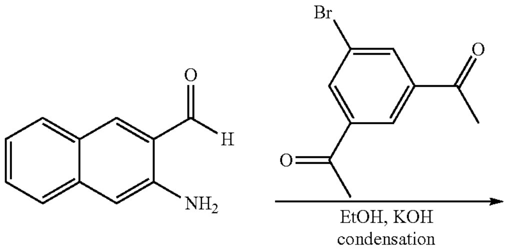

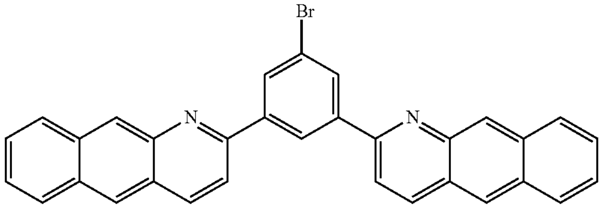

3-2

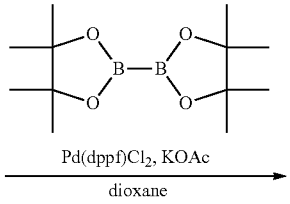

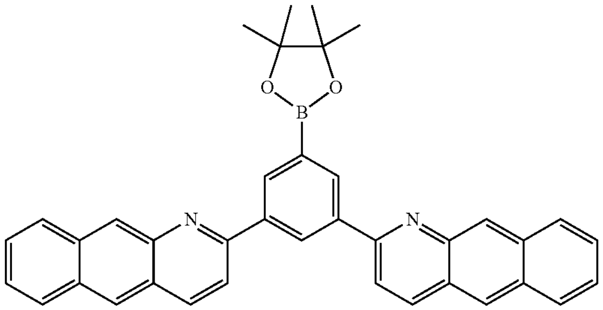

3-1

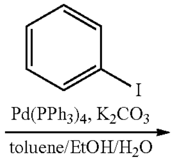

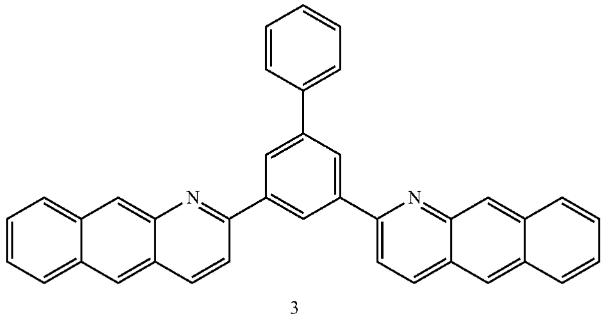

3

1) Preparation of Compound 3-2

A 3-amino-2-naphthaldehyde compound (16.8 g, 85 mmol) and 1,1'-(5-bromo-1,3-phenylene)diethanone (12.5 g, 40 mmol) were introduced to EtOH (300 mL), 5 mL of a KOH solution saturated in EtOH was added dropwise thereto, and then the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 3-2 (27 g, 95%).

2) Preparation of Compound 3-1

After placing Compound 3-2 (13.5 g, 40 mmol), 4,4,4',4',5,5,5',5'-octamethyl-2,2'-bi(1,3,2-dioxaborolane) (20 g, 80 mmol), $Pd(dppf)_2Cl_2$ (1.4 g, 2 mmol) and KOAc (11.7 g, 120 mmol) in a reactor, 0.3 M dioxane was added thereto, and the result was refluxed for 12 hours. After the reaction was completed, the result was cooled to room temperature, and extracted with distilled water and EA. After the organic layer was dried with anhydrous $Na_2O_4$, the solvent was removed using a rotary evaporator, and the result was purified using column chromatography with dichloromethane and hexane as a developing solvent to obtain target Compound 3-1 (12.2 g, 80%).

3) Preparation of Compound 3

Compound 3-1 (7.6 g, 20 mmol) and iodobenzene (5.7 g, 20 mmol) were dissolved in toluene (80 mL), then $Pd(PPh_3)_4$ (1.1 g, 1 mmol) and $K_2CO_3$ (8.3 g, 60 mmol) were added thereto, and the result was stirred for 10 minutes. After that, $H_2O$ (16 mL) and EtOH (16 mL) were added thereto, and the result was refluxed for 12 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 3 (8.3 g, 95%).

Target Compound A was synthesized in the same manner as the preparation of Compound 3 except that, in Preparation Example 1, Intermediate A of the following Table 1 was used instead of iodobenzene.

TABLE 1

| Compound Number | Intermediate A | Target Compound A | Yield |
|---|---|---|---|
| 57 | 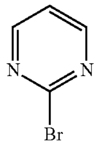 | 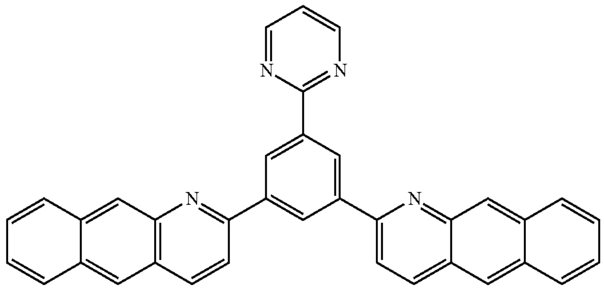 [SMILES: c1cnc(-c2cc(-c3ccc4cc5ccccc5cc4n3)cc(-c3ccc4cc5ccccc5cc4n3)c2)nc1] | 85% |
| 62 | 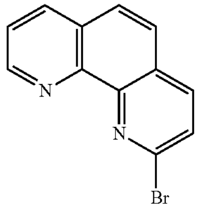 [SMILES: Brc1ccc2ccc3cccnc3c2n1] | 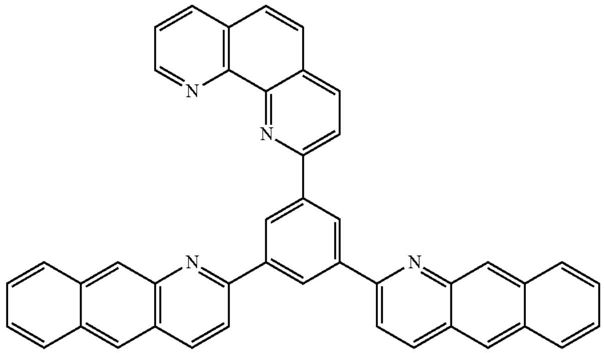 [SMILES: c1ccc2cc3nc(-c4cc(-c5ccc6cc7ccccc7cc6n5)cc(-c5ccc6ccc7cccnc7c6n5)c4)ccc3cc2c1] | 82% |
| 63 | 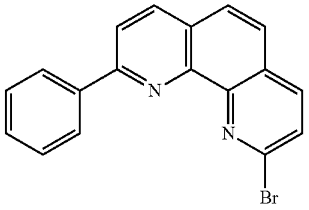 [SMILES: Brc1ccc2ccc3ccc(-c4ccccc4)nc3c2n1] | 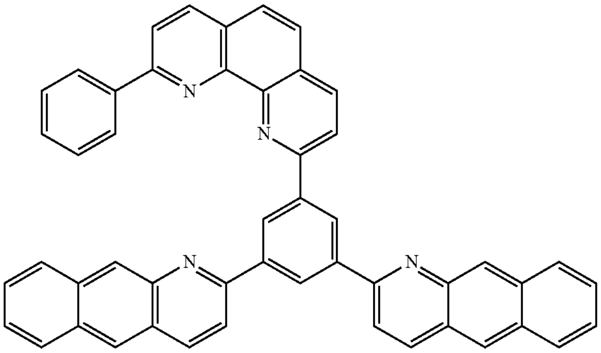 [SMILES: c1ccc(-c2ccc3ccc4ccc(-c5cc(-c6ccc7cc8ccccc8cc7n6)cc(-c6ccc7cc8ccccc8cc7n6)c5)nc4c3n2)cc1] | 88% |

TABLE 1-continued
| Compound Number | Intermediate A | Target Compound A | Yield |
| --- | --- | --- | --- |
| 138 | 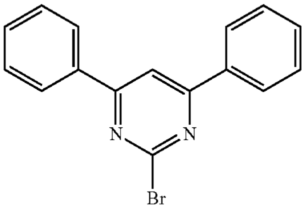 [SMILES: Brc1nc(-c2ccccc2)cc(-c2ccccc2)n1] | 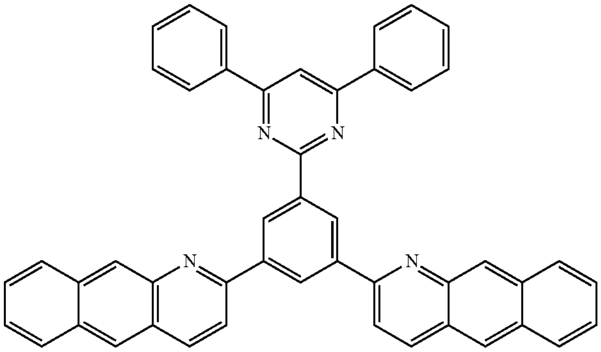 | 78% |
| 142 | 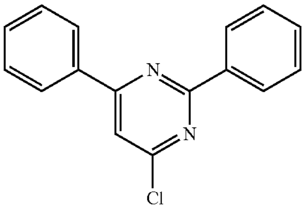 [SMILES: Clc1cc(-c2ccccc2)nc(-c2ccccc2)n1] | 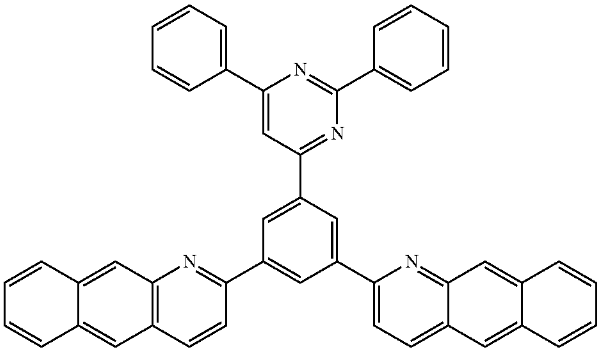 [SMILES: c1ccc(-c2cc(-c3cc(-c4ccc5cc6ccccc6cc5n4)cc(-c4ccc5cc6ccccc6cc5n4)c3)nc(-c3ccccc3)n2)cc1] | 72% |
| 147 | 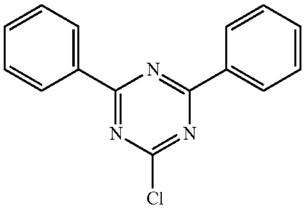 [SMILES: Clc1nc(-c2ccccc2)nc(-c2ccccc2)n1] | 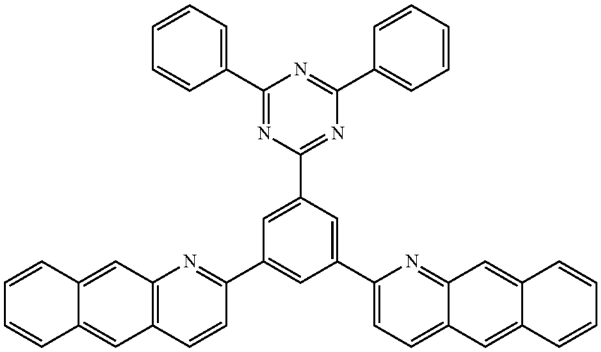 [SMILES: c1ccc(-c2nc(-c3ccccc3)nc(-c3cc(-c4ccc5cc6ccccc6cc5n4)cc(-c4ccc5cc6ccccc6cc5n4)c3)n2)cc1] | 81% |
| 148 | 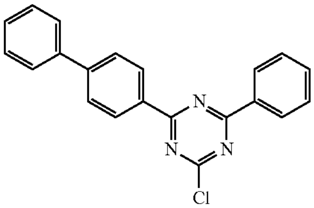 [SMILES: Clc1nc(-c2ccccc2)nc(-c2ccc(-c3ccccc3)cc2)n1] | 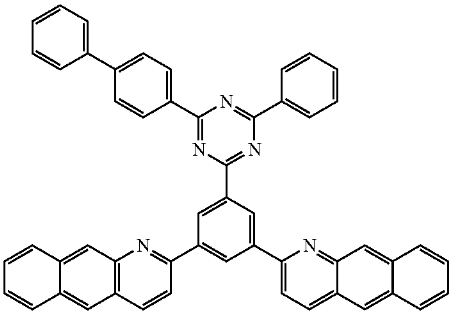 [SMILES: c1ccc(-c2ccc(-c3nc(-c4ccccc4)nc(-c4cc(-c5ccc6cc7ccccc7cc6n5)cc(-c5ccc6cc7ccccc7cc6n5)c4)n3)cc2)cc1] | 83% |

<Preparation Example 2> Preparation of Compound 41

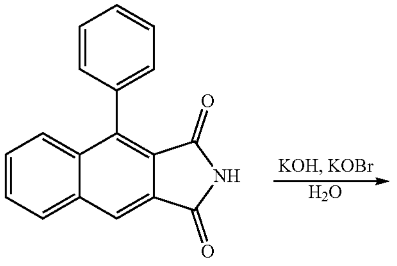

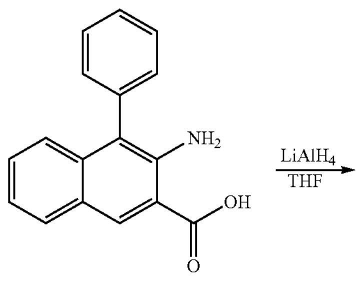

41-3

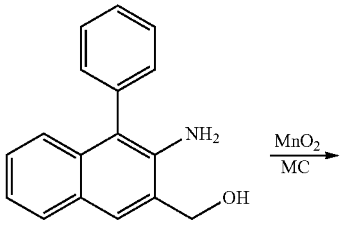

41-2

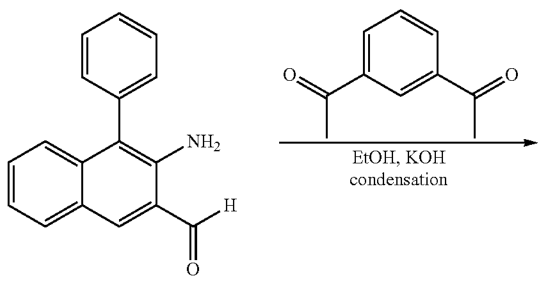

41-1

-continued

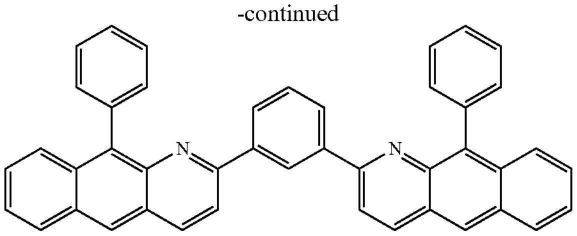

41

1) Preparation of Compound 41-3

A 4-phenyl-1H-benzo[f]isoindole-1,3(2H)-dione compound (20 g, 73 mmol), KOBr (9.9 g, 73 mmol) and KOH (10.2 g, 183 mMol) were introduced to $H_2O$ (300 mL), and the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 41-3 (15 g, 78%).

2) Preparation of Compound 41-2

$LiAlH_4$ (3.5 g, 91 mmol) was introduced to THF (50 mL), and the temperature was maintained at 0° C. Compound 41-3 (15 g, 57 mmol) was dissolved in THF (50 mL) and slowly added dropwise thereto. After that, the temperature was slowly raised to room temperature, and the result was stirred for 12 hours. After the reaction was completed, the result was extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 41-2 (13 g, 92%).

3) Preparation of Compound 41-1

After dissolving Compound 41-2 (13 g, 52 mmol) in MC (250 mL), $MnO_2$ (18 g, 208 mmol) was slowly added thereto, and the result was stirred for 1 hour at room temperature. After the reaction was completed, the result was Celite filtered, and the organic layer was rotary evaporated to remove the solvent. The result was purified using column chromatography with ethyl acetate and hexane as a developing solvent to obtain target Compound 41-1 (10 g, 77%).

4) Preparation of Compound 41

Compound 41-1 (10 g, 40 mmol) and 1,1'-(1,3-phenylene) diethanone (3.5 g, 20 mmol) were introduced to EtOH (50 mL), 5 mL of a KOH solution saturated in EtOH was added dropwise thereto, and then the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 41 (7 g, 60%).

Target Compound B was synthesized in the same manner as the preparation of Compound 41 except that, in Preparation Example 2, Intermediate B of the following Table 2 was used instead of 1,1'-(1,3-phenylene)diethanone.

TABLE 2
| Compound Number | Intermediate B | Target Compound B | Yield |
|---|---|---|---|
| 42 | 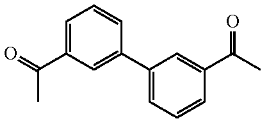 [SMILES: CC(=O)c1cccc(-c2cccc(C(C)=O)c2)c1] | 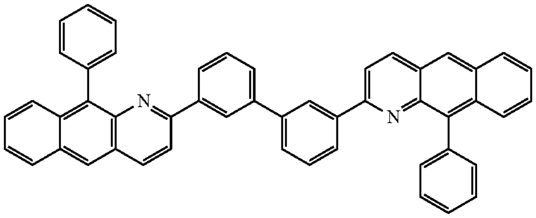 [SMILES: c1ccc(-c2c3ccccc3cc3ccc(-c4cccc(-c5cccc(-c6ccc7cc8ccccc8c(-c8ccccc8)c7n6)c5)c4)nc23)cc1] | 55% |
| 43 | 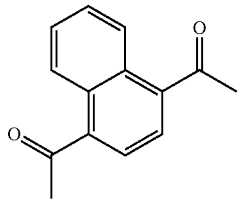 [SMILES: CC(=O)c1ccc(C(C)=O)c2ccccc12] | 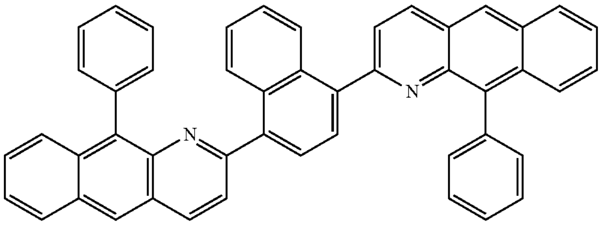 [SMILES: c1ccc(-c2c3ccccc3cc3ccc(-c4ccc(-c5ccc6cc7ccccc7c(-c7ccccc7)c6n5)c5ccccc45)nc23)cc1] | 65% |
| 44 | 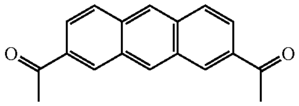 [SMILES: CC(=O)c1ccc2cc3ccc(C(C)=O)cc3cc2c1] | 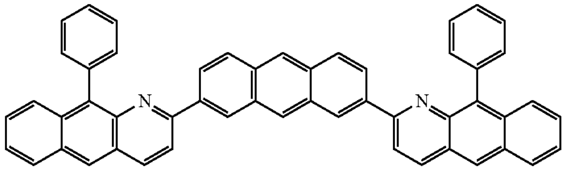 [SMILES: c1ccc(-c2c3ccccc3cc3ccc(-c4ccc5cc6ccc(-c7ccc8cc9ccccc9c(-c9ccccc9)c8n7)cc6cc5c4)nc23)cc1] | 68% |
| 45 | 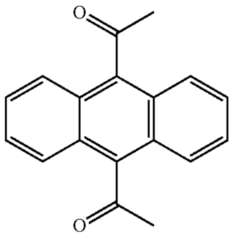 [SMILES: CC(=O)c1c2ccccc2c(C(C)=O)c2ccccc12] | 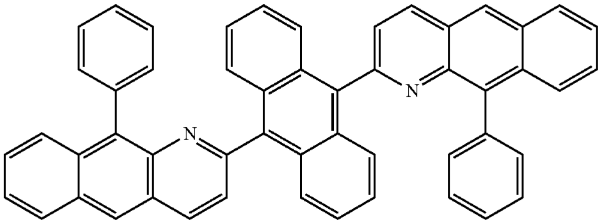 [SMILES: c1ccc(-c2c3ccccc3cc3ccc(-c4c5ccccc5c(-c5ccc6cc7ccccc7c(-c7ccccc7)c6n5)c5ccccc45)nc23)cc1] | 50% |
| 46 | 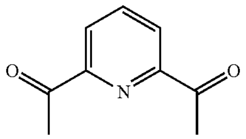 | 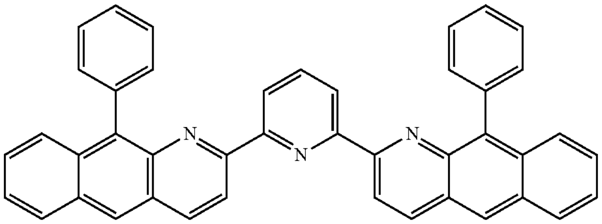 [SMILES: c1ccc(-c2c3ccccc3cc3ccc(-c4cccc(-c5ccc6cc7ccccc7c(-c7ccccc7)c6n5)n4)nc23)cc1] | 54% |
| 47 | 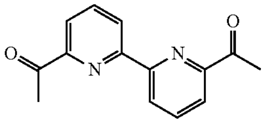 [SMILES: CC(=O)c1cccc(-c2cccc(C(C)=O)n2)n1] | 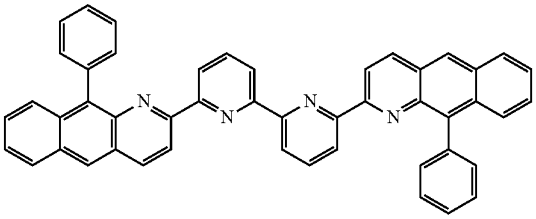 [SMILES: c1ccc(-c2c3ccccc3cc3ccc(-c4cccc(-c5cccc(-c6ccc7cc8ccccc8c(-c8ccccc8)c7n6)n5)n4)nc23)cc1] | 61% |

<Preparation Example 3> Preparation of Compound 88

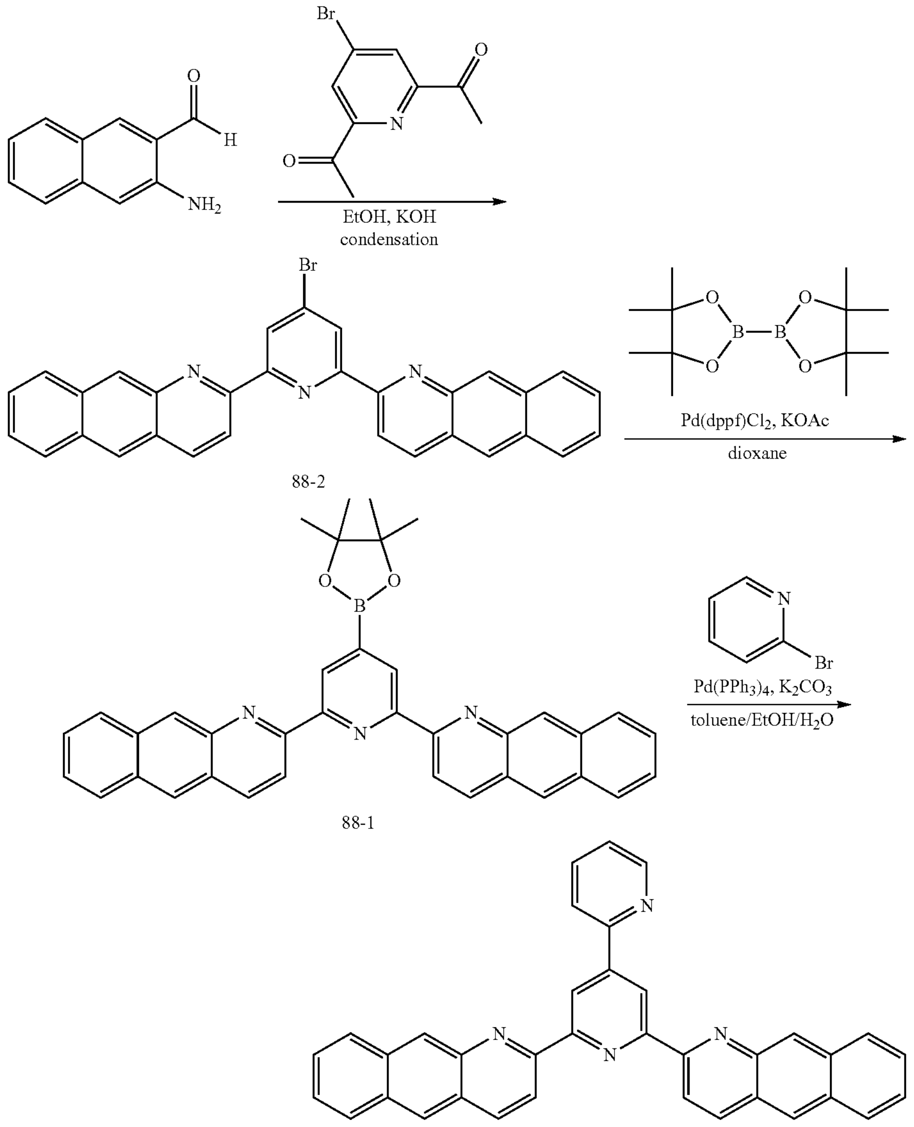

88

1) Preparation of Compound 88-2

A 3-amino-2-naphthaldehyde compound (16.8 g, 85 mmol) and 1,1'-(4-bromopyridine-2,6-diyl) diethanone (12.5 g, 40 mmol) were introduced to EtOH (300 mL), 5 mL of a KOH solution saturated in EtOH was added dropwise thereto, and then the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 88-2 (27 g, 95%).

2) Preparation of Compound 88-1

After placing Compound 88-2 (13.5 g, 40 mmol), 4,4,4',4',5,5,5',5'-octamethyl-2,2'-bi(1,3,2-dioxaborolane) (20 g, 80 mmol), $Pd(dppf)_2Cl_2$ (1.4 g, 2 mmol) and KOAc (11.7 g, 120 mmol) in a reactor, 0.3 M dioxane was added thereto, and the result was refluxed for 12 hours. After the reaction was completed, the result was cooled to room temperature, and extracted with distilled water and EA. After the organic layer was dried with anhydrous $Na_2O_4$, the solvent was removed using a rotary evaporator, and the result was purified using column chromatography with dichloromethane and hexane as a developing solvent to obtain target Compound 88-1 (14 g, 90%).

3) Preparation of Compound 88

Compound 88-1 (7.6 g, 20 mmol) and 2-bromopyridine (4.7 g, 20 mmol) were dissolved in toluene (80 mL), then $Pd(PPh_3)_4$ (1.1 g, 1 mmol) and $K_2CO_3$ (8.3 g, 60 mmol) were added thereto, and the result was stirred for 10 minutes. After that, $H_2O$ (16 mL) and EtOH (16 mL) were added thereto, and the result was refluxed for 12 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 88 (7.3 g, 85%).

Target Compound C was synthesized in the same manner as the preparation of Compound 88 except that, in Preparation Example 3, Intermediate C of the following Table 3 was used instead of 2-bromopyridine.

TABLE 3

| Compound Number | Intermediate C | Target Compound C | Yield |
|---|---|---|---|
| 89 | 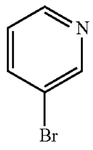 | 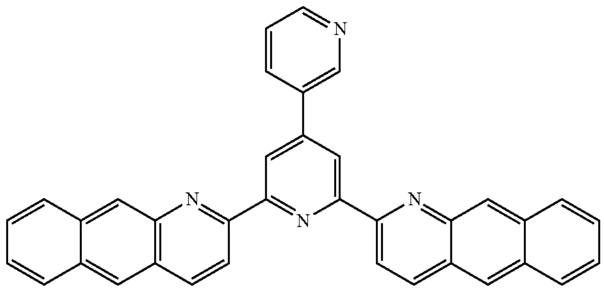 [SMILES: c1cncc(-c2cc(-c3ccc4cc5ccccc5cc4n3)nc(-c3ccc4cc5ccccc5cc4n3)c2)c1] | 78% |
| 90 | 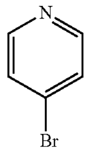 | 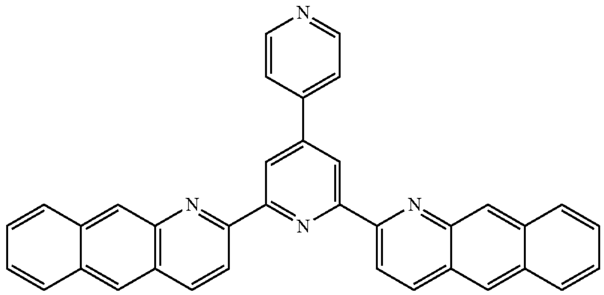 [SMILES: c1ccc2cc3nc(-c4cc(-c5ccncc5)cc(-c5ccc6cc7ccccc7cc6n5)n4)ccc3cc2c1] | 81% |
| 91 | 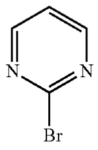 | 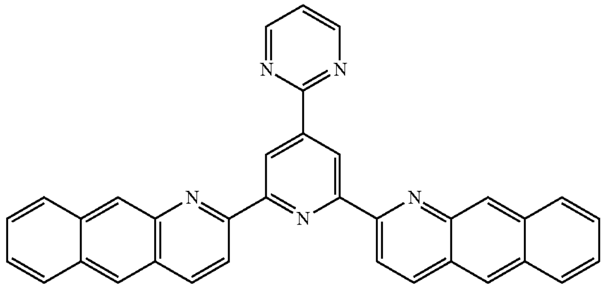 [SMILES: c1cnc(-c2cc(-c3ccc4cc5ccccc5cc4n3)nc(-c3ccc4cc5ccccc5cc4n3)c2)nc1] | 91% |
| 92 | 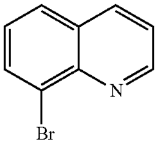 [SMILES: Brc1cccc2cccnc12] | 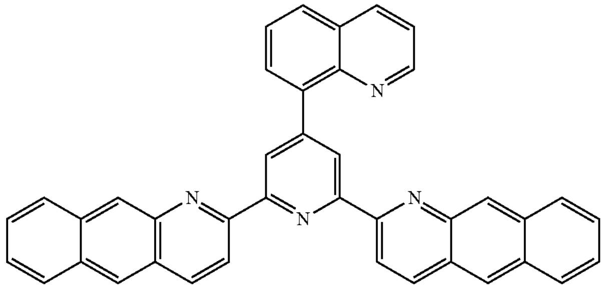 [SMILES: c1ccc2cc3nc(-c4cc(-c5cccc6cccnc56)cc(-c5ccc6cc7ccccc7cc6n5)n4)ccc3cc2c1] | 78% |

TABLE 3-continued
| Compound Number | Intermediate C | Target Compound C | Yield |
|---|---|---|---|
| 93 | 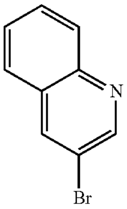 [SMILES: Brc1cnc2ccccc2c1] | 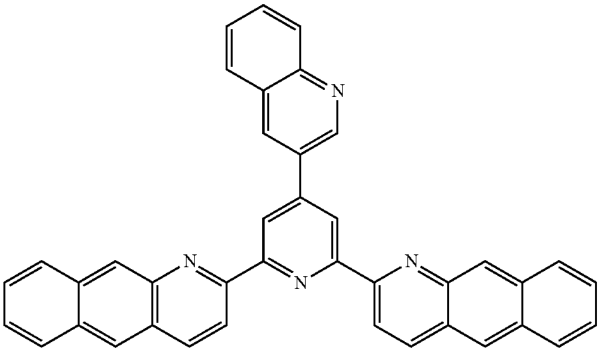 [SMILES: c1ccc2cc3nc(-c4cc(-c5cnc6ccccc6c5)cc(-c5ccc6cc7ccccc7cc6n5)n4)ccc3cc2c1] | 72% |
| 94 | 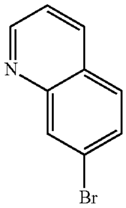 [SMILES: Brc1ccc2cccnc2c1] | 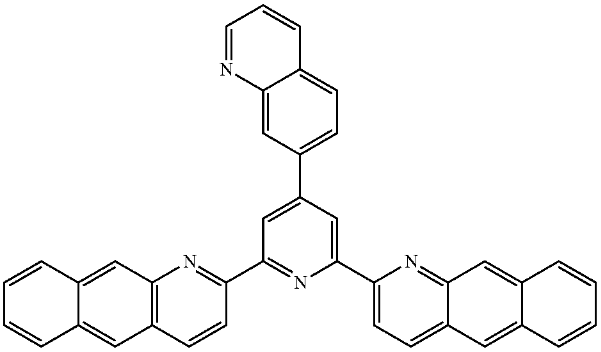 [SMILES: c1ccc2cc3nc(-c4cc(-c5ccc6cccnc6c5)cc(-c5ccc6cc7ccccc7cc6n5)n4)ccc3cc2c1] | 81% |
| 95 | 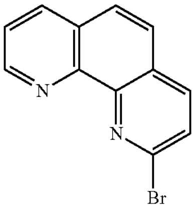 [SMILES: Brc1ccc2ccc3cccnc3c2n1] | 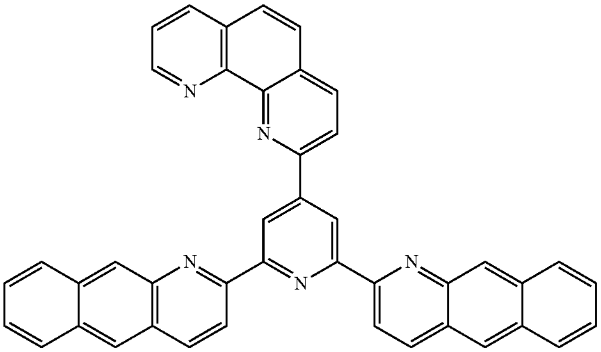 [SMILES: c1ccc2cc3nc(-c4cc(-c5ccc6ccc7cccnc7c6n5)cc(-c5ccc6cc7ccccc7cc6n5)n4)ccc3cc2c1] | 83% |
<Preparation Example 4> Preparation of Compound 164
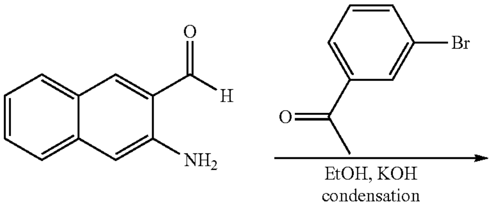

-continued

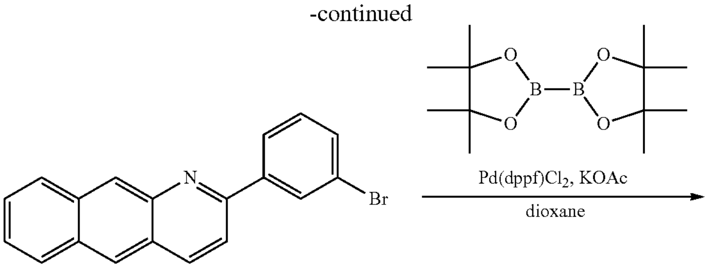

164-2

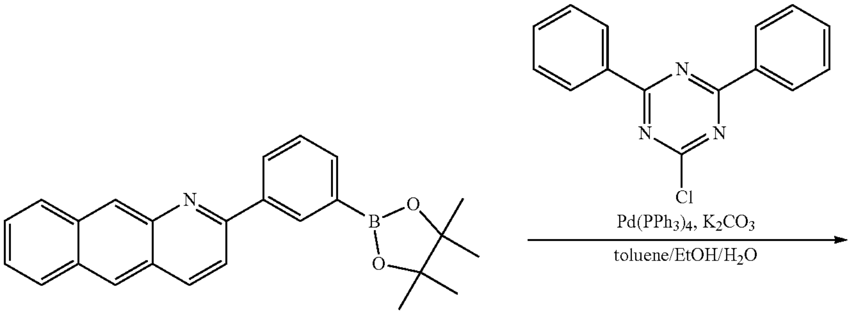

164-1

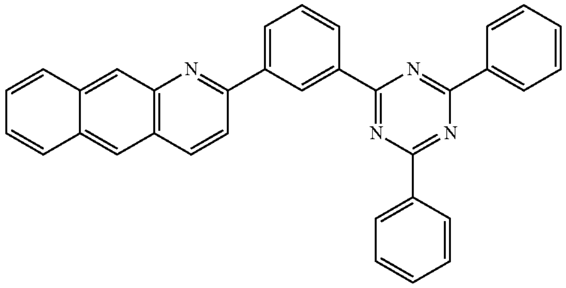

164

1) Preparation of Compound 164-2

A 3-amino-2-naphthaldehyde compound (16.8 g, 85 mmol) and 1-(3-bromophenyl)ethan-1-one (16.9 g, 85 mmol) were introduced to EtOH (300 mL), 5 mL of a KOH solution saturated in EtOH was added dropwise thereto, and then the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 164-2 (27 g, 95%).

2) Preparation of Compound 164-1

After placing Compound 164-2 (13.5 g, 40 mmol), 4,4,4',4',5,5,5',5'-octamethyl-2,2'-bi(1,3,2-dioxaborolane) (20 g, 80 mmol), $Pd(dppf)_2Cl_2$ (1.4 g, 2 mmol) and KOAc (11.7 g, 120 mmol) in a reactor, 0.3 M dioxane was added thereto, and the result was refluxed for 12 hours. After the reaction was completed, the result was cooled to room temperature, and extracted with distilled water and EA. After the organic layer was dried with anhydrous $Na_2O_4$, the solvent was removed using a rotary evaporator, and the result was purified using column chromatography with dichloromethane and hexane as a developing solvent to obtain target Compound 164-1 (12.2 g, 80%).

3) Preparation of Compound 164

Compound 164-1 (7.6 g, 20 mmol) and 2-chloro-4,6-diphenyl-1,3,5-triazine (5.7 g, 20 mmol) were dissolved in toluene (80 mL), then $Pd(PPh_3)_4$ (1.1 g, 1 mmol) and $K_2CO_3$ (8.3 g, 60 mmol) were added thereto, and the result was stirred for 10 minutes. After that, $H_2O$ (16 mL) and EtOH (16 mL) were added thereto, and the result was refluxed for 12 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 164 (7 g, 75%).

Target Compound D was synthesized in the same manner as the preparation of Compound 164 except that, in Preparation Example 4, Intermediate D of the following Table 4 was used instead of 2-chloro-4,6-diphenyl-1,3,5-triazine.

TABLE 4
| Compound Number | Intermediate D | Target Compound D | Yield |
|---|---|---|---|
| 169 | 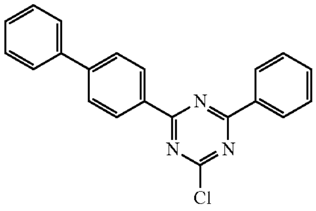 [SMILES: Clc1nc(-c2ccccc2)nc(-c2ccc(-c3ccccc3)cc2)n1] | 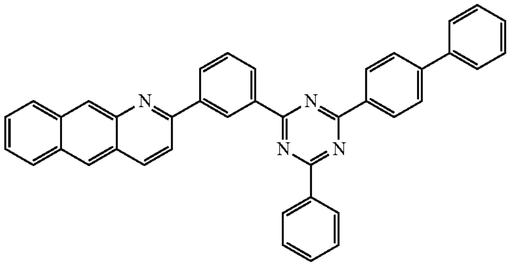 [SMILES: c1ccc(-c2ccc(-c3nc(-c4ccccc4)nc(-c4cccc(-c5ccc6cc7ccccc7cc6n5)c4)n3)cc2)cc1] | 75% |
| 192 | 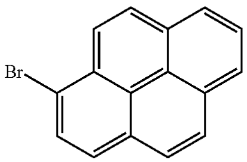 [SMILES: Brc1ccc2ccc3cccc4ccc1c2c34] | 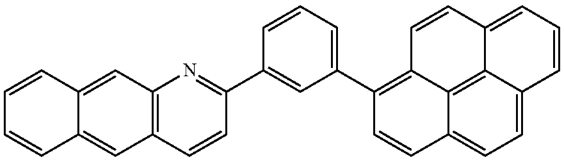 [SMILES: c1cc(-c2ccc3cc4ccccc4cc3n2)cc(-c2ccc3ccc4cccc5ccc2c3c45)c1] | 90% |
| 193 | 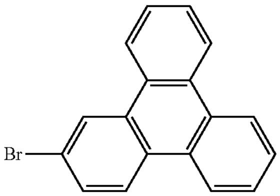 [SMILES: Brc1ccc2c3ccccc3c3ccccc3c2c1] | 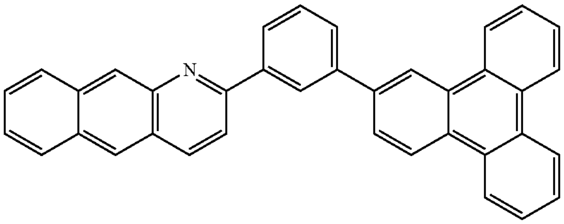 [SMILES: c1cc(-c2ccc3c4ccccc4c4ccccc4c3c2)cc(-c2ccc3cc4ccccc4cc3n2)c1] | 83% |
| 210 | 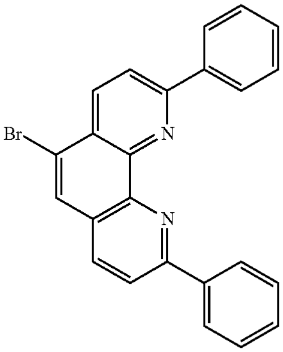 [SMILES: Brc1cc2ccc(-c3ccccc3)nc2c2nc(-c3ccccc3)ccc12] | 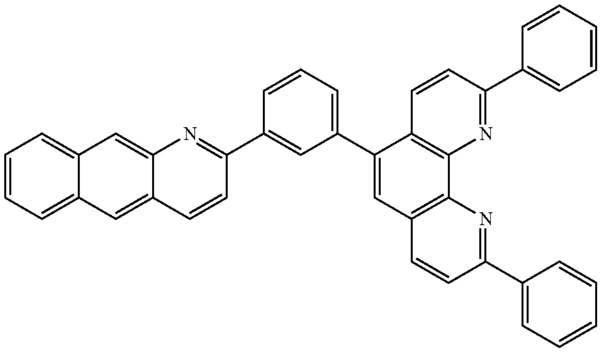 [SMILES: c1ccc(-c2ccc3cc(-c4cccc(-c5ccc6cc7ccccc7cc6n5)c4)c4ccc(-c5ccccc5)nc4c3n2)cc1] | 81% |
| 228 | 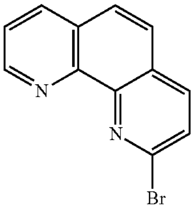 [SMILES: Brc1ccc2ccc3cccnc3c2n1] | 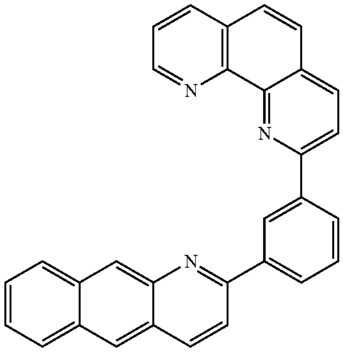 [SMILES: c1cc(-c2ccc3cc4ccccc4cc3n2)cc(-c2ccc3ccc4cccnc4c3n2)c1] | 83% |

TABLE 4-continued

| Compound Number | Intermediate D | Target Compound D | Yield |
|---|---|---|---|
| 230 | 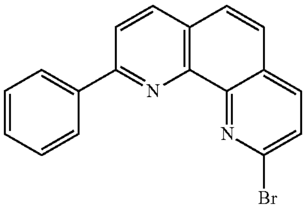 [SMILES: Brc1ccc2ccc3ccc(-c4ccccc4)nc3c2n1] | 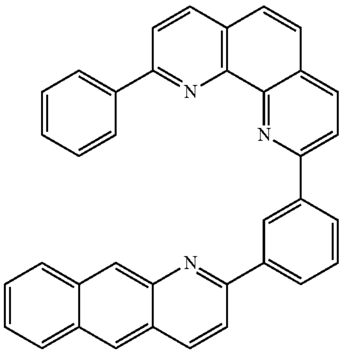 [SMILES: c1ccc(-c2ccc3ccc4ccc(-c5cccc(-c6ccc7cc8ccccc8cc7n6)c5)nc4c3n2)cc1] | 85% |
| 247 | 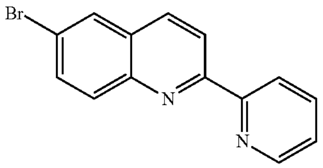 [SMILES: Brc1ccc2nc(-c3ccccn3)ccc2c1] | 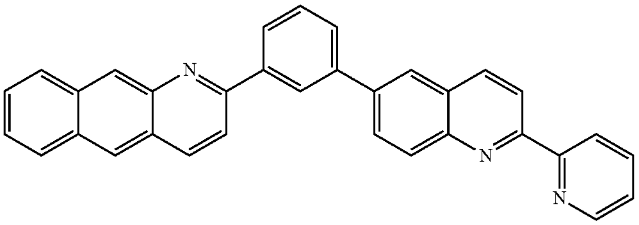 [SMILES: c1ccc(-c2ccc3cc(-c4cccc(-c5ccc6cc7ccccc7cc6n5)c4)ccc3n2)nc1] | 89% |

<Preparation Example 5> Preparation of Compound 226

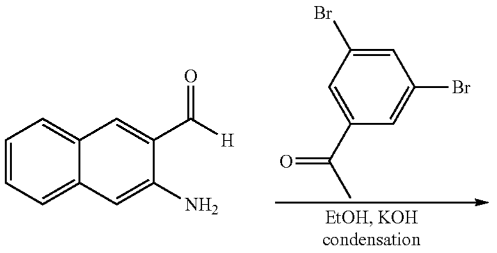

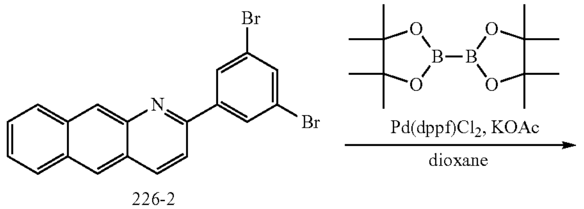

226-2

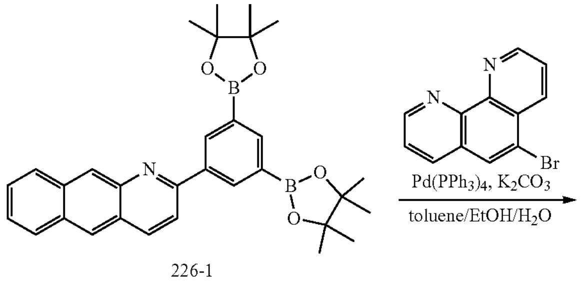

226-1

-continued

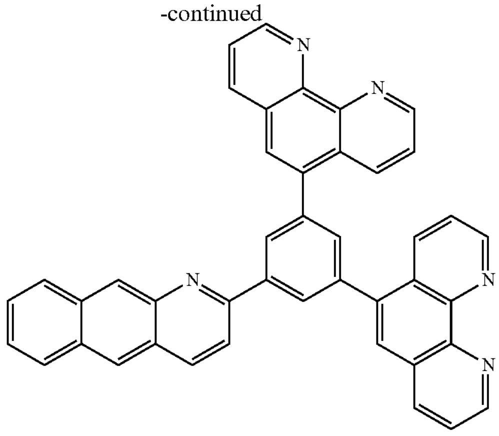

226

1) Preparation of Compound 226-2

A 1-(3,5-dibromophenyl)ethan-1-one compound (11.1 g, 40 mmol) and 2-amino-5-bromobenzaldehyde (6.8 g, 40 mmol) were introduced to EtOH (300 mL), 2 mL of a KOH solution saturated in EtOH was added dropwise thereto, and then the result was refluxed for 4 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 226-2 (11.5 g, 70%).

2) Preparation of Compound 226-1

After placing Compound 226-2 (13.5 g, 40 mmol), 4,4,4',4',5,5,5',5'-octamethyl-2,2'-bi(1,3,2-dioxaborolane) (25 g, 100 mmol), $Pd(dppf)_2Cl_2$ (1.4 g, 2 mmol) and KOAc (11.7 g, 120 mmol) in a reactor, 0.3 M dioxane was added thereto, and the result was refluxed for 12 hours. After the reaction was completed, the result was cooled to room temperature, and extracted with distilled water and EA. After the organic layer was dried with anhydrous $Na_2O_4$, the solvent was removed using a rotary evaporator, and the result was purified using column chromatography with dichloromethane and hexane as a developing solvent to obtain target Compound 226-1 (12.2 g, 80%).

3) Preparation of Compound 226

Compound 226-1 (4.1 g, 10 mmol) and 5-bromo-1,10-phenanthroline (3.3 g, 10 mmol) were dissolved in toluene (30 mL), then $Pd(PPh_3)_4$ (0.6 g, 0.5 mmol) and $K_2CO_3$ (2.8 g, 30 mmol) were added thereto, and the result was stirred for 10 minutes. After that, $H_2O$ (6 mL) and EtOH (6 mL) were added thereto, and the result was refluxed for 12 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 226 (5.0 g, 76%).

4) Preparation of Compound 203

Compound 226-2 (8 g, 20 mmol) and 9H-carbazole (3.4 g, 20 mmol) were dissolved in toluene (310 mL), then $Pd_2dba_3$ (0.2 g, 0.2 mmol), 2 M $(t\text{-}Bu)_3P$ (0.2 mL, 0.4 mmol) and NaOt-Bu (5.4 g, 60 mmol) were added thereto, and the result was refluxed for 12 hours. After the reaction was completed, the result was cooled to room temperature, and extracted with distilled water and Mc. After the organic layer was dried with anhydrous $Na_2SO_4$, the solvent was removed using a rotary evaporator, and the result was purified using column chromatography with ethyl acetate and hexane as a developing solvent to obtain target Compound 203 (10.4 g, 89%).

Target Compound E was synthesized in the same manner as the preparation of Compound 226 except that, in Preparation Example 5, Intermediate E of the following Table 5 was used instead of 5-bromo-1,10-phenanthroline.

TABLE 5

| Compound Number | Intermediate E | Target Compound E | Yield |
|---|---|---|---|
| 203 | 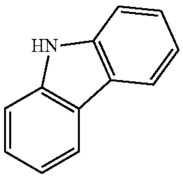 [SMILES: c1ccc2c(c1)[nH]c1ccccc12] | 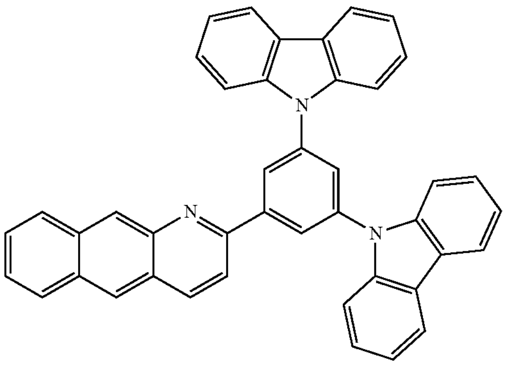 [SMILES: c1ccc2cc3nc(-c4cc(-n5c6ccccc6c6ccccc65)cc(-n5c6ccccc6c6ccccc65)c4)ccc3cc2c1] | 89% |
| 260 | 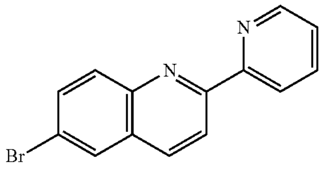 [SMILES: Brc1ccc2nc(-c3ccccn3)ccc2c1] | 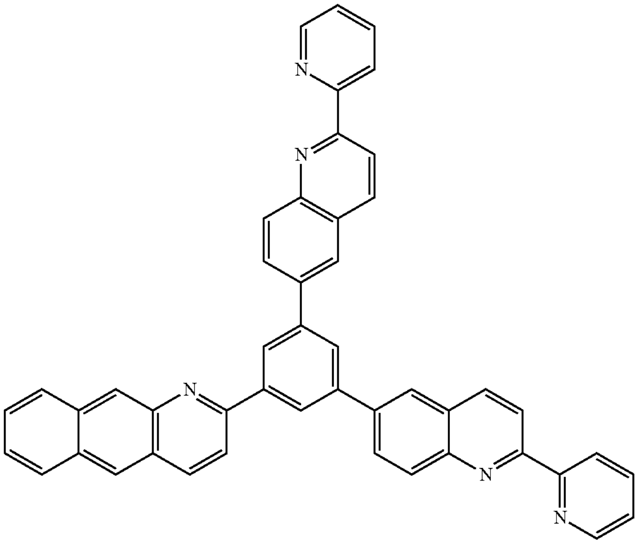 [SMILES: c1ccc(-c2ccc3cc(-c4cc(-c5ccc6nc(-c7ccccn7)ccc6c5)cc(-c5ccc6cc7ccccc7cc6n5)c4)ccc3n2)nc1] | 78% |

TABLE 5-continued

| Compound Number | Intermediate E | Target Compound E | Yield |
| --- | --- | --- | --- |
| 261 | 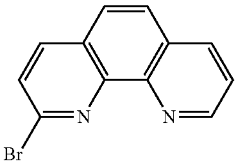 [SMILES: Brc1ccc2ccc3cccnc3c2n1] | 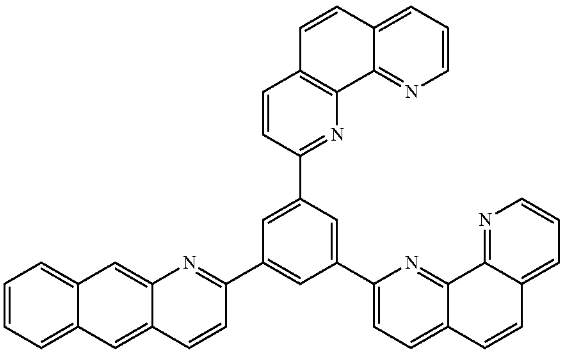 [SMILES: c1ccc2cc3nc(-c4cc(-c5ccc6ccc7cccnc7c6n5)cc(-c5ccc6ccc7cccnc7c6n5)c4)ccc3cc2c1] | 86% |

<Preparation Example 6> Preparation of Compound 195

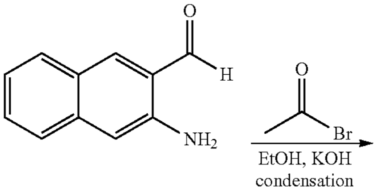

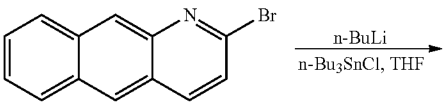

195-2

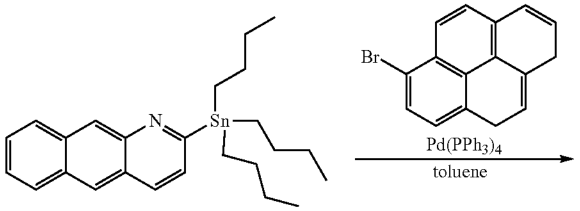

195-1

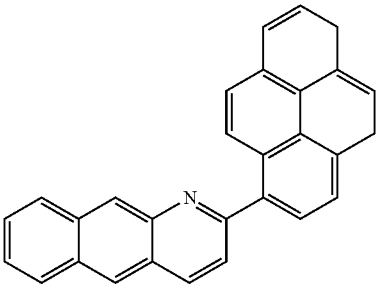

195

1) Preparation of Compound 195-2

A 3-amino-2-naphthaldehyde compound (16.8 g, 85 mmol) and acetyl bromide (10.5 g, 85 mmol) were introduced to EtOH (300 mL), 5 mL of a KOH solution saturated in EtOH was added dropwise thereto, and then the result was refluxed for 2 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 195-2 (19.7 g, 90%).

2) Preparation of Compound 195-1

Compound 195-2 (19.7 g, 74 mmol) was introduced to THF (200 mL), and the temperature was maintained at −78° C. At −78° C., 2.5 M n-BuLi (36 mL, 89 mmol) was slowly added dropwise thereto. After 30 minutes, n-$Bu_3SnCl$ (22 mL, 81.4 mmol) was added thereto, and the temperature was maintained for 2 hours. After that, the temperature was slowly raised to room temperature, and the result was quenched with an aqueous $NH_4Cl$ solution. The result was extracted with distilled water and Mc, and after the organic layer was dried with anhydrous $Na_2O_4$, the solvent was removed using a rotary evaporator to obtain target Compound 195-1 (33 g, 95%).

3) Preparation of Compound 195

Compound 195-1 (10 g, 20.5 mmol) and 6-bromo-1,9-dihydropyrene (5.8 g, 20.5 mmol) were dissolved in toluene (80 mL), then $Pd(PPh_3)_4$ (1.2 g, 1 mmol) was were added thereto, and the result was refluxed for 24 hours. After the reaction was completed, the result was cooled to room temperature, and extracted with distilled water and Mc. After the organic layer was dried with anhydrous $Na_2O_4$, the solvent was removed using a rotary evaporator, and the result was purified using column chromatography with ethyl acetate and hexane as a developing solvent to obtain target Compound 195 (5.5 g, 70%).

Target Compound F was synthesized in the same manner as the preparation of Compound 195 except that, in Preparation Example 6, Intermediate F of the following Table 6 was used instead of 6-bromo-1,9-dihydropyrene.

TABLE 6

| Compound Number | Intermediate F | Target Compound F | Yield |
| --- | --- | --- | --- |
| 207 | 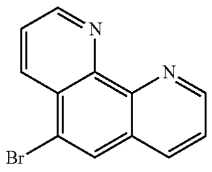 [SMILES: Brc1cc2cccnc2c2ncccc12] | 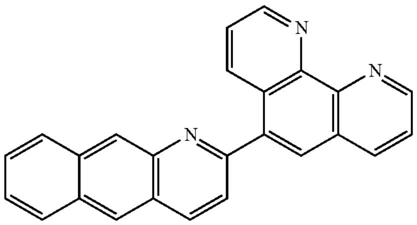 [SMILES: c1ccc2cc3nc(-c4cc5cccnc5c5ncccc45)ccc3cc2c1] | 66% |
| 213 | 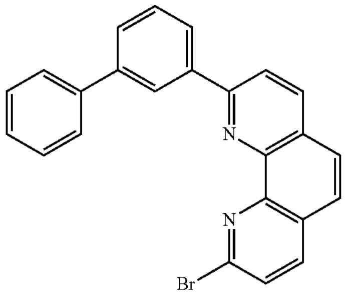 [SMILES: Brc1ccc2ccc3ccc(-c4cccc(-c5ccccc5)c4)nc3c2n1] | 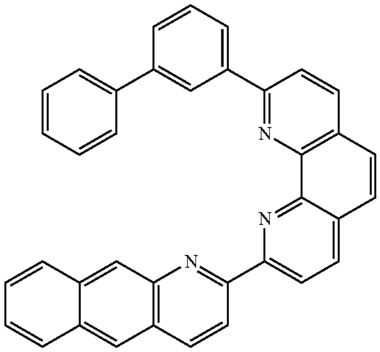 [SMILES: c1ccc(-c2cccc(-c3ccc4ccc5ccc(-c6ccc7cc8ccccc8cc7n6)nc5c4n3)c2)cc1] | 72% |
| 217 | 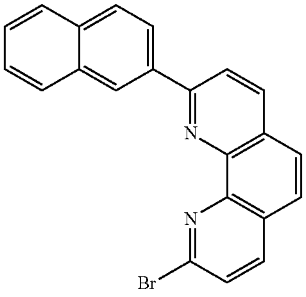 [SMILES: Brc1ccc2ccc3ccc(-c4ccc5ccccc5c4)nc3c2n1] | 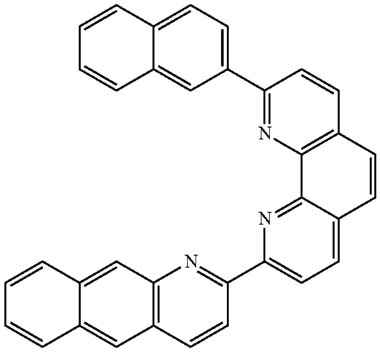 [SMILES: c1ccc2cc(-c3ccc4ccc5ccc(-c6ccc7cc8ccccc8cc7n6)nc5c4n3)ccc2c1] | 59% |

Compounds were prepared in the same manner as in the preparation examples, and the synthesis identification results are shown in Table 7 and Table 8. Table 7 shows measurement values of 1H NMR ($CDCl_3$, 200 MHz), and Table 8 shows measurement values of field desorption mass spectrometry (FD-MS).

TABLE 7

| Example | $^1$H NMR ($CDCl_3$, 400 MHz) |
| --- | --- |
| 3 | δ = 8.68 (s, 1H), 8.23 (s, 2H), 8.16-8.10 (m, 6H), 8.05 (d, 2H), 7.68-7.67 (m, 6H), 7.52-7.41 (m, 5H), 7.35 (d, 2H) |
| 41 | δ = 8.72 (s, 1H), 8.54 (d, 2H), 8.32 (d, 2H), 8.16 (td, 2H), 8.10 (dd, 2H), 7.67-7.63 (m, 7H), 7.52-7.51 (m, 8H), 7.41-7.35 (m, 4H) |
| 42 | δ = 8.54 (d, 2H), 8.26-8.21 (m, 4H), 8.16-8.10 (m, 4H), 7.67-7.52 (m, 16H), 7.51-7.41 (m, 6H) |
| 43 | δ = 8.55-8.54 (m, 6H), 8.16 (td, 2H), 8.10 (dd, 2H), 7.67-7.64 (m, 6H), 7.55-7.41 (m, 14H) |
| 44 | δ = 8.64 (t, 2H), 8.54 (d, 2H), 8.31 (s, 2H), 8.16-8.10 (m, 6H), 8.00 (d, 2H), 7.67-7.64 (m, 6H), 7.52-7.35 (m, 12H) |
| 45 | δ = 8.54 (t, 2H), 8.16-8.10 (m, 4H), 7.91 (q, 4H), 7.67-7.64 (m, 6H), 7.52-7.39 (m, 16H) |
| 46 | δ = 9.04 (d, 2H), 8.54 (t, 2H), 8.30 (d, 4H), 8.16 (dd, 2H), 7.82 (t, 1H), 7.67-7.64 (m, 6H), 7.52-7.41 (m, 10H) |

TABLE 7-continued

| Example | $^1$H NMR ($CDCl_3$, 400 MHz) |
| --- | --- |
| 47 | δ = 9.04 (d, 4H), 8.54 (d, 2H), 8.30 (d, 4H), 8.16 (dd, 2H), 7.82 (t, 2H), 7.67-7.64 (m, 6H), 7.52-7.41 (m, 10H) |
| 57 | δ = 8.86 (d, 2H), 8.68 (s, 1H), 8.23 (s, 2H), 8.16-8.10 (m, 6H), 8.05 (d, 2H), 7.68-7.67 (m, 6H), 7.35-7.31 (m, 3H) |
| 62 | δ = 8.83 (d, 1H), 8.74 (s, 3H), 8.38 (d, 1H), 8.16-8.05 (m, 8H), 7.81 (d, 1H), 7.68-7.67 (m, 6H), 7.58 (t, 1H), 7.35 (d, 3H) |
| 63 | δ = 8.74 (s, 3H), 8.30 (d, 2H), 8.16-8.05 (m, 11H), 7.81 (d, 1H), 7.68-7.67 (m, 6H), 7.35 (d, 4H) |
| 88 | δ = 9.66 (s, 2H), 8.59 (d, 1H), 8.30 (d, 4H), 8.16 (td, 4H), 8.05 (s, 2H), 7.85 (t, 1H), 7.68-7.67 (m, 6H), 7.36-7.32 (dd, 2H) |
| 89 | δ = 9.24 (s, 1H), 9.15 (s, 2H), 8.70 (d, 1H), 8.30 (d, 4H), 8.16 (td, 4H), 8.05 (s, 2H), 7.85 (t, 1H), 7.68-7.67 (m, 6H) |
| 90 | δ = 9.15 (s, 2H), 8.75 (d, 2H), 8.30 (d, 4H), 8.16 (td, 4H), 8.05-7.99 (m, 4H), 7.68-7.67 (m, 6H) |
| 91 | δ = 9.15 (s, 2H), 9.08 (d, 2H), 8.30 (d, 4H), 8.16 (td, 4H), 8.05 (s, 2H), 7.68-7.67 (m, 7H) |
| 92 | δ = 9.15 (s, 2H), 8.83 (d, 1H), 8.38-8.29 (m, 5H), 8.21-8.16 (m, 5H), 8.05-8.02 (m, 3H), 7.68-7.58 (m, 8H) |
| 93 | δ = 9.15 (s, 2H), 8.57 (s, 1H), 8.31-8.16 (m, 9H), 8.06-7.98 (m, 4H), 7.68-7.60 (m, 7H) |

TABLE 7-continued

| Example | $^1$H NMR ($CDCl_3$, 400 MHz) |
|---|---|
| 94 | δ = 9.15 (s, 2H), 8.83 (d, 1H), 8.38-8.27 (m, 6H), 8.16-8.03 (m, 8H), 7.68-7.58 (m, 7H) |
| 95 | δ = 9.66 (s, 2H), 8.83 (d, 1H), 8.44 (d, 1H), 8.38 (d, 1H), 8.30 (m, 4H), 8.16 (q, 4H), 8.06-8.05 (m, 3H), 7.81 (d, 1H), 7.68-7.67 (m, 6H), 7.58 (t, 1H), 7.41 (d, 1H) |
| 138 | δ = 8.68 (s, 1H), 8.23 (s, 3H), 8.16-8.05 (m, 8H), 7.79 (d, 4H), 7.68-7.67 (m, 6H), 7.51 (t, 4H), 7.41-7.35 (m, 4H) |
| 142 | δ = 8.68 (s, 1H), 8.28 (d, 2H), 8.23 (s, 3H), 8.16-8.05 (m, 8H), 7.79 (d, 2H), 7.68-7.67 (m, 6H), 7.51 (t, 4H), 7.41-7.35 (m, 4H) |
| 147 | δ = 8.68 (s, 1H), 8.28 (d, 4H), 8.23 (s, 2H), 8.16-8.05 (m, 8H), 7.68-7.67 (m, 6H), 7.51 (t, 4H), 7.41-7.35 (m, 4H) |
| 148 | δ = 8.68 (s, 1H), 8.28 (d, 2H), 8.23 (s, 2H), 8.16-8.05 (m, 8H), 7.85 (d, 2H), 7.68-7.67 (m, 6H), 7.51 (t, 4H), 7.52-7.35 (m, 10H), 7.25 (d, 2H) |
| 164 | δ = 8.30-8.28 (m, 5H), 8.26-8.10 (m, 5H), 8.05 (s, 1H), 7.68-7.67 (m, 3H), 7.60 (t, 1H), 7.51-7.41 (m, 7H) |
| 169 | δ = 8.30-8.28 (m, 5H), 8.26-8.10 (m, 5H), 8.05 (s, 1H), 7.85 (d, 2H), 7.68-7.67 (m, 3H), 7.60 (t, 1H), 7.51-7.41 (m, 6H), 7.41-7.35 (m, 3H), 7.25 (d, 2H) |
| 192 | δ = 8.26 (td, 1H), 8.21-8.05 (m, 7H), 7.80 (q, 2H), 7.71-7.54 (m, 9H), 7.35 (d, 1H) |
| 193 | δ = 9.15 (s, 1H), 8.93 (d, 2H), 8.26-8.04 (m, 10H), 7.68-7.54 (m, 5H), 7.35 (d, 1H) |
| 195 | δ = 8.55 (d, 1H), 8.21-8.05 (m, 7H), 7.88-7.82 (m, 2H), 7.71-7.67 (m, 7H), 7.35 (d, 1H) |
| 203 | δ = 9.15 (s, 2H), 8.52 (d, 8H), 8.17-8.04 (m, 10H), 7.85 (t, 8H), 7.72-7.67 (m, 4H), 7.35 (d, 1H) |
| 207 | δ = 8.83 (d, 2H), 8.38 (d, 2H), 8.16-8.05 (m, 5H), 7.68-7.67 (m, 3H), 7.58 (t, 2H), 7.35 (d, 1H) |
| 210 | δ = 8.30-8.05 (m, 12H), 7.68-7.47 (m, 12H), 7.35 (d, 3H) |
| 213 | δ = 8.26-8.05 (m, 11H), 7.81 (d, 1H), 8.38 (d, 2H), 7.68-7.51 (m, 9H), 7.41-7.35 (m, 2H) |
| 217 | δ = 8.85 (s, 1H), 8.38-8.29 (m, 5H), 8.16-8.00 (m, 8H), 7.81 (d, 1H), 7.68-7.67 (m, 3H), 7.59 (dd, 2H), 7.35 (d, 1H) |
| 226 | δ = 8.83 (d, 4H), 8.38 (d, 4H), 8.17-8.05 (m, 6H), 7.72-7.58 (m, 10H), 7.35 (d, 1H) |
| 228 | δ = 8.83 (d, 1H), 8.72 (s, 1H), 8.83 (d, 1H), 8.32 (d, 2H), 8.16-8.05 (m, 6H), 7.61 (d, 1H), 7.68-7.58 (m, 5H), 7.35 (d, 2H) |
| 230 | δ = 8.72 (s, 1H), 8.32 (d, 2H), 8.30 (d, 2H), 8.16-8.05 (m, 7H), 7.81 (d, 1H), 7.68-7.63 (m, 4H), 7.54-7.47 (m, 3H), 7.35 (d, 3H) |
| 247 | δ = 9.30 (d, 1H), 8.53 (d, 1H), 8.31-8.05 (m, 10H), 7.90 (s, 1H), 7.70-7.54 (m, 6H), 7.35d (, 1H), 7.14 (t, 1H) |
| 260 | δ = 9.30 (d, 2H), 8.53 (d, 2H), 8.31 (d, 2H), 8.29-8.05 (m, 10H), 8.04 (d, 2H), 7.90 (s, 1H), 7.70-7.67 (m, 6H), 7.35 (d, 1H), 7.14 (t, 2H) |
| 261 | δ = 8.83 (d, 2H), 8.74 (s, 3H), 8.38 (d, 2H), 8.16-8.05 (m, 8H), 7.81 (d, 2H), 7.68-7.67 (m, 3H), 7.58 (t, 2H), 7.35 (d, 3H) |

TABLE 8

| Compound | FD-Mass | Compound | FD-Mass |
|---|---|---|---|
| 1 | m/z = 432.51 (C32H20N2 = 432.16) | 2 | m/z = 508.61 (C38H24N2 = 508.19) |
| 3 | m/z = 508.61 (C38H24N2 = 508.19) | 4 | m/z = 482.57 (C36H22N2 = 482.18) |
| 5 | m/z = 482.57 (C36H22N2 = 482.18) | 6 | m/z = 482.57 (C36H22N2 = 482.18) |
| 7 | m/z = 520.62 (C39H24N2 = 520.19) | 8 | m/z = 532.63 (C40H24N2 = 532.19) |
| 9 | m/z = 532.63 (C40H24N2 = 532.19) | 10 | m/z = 584.71 (C44H28N2 = 584.23) |
| 11 | m/z = 585.69 (C43H27N3 = 585.22) | 12 | m/z = 556.65 (C42H24N2 = 556.19) |
| 13 | m/z = 556.65 (C42H24N2 = 556.19) | 14 | m/z = 556.65 (C42H24N2 = 556.19) |
| 15 | m/z = 508.61 (C38H24N2 = 508.19) | 16 | m/z = 532.63 (C40H24N2 = 532.19) |
| 17 | m/z = 533.62 (C39H23N3 = 533.19) | 18 | m/z = 433.50 (C31H19N3 = 433.16) |

TABLE 8-continued

| Compound | FD-Mass | Compound | FD-Mass |
|---|---|---|---|
| 19 | m/z = 434.49 (C30H18N4 = 434.15) | 20 | m/z = 483.56 (C35H21N3 = 483.17) |
| 21 | m/z = 483.56 (C35H21N3 = 483.17) | 22 | m/z = 483.56 (C35H21N3 = 483.17) |
| 23 | m/z = 510.59 (C36H22N4 = 510.18) | 24 | m/z = 558.67 (C42H26N2 = 558.21) |
| 25 | m/z = 559.66 (C41H25N3 = 559.20) | 26 | m/z = 560.65 (C40H24N4 = 560.20) |
| 27 | m/z = 559.66 (C41H25N3 = 559.20) | 28 | m/z = 608.73 (C46H28N2 = 608.23) |
| 29 | m/z = 609.72 (C45H27N3 = 609.22) | 30 | m/z = 610.70 (C44H26N4 = 610.22) |
| 31 | m/z = 610.70 (C44H26N4 = 610.22) | 32 | m/z = 608.73 (C46H28N2 = 608.23) |
| 33 | m/z = 609.72 (C45H27N3 = 609.22) | 34 | m/z = 658.79 (C50H30N2 = 658.24) |
| 35 | m/z = 659.77 (C49H29N3 = 659.24) | 36 | m/z = 534.61 (C38H22N4 = 534.18) |
| 37 | m/z = 558.67 (C42H26N2 = 558.21) | 38 | m/z = 559.66 (C41H25N3 = 559.20) |
| 39 | m/z = 608.73 (C46H28N2 = 608.23) | 40 | m/z = 708.85 (C54H32N2 = 708.26) |
| 41 | m/z = 584.71 (C44H28N2 = 584.23) | 42 | m/z = 660.80 (C50H32N2 = 660.26) |
| 43 | m/z = 634.77 (C48H30N2 = 634.24) | 44 | m/z = 684.82 (C52H32N2 = 684.26) |
| 45 | m/z = 684.82 (C52H32N2 = 684.26) | 46 | m/z = 585.69 (C43H27N3 = 585.22) |
| 47 | m/z = 662.78 (C48H30N4 = 662.25) | 48 | m/z = 711.85 (C53H33N3 = 711.27) |
| 49 | m/z = 584.71 (C44H28N2 = 584.23) | 50 | m/z = 660.80 (C50H32N2 = 660.26) |
| 51 | m/z = 634.77 (C48H30N2 = 634.24) | 52 | m/z = 684.82 (C52H32N2 = 684.26) |
| 53 | m/z = 784.94 (C60H36N2 = 784.29) | 54 | m/z = 509.60 (C37H23N3 = 509.19) |
| 55 | m/z = 509.60 (C37H23N3 = 509.19) | 56 | m/z = 509.60 (C37H23N3 = 509.19) |
| 57 | m/z = 510.59 (C36H22N4 = 510.18) | 58 | m/z = 509.60 (C37H23N3 = 509.19) |
| 59 | m/z = 559.66 (C41H25N3 = 559.20) | 60 | m/z = 559.66 (C41H25N3 = 559.20) |
| 61 | m/z = 559.66 (C41H25N3 = 559.20) | 62 | m/z = 610.70 (C44H26N4 = 610.22) |
| 63 | m/z = 686.80 (C50H30N4 = 686.25) | 64 | m/z = 687.79 (C49H29N5 = 687.24) |
| 65 | m/z = 624.73 (C45H28N4 = 624.23) | 66 | m/z = 700.83 (C51H32N4 = 700.26) |
| 67 | m/z = 762.90 (C56H34N4 = 762.28) | 68 | m/z = 533.62 (C39H23N3 = 533.19) |
| 69 | m/z = 608.73 (C46H28N2 = 608.23) | 70 | m/z = 684.82 (C52H32N2 = 684.26) |
| 71 | m/z = 609.72 (C45H27N3 = 609.22) | 72 | m/z = 735.87 (C55H33N3 = 735.27) |
| 73 | m/z = 785.93 (C59H35N3 = 785.28) | 74 | m/z = 685.81 (C51H31N3 = 685.25) |
| 75 | m/z = 735.87 (C55H33N3 = 735.27) | 76 | m/z = 685.81 (C51H31N3 = 685.25) |
| 77 | m/z = 786.92 (C58H34N4 = 786.28) | 78 | m/z = 863.01 (C64H38N4 = 862.31) |
| 79 | m/z = 685.81 (C51H31N3 = 685.25) | 80 | m/z = 735.87 (C55H33N3 = 735.27) |
| 81 | m/z = 635.75 (C47H29N3 = 635.24) | 82 | m/z = 685.81 (C51H31N3 = 685.25) |
| 83 | m/z = 635.75 (C47H29N3 = 635.24) | 84 | m/z = 686.80 (C50H30N4 = 686.25) |
| 85 | m/z = 838.99 (C62H38N4 = 838.31) | 86 | m/z = 762.90 (C56H34N4 = 762.28) |
| 87 | m/z = 762.90 (C56H34N4 = 762.28) | 88 | m/z = 510.59 (C36H22N4 = 510.18) |
| 89 | m/z = 510.59 (C36H22N4 = 510.18) | 90 | m/z = 510.59 (C36H22N4 = 510.18) |
| 91 | m/z = 511.57 (C35H21N5 = 511.18) | 92 | m/z = 560.65 (C40H24N4 = 560.20) |
| 93 | m/z = 560.65 (C40H24N4 = 560.20) | 94 | m/z = 560.65 (C40H24N4 = 560.20) |
| 95 | m/z = 611.69 (C43H25N5 = 611.21) | 96 | m/z = 687.79 (C49H29N5 = 687.24) |

TABLE 8-continued

| Compound | FD-Mass | Compound | FD-Mass |
|---|---|---|---|
| 97 | m/z = 688.78 (C48H28N6 = 688.24) | 98 | m/z = 625.72 (C44H27N5 = 625.23) |
| 99 | m/z = 701.81 (C50H31N5 = 701.26) | 100 | m/z = 763.88 (C55H33N5 = 763.27) |
| 101 | m/z = 609.72 (C45H27N3 = 609.22) | 102 | m/z = 686.80 (C50H30N4 = 686.25) |
| 103 | m/z = 685.81 (C51H31N3 = 685.25) | 104 | m/z = 610.70 (C44H26N4 = 610.22) |
| 105 | m/z = 736.86 (C54H32N4 = 736.26) | 106 | m/z = 786.92 (C58H34N4 = 786.28) |
| 107 | m/z = 686.80 (C50H30N4 = 686.25) | 108 | m/z = 736.86 (C54H32N4 = 736.26) |
| 109 | m/z = 737.85 (C53H31N5 = 737.26) | 110 | m/z = 686.80 (C50H30N4 = 686.25) |
| 111 | m/z = 687.79 (C49H29N5 = 687.24) | 112 | m/z = 787.91 (C57H33N5 = 787.27) |
| 113 | m/z = 864.00 (C63H37N5 = 863.30) | 114 | m/z = 864.99 (C62H36N6 = 864.30) |
| 115 | m/z = 686.80 (C50H30N4 = 686.25) | 116 | m/z = 736.86 (C54H32N4 = 736.26) |
| 117 | m/z = 636.74 (C46H28N4 = 636.23) | 118 | m/z = 686.80 (C50H30N4 = 686.25) |
| 119 | m/z = 636.74 (C46H28N4 = 636.23) | 120 | m/z = 637.73 (C45H27N5 = 637.23) |
| 121 | m/z = 687.79 (C49H29N5 = 687.24) | 122 | m/z = 839.98 (C61H37N5 = 839.30) |
| 123 | m/z = 839.98 (C61H37N5 = 839.30) | 124 | m/z = 763.88 (C55H33N5 = 763.27) |
| 125 | m/z = 764.87 (C54H32N6 = 764.27) | 126 | m/z = 763.88 (C55H33N5 = 763.27) |
| 127 | m/z = 764.87 (C54H32N6 = 764.27) | 128 | m/z = 635.75 (C47H29N3 = 635.24) |
| 129 | m/z = 685.81 (C51H31N3 = 685.25) | 130 | m/z = 712.84 (C52H32N4 = 712.26) |
| 131 | m/z = 585.69 (C43H27N3 = 585.22) | 132 | m/z = 662.78 (C48H30N4 = 662.25) |
| 133 | m/z = 635.75 (C47H29N3 = 635.24) | 134 | m/z = 658.79 (C50H30N4 = 686.25) |
| 135 | m/z = 686.80 (C50H30N4 = 686.25) | 136 | m/z = 686.80 (C50H30N4 = 686.25) |
| 137 | m/z = 786.92 (C58H34N4 = 786.28) | 138 | m/z = 662.78 (C48H30N4 = 662.25) |
| 139 | m/z = 738.87 (C54H34N4 = 738.28) | 140 | m/z = 814.97 (C60H38N4 = 814.31) |
| 141 | m/z = 762.90 (C56H34N4 = 762.28) | 142 | m/z = 662.78 (C48H30N4 = 662.25) |
| 143 | m/z = 738.87 (C54H34N4 = 738.28) | 144 | m/z = 738.87 (C54H34N4 = 738.28) |
| 145 | m/z = 814.97 (C60H38N4 = 814.31) | 146 | m/z = 762.90 (C56H34N4 = 762.28) |
| 147 | m/z = 663.77 (C47H29N5 = 663.24) | 148 | m/z = 739.86 (C53H33N5 = 739.27) |
| 149 | m/z = 815.96 (C59H37N5 = 815.30) | 150 | m/z = 763.88 (C55H33N5 = 763.27) |
| 151 | m/z = 663.77 (C47H29N5 = 663.24) | 152 | m/z = 739.86 (C53H33N5 = 739.27) |
| 153 | m/z = 763.88 (C55H33N5 = 763.27) | 154 | m/z = 663.77 (C47H29N5 = 663.24) |
| 155 | m/z = 739.86 (C53H33N5 = 739.27) | 156 | m/z = 739.86 (C53H33N5 = 739.27) |
| 157 | m/z = 815.96 (C59H37N5 = 815.30) | 158 | m/z = 763.88 (C55H33N5 = 763.27) |
| 159 | m/z = 664.75 (C46H28N6 = 664.24) | 160 | m/z = 740.85 (C52H32N6 = 740.27) |
| 161 | m/z = 816.95 (C58H36N6 = 816.30) | 162 | m/z = 764.87 (C54H32N6 = 764.27) |
| 163 | m/z = 486.57 (C34H22N4 = 486.18) | 164 | m/z = 486.57 (C34H22N4 = 486.18) |
| 165 | m/z = 485.58 (C41H25N3 = 485.19) | 166 | m/z = 485.58 (C35H23N3 = 485.19) |
| 167 | m/z = 485.58 (C35H23N3 = 485.19) | 168 | m/z = 485.58 (C35H23N3 = 485.19) |
| 169 | m/z = 562.66 (C40H26N4 = 562.22) | 170 | m/z = 638.76 (C46H30N4 = 638.25) |
| 171 | m/z = 561.67 (C41H27N3 = 561.22) | 172 | m/z = 561.67 (C41H27N3 = 561.22) |
| 173 | m/z = 816.95 (C58H36N6 = 816.30) | 174 | m/z = 764.87 (C54H32N6 = 764.27) |

TABLE 8-continued

| Compound | FD-Mass | Compound | FD-Mass |
|---|---|---|---|
| 175 | m/z = 486.57 (C34H22N4 = 486.18) | 176 | m/z = 486.57 (C34H22N4 = 486.18) |
| 177 | m/z = 485.58 (C35H23N3 = 485.19) | 178 | m/z = 485.58 (C35H23N3 = 485.19) |
| 179 | m/z = 485.58 (C35H23N3 = 485.19) | 180 | m/z = 485.58 (C35H23N3 = 485.19) |
| 181 | m/z = 562.66 (C40H26N4 = 562.22) | 182 | m/z = 562.66 (C40H26N4 = 562.22) |
| 183 | m/z = 638.76 (C46H30N4 = 638.25) | 184 | m/z = 638.76 (C46H30N4 = 638.25) |
| 185 | m/z = 561.67 (C41H27N3 = 561.22) | 186 | m/z = 561.67 (C41H27N3 = 561.22) |
| 187 | m/z = 561.67 (C41H27N3 = 561.22) | 188 | m/z = 561.67 (C41H27N3 = 561.22) |
| 189 | m/z = 561.67 (C41H27N3 = 561.22) | 190 | m/z = 561.67 (C41H27N3 = 561.22) |
| 191 | m/z = 431.53 (C33H21N = 431.17) | 192 | m/z = 455.55 (C35H21N = 455.17) |
| 193 | m/z = 481.59 (C37H23N = 481.18) | 194 | m/z = 505.61 (C39H23N = 505.18) |
| 195 | m/z = 379.45 (C29H17N = 379.14) | 196 | m/z = 457.56 (C35H23N = 457.18) |
| 197 | m/z = 507.62 (C39H25N = 507.20) | 198 | m/z = 557.68 (C43H27N = 557.21) |
| 199 | m/z = 557.68 (C43H27N = 557.21) | 200 | m/z = 557.68 (C43H27N = 557.21) |
| 201 | m/z = 607.74 (C47H29N = 607.23) | 202 | m/z = 655.78 (C51H29N = 655.23) |
| 203 | m/z = 665.22 (C49H35N3 = 665.28) | 204 | m/z = 659.81 (C51H33N = 659.26) |
| 205 | m/z = 659.81 (C51H33N = 659.26) | 206 | m/z = 589.20 (C43H31N3 = 589.25) |
| 207 | m/z = 357.41 (C25H15N3 = 357.13) | 208 | m/z = 433.50 (C31H19N3 = 433.16) |
| 209 | m/z = 509.60 (C37H23N3 = 509.19) | 210 | m/z = 585.69 (C43H27N3 = 585.22) |
| 211 | m/z = 511.57 (C35H21N5 = 511.18) | 212 | m/z = 407.47 (C29H17N3 = 407.14) |
| 213 | m/z = 509.60 (C37H23N3 = 509.19) | 214 | m/z = 610.70 (C44H26N4 = 610.22) |
| 215 | m/z = 559.66 (C41H25N3 = 559.20) | 216 | m/z = 701.81 (C50H31N5 = 701.26) |
| 217 | m/z = 483.56 (C35H21N3 = 483.17) | 218 | m/z = 510.59 (C36H22N4 = 510.18) |
| 219 | m/z = 482.57 (C36H22N2 = 482.18) | 220 | m/z = 482.57 (C36H22N2 = 482.18) |
| 221 | m/z = 609.72 (C45H27N3 = 609.22) | 222 | m/z = 511.57 (C35H21N5 = 511.18) |
| 223 | m/z = 587.67 (C41H25N5 = 587.21) | 224 | m/z = 461.56 (C33H23N3 = 461.19) |
| 225 | m/z = 685.81 (C51H31N3 = 685.25) | 226 | m/z = 611.69 (C43H25N5 = 611.21) |
| 227 | m/z = 667.80 (C47H33N5 = 667.27) | 228 | m/z = 433.50 (C31H19N3 = 433.16) |
| 229 | m/z = 447.53 (C32H21N3 = 447.17) | 230 | m/z = 509.60 (C37H23N3 = 509.19) |
| 231 | m/z = 434.49 (C30H18N4 = 434.15) | 232 | m/z = 448.52 (C31H20N4 = 448.17) |
| 233 | m/z = 510.59 (C36H22N4 = 510.18) | 234 | m/z = 511.57 (C35H21N5 = 511.18) |
| 235 | m/z = 637.73 (C45H27N5 = 637.23) | 236 | m/z = 687.79 (C49H29N5 = 687.24) |
| 237 | m/z = 587.67 (C41H25N5 = 587.21) | 238 | m/z = 483.56 (C35H21N3 = 483.17) |
| 239 | m/z = 559.66 (C41H25N3 = 559.20) | 240 | m/z = 560.65 (C40H24N4 = 560.20) |
| 241 | m/z = 484.55 (C34H20N4 = 484.17) | 242 | m/z = 560.65 (C40H24N4 = 560.20) |
| 243 | m/z = 561.63 (C39H23N5 = 561.20) | 244 | m/z = 560.65 (C40H24N4 = 558.21) |
| 245 | m/z = 636.74 (C46H28N4 = 636.23) | 246 | m/z = 637.73 (C45H27N5 = 637.23) |
| 247 | m/z = 459.54 (C33H21N3 = 459.17) | 248 | m/z = 612.72 (C44H28N4 = 612.23) |
| 249 | m/z = 612.72 (C44H28N4 = 612.23) | 250 | m/z = 712.84 (C52H32N4 = 712.26) |
| 251 | m/z = 582.69 (C44H26N2 = 582.21) | 252 | m/z = 585.69 (C43H27N3 = 585.22) |

TABLE 8-continued

| Compound | FD-Mass | Compound | FD-Mass |
|---|---|---|---|
| 253 | m/z = 585.69 (C43H27N3 = 585.22) | 254 | m/z = 460.53 (C32H20N4 = 460.17) |
| 255 | m/z = 613.71 (C43H27N5 = 613.23) | 256 | m/z = 613.71 (C43H27N5 = 613.23) |
| 257 | m/z = 583.68 (C43H25N3 = 583.20) | 258 | m/z = 586.68 (C42H26N4 = 586.22) |
| 259 | m/z = 509.60 (C37H23N3 = 509.19) | 260 | m/z = 663.77 (C47H29N5 = 663.24) |
| 261 | m/z = 612.68 (C42H24N6 = 612.21) | 262 | m/z = 656.77 (C50H28N2 = 656.23) |
| 263 | m/z = 708.85 (C54H32N2 = 708.26) | 264 | m/z = 662.78 (C48H30N4 = 662.25) |
| 265 | m/z = 664.75 (C46H28N6 = 664.24) | 266 | m/z = 510.59 (C36H22N4 = 510.18) |
| 267 | m/z = 455.55 (C35H21N = 455.17) | 268 | m/z = 431.53 (C33H21N = 431.17) |
| 269 | m/z = 431.53 (C33H21N = 431.17) | 270 | m/z = 431.53 (C33H21N = 431.17) |
| 271 | m/z = 507.62 (C39H25N = 507.20) | 272 | m/z = 509.60 (C37H23N3 = 509.19) |
| 273 | m/z = 661.79 (C49H31N3 = 661.25) | 274 | m/z = 587.67 (C41H25N5 = 587.21) |
| 275 | m/z = 559.66 (C41H25N3 = 559.20) | 276 | m/z = 558.67 (C42H26N2 = 558.21) |
| 277 | m/z = 685.81 (C51H31N3 = 685.25) | 278 | m/z = 537.65 (C39H27N3 = 537.22) |
| 279 | m/z = 687.79 (C49H29N5 = 687.24) | 280 | m/z = 509.60 (C37H23N3 = 509.19) |
| 281 | m/z = 510.59 (C36H22N4 = 510.18) | 282 | m/z = 559.66 (C41H25N3 = 559.20) |
| 283 | m/z = 599.72 (C44H29N3 = 599.24) | 284 | m/z = 561.67 (C41H27N3 = 561.22) |
| 285 | m/z = 561.67 (C41H27N3 = 561.22) | 286 | m/z = 562.66 (C40H26N4 = 562.22) |
| 287 | m/z = 561.67 (C41H27N3 = 561.22) | 288 | m/z = 561.67 (C41H27N3 = 561.22) |
| 289 | m/z = 562.66 (C40H26N4 = 562.22) | 290 | m/z = 523.63 (C38H25N3 = 523.20) |
| 291 | m/z = 675.82 (C50H33N3 = 675.27) | 292 | m/z = 583.18 (C45H29N = 583.23) |
| 293 | m/z = 583.18 (C45H29N = 583.23) | 294 | m/z = 587.13 (C43H25NO2 = 587.19) |
| 295 | m/z = 619.08 (C43H25NS2 = 619.14) | 296 | m/z = 652.18 (C46H28N4O = 652.23) |
| 297 | m/z = 668.15 (C46H28N4S = 668.20) | 298 | m/z = 651.17 (C46H29N5 = 651.24) |
| 299 | m/z = 652.18 (C46H28N4O = 652.23) | 300 | m/z = 728.20 (C52H32N4O = 728.26) |
| 301 | m/z = 744.17 (C52H32N4S = 744.23) | 302 | m/z = 727.21 (C52H33N5 = 727.27) |
| 303 | m/z = 728.21 (C52H32N4O = 728.26) | 304 | m/z = 727.21 (C53H33N3O = 727.26) |
| 305 | m/z = 743.19 (C53H33N3S = 743.24) | 306 | m/z = 726.23 (C53H34N4 = 726.28) |
| 307 | m/z = 727.21 (C53H33N3O = 727.26) | 308 | m/z = 651.18 (C47H29N3O = 651.23) |
| 309 | m/z = 667.15 (C47H29N3S = 667.21) | 310 | m/z = 650.20 (C47H30N4 = 650.25) |
| 311 | m/z = 651.17 (C47H29N3O = 651.23) | | |

EXPERIMENTAL EXAMPLE

Experimental Example 1

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition.

On the ITO transparent electrode (anode), organic materials were formed in a two-stack white organic light emitting diode (WOLED) structure. As for the first stack, a hole transfer layer was formed first by thermal vacuum depositing TAPC to a thickness of 300 Å. After forming the hole transfer layer, a light emitting layer was thermal vacuum deposited thereon as follows. The light emitting layer was deposited to 300 Å by doping FIrpic in 8% as a blue phosphorescent dopant to TCzl, a host. An electron transfer layer was formed to 400 Å using TmPyPB, and then a charge generation layer was formed to 100 Å by doping $Cs_2CO_3$ in 20% to a compound described in the following Table 9.

As for the second stack, a hole injection layer was formed first by thermal vacuum depositing $MoO_3$ to a thickness of 50 Å. A hole transfer layer, a common layer, was formed by doping $MoO_3$ to TAPC in 20% and forming to 100 Å, and then depositing TAPC to 300 Å. After depositing a light emitting layer to 300 Å thereon by doping $Ir(ppy)_3$, a green phosphorescent dopant, in 8% to TCzl, a host, an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED device were vacuum sublimation purified under $10^{-6}$ torr to $10^{-8}$ torr by each material to be used in the OLED manufacture.

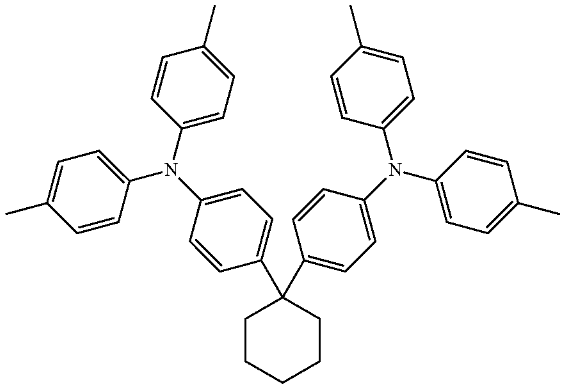

TAPC

-continued
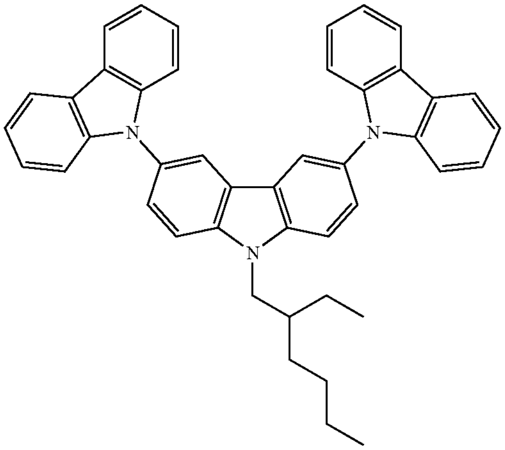
TCz1
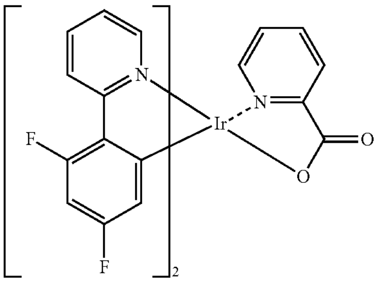
FIrpic
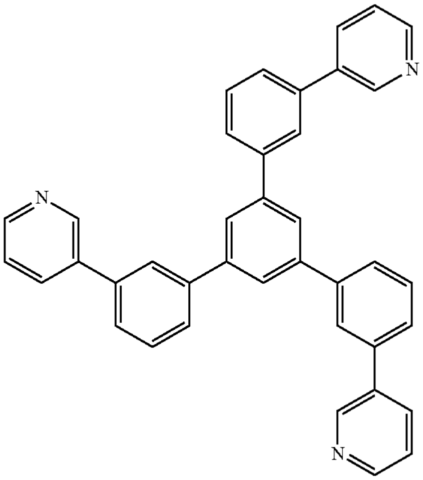
TmPyPB
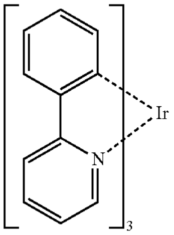
Ir(ppy)3
-continued
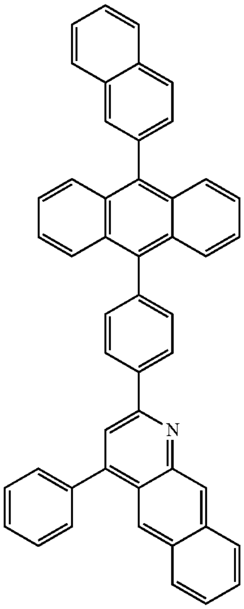
N-ADN2
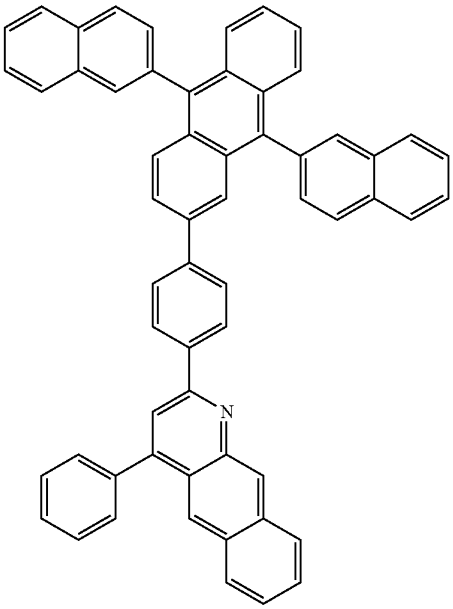
N-ADN5

-continued

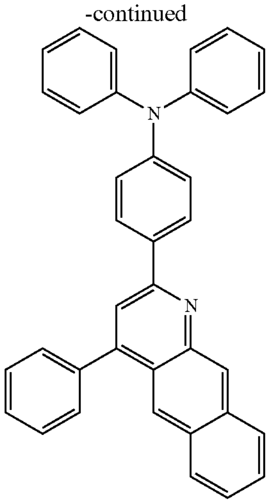

N-AN9

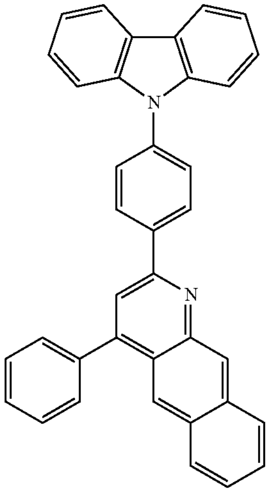

N-AN11

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, T95 when standard luminance was 3,500 cd/$m^2$ was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 9.

TABLE 9

| | Compound | Driving Voltage (V) | Light Emission Efficiency (cd/A) | CIE (x, y) | Lifespan (T95) |
|---|---|---|---|---|---|
| Example 1 | 3 | 7.89 | 59.32 | (0.221, 0.434) | 28 |
| Example 2 | 5 | 7.96 | 59.45 | (0.220, 0.430) | 27 |

TABLE 9-continued

| | Compound | Driving Voltage (V) | Light Emission Efficiency (cd/A) | CIE (x, y) | Lifespan (T95) |
|---|---|---|---|---|---|
| Example 3 | 7 | 7.82 | 58.98 | (0.219, 0.422) | 28 |
| Example 4 | 41 | 7.88 | 61.78 | (0.221, 0.427) | 29 |
| Example 5 | 42 | 7.93 | 58.66 | (0.225, 0.424) | 25 |
| Example 6 | 43 | 7.88 | 59.74 | (0.219, 0.425) | 24 |
| Example 7 | 44 | 7.79 | 59.42 | (0.222, 0.430) | 27 |
| Example 8 | 45 | 7.90 | 60.17 | (0.221, 0.415) | 26 |
| Example 9 | 46 | 7.91 | 59.87 | (0.228, 0.430) | 28 |
| Example 10 | 47 | 7.95 | 58.26 | (0.218, 0.411) | 28 |
| Example 11 | 57 | 7.99 | 60.11 | (0.223, 0.422) | 28 |
| Example 12 | 62 | 7.06 | 69.82 | (0.221, 0.440) | 42 |
| Example 13 | 63 | 7.08 | 69.45 | (0.220, 0.430) | 40 |
| Example 14 | 64 | 7.12 | 68.55 | (0.216, 0.426) | 35 |
| Example 15 | 65 | 7.06 | 66.75 | (0.225, 0.430) | 36 |
| Example 16 | 66 | 7.01 | 68.21 | (0.220, 0.415) | 34 |
| Example 17 | 67 | 7.11 | 67.99 | (0.217, 0.413) | 35 |
| Example 18 | 89 | 7.99 | 58.73 | (0.211, 0.421) | 26 |
| Example 19 | 90 | 7.97 | 59.02 | (0.218, 0.425) | 27 |
| Example 20 | 91 | 7.99 | 59.64 | (0.211, 0.423) | 31 |
| Example 21 | 92 | 7.88 | 58.98 | (0.227, 0.422) | 23 |
| Example 22 | 93 | 7.89 | 58.77 | (0.230, 0.431) | 29 |
| Example 23 | 94 | 7.96 | 59.25 | (0.230, 0.424) | 22 |
| Example 24 | 95 | 7.12 | 68.55 | (0.215, 0.422) | 44 |
| Example 25 | 96 | 7.23 | 67.58 | (0.221, 0.422) | 39 |
| Example 26 | 97 | 7.20 | 69.45 | (0.223, 0.426) | 37 |
| Example 27 | 100 | 7.11 | 67.44 | (0.215, 0.422) | 38 |
| Example 28 | 138 | 7.90 | 60.91 | (0.220, 0.428) | 29 |
| Example 29 | 142 | 7.77 | 64.77 | (0.216, 0.430) | 30 |
| Example 30 | 147 | 7.82 | 59.99 | (0.216, 0.422) | 31 |
| Example 31 | 148 | 7.80 | 61.74 | (0.220, 0.432) | 31 |
| Example 32 | 164 | 7.90 | 63.52 | (0.210, 0.430) | 32 |
| Example 33 | 169 | 7.96 | 58.77 | (0.221, 0.422) | 26 |
| Example 34 | 192 | 7.98 | 63.35 | (0.223, 0.424) | 29 |
| Example 35 | 193 | 7.74 | 64.20 | (0.224, 0.424) | 29 |
| Example 36 | 195 | 7.85 | 60.57 | (0.226, 0.433) | 27 |
| Example 37 | 203 | 7.82 | 60.65 | (0.210, 0.423) | 31 |
| Example 38 | 207 | 7.08 | 68.21 | (0.214, 0.422) | 45 |

TABLE 9-continued

| | Compound | Driving Voltage (V) | Light Emission Efficiency (cd/A) | CIE (x, y) | Lifespan (T95) |
|---|---|---|---|---|---|
| Example 39 | 208 | 7.02 | 67.44 | (0.212, 0.417) | 40 |
| Example 40 | 209 | 7.09 | 68.01 | (0.211, 0.422) | 42 |
| Example 41 | 210 | 7.01 | 69.67 | (0.223, 0.429) | 40 |
| Example 42 | 213 | 7.21 | 68.96 | (0.215, 0.426) | 39 |
| Example 43 | 217 | 7.05 | 67.93 | (0.221, 0.428) | 50 |
| Example 44 | 226 | 7.11 | 69.44 | (0.223, 0.428) | 41 |
| Example 45 | 228 | 7.02 | 68.08 | (0.222, 0.430) | 42 |
| Example 46 | 230 | 7.04 | 69.11 | (0.231, 0.434) | 40 |
| Example 47 | 233 | 7.25 | 68.11 | (0.221, 0.430) | 38 |
| Example 48 | 234 | 7.13 | 69.24 | (0.214, 0.421) | 39 |
| Example 49 | 238 | 7.22 | 67.88 | (0.222, 0.413 | 42 |
| Example 50 | 242 | 7.01 | 68.43 | (0.212, 0.431) | 41 |
| Example 51 | 247 | 7.29 | 65.55 | (0.220, 0.432) | 53 |
| Example 52 | 260 | 7.31 | 66.32 | (0.221, 0.433) | 51 |
| Example 53 | 261 | 7.10 | 69.22 | (0.229, 0.432) | 40 |
| Example 54 | 272 | 7.22 | 68.46 | (0.228, 0.421) | 41 |
| Example 55 | 279 | 7.14 | 69.21 | (0.219, 0.430) | 39 |
| Example 56 | 280 | 7.20 | 67.88 | (0.226, 0.416) | 44 |
| Example 57 | 296 | 7.87 | 57.56 | (0.220, 0.420) | 26 |
| Example 58 | 302 | 7.93 | 59.67 | (0.226, 0.423) | 28 |
| Example 59 | 305 | 7.85 | 58.69 | (0.217, 0.419) | 26 |
| Example 60 | 310 | 7.79 | 59.11 | (0.230, 0.425) | 27 |
| Comparative Example 1-1 | TmPyPB | 8.50 | 57.63 | (0.213, 0.431) | 25 |
| Comparative Example 1-2 | N-ADN2 | 8.05 | 58.45 | (0.211, 0.427) | 26 |
| Comparative Example 1-3 | N-ADN5 | 8.11 | 57.12 | (0.220, 0.421) | 25 |
| Comparative Example 1-4 | N-AN9 | 8.38 | 58.11 | (0.218, 0.439) | 26 |
| Comparative Example 1-5 | N-AN11 | 8.34 | 57.55 | (0.234, 0.423) | 24 |

As shown from the results of Table 9, the organic electroluminescent devices using the charge generation layer material of the 2-stack white organic electroluminescent device of the present disclosure had a low driving voltage and improved light emission efficiency compared to Comparative Examples 1-1, 1-2, 1-3, 1-4 and 1-5. Particularly, it was identified that Compounds 62, 63, 95, 207, 210, 217, 226, 228, 230, 247, 260 and 261 were significantly excellent in all of driving, efficiency and lifespan.

The presumed reason for such results is that the compound of the present disclosure used as an N-type charge generation layer formed with an invented skeleton having proper length, strength and flat property and a proper hetero-compound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 2

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition. On the ITO transparent electrode (anode), organic materials were formed in a single-stack structure. As a hole injection layer, HAT-CN was deposited to a thickness of 50 Å, and subsequently, a hole transfer layer was formed by doping DNTPD within 10% to NPD, depositing the result to a thickness of 1500 Å, and continuously depositing TCTA to a thickness of 200 Å. Subsequently, a light emitting layer comprising a t-Bu-perylene dopant in an ADN host was formed to a thickness of 250 Å. Next, $Alq_3$, an electron transfer layer, was formed to a thickness of 250 Å, and an N-type charge transfer layer was formed to a thickness of 100 Å by doping Li, an alkali metal, to a compound described in the following Table 10, and Al, a cathode, was formed to a thickness of approximately 1,000 Å to manufacture an organic electroluminescent device.

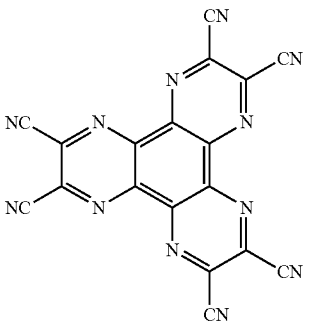

HAT-CN

-continued
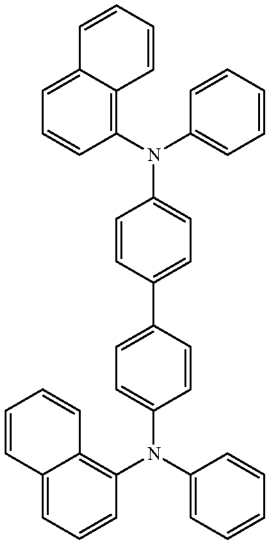
NPD
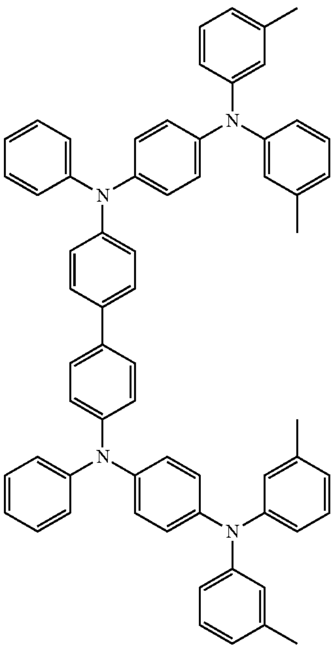
DNTPD
-continued
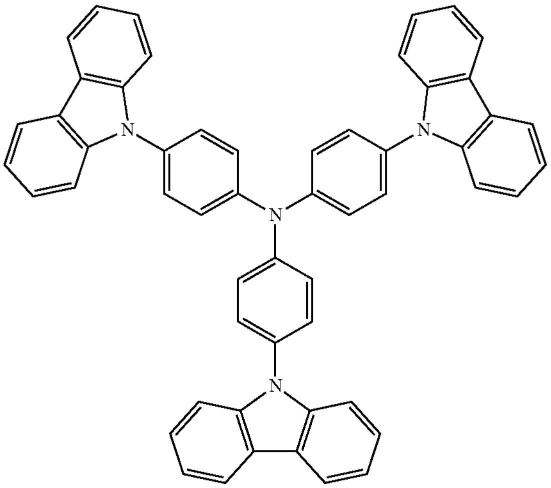
TCTA
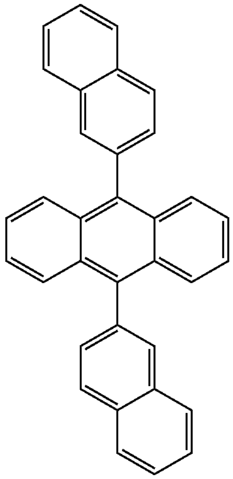
ADN
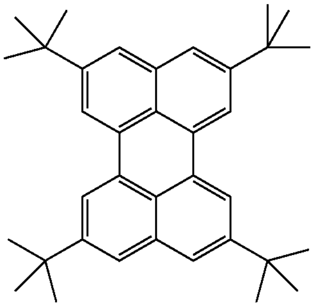
t-Bu-Perylene
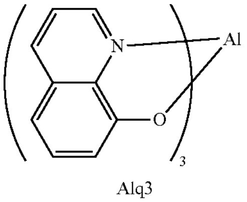
Alq3
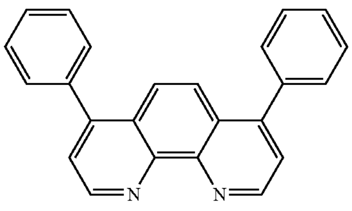
Bphen -continued

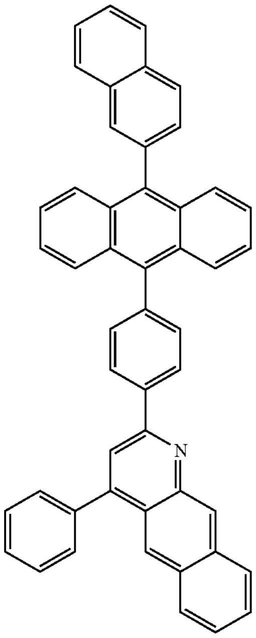

N-ADN2

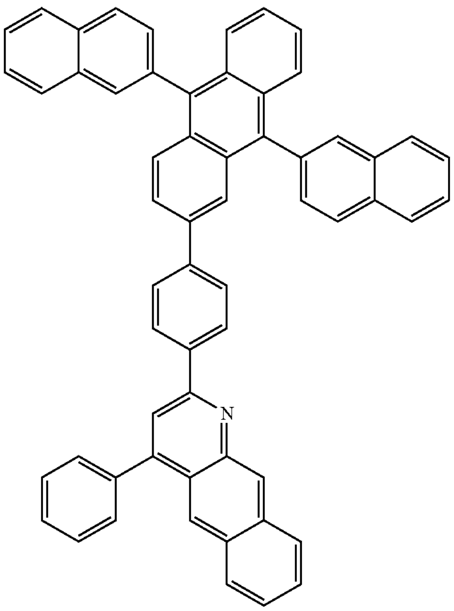

N-ADN5

-continued

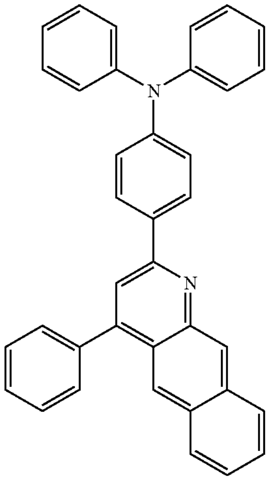

N-AN9

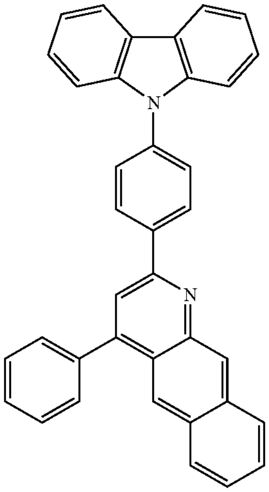

N-AN11

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, $T_{95}$ when standard luminance was 750 cd/$m^2$ was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 10.

TABLE 10

| | Compound | Driving Voltage (V) | Light Emission Efficiency (cd/A) | CIE (x, y) | Lifespan (T95) |
|---|---|---|---|---|---|
| Example 61 | 3 | 5.68 | 6.42 | (0.134 0.102) | 30 |
| Example 62 | 5 | 5.75 | 6.38 | (0.134 0.102) | 29 |
| Example 63 | 7 | 5.62 | 6.32 | (0.134 0.101) | 32 |
| Example 64 | 41 | 5.58 | 6.33 | (0.134, 0.104) | 29 |
| Example 65 | 42 | 5.79 | 6.21 | (0.134, 0.099) | 28 |
| Example 66 | 43 | 5.83 | 6.15 | (0.132, 0.100) | 29 |
| Example 67 | 44 | 5.65 | 6.07 | (0.128, 0.095) | 25 |
| Example 68 | 45 | 5.77 | 6.21 | (0.134, 0.099) | 30 |
| Example 69 | 46 | 5.85 | 6.43 | (0.134, 0.100 | 28 |
| Example 70 | 47 | 5.86 | 6.22 | (0.131, 0.098) | 30 |
| Example 71 | 57 | 5.87 | 6.31 | (0.130, 0.0910 | 29 |
| Example 72 | 62 | 4.48 | 6.89 | (0.134 0.100) | 41 |
| Example 73 | 63 | 4.51 | 6.90 | (0.134 0.100) | 40 |
| Example 74 | 64 | 4.61 | 6.75 | (0.132, 0.095) | 42 |

TABLE 10-continued

| | Compound | Driving Voltage (V) | Light Emission Efficiency (cd/A) | CIE (x, y) | Lifespan (T95) |
|---|---|---|---|---|---|
| Example 75 | 65 | 4.72 | 6.71 | (0.131, 0.100) | 39 |
| Example 76 | 66 | 4.55 | 6.66 | (0.129, 0.098) | 40 |
| Example 77 | 67 | 4.60 | 6.70 | (0.130, 0.100) | 40 |
| Example 78 | 89 | 5.79 | 6.11 | (0.133, 0.102 | 29 |
| Example 79 | 90 | 5.91 | 6.03 | (0.130, 0.099) | 27 |
| Example 80 | 91 | 5.91 | 6.17 | (0.134, 0.101) | 31 |
| Example 81 | 92 | 5.87 | 6.21 | (0.128, 0.103) | 30 |
| Example 82 | 93 | 5.67 | 6.35 | (0.134, 0.103) | 29 |
| Example 83 | 94 | 5.78 | 6.22 | (0.130, 0.099) | 31 |
| Example 84 | 95 | 4.51 | 6.89 | (0.134, 0.100) | 49 |
| Example 85 | 96 | 4.62 | 6.91 | (0.132, 0.102) | 42 |
| Example 86 | 97 | 4.68 | 6.75 | (0.129, 0.098) | 40 |
| Example 87 | 100 | 4.82 | 6.64 | (0.128, 0.102) | 43 |
| Example 88 | 138 | 5.65 | 6.46 | (0.134 0.101) | 31 |
| Example 89 | 142 | 5.70 | 6.57 | (0.134 0.100) | 29 |
| Example 90 | 147 | 5.50 | 6.39 | (0.134 0.100) | 30 |
| Example 91 | 148 | 5.56 | 6.47 | (0.134 0.100) | 30 |
| Example 92 | 164 | 5.62 | 6.43 | (0.134 0.101) | 32 |
| Example 93 | 169 | 5.78 | 6.27 | (0.130, 0.102) | 28 |
| Example 94 | 192 | 5.46 | 6.34 | (0.134 0.102) | 32 |
| Example 95 | 193 | 5.76 | 6.51 | (0.134 0.101) | 34 |
| Example 96 | 195 | 5.76 | 6.44 | (0.134, 0.102) | 28 |
| Example 97 | 203 | 5.62 | 6.58 | (0.134 0.102) | 35 |
| Example 98 | 207 | 4.53 | 6.79 | (0.134, 0.098) | 48 |
| Example 99 | 208 | 4.73 | 6.88 | (0.131, 0.100) | 42 |
| Example 100 | 209 | 4.69 | 6.76 | (0.130, 0.102) | 40 |
| Example 101 | 210 | 4.60 | 6.90 | (0.134 0.099) | 40 |
| Example 102 | 213 | 4.77 | 6.80 | (0.128, 0.097) | 39 |
| Example 103 | 217 | 4.65 | 6.93 | (0.134, 0.100) | 49 |
| Example 104 | 226 | 4.44 | 6.89 | (0.134 0.099) | 40 |
| Example 105 | 228 | 4.57 | 6.95 | (0.134 0.100) | 41 |
| Example 106 | 230 | 4.50 | 6.98 | (0.134 0.101) | 41 |
| Example 107 | 233 | 4.69 | 6.78 | (0.130, 0.099) | 39 |
| Example 108 | 234 | 4.70 | 6.80 | (0.129, 0.100) | 38 |
| Example 109 | 238 | 4.65 | 6.62 | (0.128, 0.101) | 40 |
| Example 110 | 242 | 4.89 | 6.79 | (0.130, 0.100) | 40 |
| Example 111 | 247 | 4.83 | 6.67 | (0.134 0.103) | 48 |

TABLE 10-continued

| | Compound | Driving Voltage (V) | Light Emission Efficiency (cd/A) | CIE (x, y) | Lifespan (T95) |
|---|---|---|---|---|---|
| Example 112 | 260 | 4.90 | 6.58 | (0.134 0.103) | 47 |
| Example 113 | 261 | 4.51 | 6.99 | (0.134 0.100) | 42 |
| Example 114 | 272 | 4.91 | 6.78 | (0.131, 0.102) | 38 |
| Example 115 | 279 | 4.78 | 6.80 | (0.128, 0.099) | 42 |
| Example 116 | 280 | 4.69 | 6.82 | (0.130, 0.098) | 40 |
| Example 117 | 296 | 5.88 | 6.21 | (0.133, 0.103) | 25 |
| Example 118 | 302 | 5.97 | 6.01 | (0.127, 0.101) | 29 |
| Example 119 | 305 | 5.79 | 6.15 | (0.129, 0.100) | 27 |
| Example 120 | 310 | 5.80 | 6.23 | (0.130, 0.098) | 30 |
| Comparative Example 2-1 | Bphen | 5.82 | 6.23 | (0.134 0.110) | 27 |
| Comparative Example 2-2 | N-ADN2 | 5.79 | 6.31 | (0.134, 0.100) | 31 |
| Comparative Example 2-3 | N-ADN5 | 5.68 | 6.24 | (0.134, 0.100) | 29 |
| Comparative Example 2-4 | N-AN9 | 5.83 | 6.15 | (0.134, 0.104) | 27 |
| Comparative Example 2-5 | N-AN11 | 5.86 | 6.26 | (0.134, 0.103) | 26 |

As shown from the results of Table 10, the organic electroluminescent devices using the charge generation layer material of the blue organic electroluminescent device of the present disclosure had a low driving voltage and improved light emission efficiency compared to Comparative Examples 2-1, 2-2, 2-3, 2-4 and 2-5. Particularly, it was identified that Compounds 62, 63, 95, 207, 210, 217, 226, 228, 230, 247, 260 and 261 were significantly excellent in all of driving, efficiency and lifespan.

The presumed reason for such results is that the compound of the present disclosure used as an N-type charge generation layer formed with an invented skeleton having proper length, strength and flat property and a proper hetero-compound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 3

1) Manufacture of Organic Light Emitting Device

A transparent electrode ITO thin film obtained from glass for an OLED (manufactured by Samsung Corning Advanced Glass) was ultrasonic cleaned consecutively using trichloroethylene, acetone, ethanol and distilled water for 5 minutes each, placed in isopropanol and stored, and then used.

Next, the ITO substrate was installed in a substrate folder of vacuum deposition equipment, and the following 4,4',4"-tris(N,N-(2-naphthyl)-phenylamino)triphenyl amine (2-TNATA) was introduced to a cell in the vacuum deposition equipment.

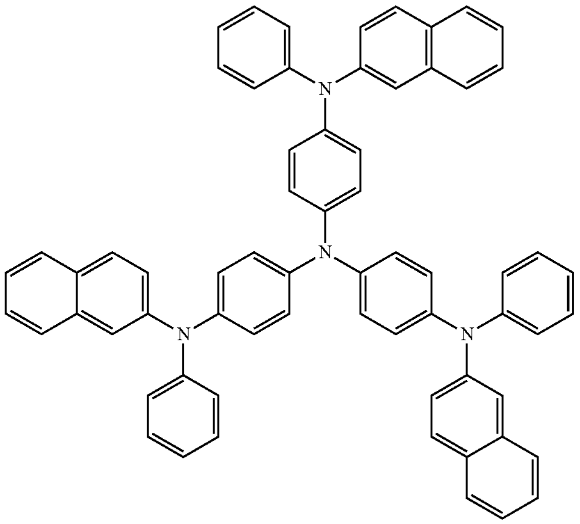

2-TNATA

Subsequently, the chamber was exhausted until the degree of vacuum inside the chamber reached $10^{-6}$ torr, and then a current was applied to the cell to evaporate the 2-TNATA to deposit a hole injection layer having a thickness of 600 Å on the ITO substrate.

The following N,N'-bis(α-naphthyl)-N,N'-diphenyl-4,4'-diamine (NPB) was introduced to a different cell in the vacuum deposition equipment, a current was applied to the cell to evaporate to deposit a hole transfer layer having a thickness of 300 Å on the hole injection layer.

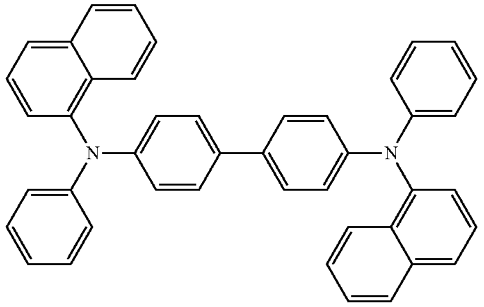

NPB

After forming the hole injection layer and the hole transfer layer as above, a blue light emitting material having a structure as follows was deposited thereon as a light emitting layer. Specifically, H1, a blue light emitting host material, was vacuum deposited to a thickness of 200 Å on one cell in the vacuum deposition equipment, and D1, a blue light emitting dopant material, was vacuum deposited thereon in 5% with respect to the host material.

H1

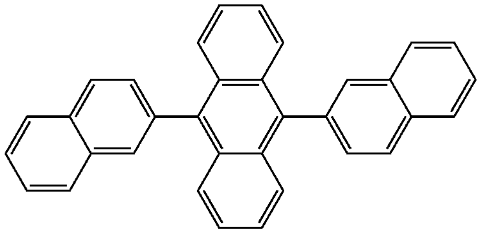

D1

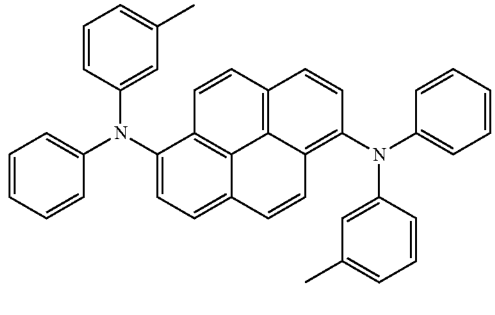

Subsequently, compounds of the following structural formulae E1, N-ADN2, N-ADN5, N-AN9 and N-AN11 were deposited to a thickness of 300 Å as an electron transfer layer.

E1

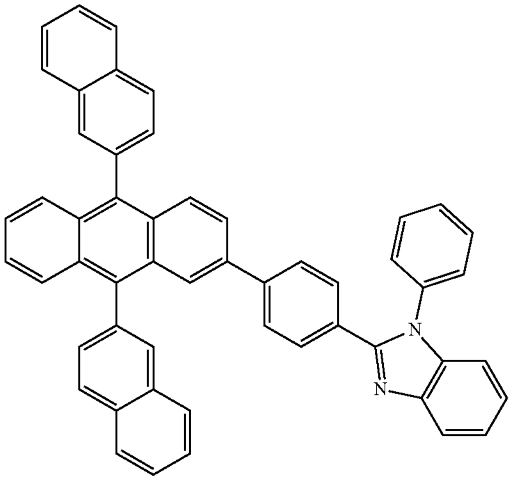

-continued

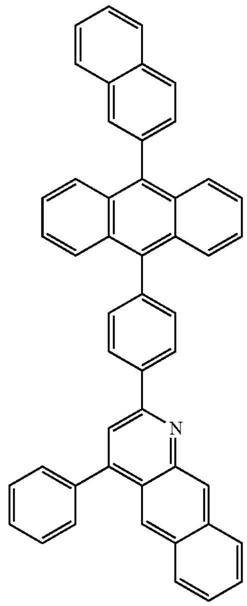

N-ADN2

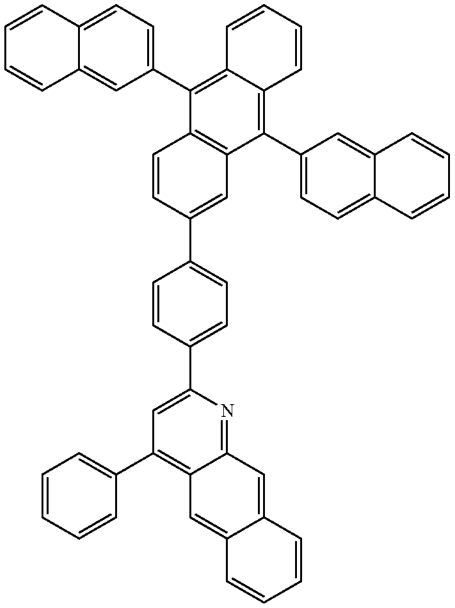

N-ADN5

-continued

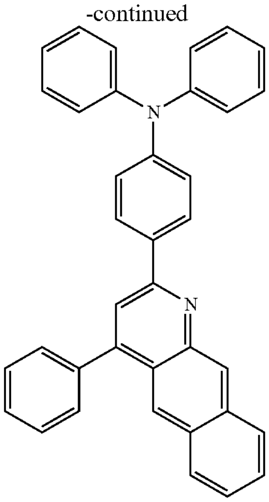

N-AN9

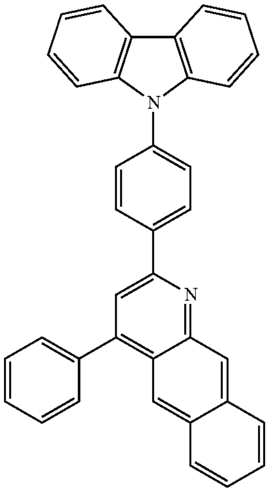

N-AN11

As an electron injection layer, lithium fluoride (LiF) was deposited to a thickness of 10 Å, and an Al cathode was formed to a thickness of 1000 Å to manufacture an OLED device.

Meanwhile, all the organic compounds required to manufacture the OLED device were vacuum sublimation purified under $10^{-6}$ torr to $10^{-8}$ torr by each material to be used in the OLED manufacture.

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, Tss when standard luminance was 700 cd/$m^2$ was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 11.

TABLE 11

| | Compound | Driving Voltage (V) | Light Emission Efficiency (cd/A) | CIE (x, y) | Lifespan (T95) |
|---|---|---|---|---|---|
| Example 121 | 3 | 4.42 | 6.93 | (0.134 0.099) | 40 |
| Example 122 | 5 | 4.48 | 6.86 | (0.134 0.099) | 41 |
| Example 123 | 7 | 4.47 | 6.87 | (0.134 0.100) | 40 |
| Example 124 | 41 | 4.51 | 7.05 | (0.134, 0.099) | 42 |
| Example 125 | 42 | 4.67 | 6.64 | (0.129, 0.100) | 38 |
| Example 126 | 43 | 4.82 | 6.55 | (0.130, 0.099) | 36 |
| Example 127 | 44 | 4.77 | 6.68 | (0.132, 0.098) | 36 |
| Example 128 | 45 | 4.44 | 6.97 | (0.134, 0.101) | 40 |
| Example 129 | 46 | 4.61 | 6.89 | (0.134, 0.103) | 40 |
| Example 130 | 47 | 4.88 | 6.72 | (0.128, 0.099) | 36 |
| Example 131 | 57 | 4.70 | 6.75 | (0.127, 0.100) | 37 |
| Example 132 | 62 | 5.35 | 6.30 | (0.134 0.102) | 33 |
| Example 133 | 63 | 5.28 | 6.28 | (0.134 0.102) | 32 |
| Example 134 | 64 | 5.61 | 6.19 | (0.130, 0.099) | 28 |
| Example 135 | 65 | 5.60 | 6.07 | (0.129, 0.100) | 29 |
| Example 136 | 66 | 5.55 | 6.10 | (0.130, 0.101) | 30 |
| Example 137 | 67 | 5.71 | 6.15 | (0.129, 0.098) | 28 |
| Example 138 | 89 | 4.57 | 6.74 | (0.128, 0.099) | 36 |
| Example 139 | 90 | 4.60 | 6.69 | (0.129, 0.102) | 36 |
| Example 140 | 91 | 4.49 | 6.96 | (0.134, 0.100) | 40 |
| Example 141 | 92 | 4.62 | 6.72 | (0.133, 0.100) | 37 |
| Example 142 | 93 | 4.55 | 6.85 | (0.134, 0.101) | 39 |
| Example 143 | 94 | 4.80 | 6.69 | (0.130, 0.100) | 38 |
| Example 144 | 95 | 5.42 | 6.13 | (0.134, 0.101) | 29 |
| Example 145 | 96 | 5.67 | 6.02 | (0.132, 0.103) | 25 |
| Example 146 | 97 | 5.58 | 6.15 | (0.130, 0.099) | 25 |
| Example 147 | 100 | 5.70 | 6.07 | (0.129, 0.100) | 28 |
| Example 148 | 138 | 4.54 | 6.92 | (0.134 0.101) | 41 |
| Example 149 | 142 | 4.30 | 6.81 | (0.134 0.101) | 41 |
| Example 150 | 147 | 4.50 | 6.98 | (0.134 0.100) | 40 |
| Example 151 | 148 | 4.44 | 7.09 | (0.134 0.100) | 39 |
| Example 152 | 164 | 4.61 | 7.01 | (0.134 0.099) | 38 |
| Example 153 | 169 | 4.60 | 6.87 | (0.131, 0.100) | 37 |
| Example 154 | 192 | 4.64 | 7.08 | (0.134 0.099) | 40 |
| Example 155 | 193 | 4.53 | 6.91 | (0.134 0.101) | 41 |
| Example 156 | 195 | 4.97 | 6.59 | (0.134, 0.100) | 34 |
| Example 157 | 203 | 4.54 | 6.95 | (0.134 0.103) | 42 |
| Example 158 | 207 | 5.33 | 6.17 | (0.134, 0.102) | 29 |
| Example 159 | 208 | 5.63 | 6.11 | (0.131, 0.098) | 28 |
| Example 160 | 209 | 5.58 | 6.23 | (0.129, 0.101) | 30 |
| Example 161 | 210 | 5.61 | 6.20 | (0.134 0.102) | 31 |
| Example 162 | 213 | 5.66 | 6.04 | (0.131, 0.102) | 30 |
| Example 163 | 217 | 5.65 | 6.08 | (0.134, 0.101) | 28 |
| Example 164 | 226 | 5.35 | 6.32 | (0.134 0.102) | 30 |
| Example 165 | 228 | 5.43 | 6.25 | (0.134 0.101) | 29 |
| Example 166 | 230 | 5.40 | 6.49 | (0.134 0.101) | 31 |
| Example 167 | 233 | 5.59 | 6.14 | (0.131, 0.101) | 28 |
| Example 168 | 234 | 5.60 | 6.22 | (0.129, 0.100) | 29 |
| Example 169 | 238 | 5.48 | 6.18 | (0.129, 0.099) | 28 |
| Example 170 | 242 | 5.59 | 6.07 | (0.128, 0.102 | 30 |
| Example 171 | 247 | 4.74 | 5.89 | (0.134 0.100) | 37 |
| Example 172 | 260 | 4.70 | 6.01 | (0.134 0.101) | 36 |
| Example 173 | 261 | 5.40 | 6.31 | (0.134 0.102) | 31 |
| Example 174 | 272 | 5.71 | 6.19 | (0.131, 0.100) | 27 |
| Example 175 | 279 | 5.63 | 6.06 | (0.128, 0.102) | 27 |
| Example 176 | 280 | 5.49 | 6.14 | (0.130, 0.101) | 29 |
| Example 177 | 296 | 4.73 | 6.78 | (0.130, 0.100) | 35 |
| Example 178 | 302 | 4.67 | 6.65 | (0.129, 0.098) | 36 |
| Example 179 | 305 | 4.69 | 6.92 | (0.130, 0.101) | 35 |
| Example 180 | 310 | 4.52 | 6.75 | (0.129, 0.097) | 37 |
| Comparative Example 3-1 | E1 | 5.79 | 6.10 | (0.134 0.100) | 27 |
| Comparative Example 3-2 | N-ADN2 | 5.54 | 6.24 | (0.134, 0.100) | 33 |
| Comparative Example 3-3 | N-ADN5 | 5.68 | 6.21 | (0.134, 0.104) | 31 |
| Comparative Example 3-4 | N-AN9 | 5.77 | 6.18 | (0.134, 0.103) | 33 |
| Comparative Example 3-5 | N-AN11 | 5.72 | 6.14 | (0.134, 0.100) | 35 |

As shown from the results of Table 11, the organic electroluminescent devices using the electron transfer layer material of the blue organic electroluminescent device of the present disclosure had a low driving voltage and significantly improved light emission efficiency and lifespan compared to Comparative Examples 3-1, 3-2, 3-3, 3-4 and 3-5. Particularly, it was identified that Compounds 3, 5, 7, 41, 45, 46, 91, 93, 138, 142, 147, 148, 164, 192, 193 and 203 were significantly excellent in all of driving, efficiency and lifespan.

The presumed reason for such results is that, when the invented compound having proper length, strength and flat property is used as an electron transfer layer, a compound in an excited state is produced by receiving electrons under a specific condition, and particularly, when the excited state is formed in the heteroskeleton site of the compound, excited energy moves to a stable state before the excited heteroskeleton site goes through a different reaction, and the relatively stabilized compound is capable of efficiently transferring electrons without compound decomposition or destruction. As a reference, it is considered that those having a stable state when excited are aryl or acene series compounds or multicyclic hetero-compounds. Accordingly, it is considered that the compound of the present disclosure enhances electron-transport properties or improved stability resulting in excellency in all of driving, efficiency and lifespan.

The invention claimed is:

1. A hetero-cyclic compound represented by the following Chemical Formula 1 or Chemical Formula 2:

[Chemical Formula 1]

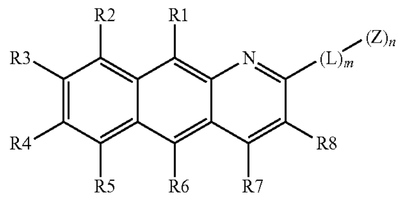

[Chemical Formula 2]

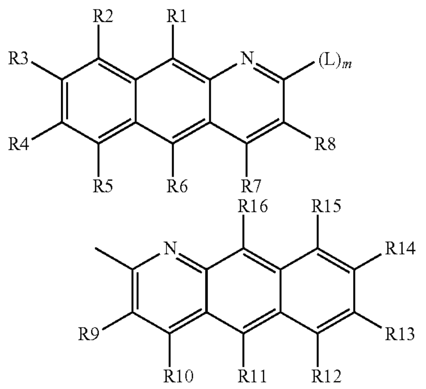

wherein, in Chemical Formulae 1 and 2,

L is a direct bond; a phenylene group unsubstituted or substituted with one or more substituents selected from the group consisting of a pyridine group, a pyrimidine group, a quinoline group, a phenanthroline group, an anthracene group, a benzoquinoline group, a naphthyl group, a phenyl group, a triazine group, a dibenzofuran group, a dibenzothiophene group and a carbazole group; an anthracene group unsubstituted or substituted with one or more substituents selected from the group consisting of a phenyl group, a naphthyl group, a pyridine group and a quinoline group; a biphenylene group; a naphthylene group; a phenalene group; a phenanthrene group; or a pyrene group, Z is selected from the group consisting of a substituted or unsubstituted biphenyl group;

a substituted or unsubstituted naphthyl group; a substituted or unsubstituted anthracene group; a substituted or unsubstituted triphenylene group; a substituted or unsubstituted pyrene group; a substituted or unsubstituted phenanthrene group; a substituted or unsubstituted perylene group; a substituted or unsubstituted triazine group; a substituted or unsubstituted pyrimidine group; a substituted or unsubstituted quinoline group; a substituted or unsubstituted phenanthroline group; a substituted or unsubstituted benzimidazole group; a substituted or unsubstituted dibenzothiophene group; a substituted or unsubstituted dibenzofuran group; and a substituted and unsubstituted carbazole group, m is an integer of 1 to 4;

n is an integer of 1 to 4;

R1 and R16, are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(═O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring;

R2 to R15 are hydrogen; or deuterium, wherein "substituted or unsubstituted" means being (a) substituted with one or more substituents selected from the group consisting a $C_1$ to $C_{60}$ alkyl group; a $C_6$ to $C_{60}$ aryl group; and a $C_2$ to $C_{60}$ heteroaryl group, or being unsubstituted, or (b) being substituted with a substituent bonding two or more of the above-mentioned substituents, or being unsubstituted, or (c) being substituted with a substituent linking two or more substituents selected from among the above-mentioned substituents, or being unsubstituted, in chemical formula 1, L is a phenylene group unsubstituted or substituted with one or more substituents selected from the group consisting of a pyridine group, a pyrimidine group, a quinoline group, a phenanthroline group, an anthracene group, a benzoquinoline group, a naphthyl group, a phenyl group, a triazine group, a dibenzofuran group, a dibenzothiophene group and a carbazole group; an anthracene group unsubstituted or substituted with one or more substituents selected from the group consisting of a phenyl group, a naphthyl group, a pyridine group and a quinoline group; a biphenylene group; a naphthylene group; a phenalene group; a phenanthrene group; or a pyrene group, when Z is a unsubstituted phenanthroline group; or a unsubstituted quinoline group, in chemical formula 2, L is direct bond; a phenylene group unsubstituted or substituted with one or more substituents selected from the group consisting of a pyridine group, a pyrimidine group, a quinoline group, a phenanthroline group, an anthracene group, a benzoquinoline group, a naphthyl group, a phenyl group, a triazine group, a dibenzofuran group, a dibenzothiophene group and a carbazole group; an anthracene group unsubstituted or substituted with one or more substituents selected from the group consisting of a phenyl group, a naphthyl group, a pyridine group and a quinoline group; a biphenylene group; a naphthylene group; a phenalene group; a phenanthrene group; or a pyrene group, in chemical formula 2, m is integer of 2 to 4, when L is a phenylene group unsubstituted or substituted by a benzoquinoline group, and R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

2. An organic light emitting device comprising:

an anode;

a cathode; and one or more organic material layers provided between the anode and the cathode, wherein one or more layers of the organic material layers comprise the hetero-cyclic compound of claim 1.

3. The organic light emitting device of claim 2, wherein the organic material layer comprises at least one of a hole blocking layer, an electron injection layer and an electron transfer layer, and at least one of the hole blocking layer, the electron injection layer and the electron transfer layer comprises the hetero-cyclic compound.

4. The organic light emitting device of claim 2, wherein the organic material layer comprises a light emitting layer, and the light emitting layer comprises the hetero-cyclic compound.

5. The organic light emitting device of claim 2, wherein the organic material layer comprises one or more of a hole injection layer, a hole transfer layer, and a layer carrying out hole injection and hole transfer at the same time, and one of the above-mentioned layers comprises the hetero-cyclic compound.

6. The organic light emitting device of claim 2, wherein the organic material layer comprises a charge generation layer, and the charge generation layer comprises the hetero-cyclic compound.

7. The organic light emitting device of claim 2, comprising:

an anode;

a first stack provided on the anode and comprising a first light emitting layer;

a charge generation layer provided on the first stack;

a second stack provided on the charge generation layer and comprising a second light emitting layer; and a cathode provided on the second stack.

8. A hetero-cyclic compound represented by any one of the following compounds:

2

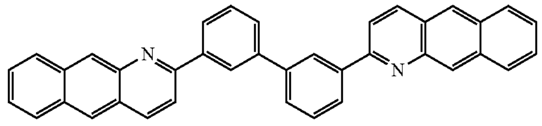

3

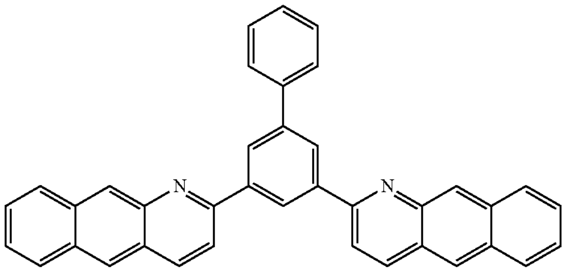

4

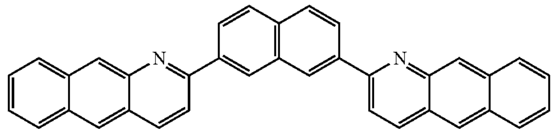

5

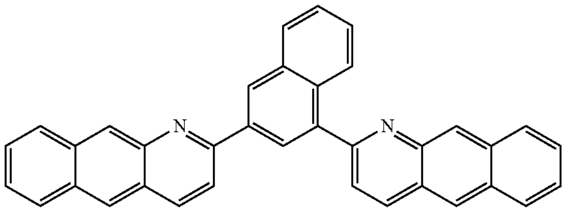

6

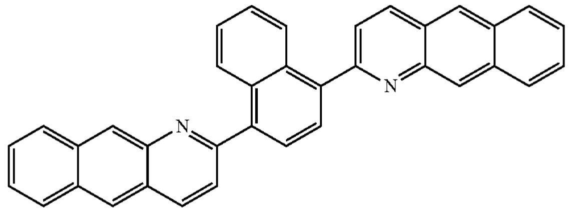

7

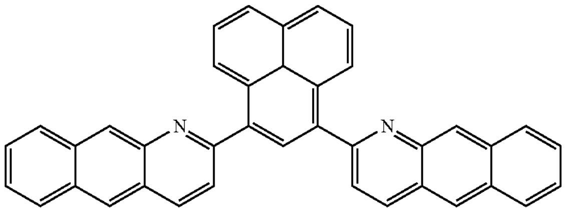

-continued
8
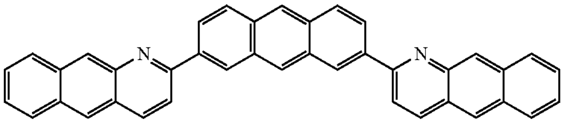
9
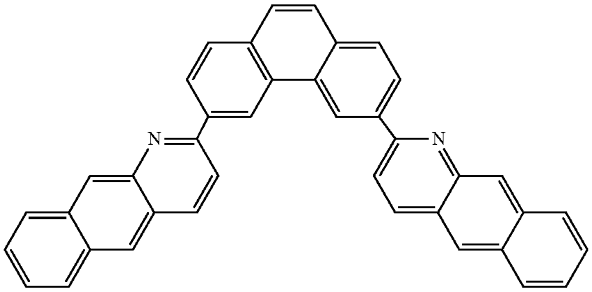
10
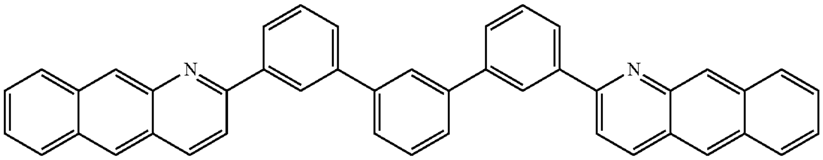
11
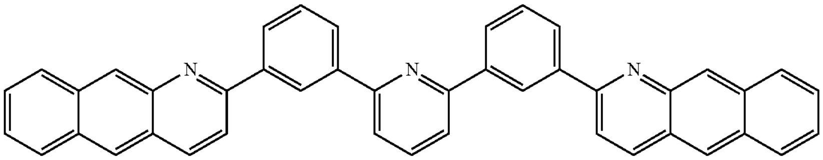
12
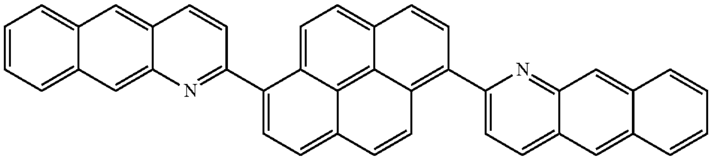
13
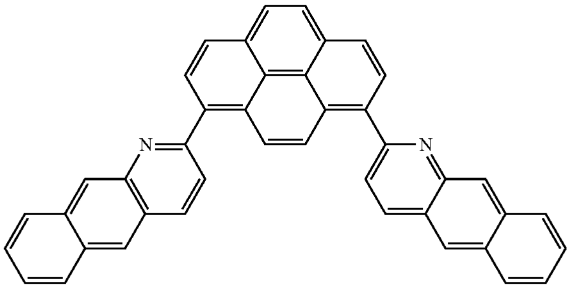
14
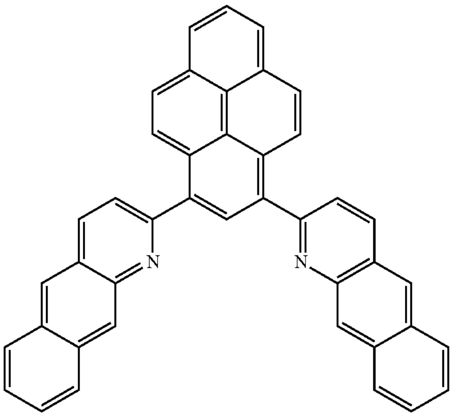
15
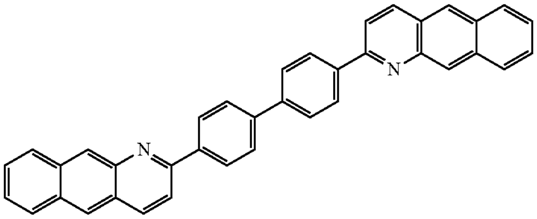
16
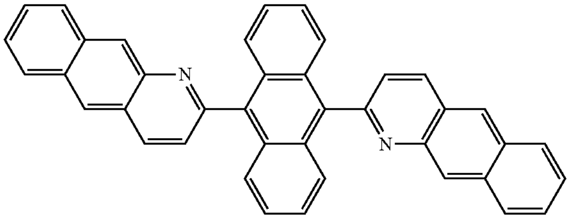

-continued
17
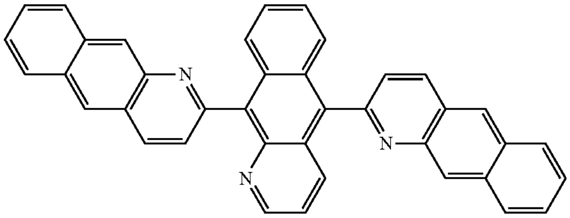
18
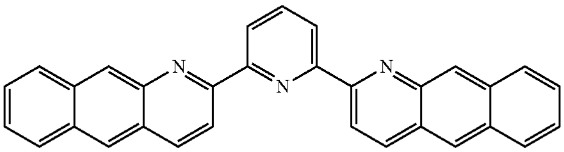
19
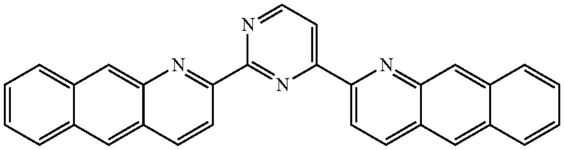
20
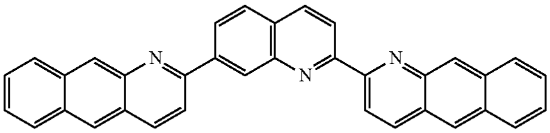
21
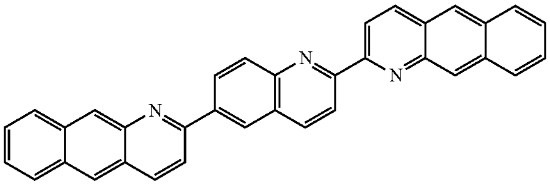
22
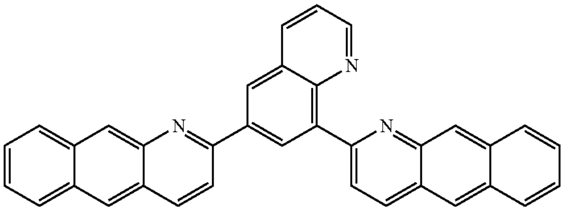
23
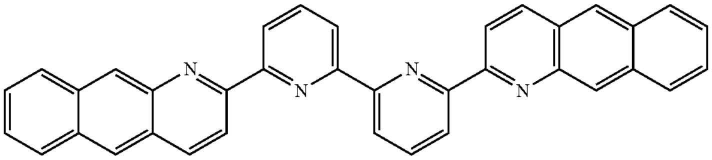
24
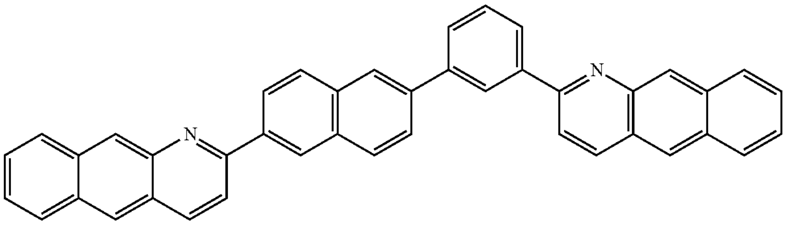
25
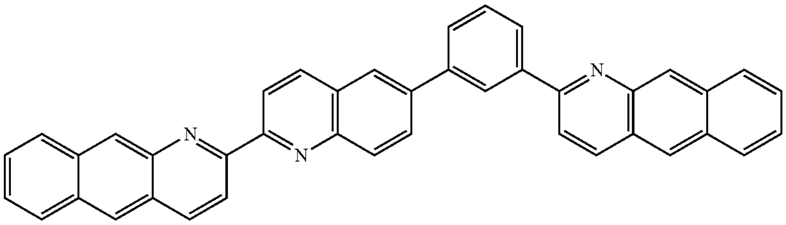
26
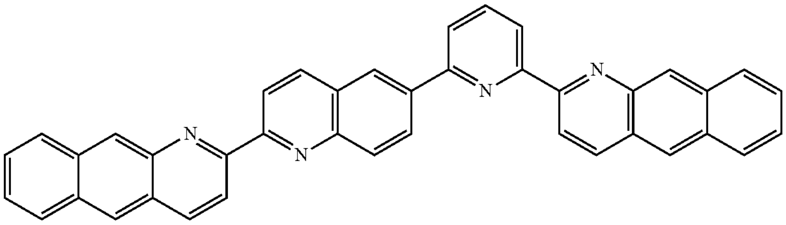

-continued
27
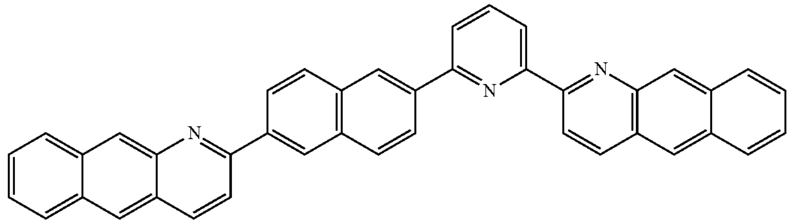
28
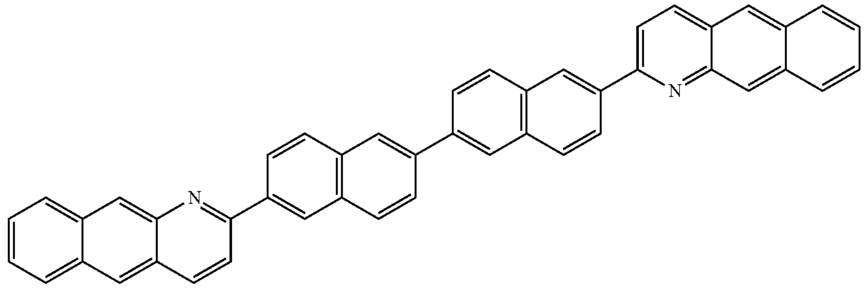
29
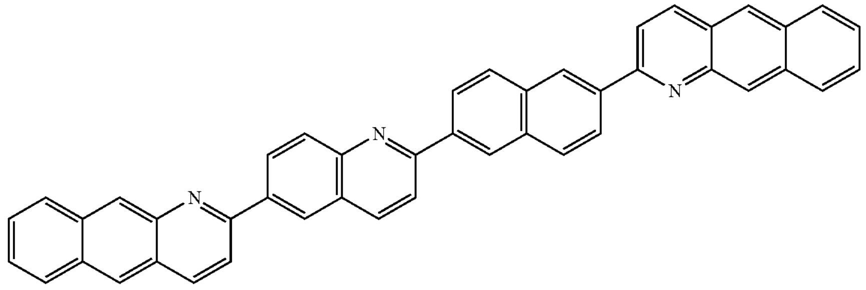
30
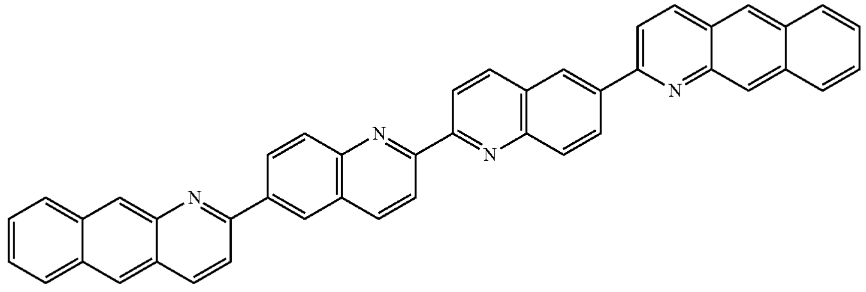
31
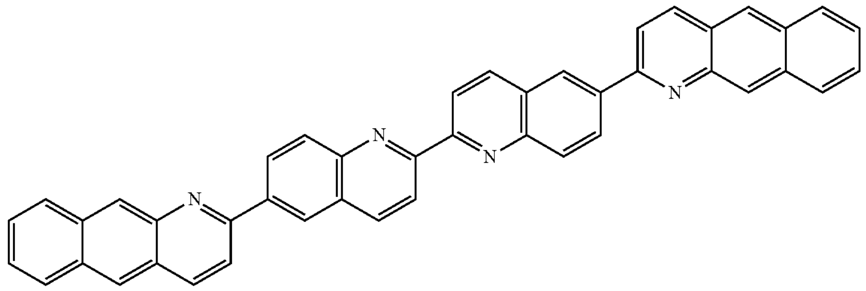

-continued
32
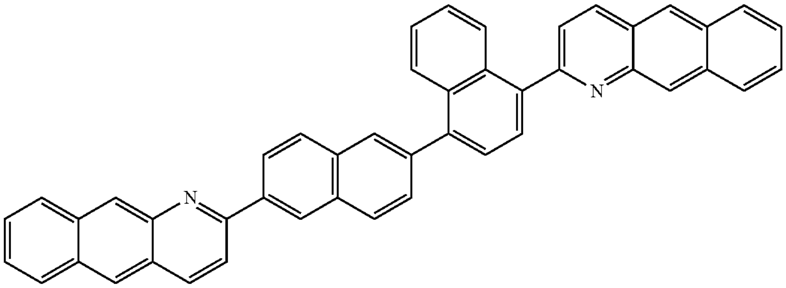
33
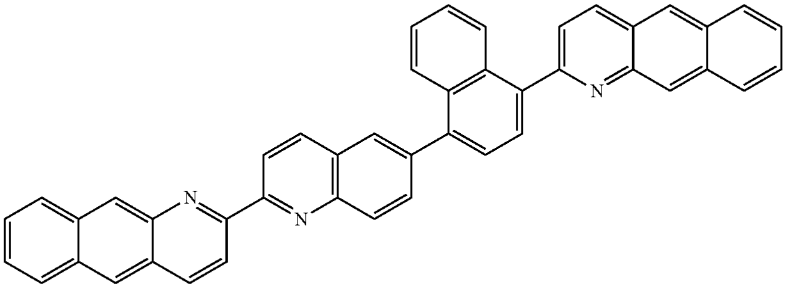
34
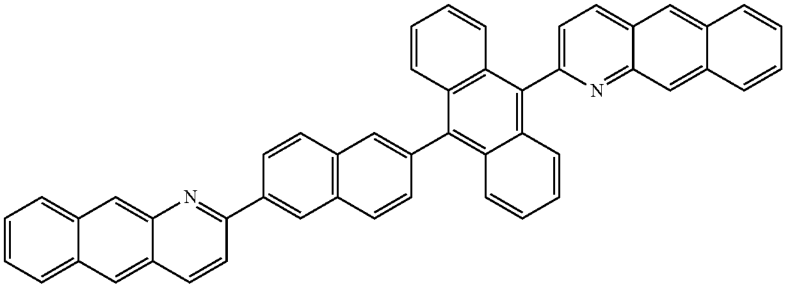
35
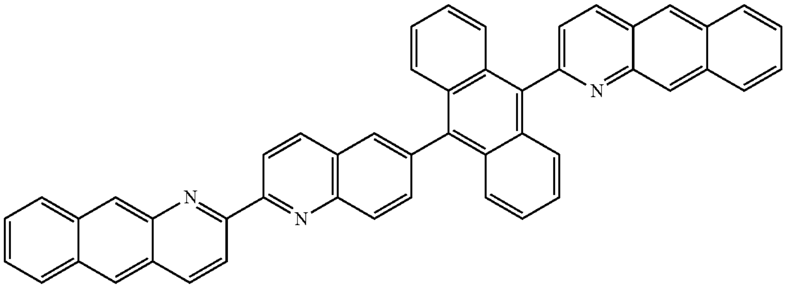
36
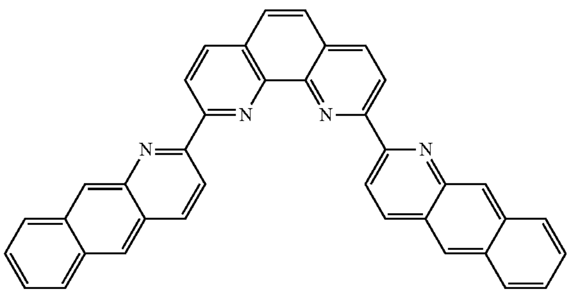
37
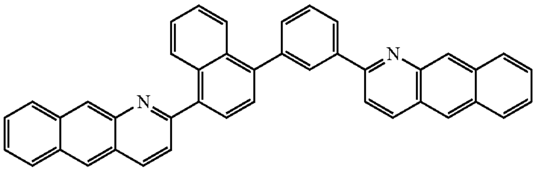

-continued
38
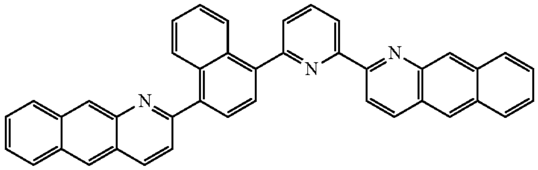
39
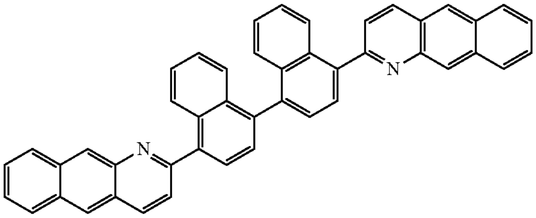
40
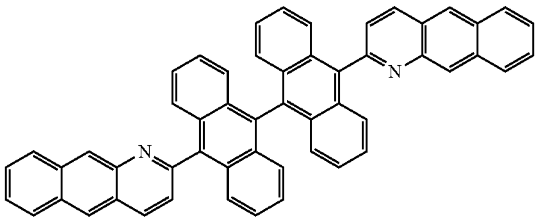
42
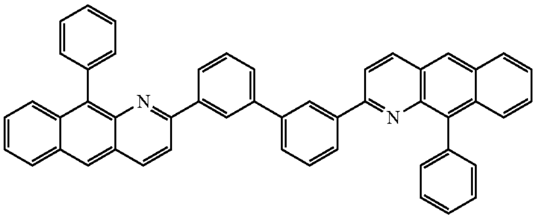
43
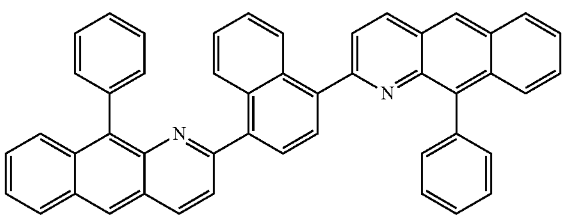
44
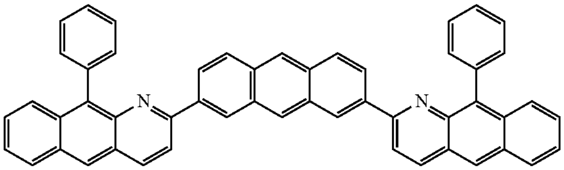
45
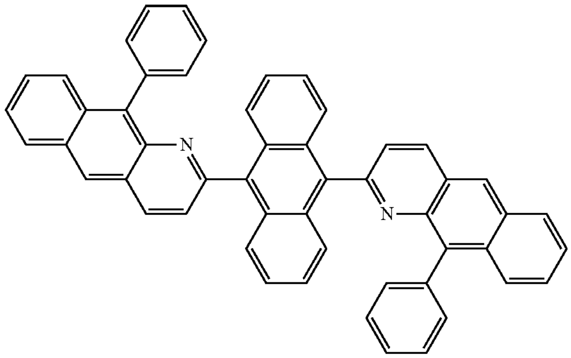
46
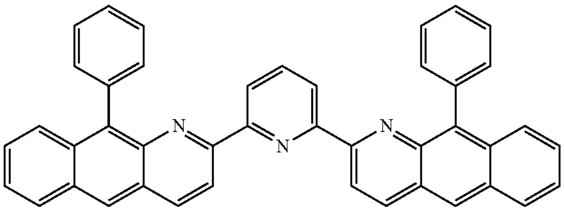
47
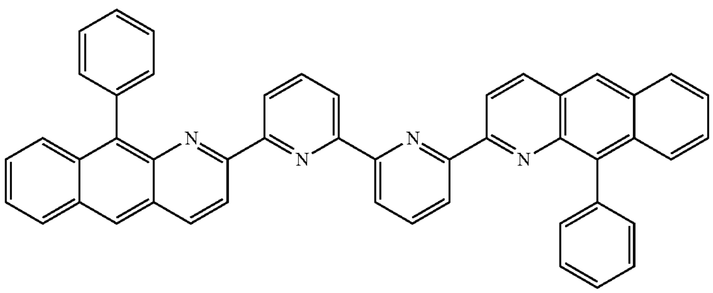

-continued
48
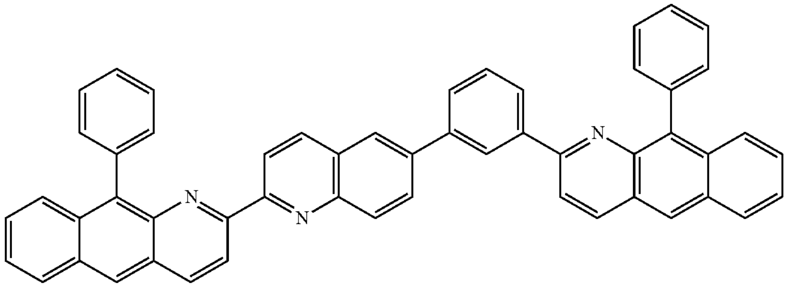
49
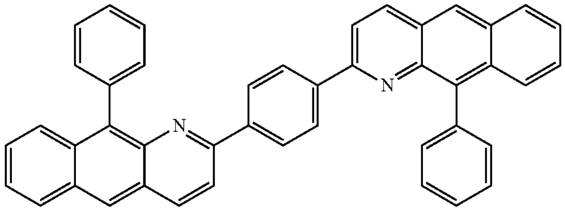
50
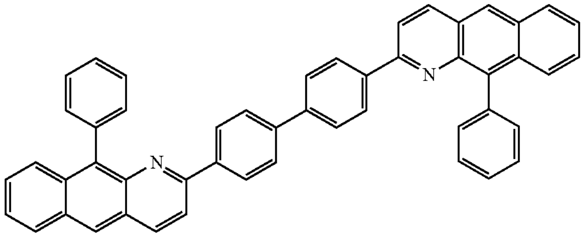
51
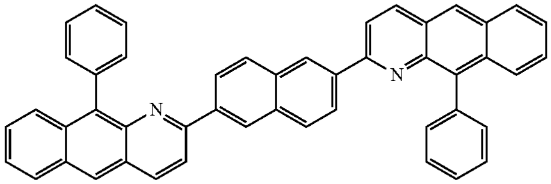
52
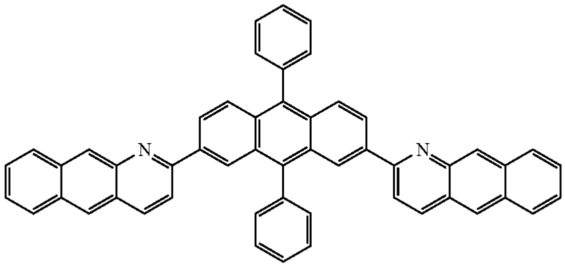
53
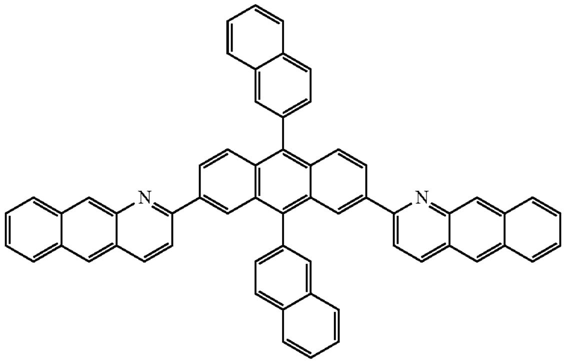
54
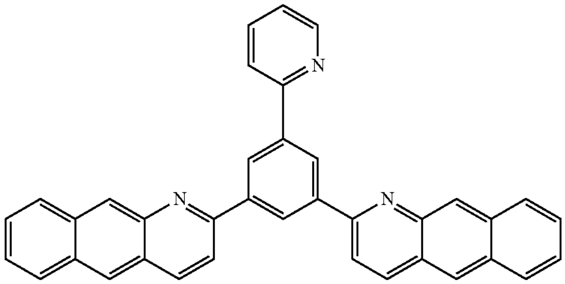
55
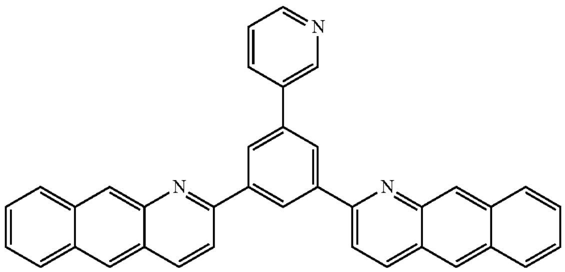
56
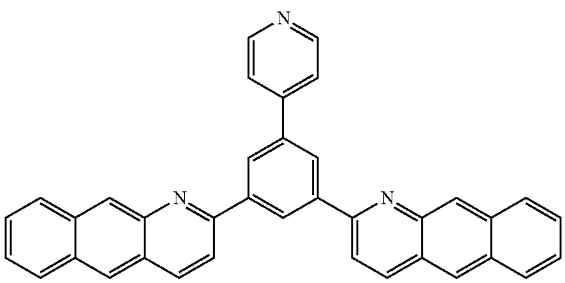

-continued
57
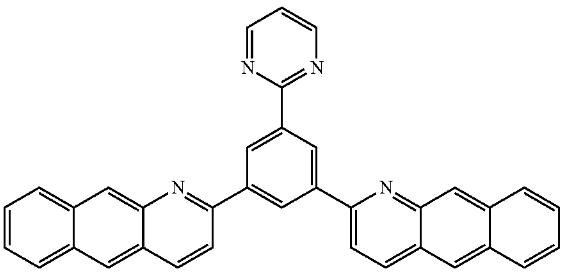
58
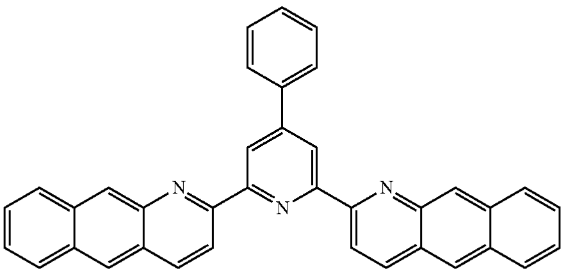
59
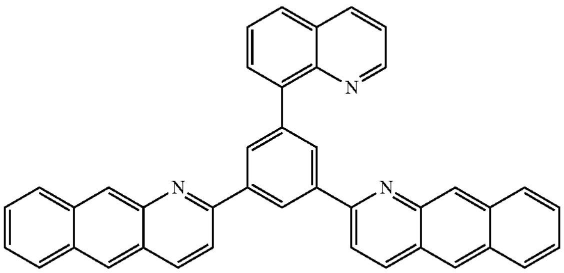
60
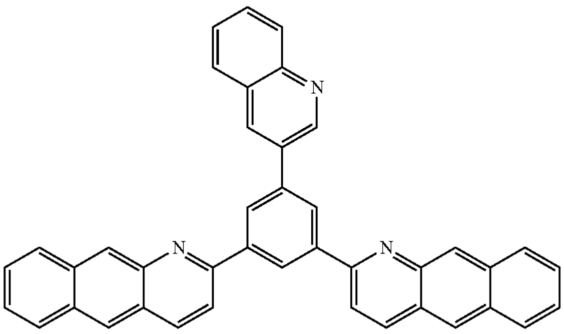
61
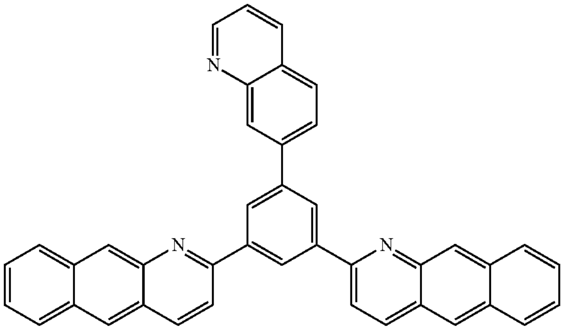
62
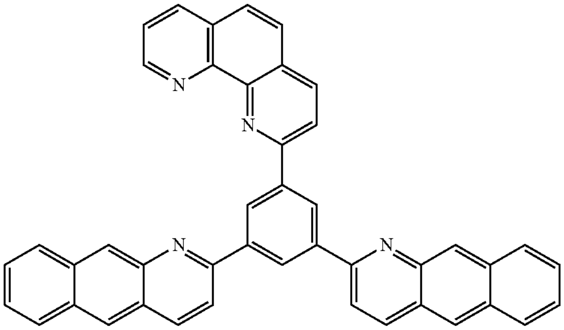
63
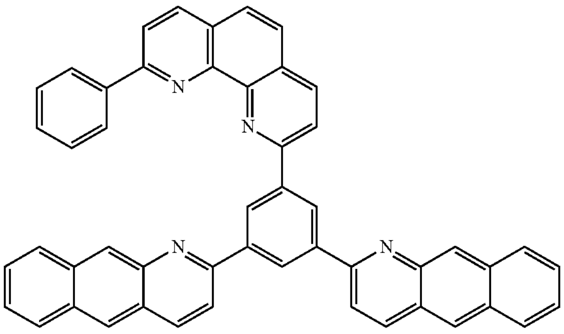
64
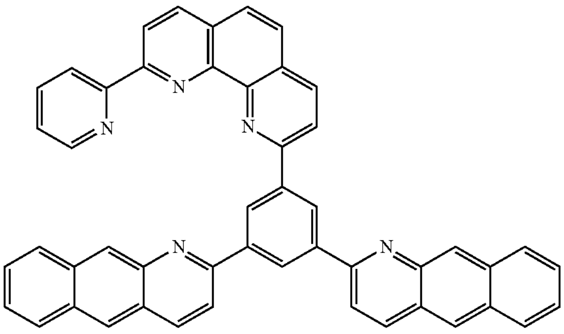

-continued
65
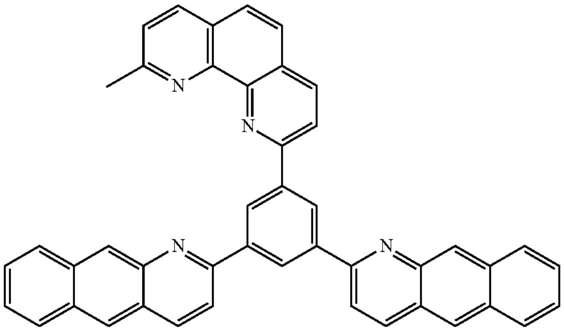
66
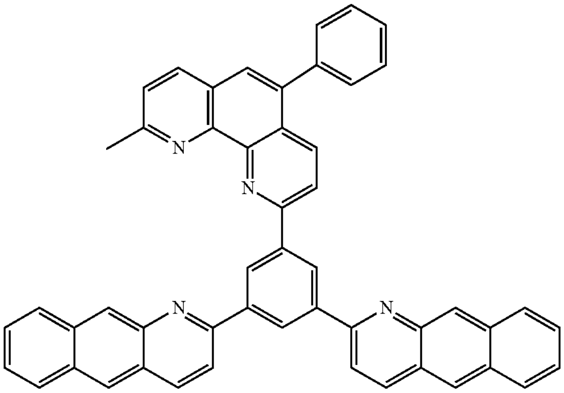
67
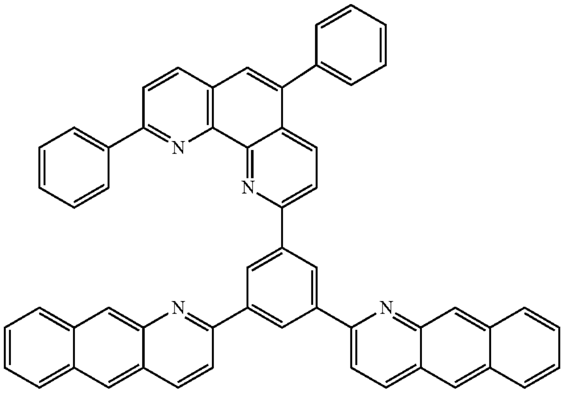
68
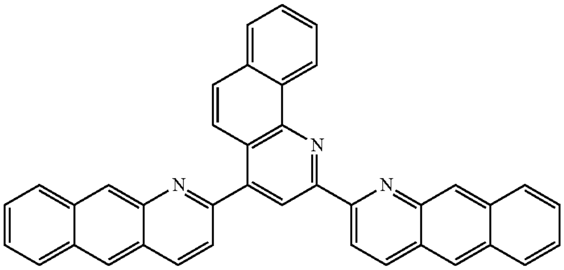
69
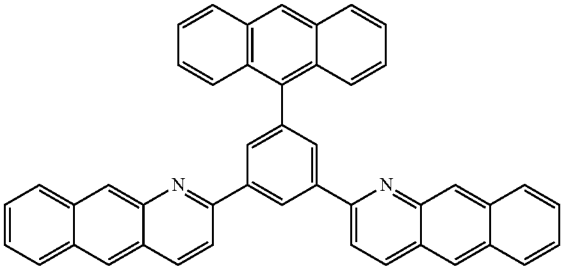
70
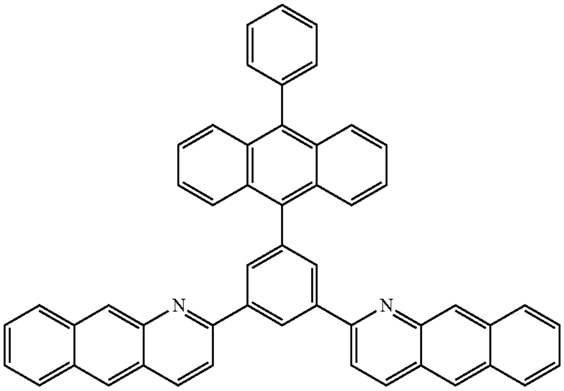

-continued
72
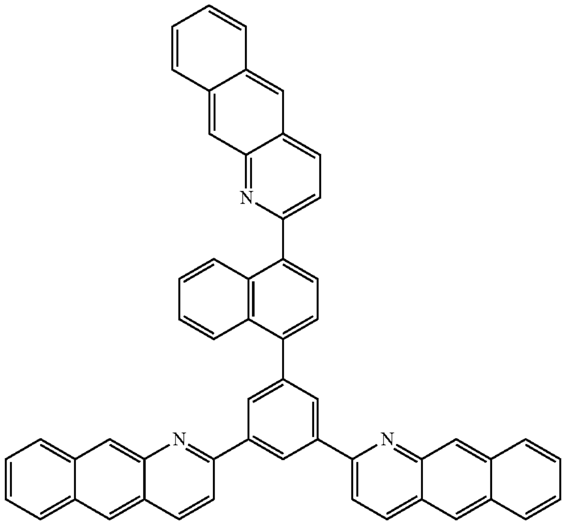
73
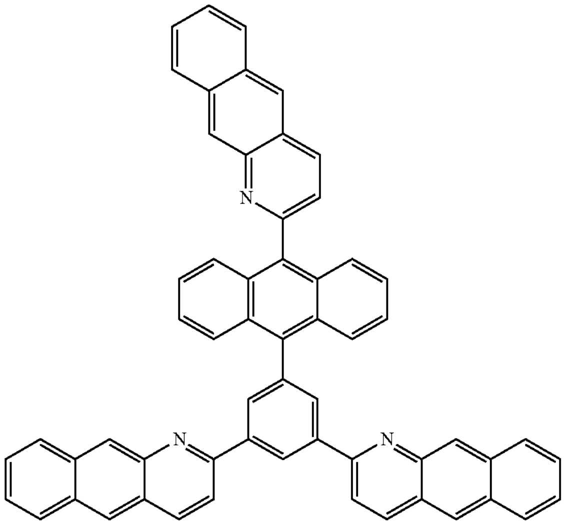
74
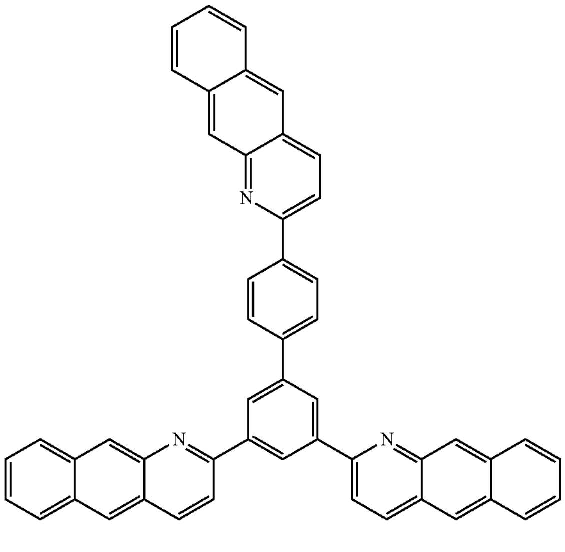
75
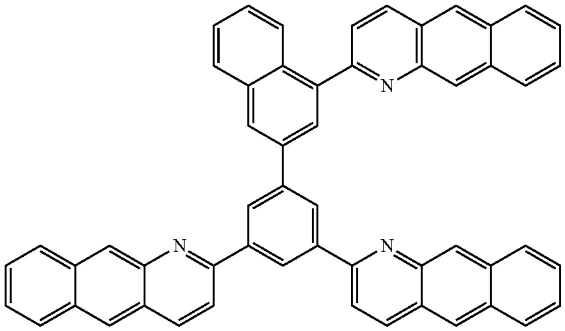
76
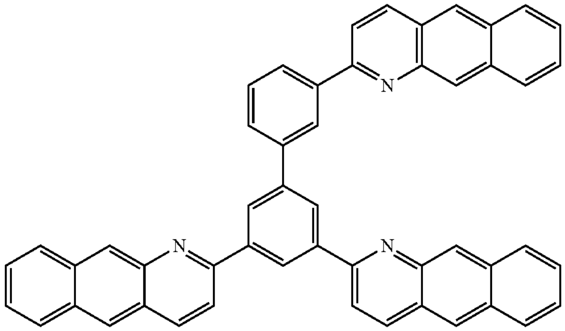
78
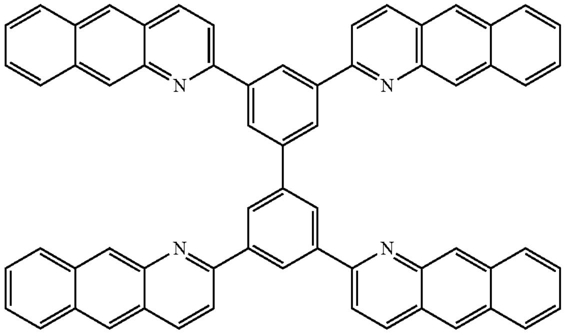

-continued
79
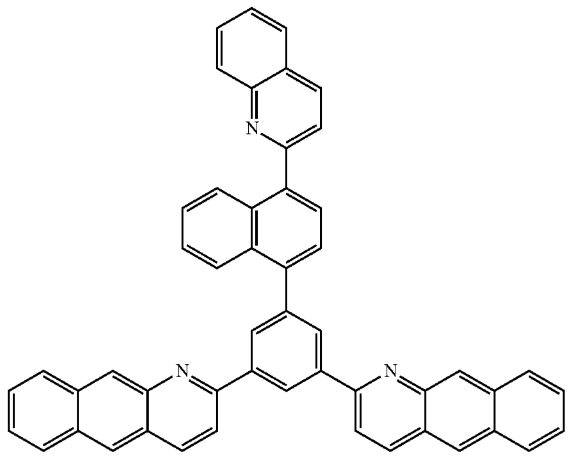
80
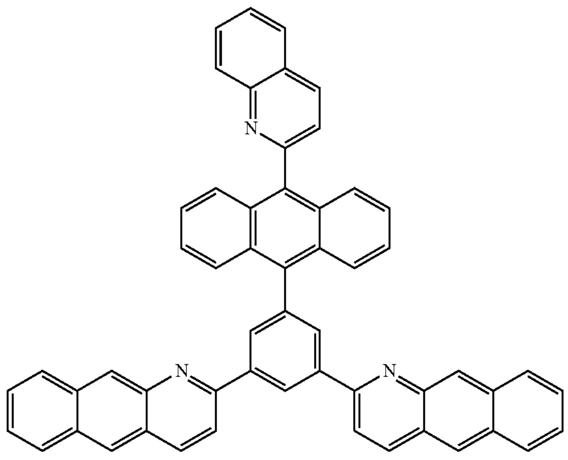
81
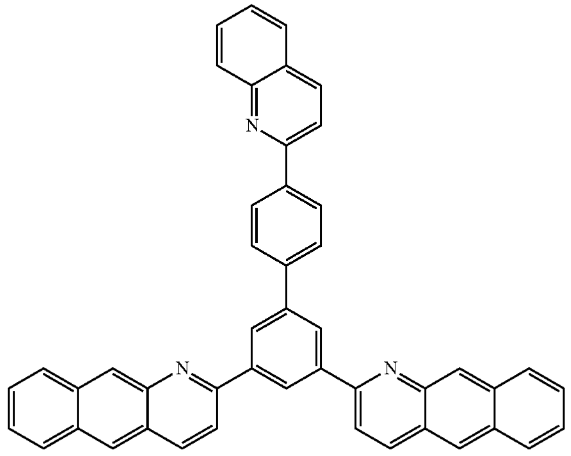
82
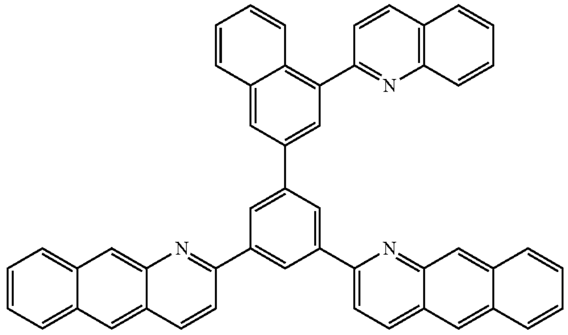
83
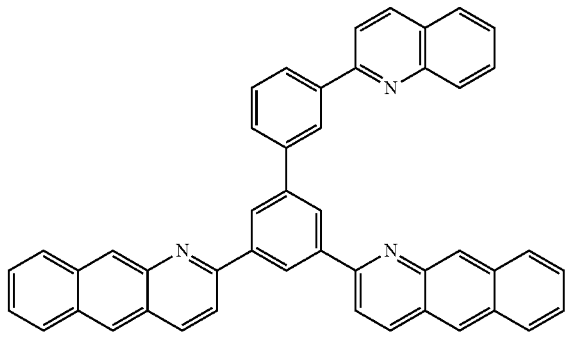
84
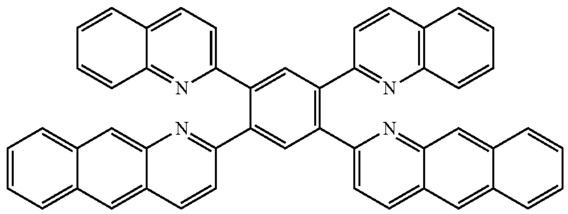

-continued
85
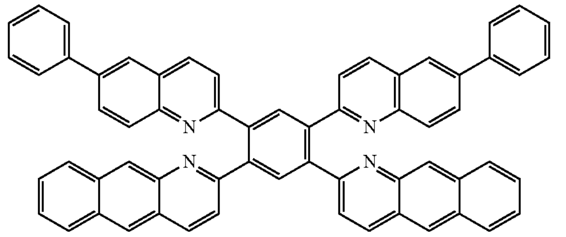
86
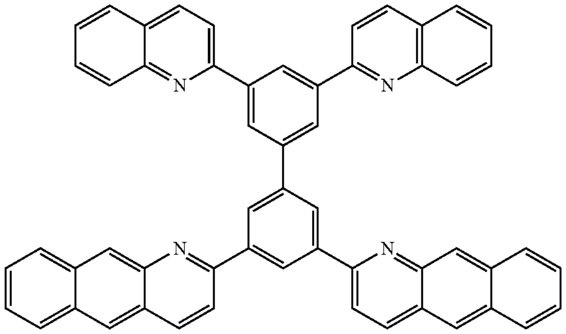
87
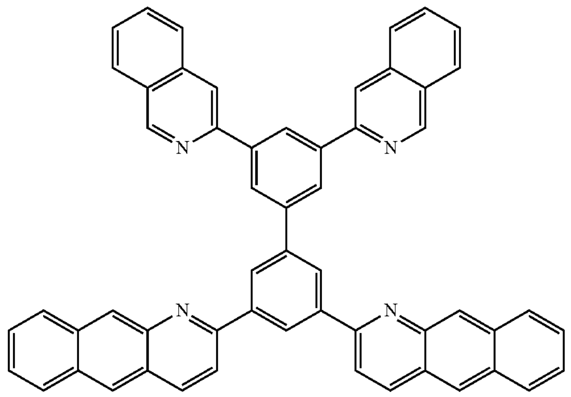
88
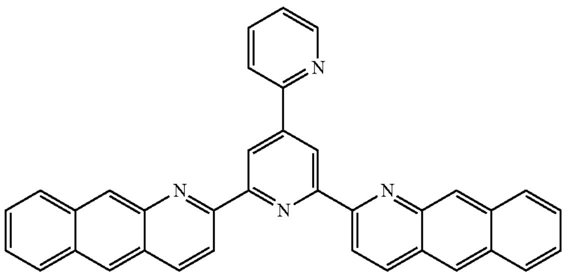
89
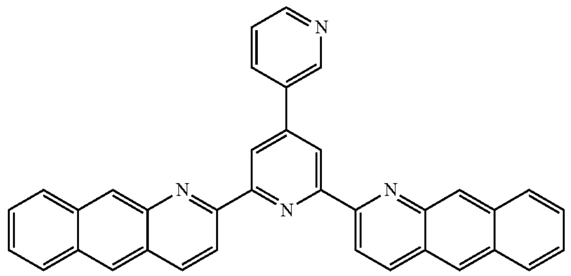
90
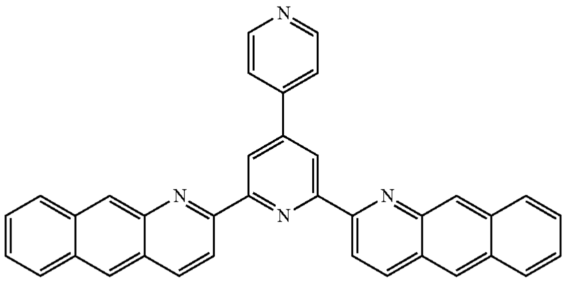
91
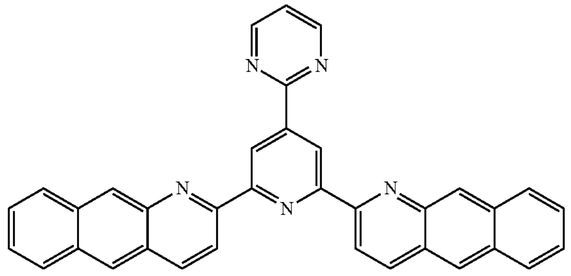
92
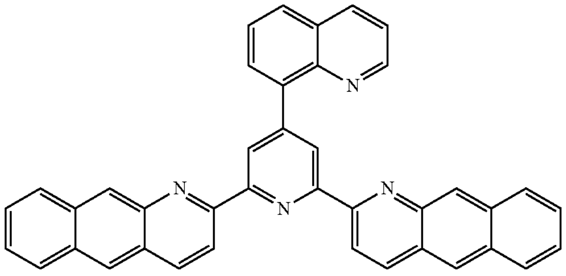

-continued
93
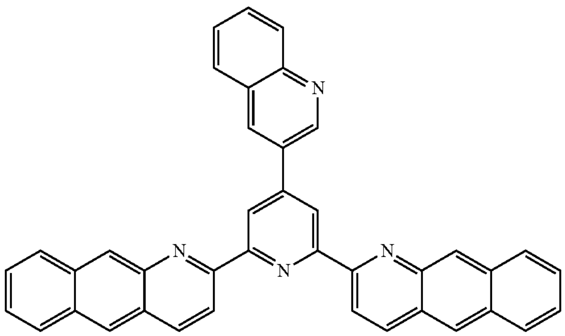
94
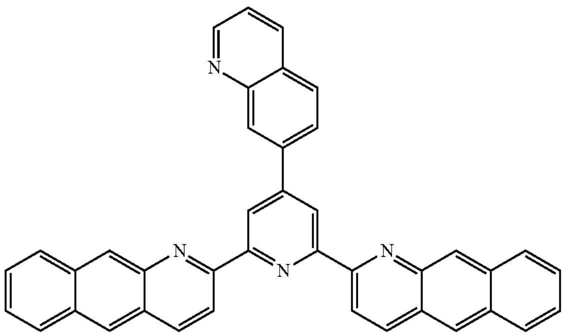
95
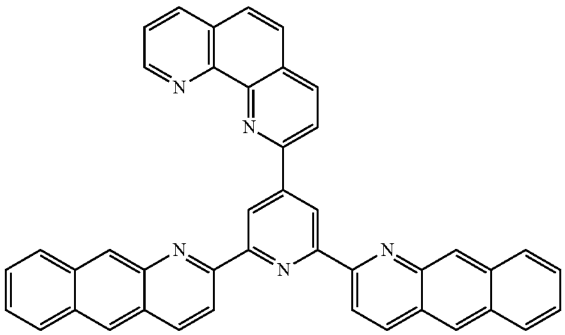
96
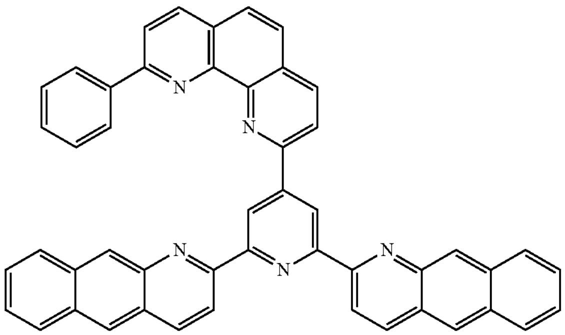
97
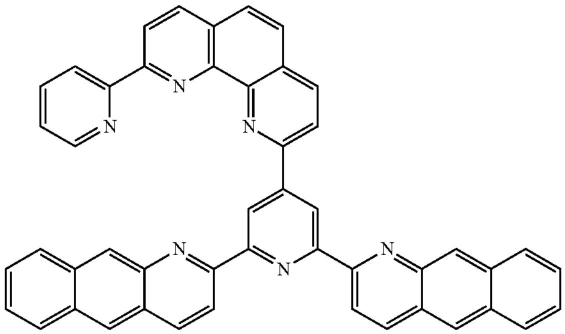
98
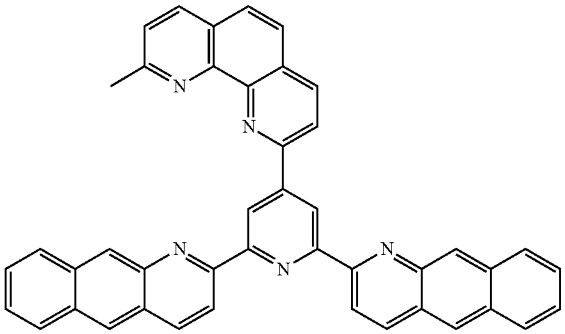
99
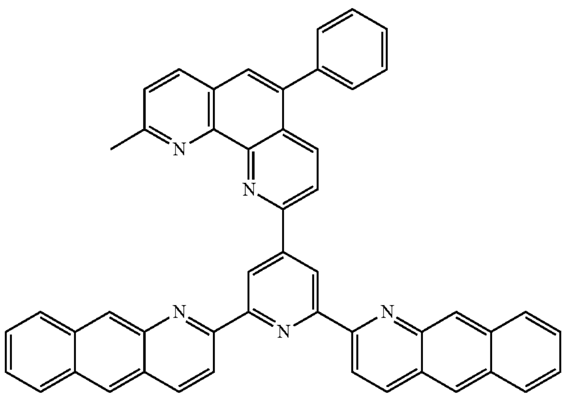
100
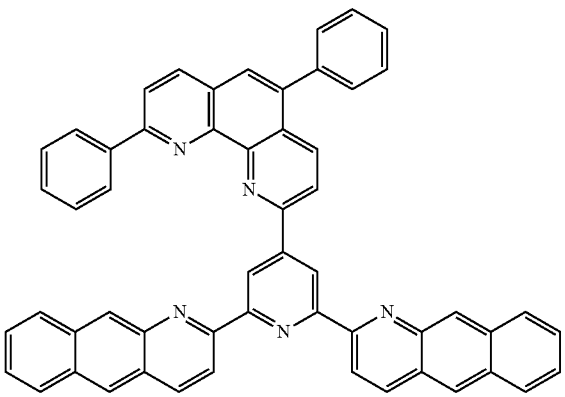

-continued
101
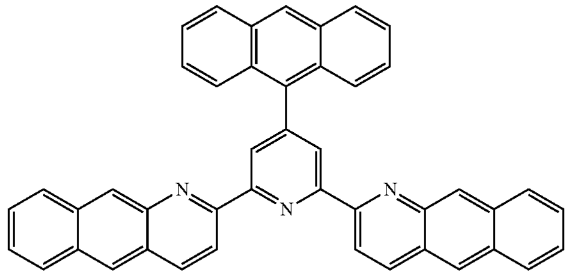
102
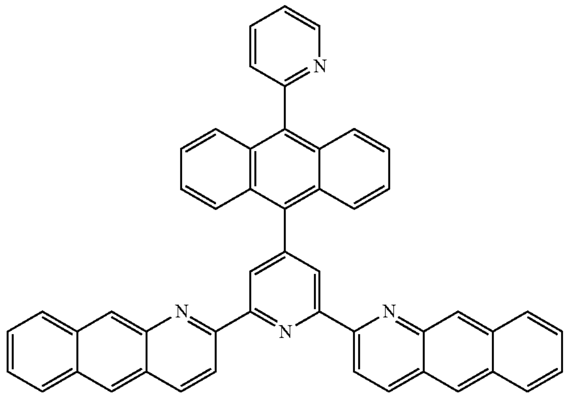
103
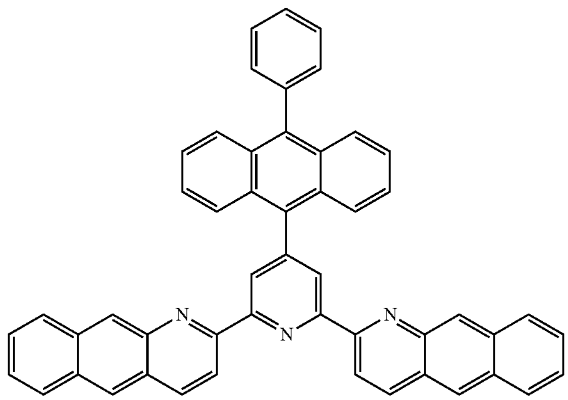
104
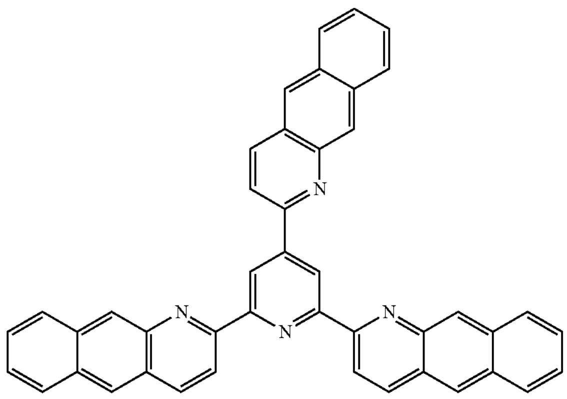
105
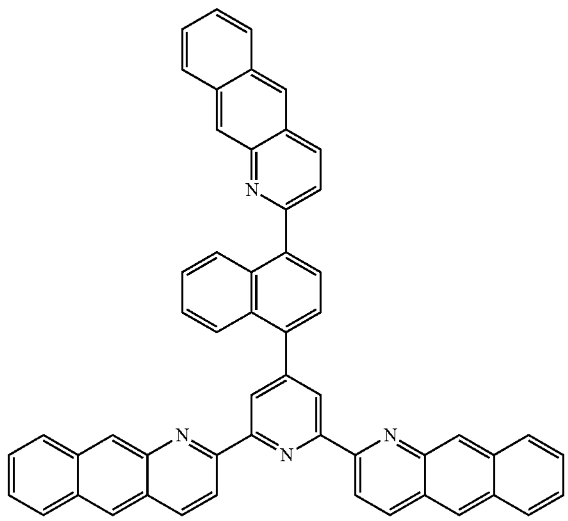
106
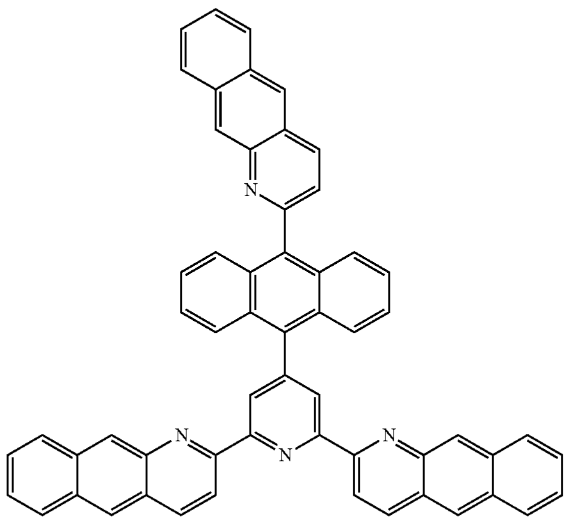

-continued
107
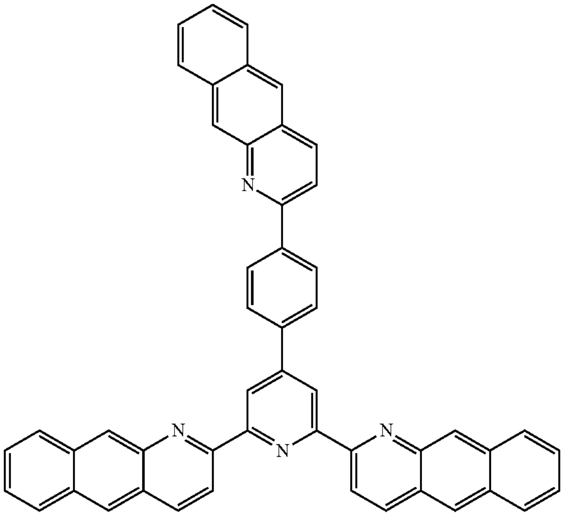
108
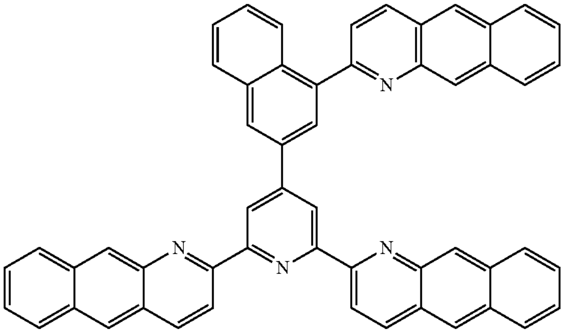
109
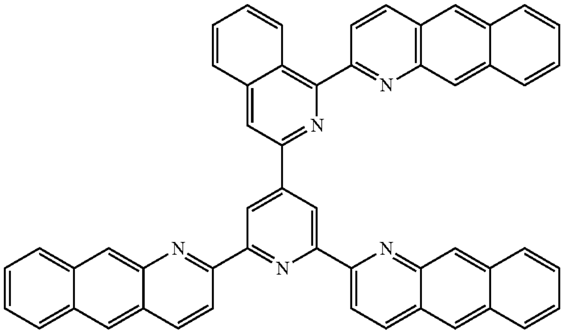
110
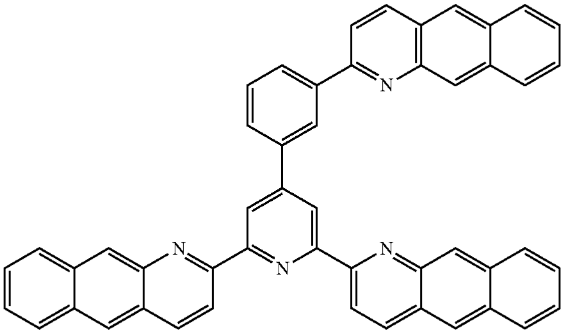
111
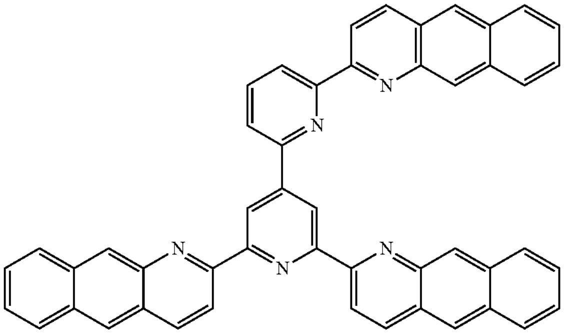
112
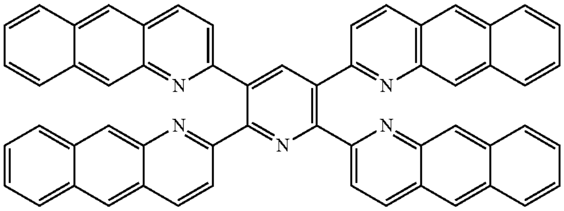
113
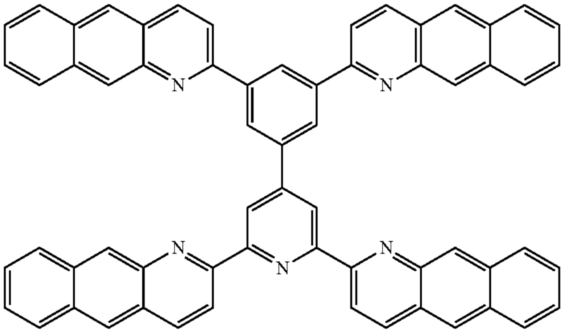
114
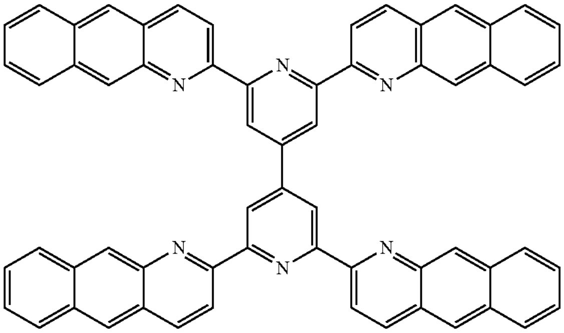

-continued
115
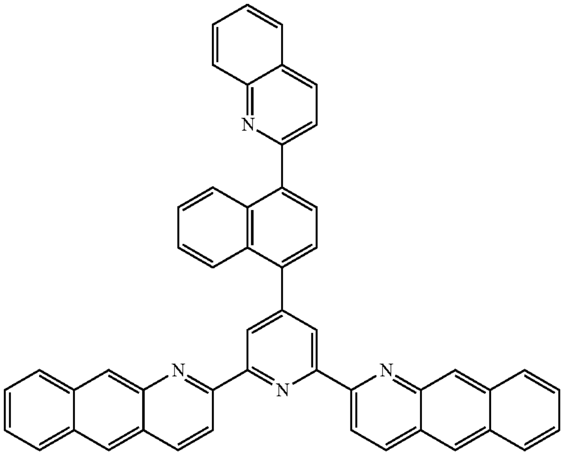
116
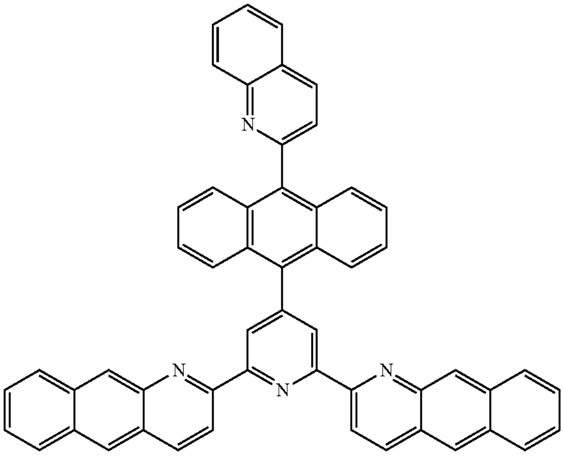
117
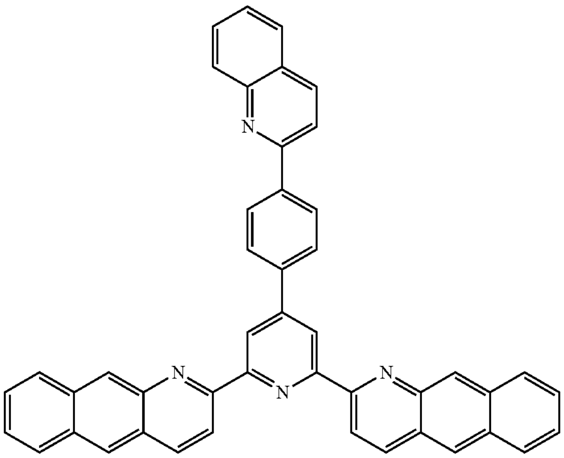
118
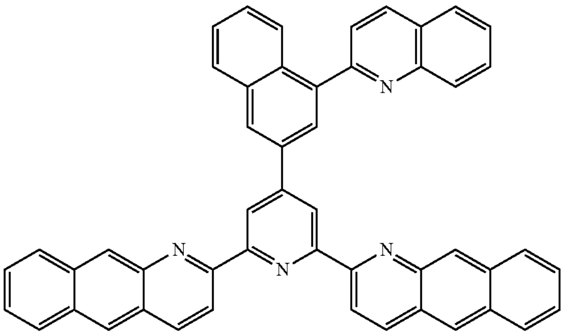
119
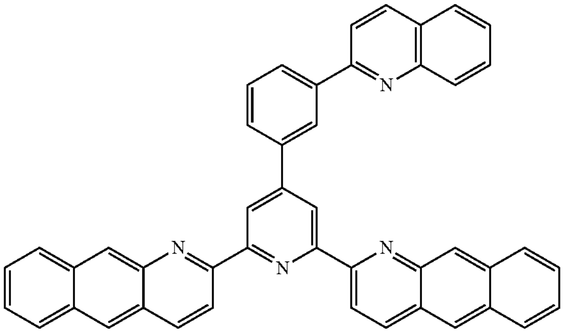
120
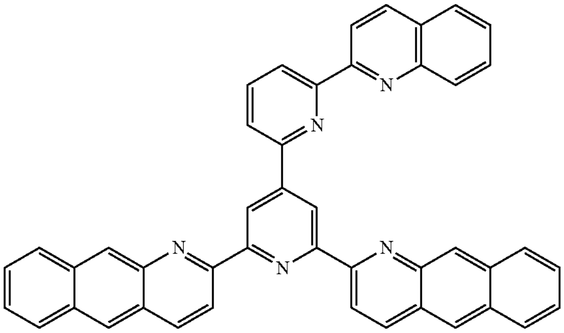
121
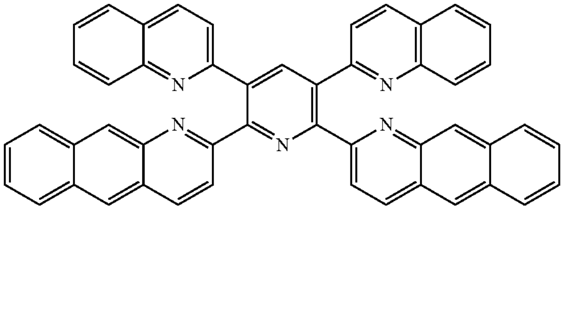
123
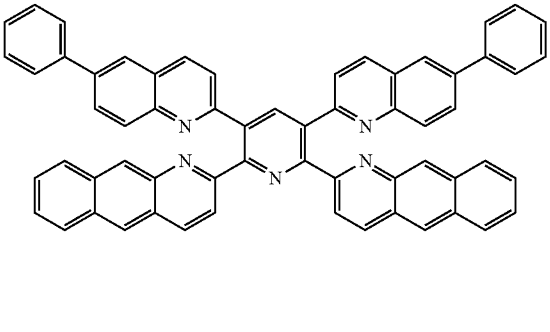

-continued
124
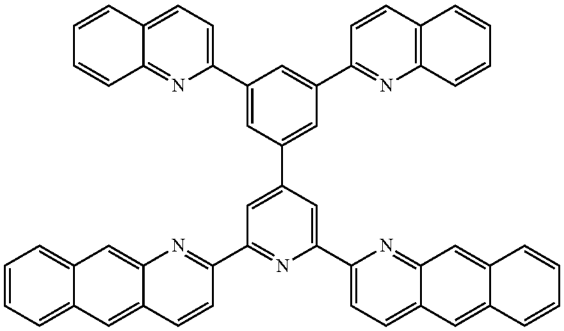
125
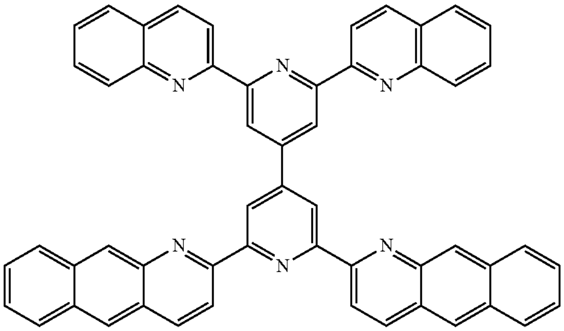
126
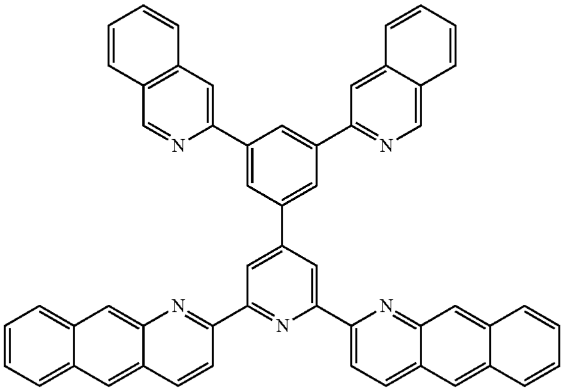
127
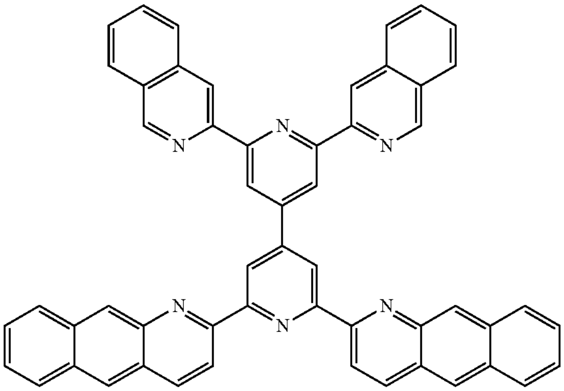
128
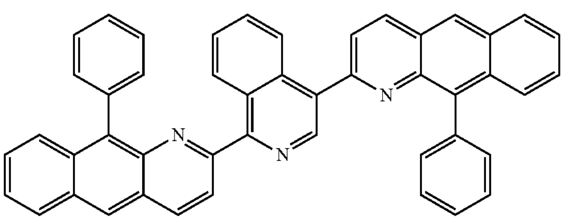
129
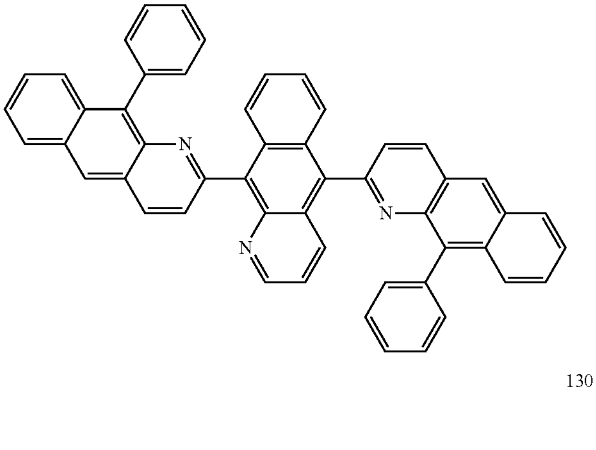
130
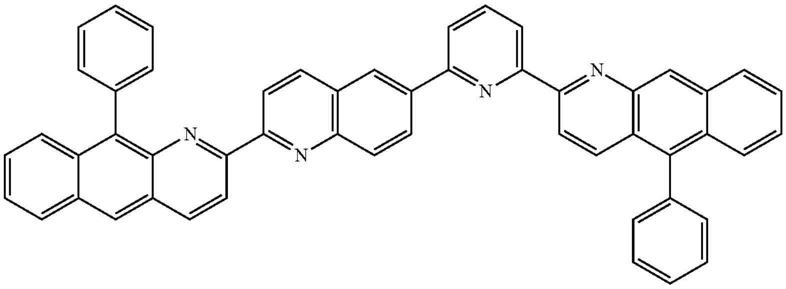

-continued
131
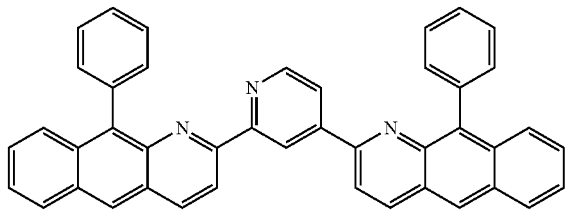
132
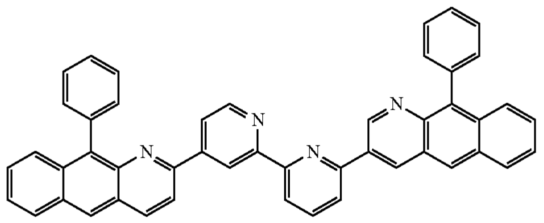
133
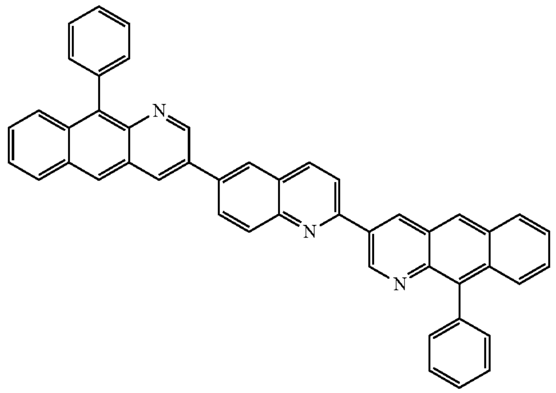
134
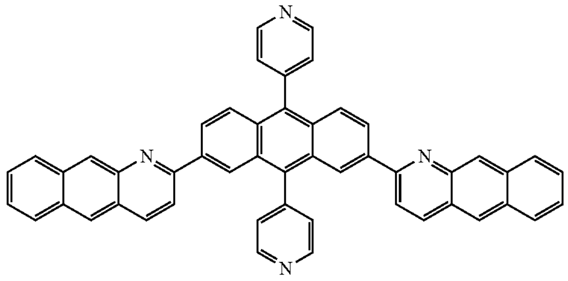
135
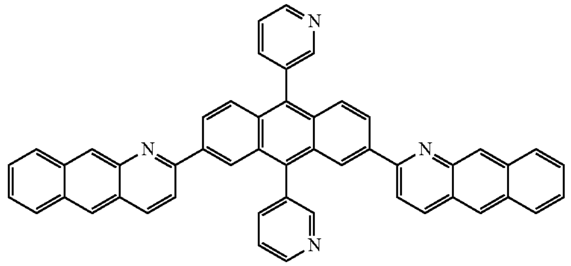
136
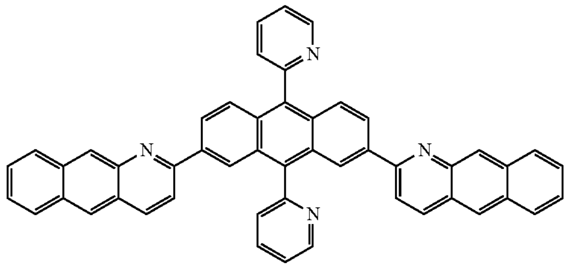
137
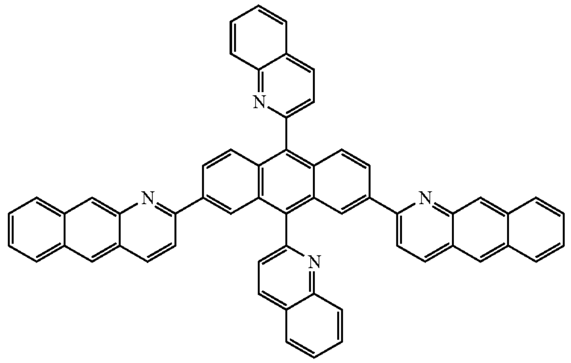
138
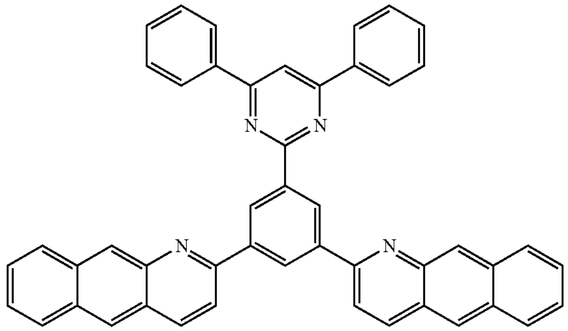

-continued
139
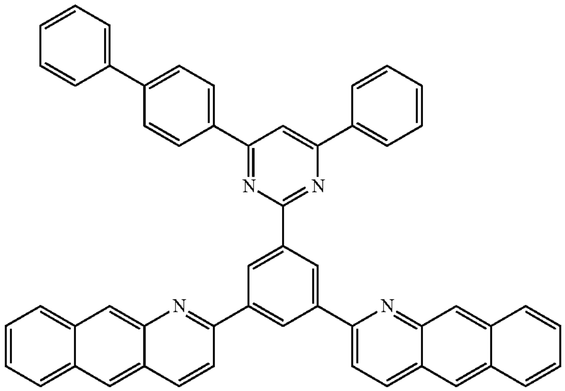
140
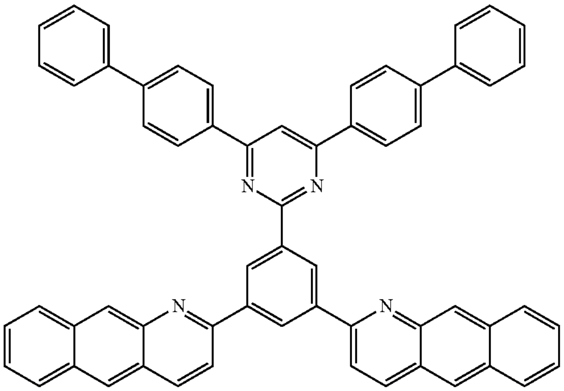
141
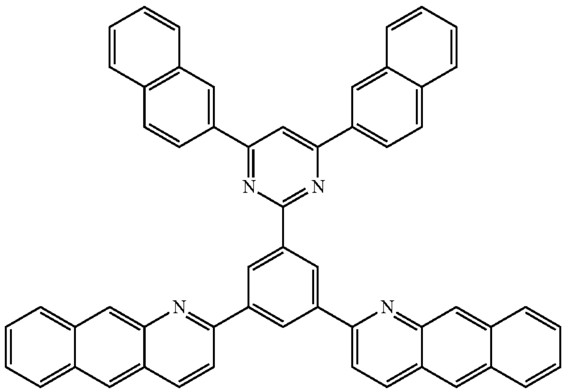
142
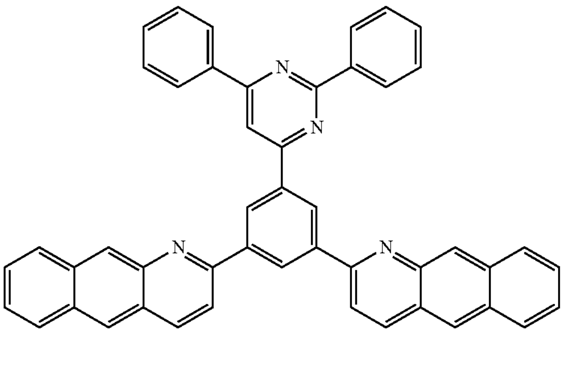
143
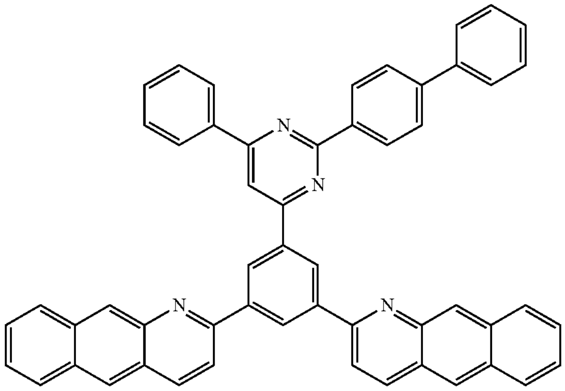
144
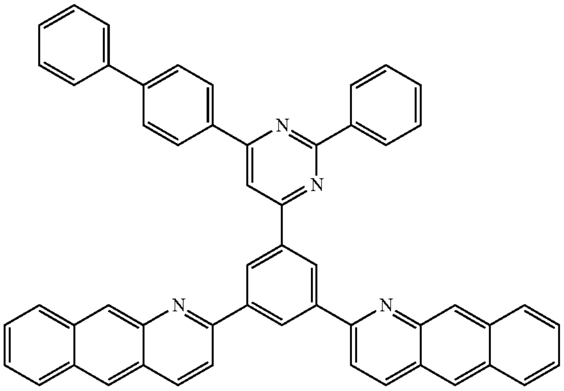
145
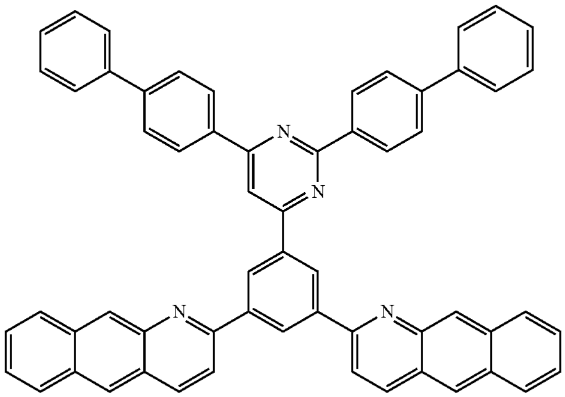
146
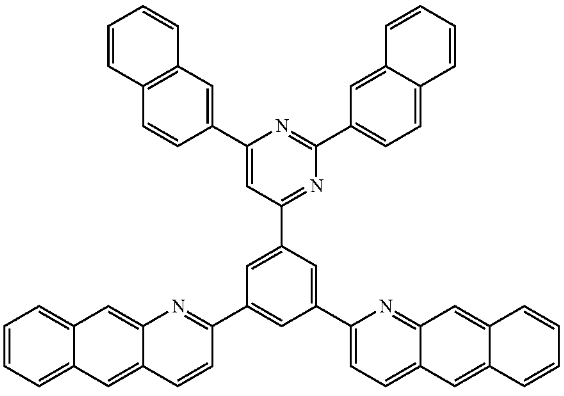

-continued
147
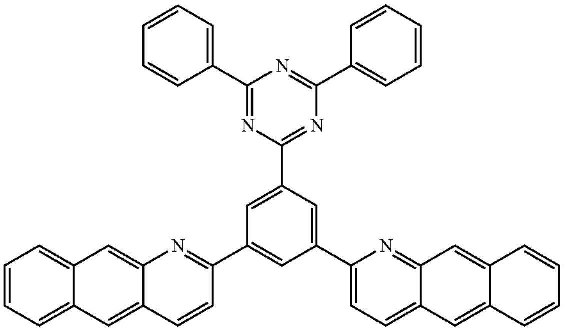
148
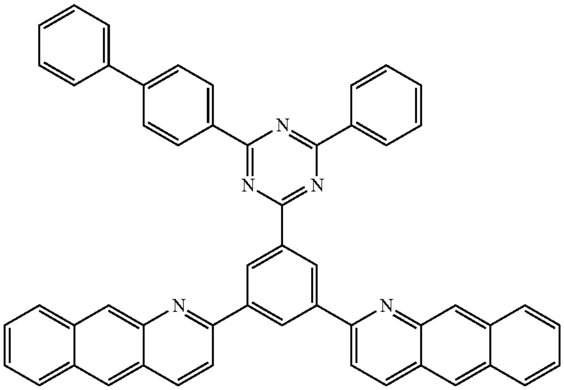
149
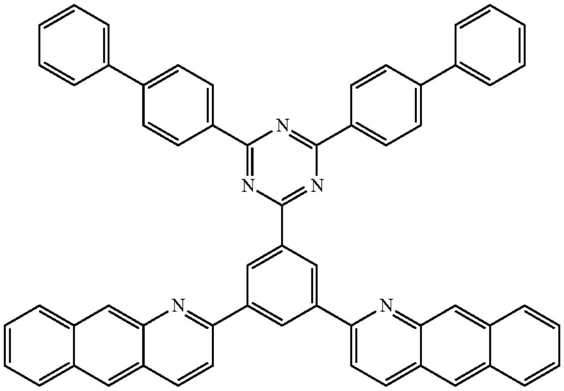
150
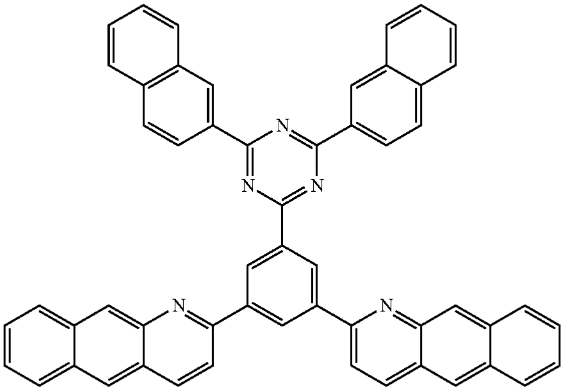
151
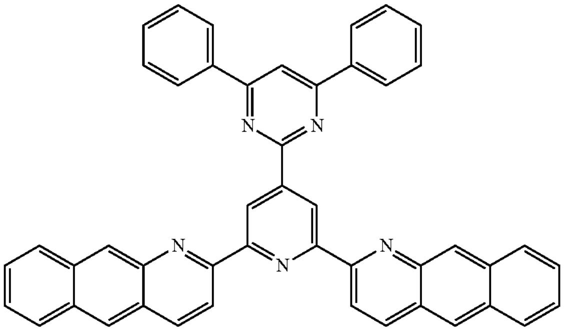
152
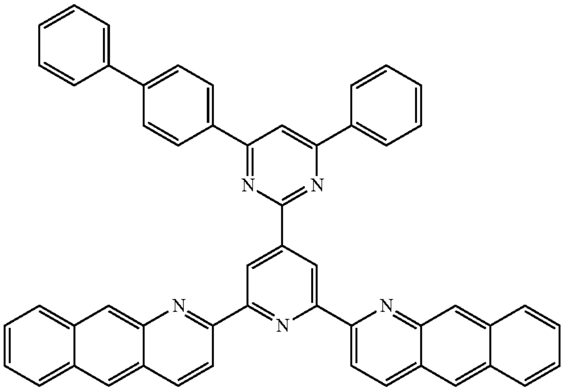
153
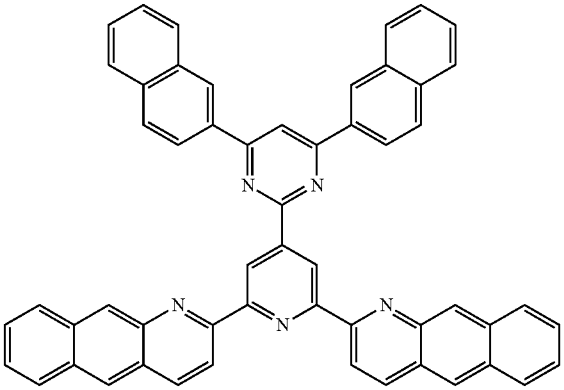
154
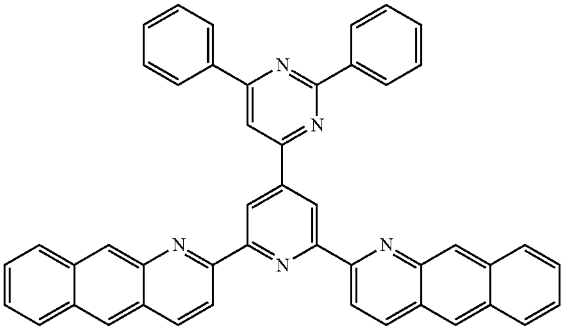

-continued
155
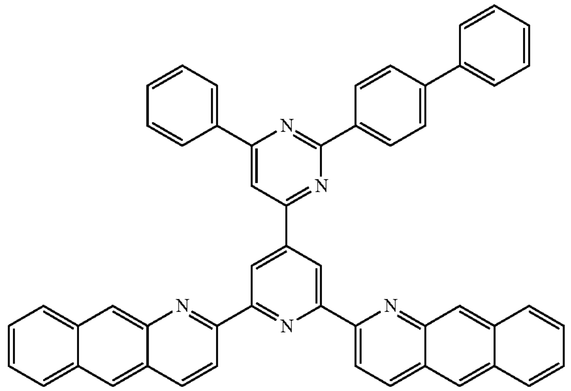
156
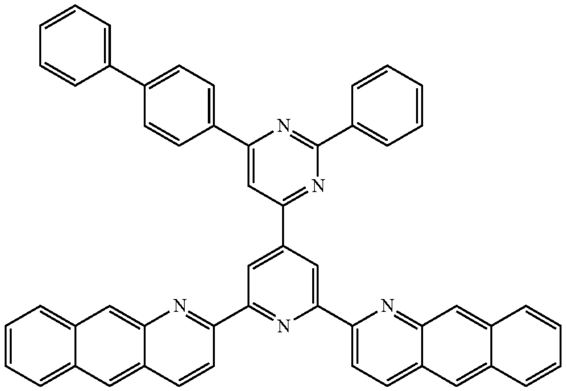
157
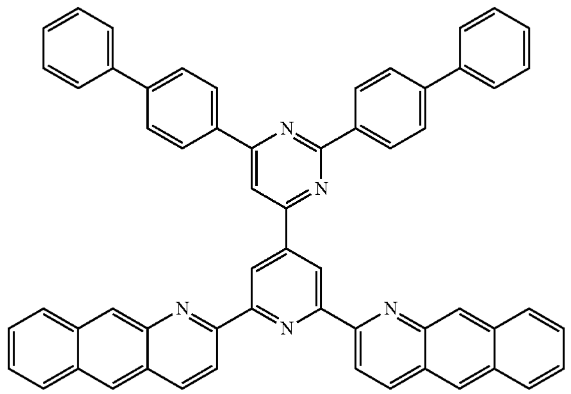
158
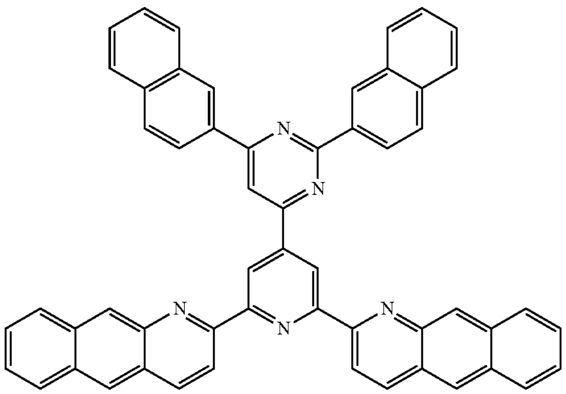
159
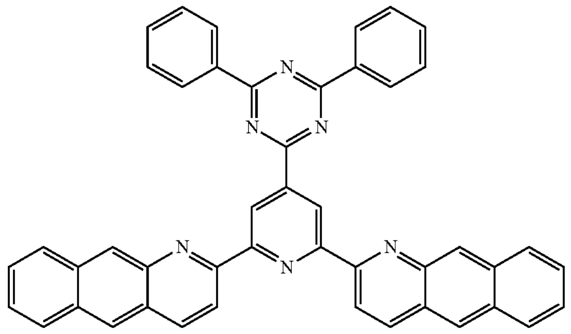
160
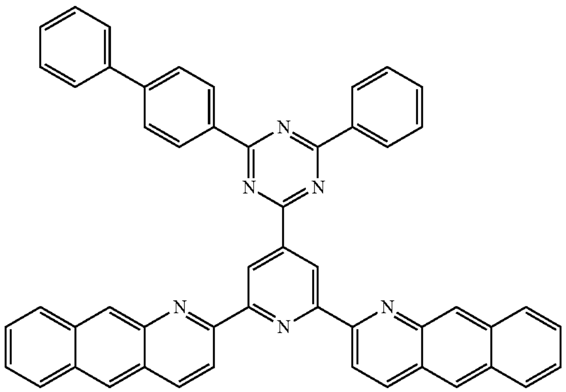
161
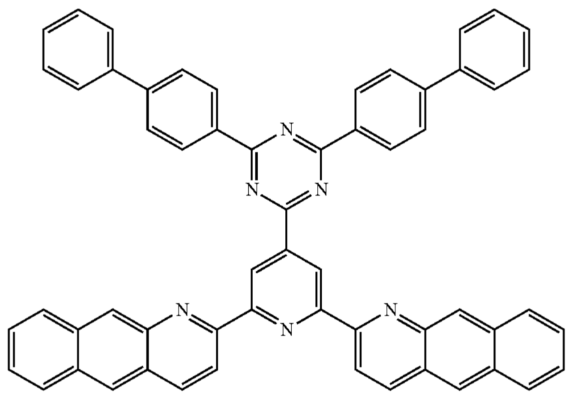
162
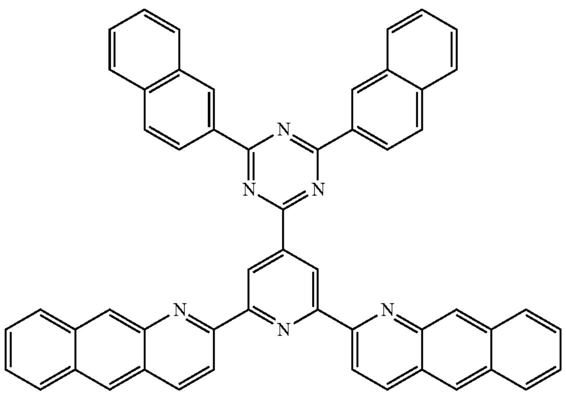

-continued
163
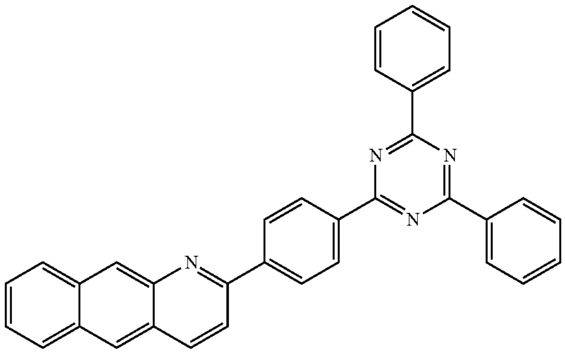
164
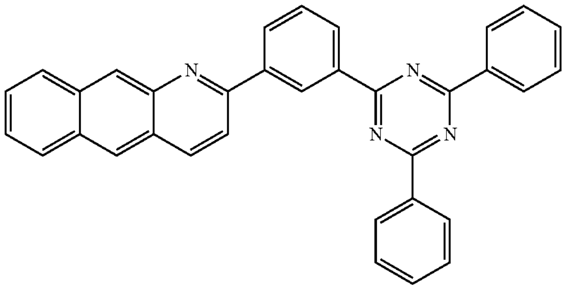
165
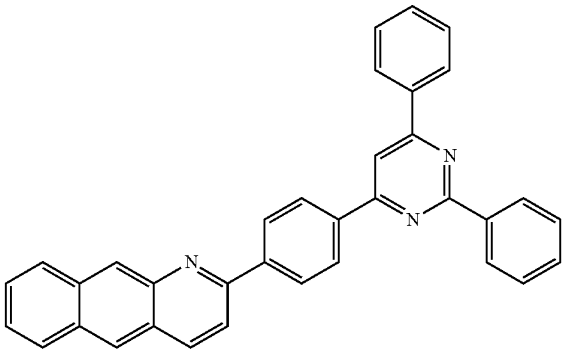
166
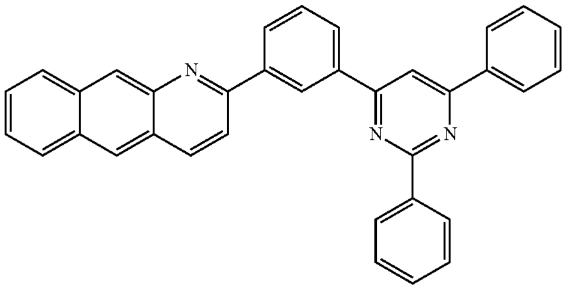
167
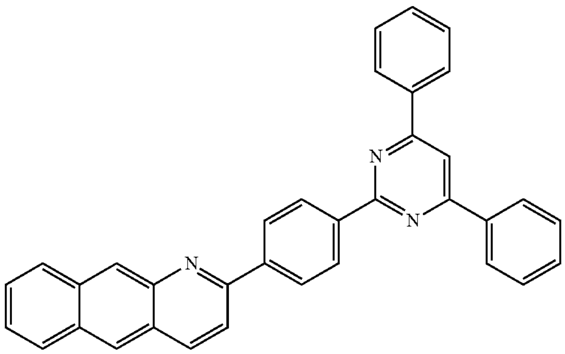
168
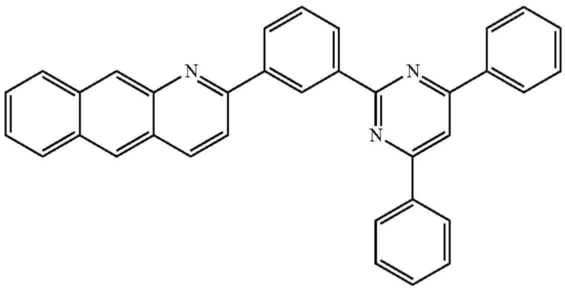
169
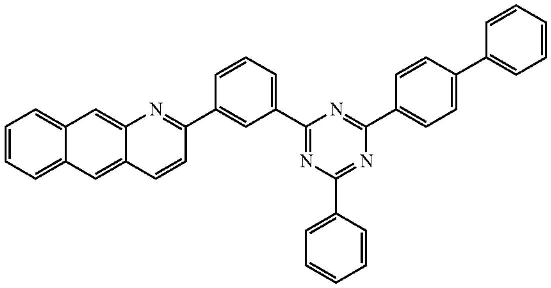
170
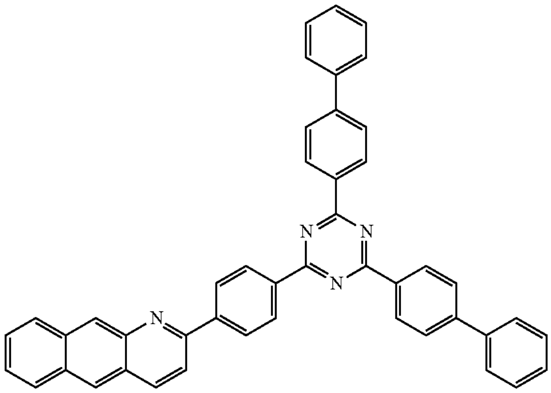

-continued
171
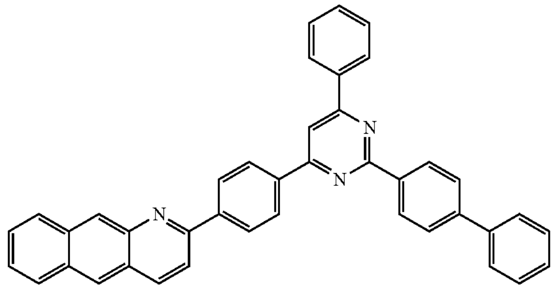
172
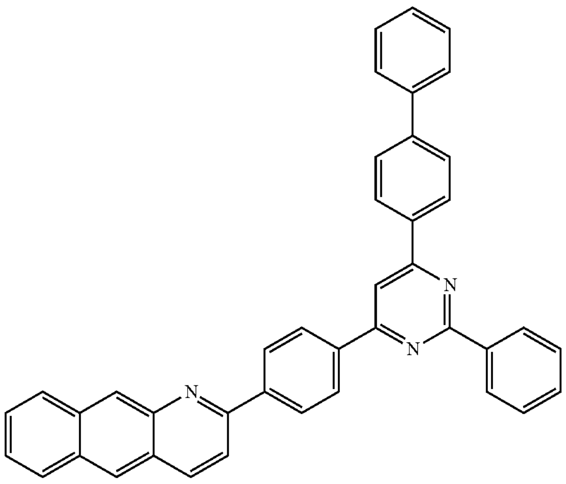
173
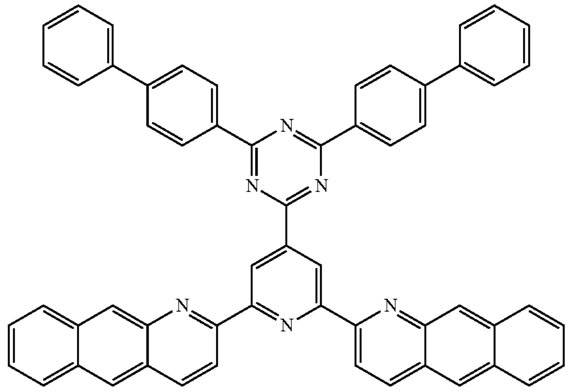
174
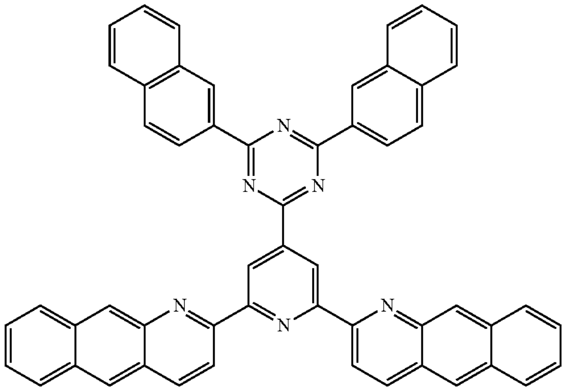
175
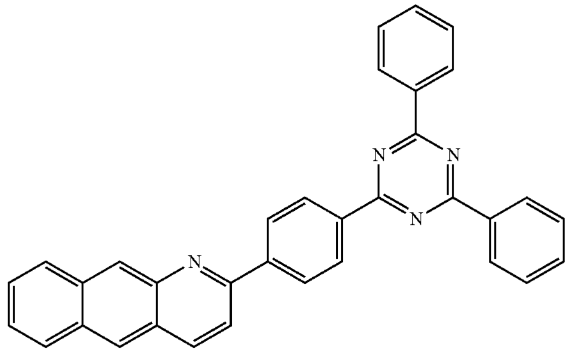
176
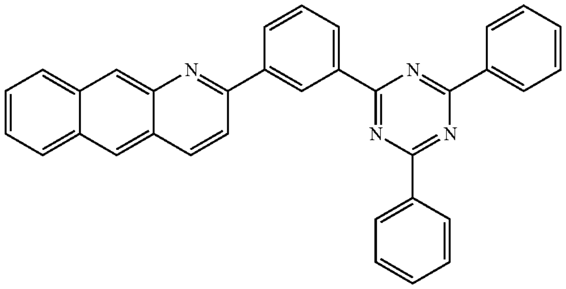

-continued
177
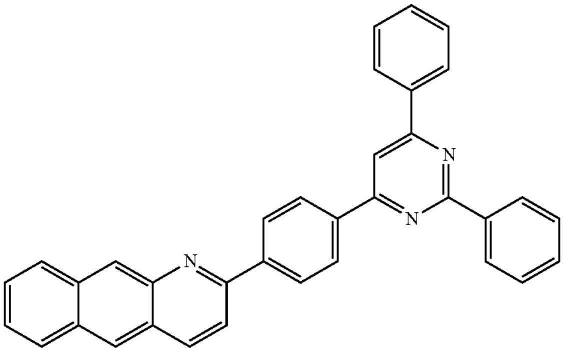
178
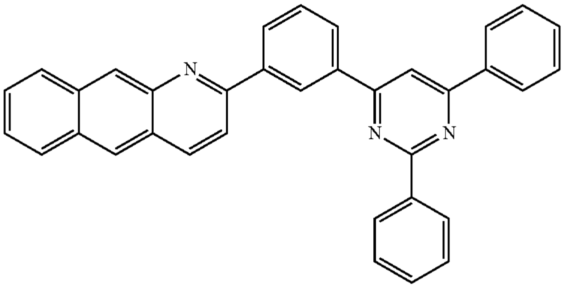
179
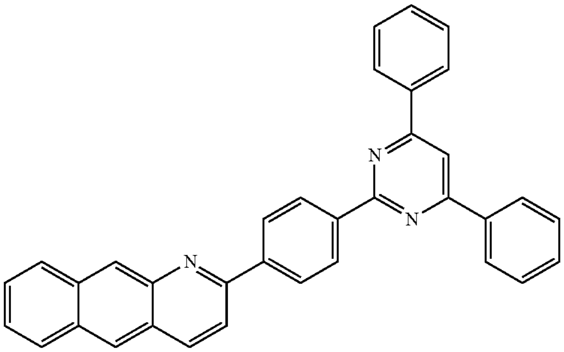
180
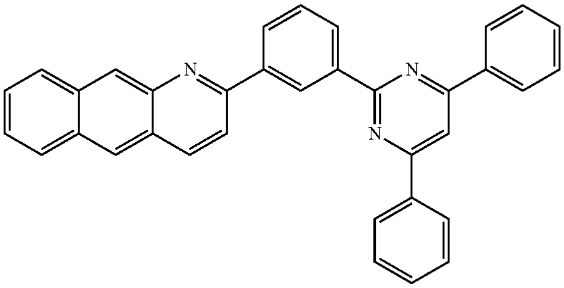
181
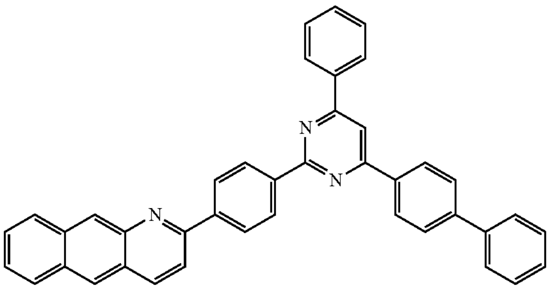
182
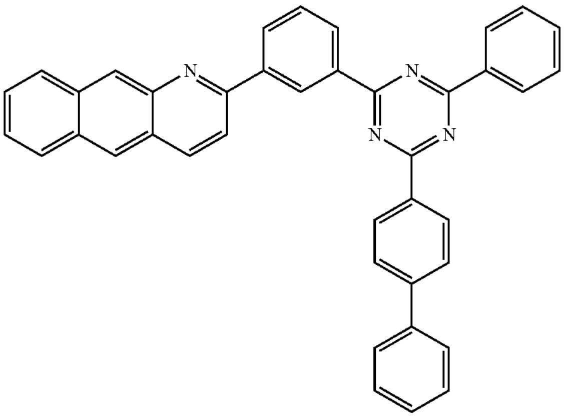
183
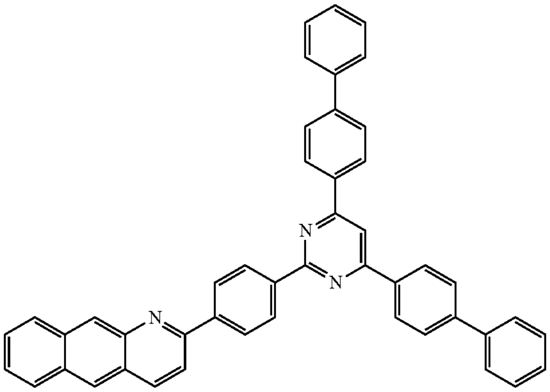
184
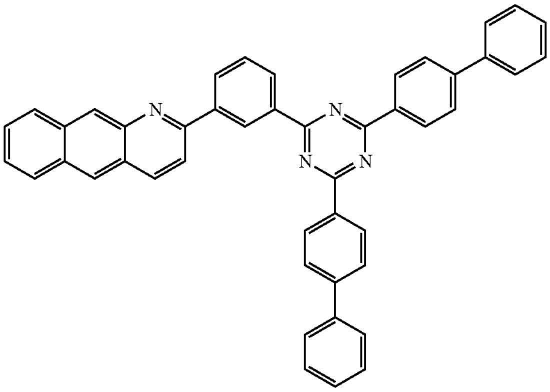

-continued
185
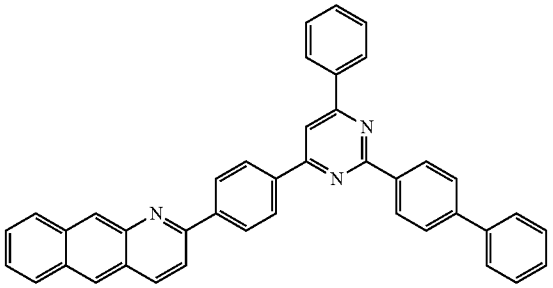
186
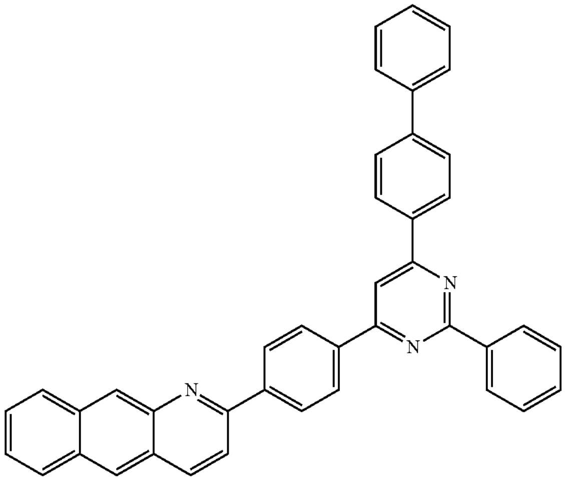
187
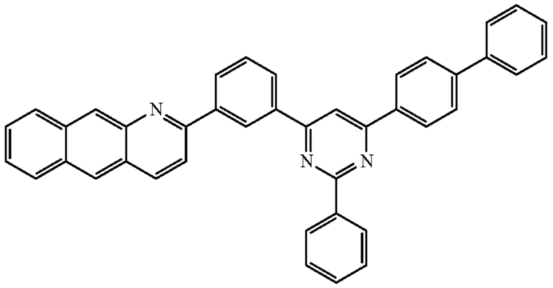
188
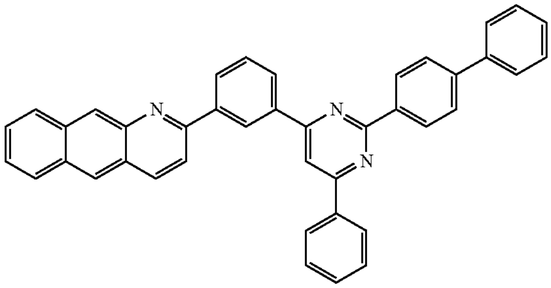
189
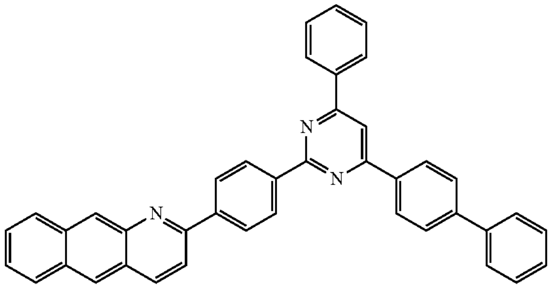
190
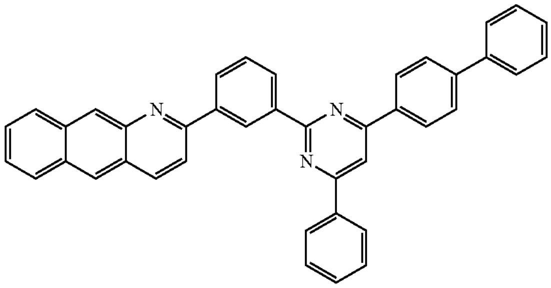
191
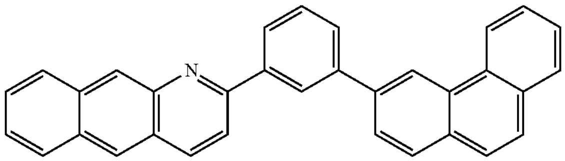
192
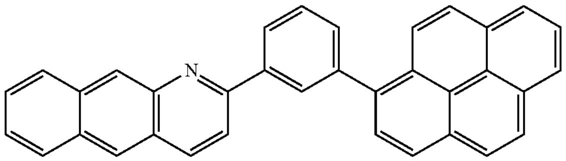
193
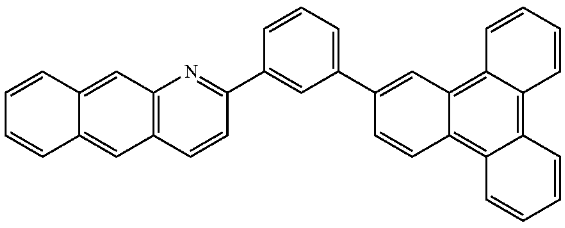
194
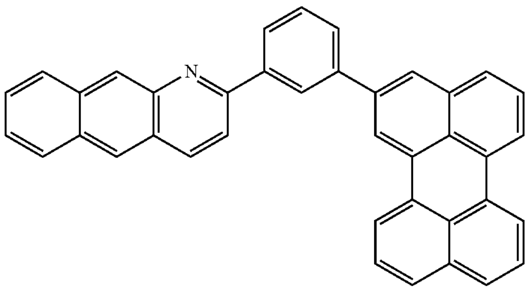

-continued
195
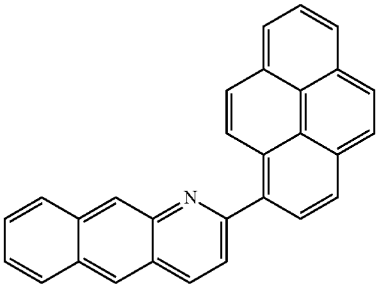
196
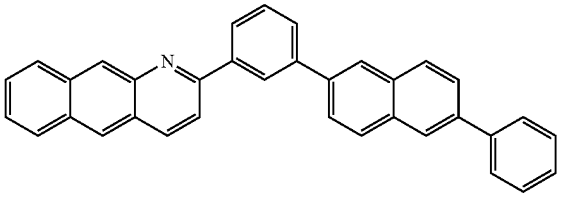
197
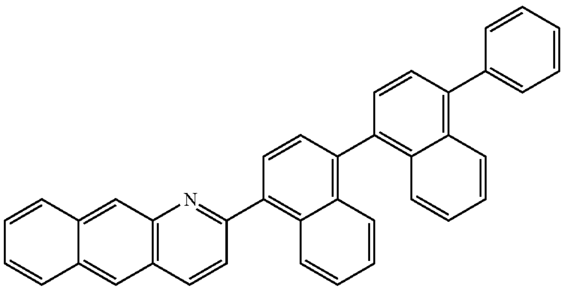
198
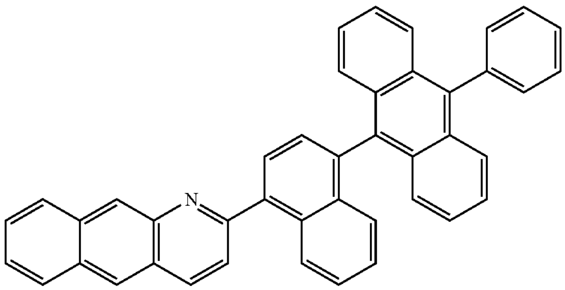
199
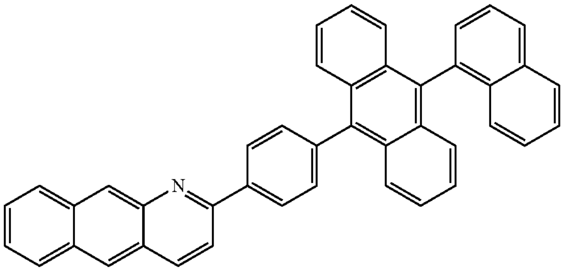
200
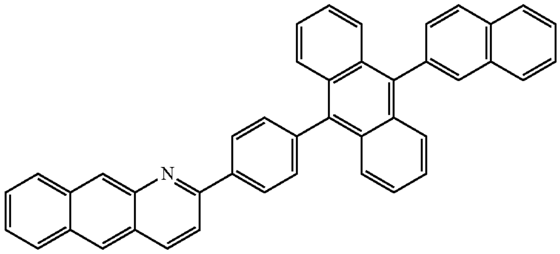
201
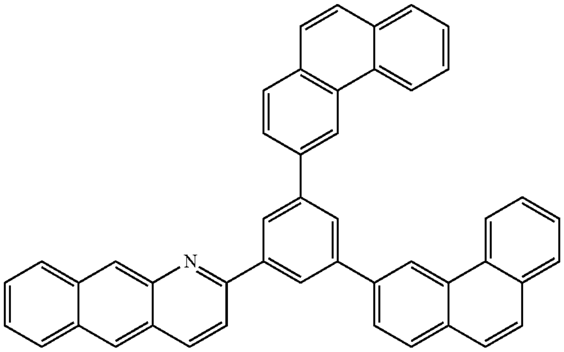
202
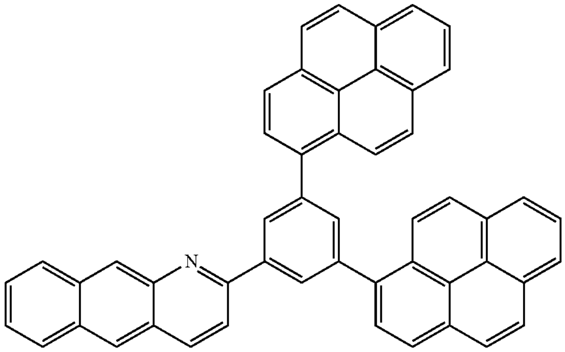

-continued
203
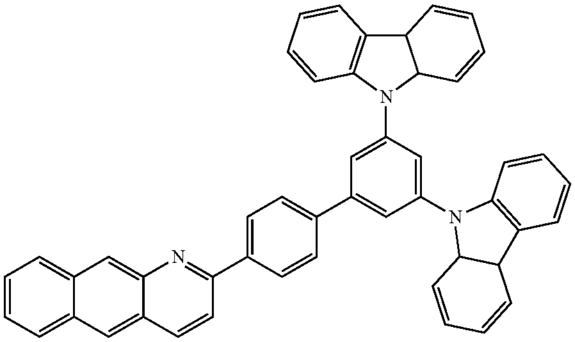
204
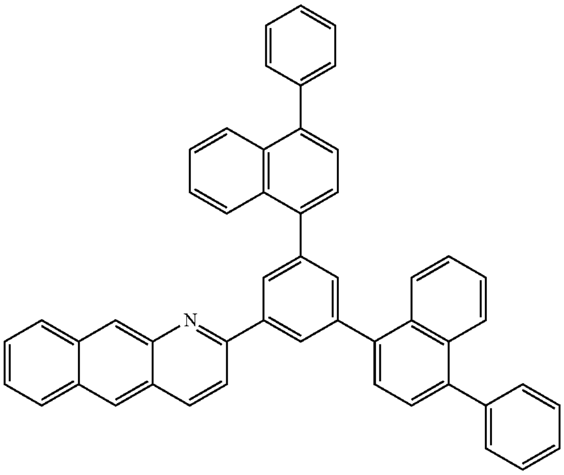
205
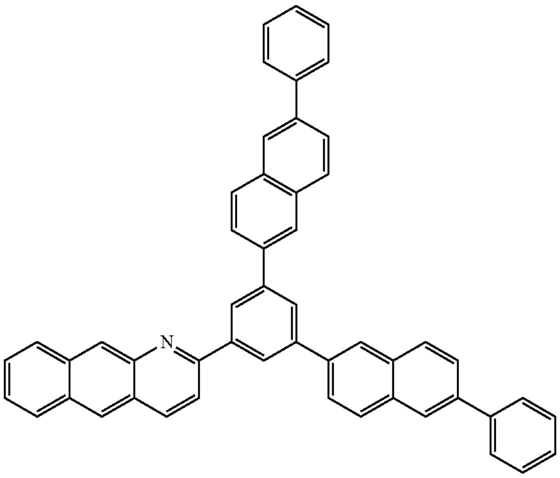
206
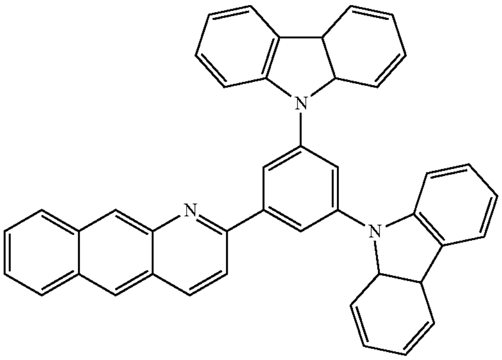
208
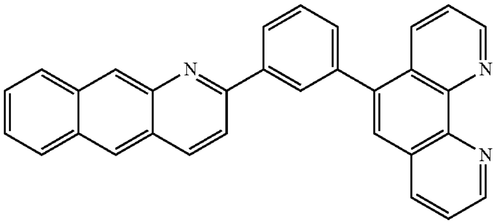
209
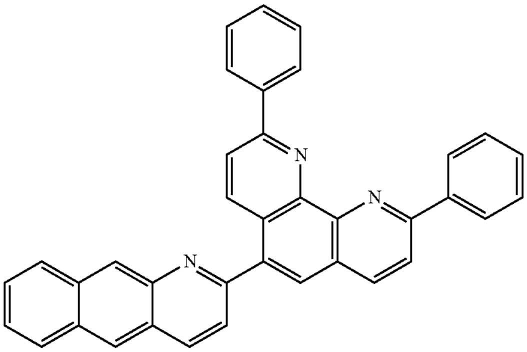

-continued
210
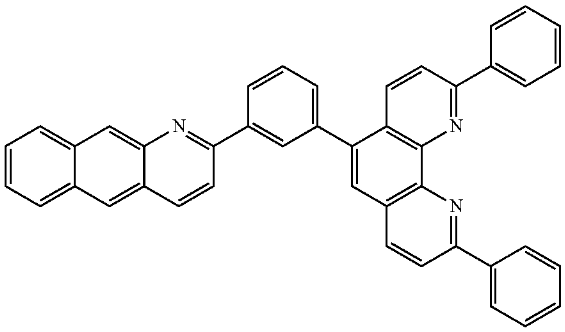
211
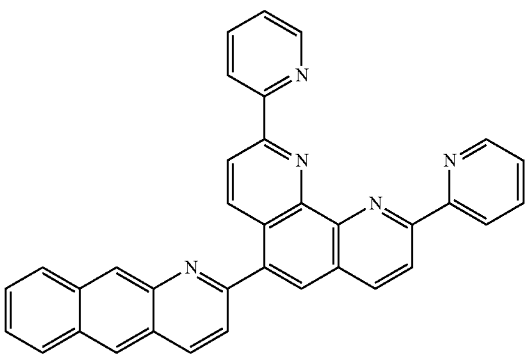
213
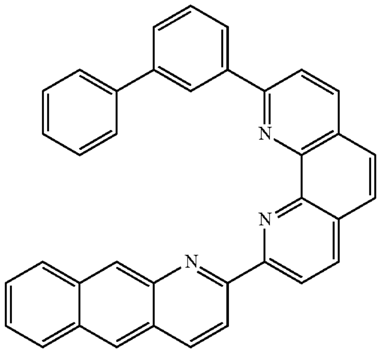
214
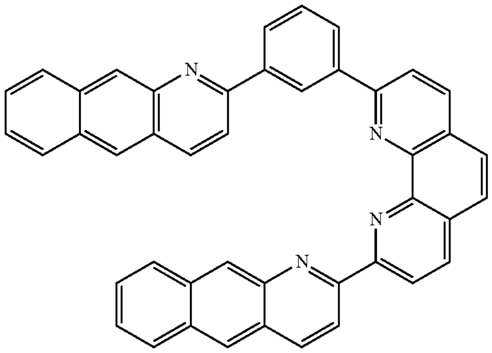
215
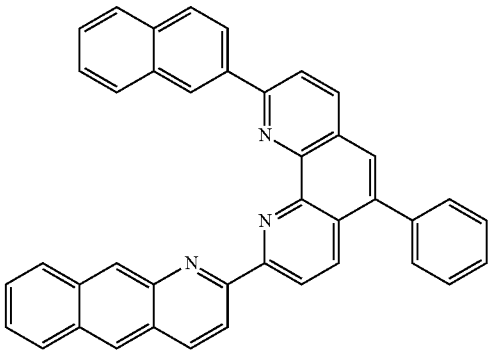
216
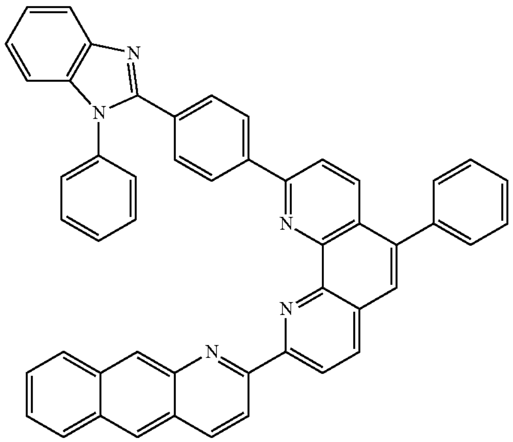
217
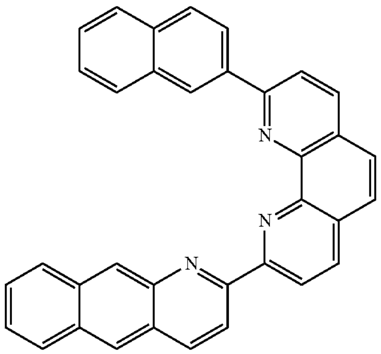
218
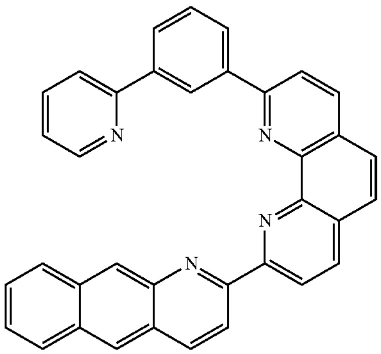

-continued
219
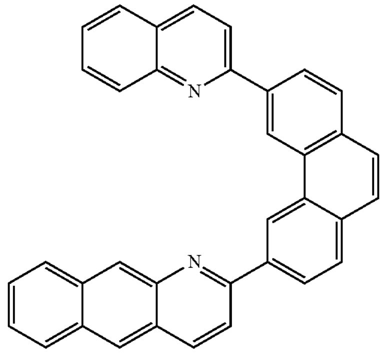
220
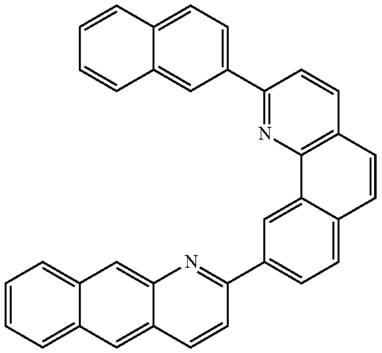
221
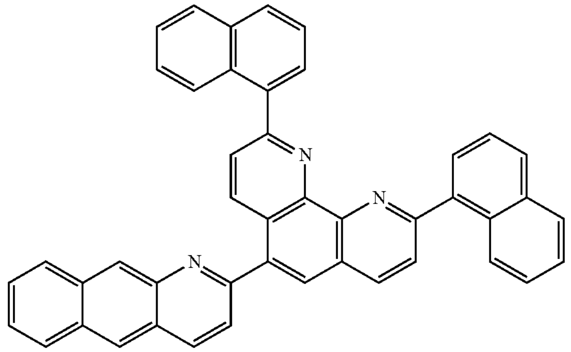
222
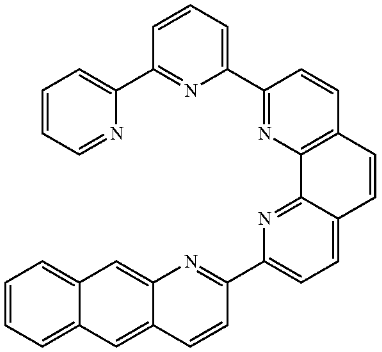
223
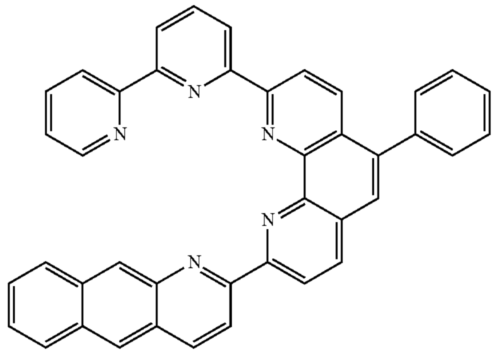
224
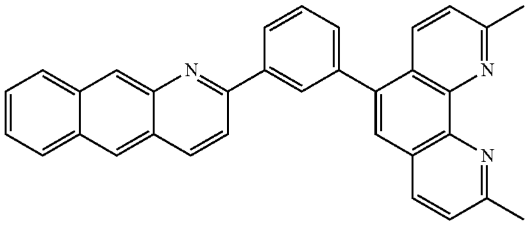
225
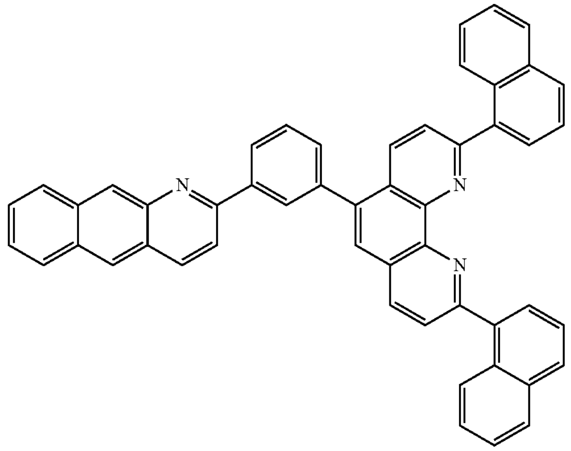
226
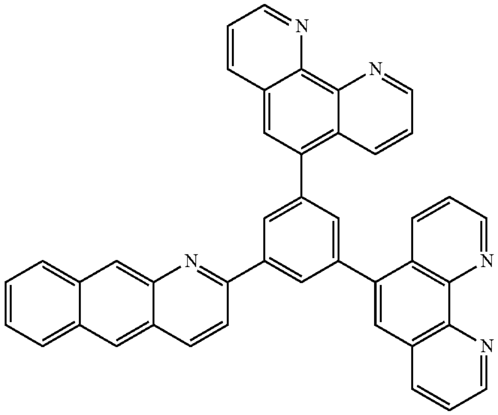

-continued
227
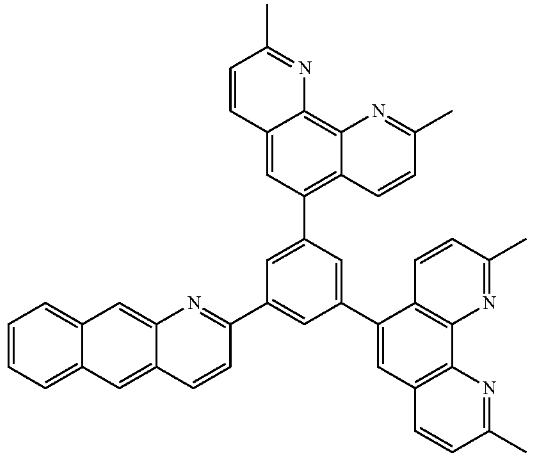
228
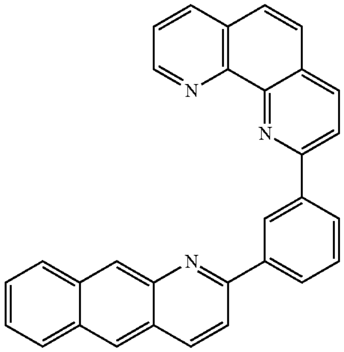
229
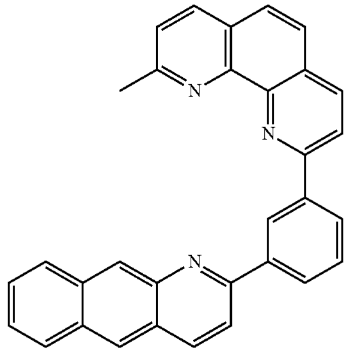
230
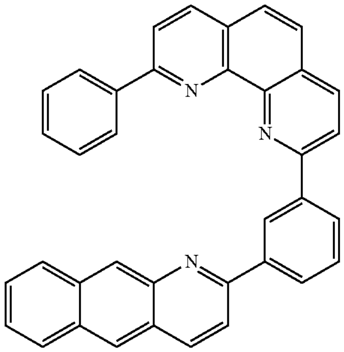
231
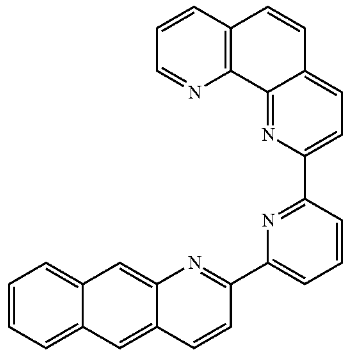
232
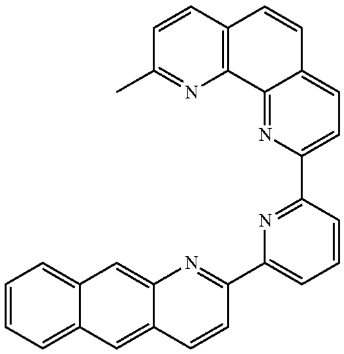
233
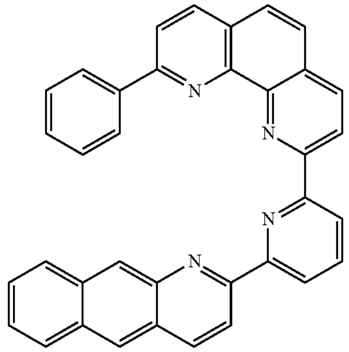
234
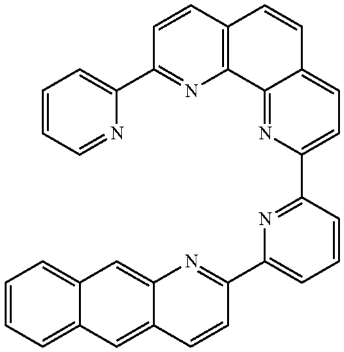

-continued
235
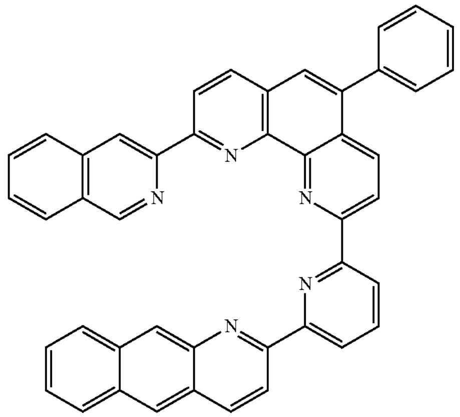
236
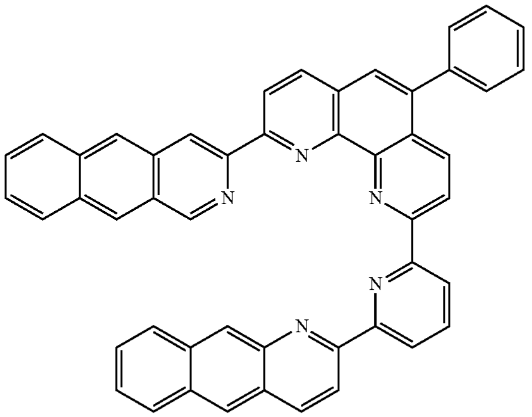
237
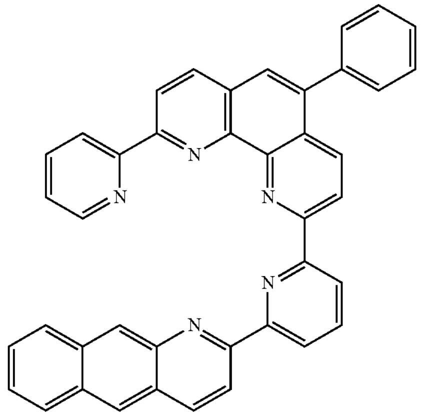
238
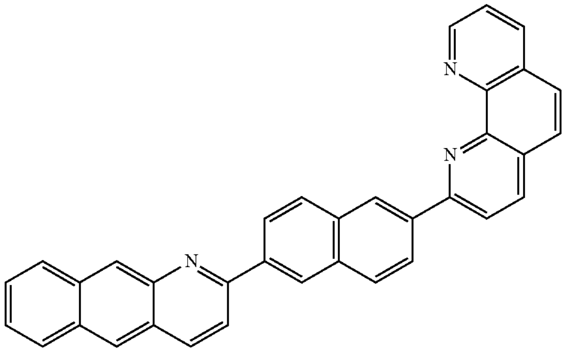
239
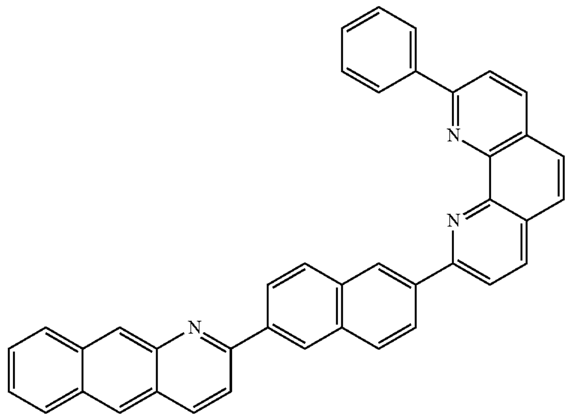
240
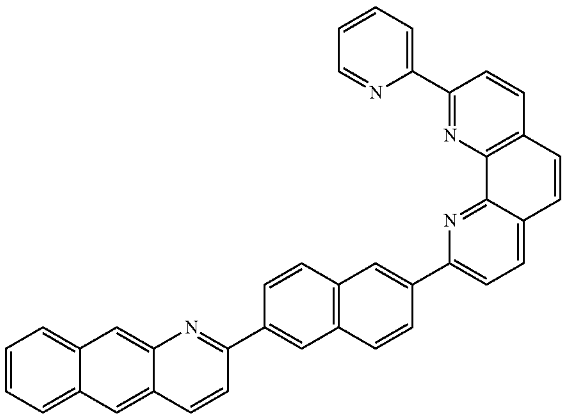

-continued
241
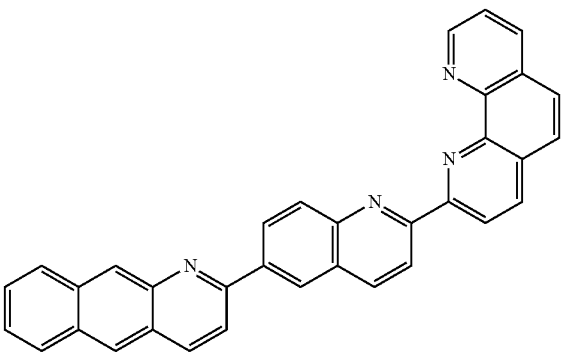
242
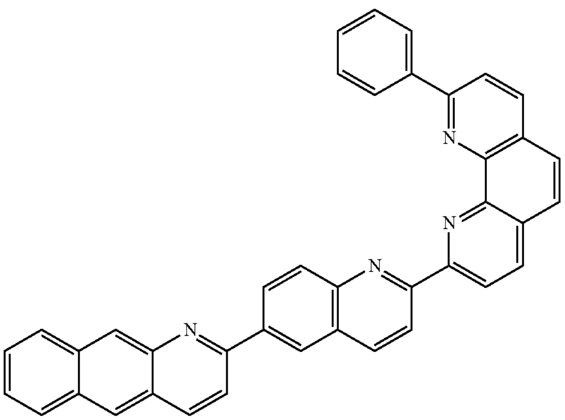
243
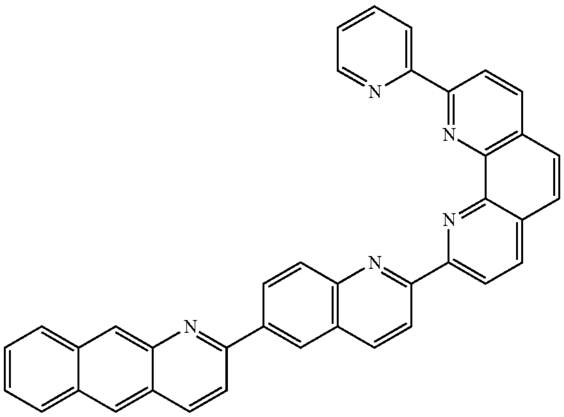
244
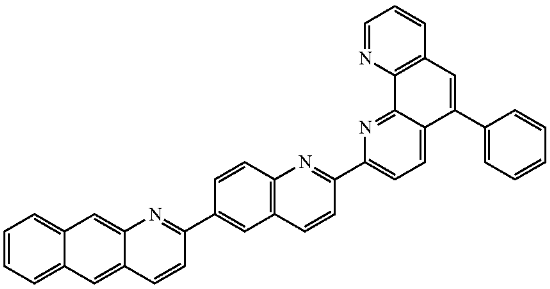
245
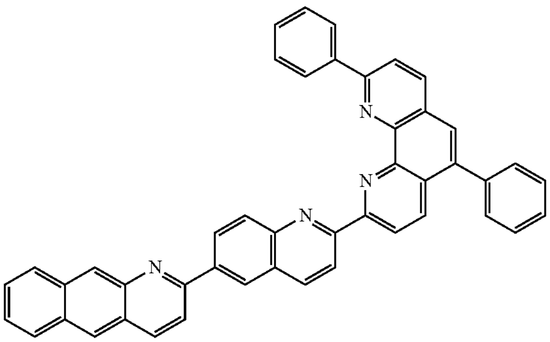
246
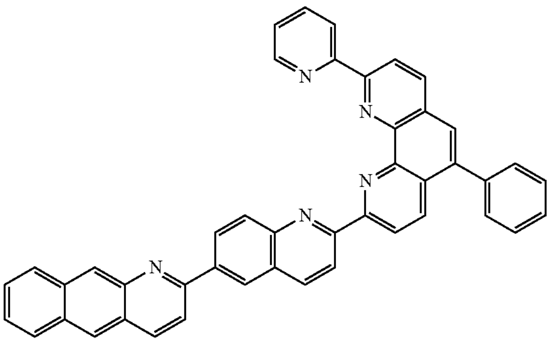
247
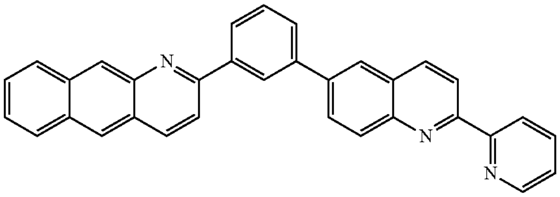
248
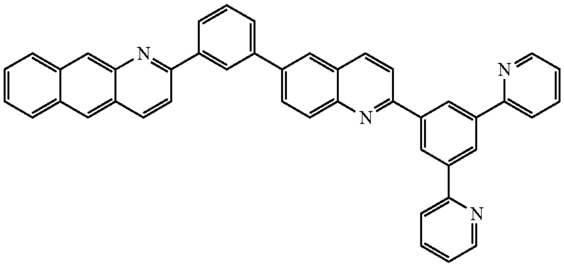

-continued
249
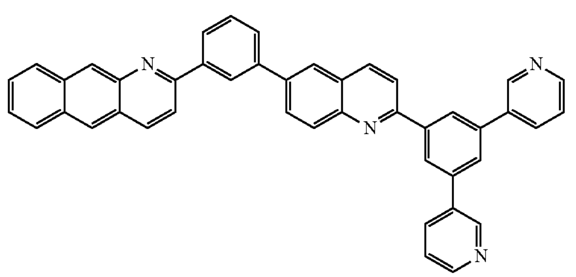
250
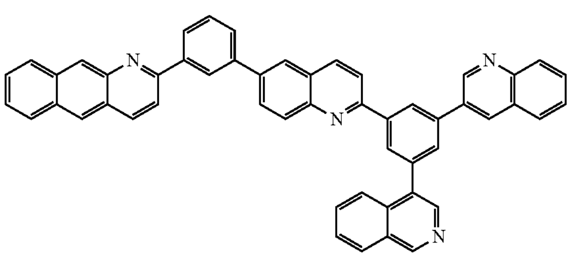
251
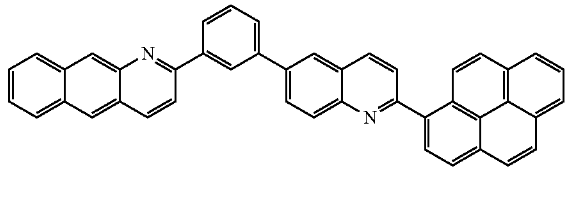
252
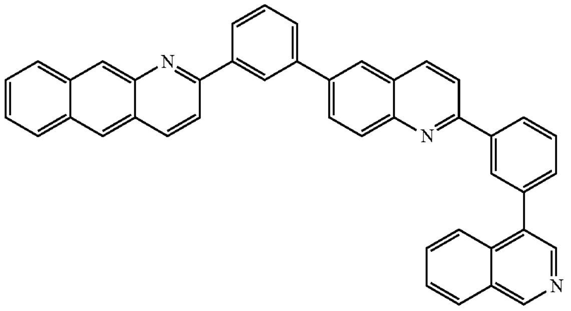
253
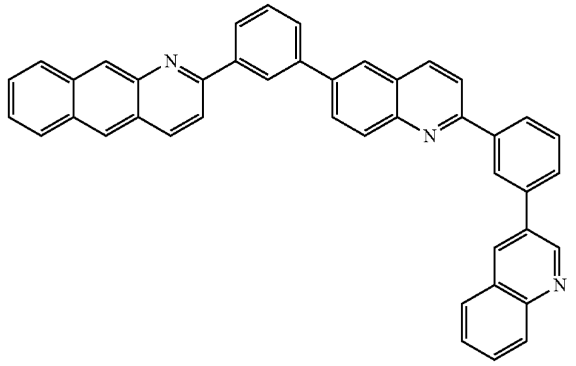
254
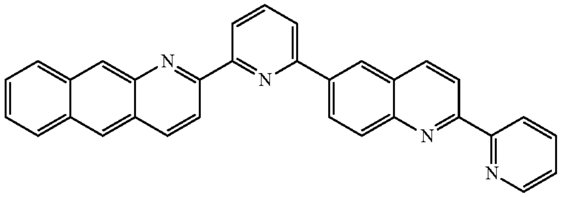
255
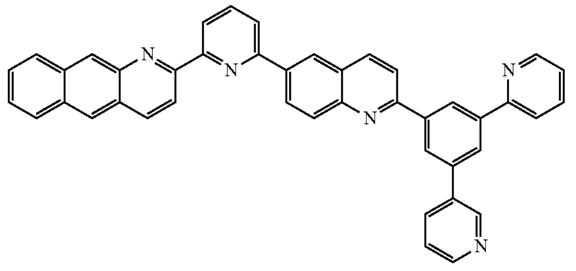
256
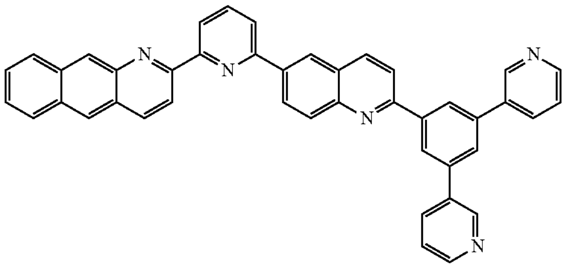
257
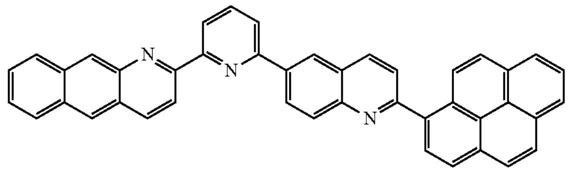
258
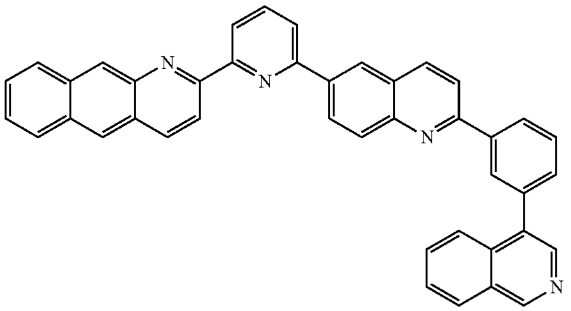

-continued
259
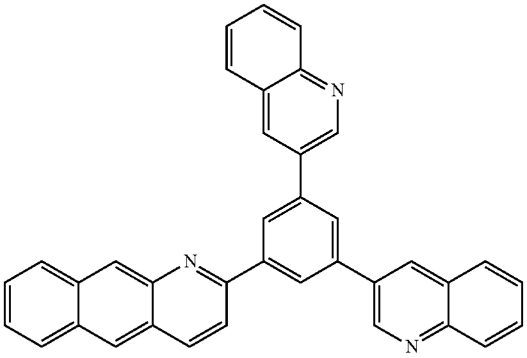
260
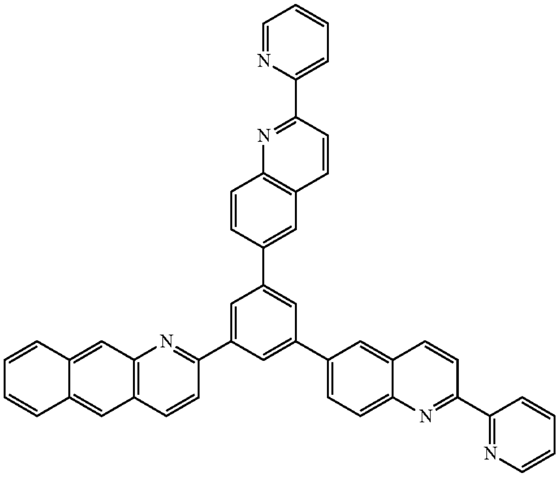
261
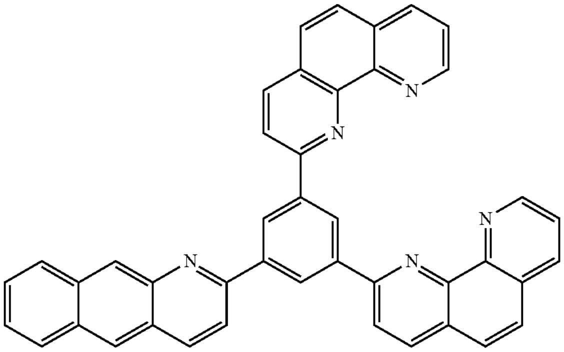
262
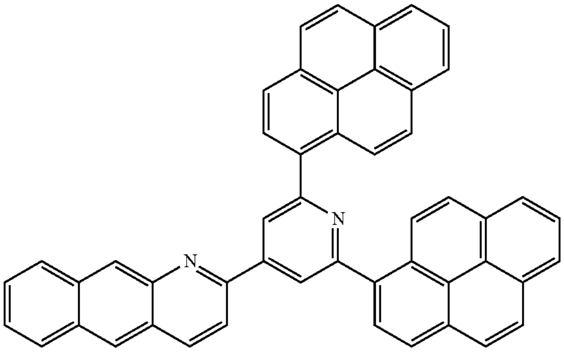
263
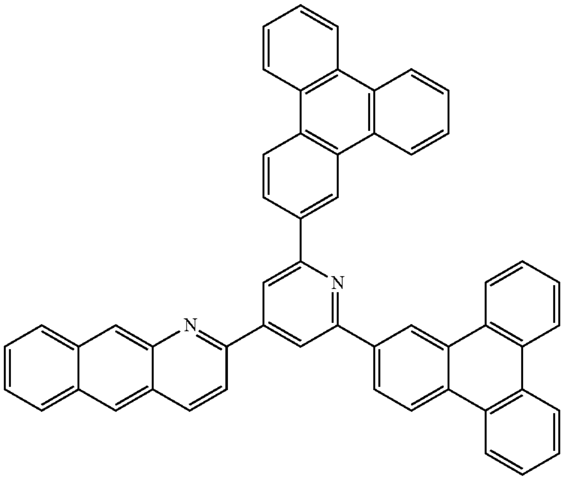
264
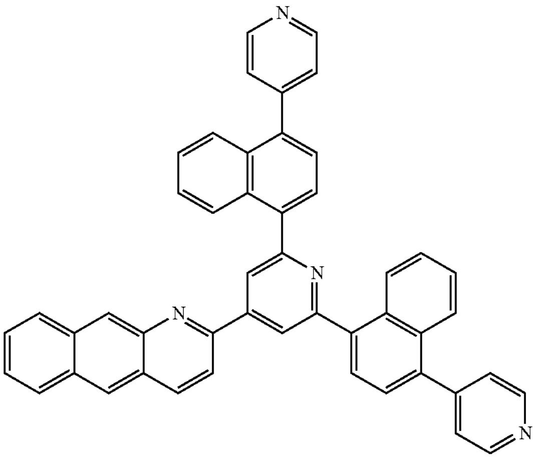

-continued
265
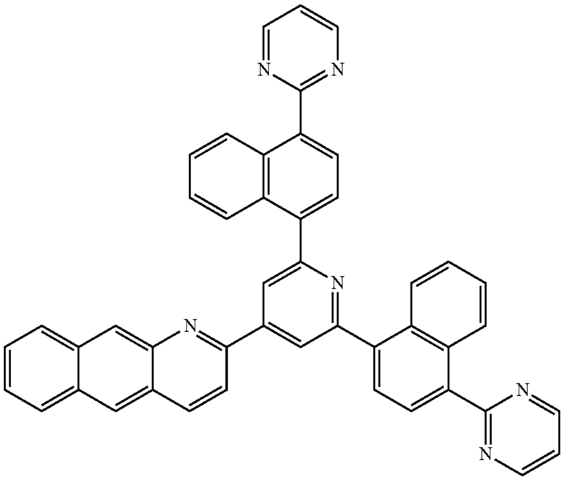
266
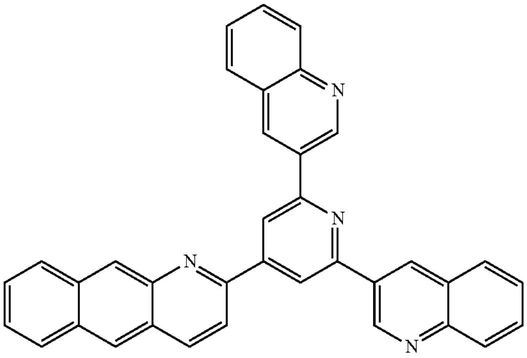
267
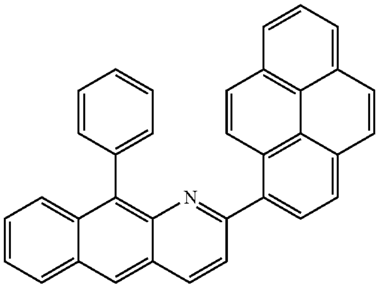
268
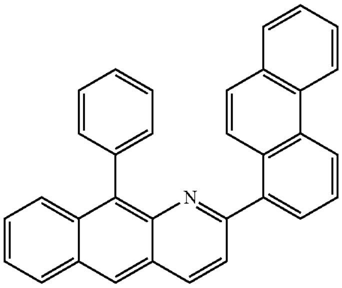
269
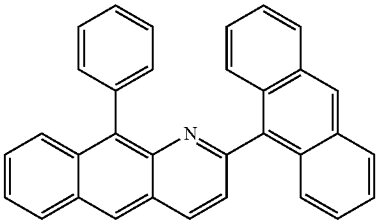
270
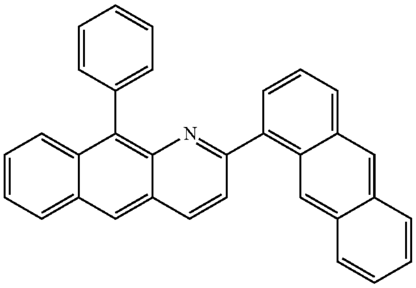
271
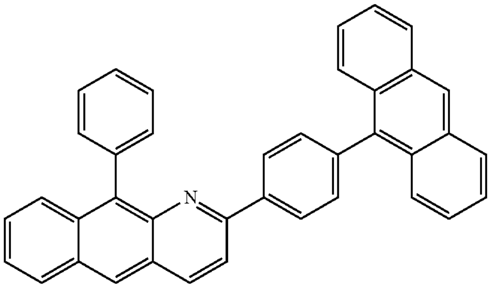
272
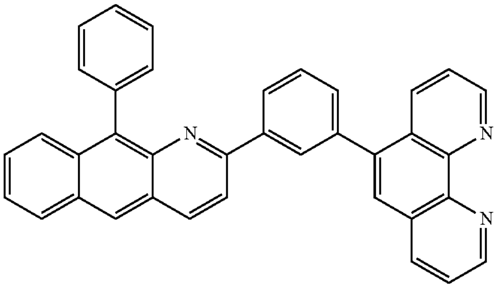

-continued
273
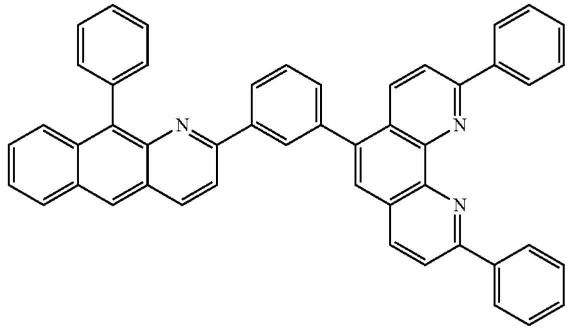
274
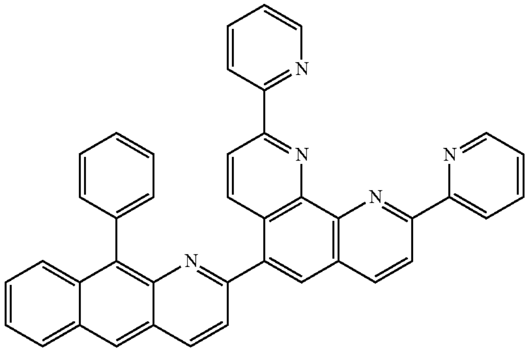
275
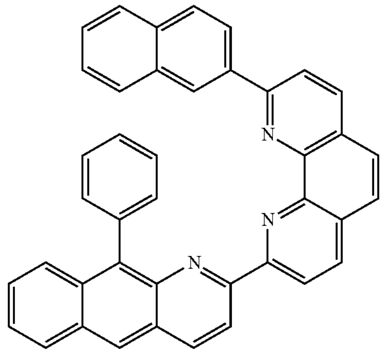
276
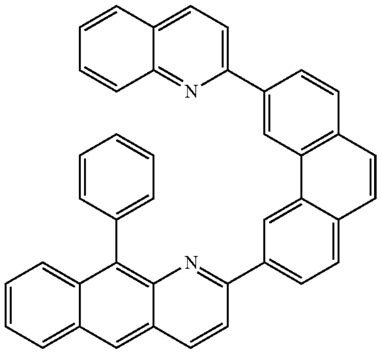
277
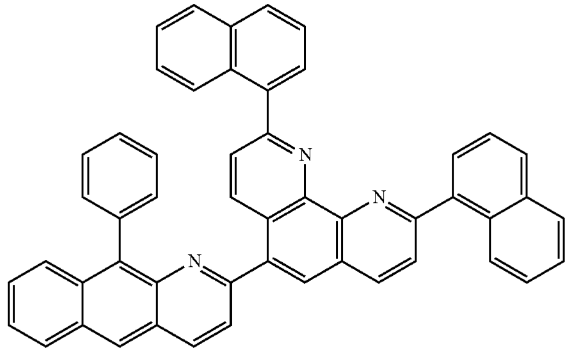
278
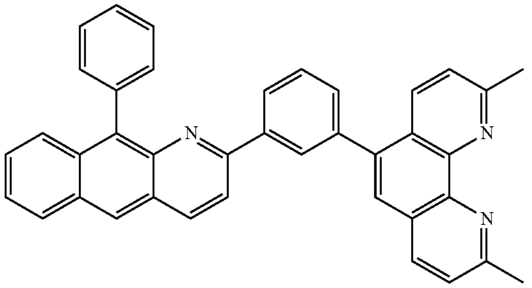
279
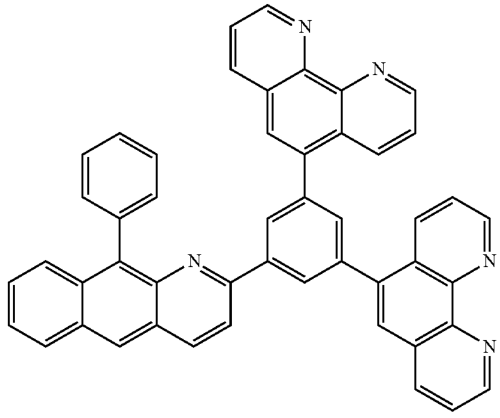
280
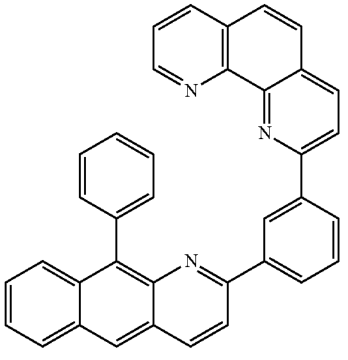

-continued
281
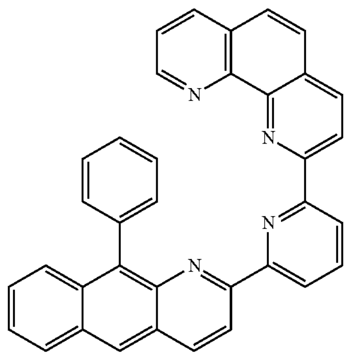
282
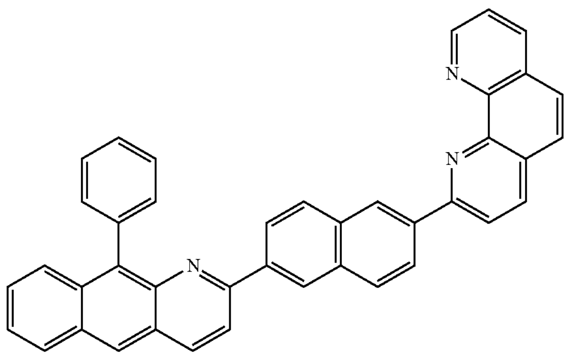
283
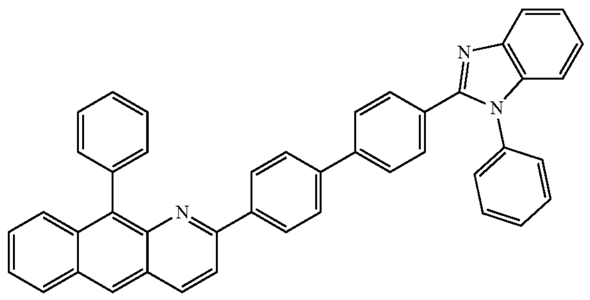
284
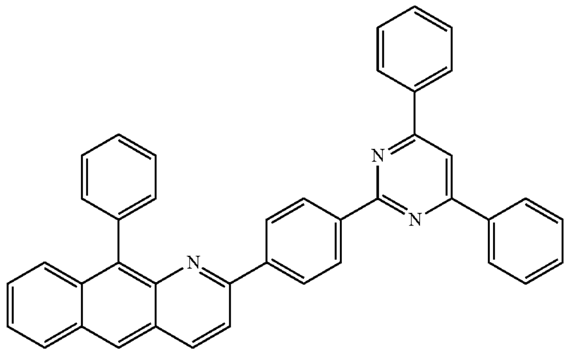
285
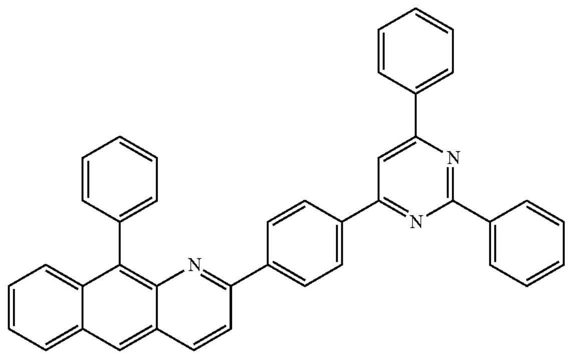
286
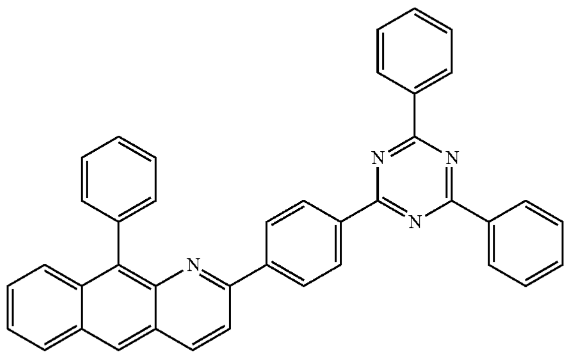
287
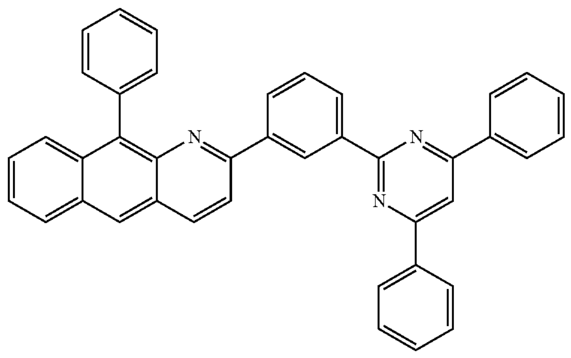
288
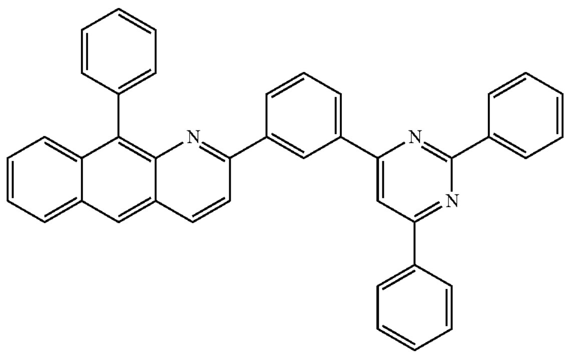

-continued
289
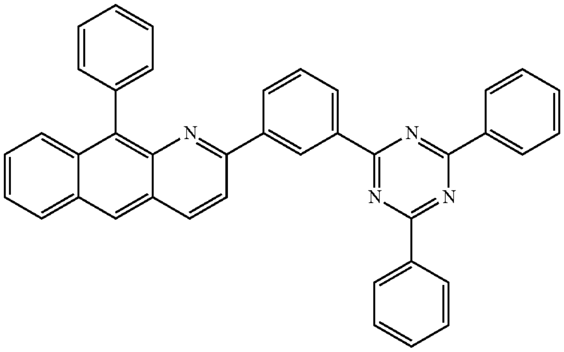
291
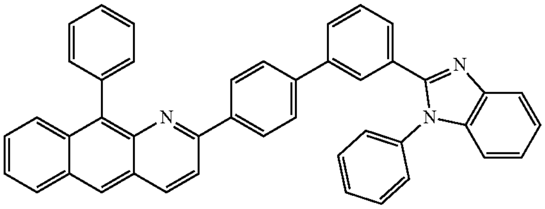
292
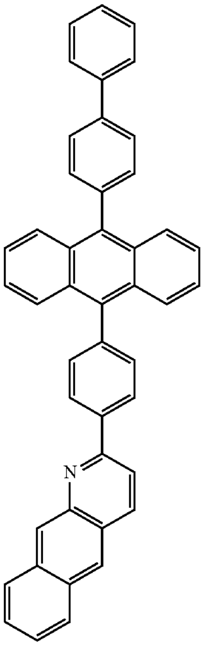
293
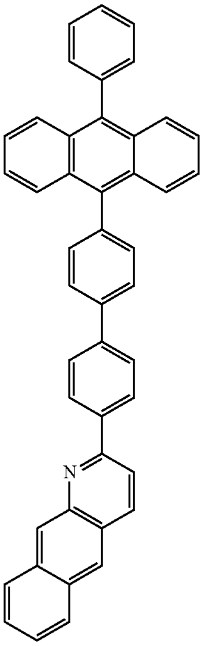
294
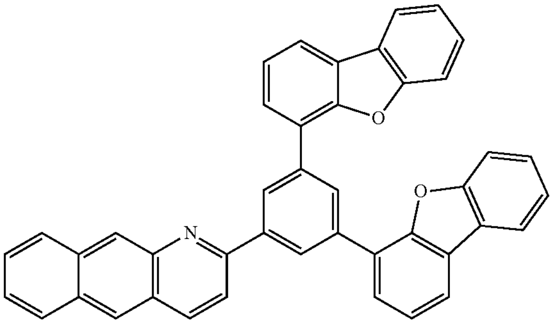
295
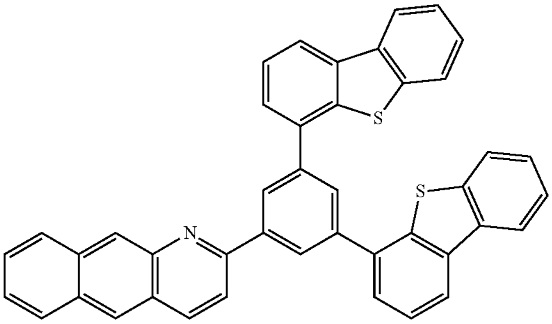

-continued
296
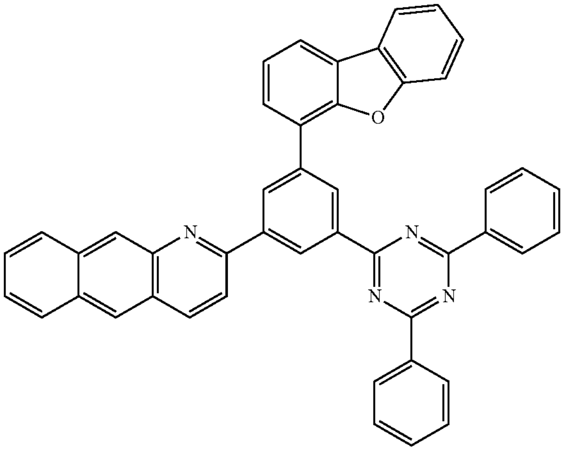
297
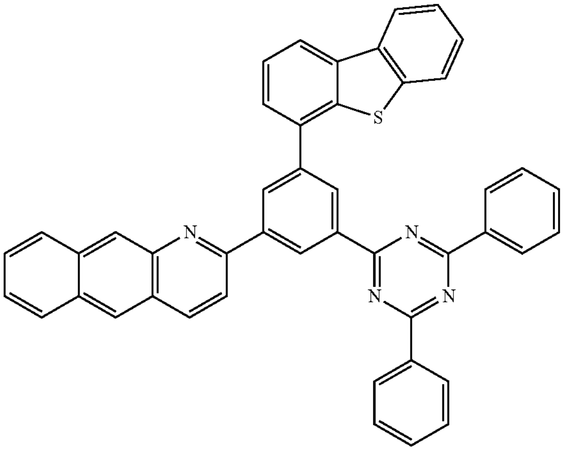
298
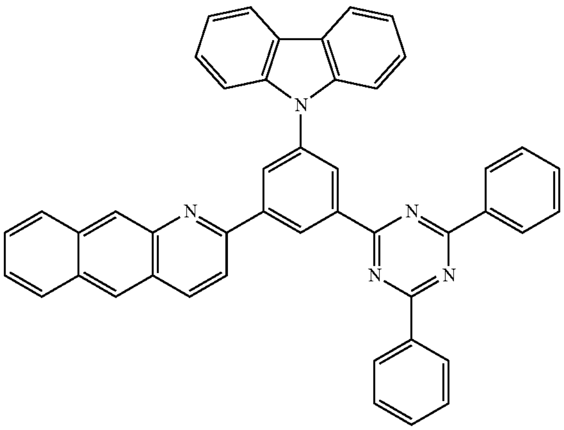
299
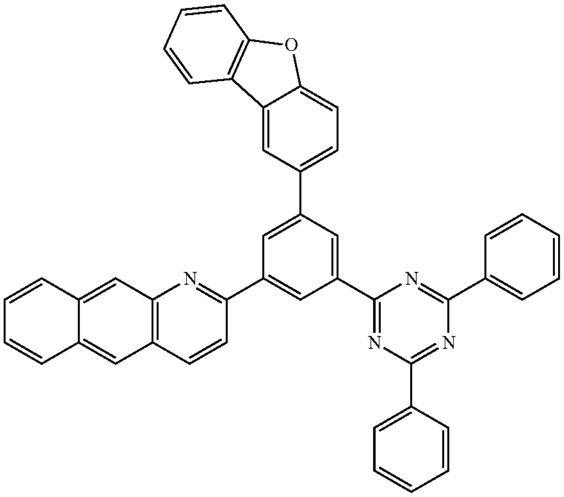
300
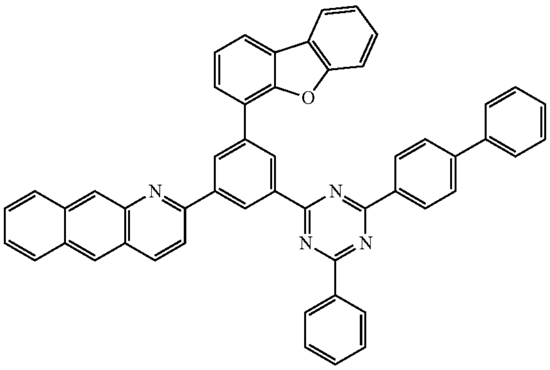
301
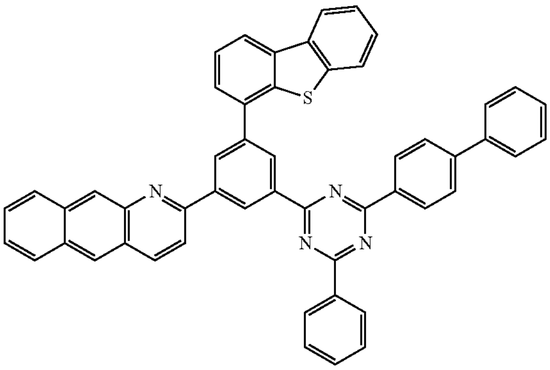

-continued
302
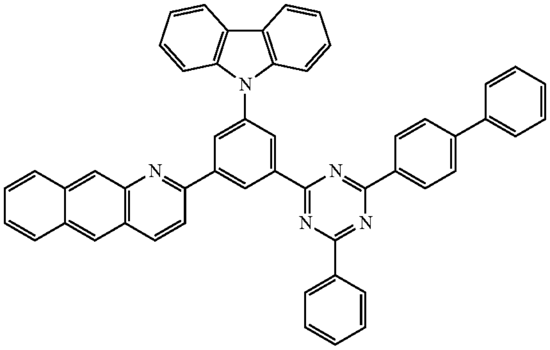
303
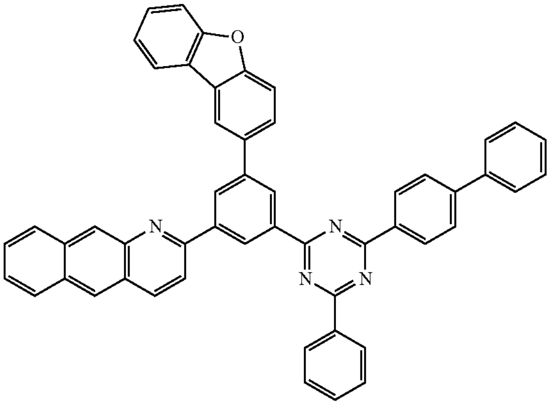
304
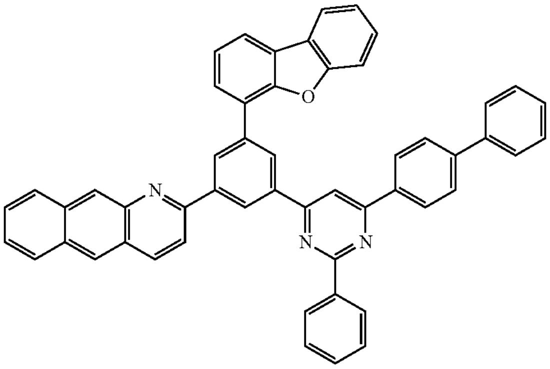
305
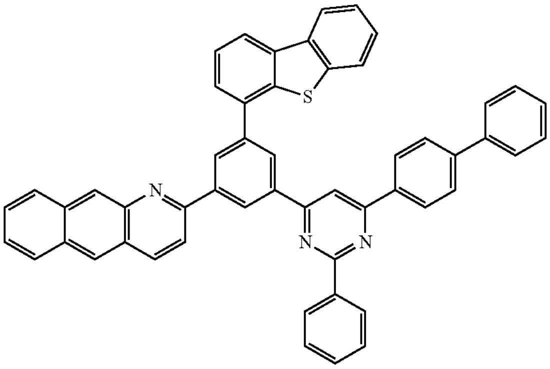
306
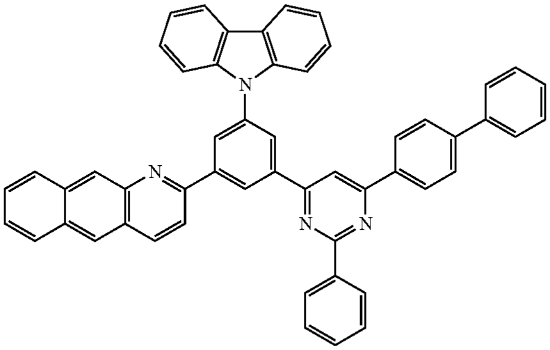
307
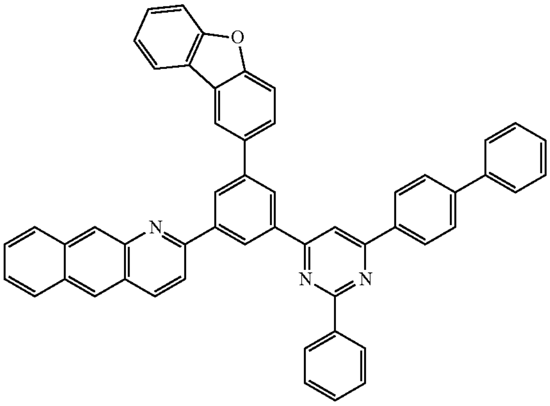

-continued
308
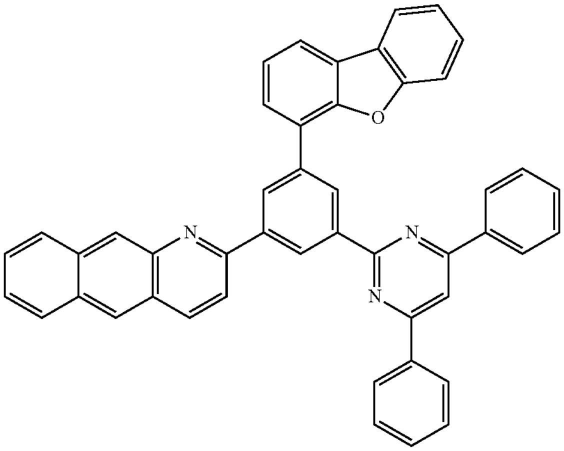
309
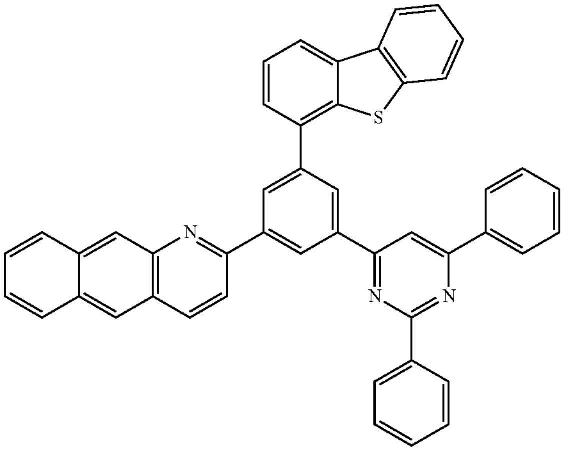
310
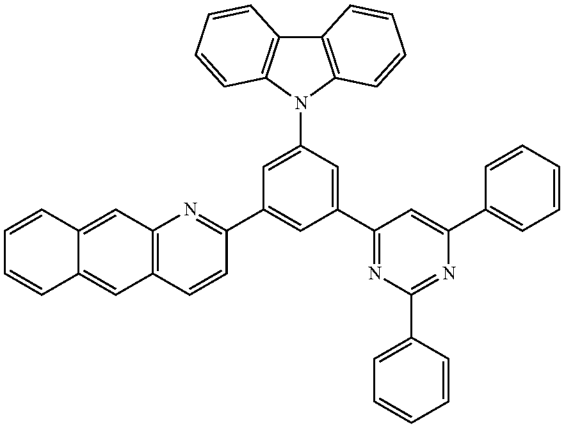
311
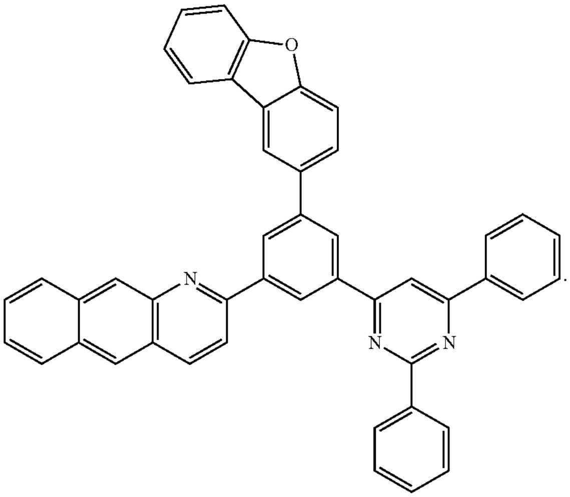
* * * * *